(12) United States Patent
Shiraishi et al.

(10) Patent No.: US 7,371,772 B2
(45) Date of Patent: May 13, 2008

(54) BICYCLIC COMPOUND, PRODUCTION AND USE THEREOF

(75) Inventors: Mitsuru Shiraishi, Amagasaki (JP); Masanori Baba, Kagoshima (JP); Katsuji Aikawa, Takatsuki (JP); Naoyuki Kanzaki, Ibaraki (JP); Masaki Seto, Ibaraki (JP); Yuji Iizawa, Muko (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 345 days.

(21) Appl. No.: 10/484,762

(22) PCT Filed: Aug. 7, 2002

(86) PCT No.: PCT/JP02/08043

§ 371 (c)(1),
(2), (4) Date: Jan. 23, 2004

(87) PCT Pub. No.: WO03/014105

PCT Pub. Date: Feb. 20, 2003

(65) Prior Publication Data

US 2004/0259876 A1 Dec. 23, 2004

(30) Foreign Application Priority Data

Aug. 8, 2001 (JP) ............................. 2001-240750
Mar. 12, 2002 (JP) ............................. 2002-066809

(51) Int. Cl.
| | |
|---|---|
| A61P 31/18 | (2006.01) |
| A61K 31/335 | (2006.01) |
| A61K 31/395 | (2006.01) |
| A61K 31/4178 | (2006.01) |
| A61K 31/4196 | (2006.01) |
| C07D 313/20 | (2006.01) |
| C07D 225/06 | (2006.01) |
| C07D 403/12 | (2006.01) |
| C07D 405/14 | (2006.01) |
| C07D 403/14 | (2006.01) |

(52) U.S. Cl. ...................... 514/383; 514/397; 514/459; 540/476

(58) Field of Classification Search ................ 514/383, 514/397, 459; 540/476
See application file for complete search history.

(56) References Cited

FOREIGN PATENT DOCUMENTS

| WO | WO-96/01267 | 1/1996 |
| WO | WO-99/32100 | 7/1999 |
| WO | WO-00/10965 | 3/2000 |

OTHER PUBLICATIONS

Horuk, Richard, Chemokine Receptors, Cytokine and Growth Factor Reviews, vol. 12, No. 4, pp. 313-335, Dec. 2001.*

R. Liu, et al., "Homozygous Defect in HIV-1 Coreceptor Accounts for Resistance of Some Multiply-Exposed Individuals to HIV-1 Infection", Cell, (1996), 86: 367-377.
M. Samson, et al., "Resistance to HIV-1 Infection in Caucasian Individuals Bearing Mutant Alleles of the CCR-5 Chemokine Receptor Gene", Nature, (1996), 382: 722-725.
M. Baba, et al., "TAK-652 Inhibits CCR5-Mediated Human Immunodeficiency Virus Type 1 Infection In Vitro and Has Favorable Pharmacokinetics in Humans", Antimicrobial Agents and Chemotherapy, (2005), pp. 4584-4591.
M. Fischereder, et al., "CC Chemokine Receptor 5 and Renal-Transplant Survival", The Lancet (2001), 357: 1758-1761.
F. Sellebjerg, et al., "CCR5 Delta 32, Matrix Metalloproteinase-9 and Disease Activity in Multiple Sclerosis", Journal of Neuroimmunology, (2000), pp. 98-106.
V. Pokorny, et al., "Evidence for Negative Association of the Chemokine Receptor CCR5 d32 Polymorphism with Rheumatoid Arthritis", Ann. Rheum. Dis., (2005), 64: 487-490.
T.C. Dawson, et al., "Absence of CC Chemokine Receptor-2 Reduces Atherosclerosis in Apolipoprotein E-Deficient Mice", Atherosclerosis, (1999), 143: 205-211.
K. Maeda, et al., "The Current Status of, and Challenges in, the Development of CCR5 Inhibitors as Therapeutics for HIV-1 Infection", Current Opinion in Pharmacology, (2004), 4: 447-452.
K. Princen, et al., "HIV Chemokine Receptor Inhibitors as Novel anti-HIV Drugs", Cytokine & Growth Factor Reviews, (2005), 16: 659-677.
W. Kazmierski, et al., "Recent Progress in Discovery of Small-Molecule CCR5 Chemokine Receptor Ligands as HIV-1 Inhibitors", Bioorganic & Medicinal Chemistry, (2003), 11: 2663-2676.
M. Baba et al. "A small-molecule, nonpeptide CCR5 antagonist with highly potent and selective anti-HIV-1 activity," Proc. Natl. Acad. Sci., vol. 96, pp. 5698-5703 (May 1999).
H. Fukushi et al., "Synthesis and Platelet-Activating Factor (PAF)-Antagonistic Activities of 1,4-Disubstituted Piperazine Derivatives," Chem. Pharm. Bull., vol. 42, No. 3, pp. 541-550 (1994).

* cited by examiner

*Primary Examiner*—Brenda L Coleman
(74) *Attorney, Agent, or Firm*—Edwards, Angell, Palmer and Dodge, LLP; David G. Conlin; Jeffrey L. Kopacz

(57) ABSTRACT

The present invention provides a new cyclic compound having a CCR antagonist activity, especially a CCR5 antagonist activity, and the use thereof. The compound of the present invention is represented by the formula:

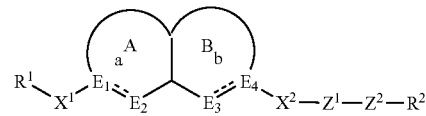

wherein, $R^1$ is a 5- to 6-membered ring group which may be substituted; $X^1$ is a bond or the like; ring A is a 5- to 6-membered ring group which may be substituted; ring B is a 8- to 10-membered ring group which may be substituted; $X^2$ is a bivalent group of 1 to 4 atoms; $Z^1$ is a bivalent cyclic ring group or the like; $Z^2$ is a bond or the like; and $R^2$ is an amino group, a nitrogen-containing heterocyclic group which may be substituted or the like, or a salt thereof.

1 Claim, No Drawings

BICYCLIC COMPOUND, PRODUCTION AND USE THEREOF

This application is the National Phase filing of International Patent Application No. PCT/JP02/08043, filed Aug. 7, 2002.

FIELD OF THE INVENTION

The present invention relates to a new cyclic compound having CCR antagonist activity, especially CCR5 antagonist activity, and use thereof.

BACKGROUND ART

Recently, HIV (human immunodeficiency virus) protease inhibitors have been developed for treatment of AIDS (acquired immune deficiency syndrome). With combined use of the protease with either of two HIV reverse transcriptase inhibitors which have been commonly used, treatment of AIDS has made remarkable progress. However, the treatment is still not efficient enough, and development of a new anti-AIDS medicine based on a different mechanism of action is desired.

As a receptor when HIV invades a target cell, CD4 has already been known. Recently, new receptors, CCR5 as a second receptor of macrophage directed HIV, and CXCR4 as a second receptor of T cell directed HIV, a G-protein conjugated chemokine receptor having a seven-transmembrane protein structure, have been found, suggesting a critical role of these chemokine receptors for infection and transmission of HIV. As a matter of fact, it has been reported that a man having resistance to infection even after repeated exposures to the virus had a mutation in which CCR5 gene was deleted homologically. Thus, the CCR5 antagonists have a potential to provide a new HIV medicine, and examples of synthesis of new anilide derivatives having CCR5 antagonist activity have been reported in, for example, PCT/JP98/05708 (WO99/32100), Japanese Patent Application No. 10-234388 (WO00/10965), and Japanese Patent Application No. 10-363404 (PCT/JP99/07148), while there has been no report of a CCR5 antagonist which has been commercialized as a therapeutic medicine for AIDS. Further, a compound having CCR5 antagonist activity has been described as useful as a preventative medicine of AIDS in JP 2001-026586 A, but said compound has a different structure from the compound of the present invention.

OBJECTS OF THE INVENTION

The present invention is to provide a new bicyclic compound that is useful for preventing and treating HIV infectious diseases, especially AIDS, due to its CCR antagonist activity, especially CCR5 antagonist activity.

SUMMARY OF THE INVENTION

The present inventors have intensively studied compounds having CCR5 antagonist activity, and found a compound of the formula [I] below or the salt thereof, (hereinafter, sometimes, referred to as compound [I]), has an excellent clinically-favorable pharmacological property including CCR antagonist activity, especially CCR5 antagonist activity, and completed the present invention.

Thus, the present invention provides:
[1] A compound of the formula:

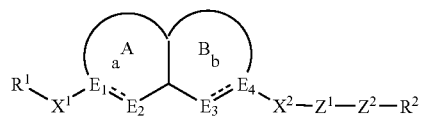

[I]

wherein $R^1$ is a cyclic 5- to 6-membered ring which may be substituted; $X^1$ is a bond or a bivalent chain group whose straight chain moiety is constituted of 1 to 4 atoms; ring A is a 5- to 6-membered ring which may be substituted; ring B is a 8- to 10-membered ring which may be substituted; each of $E_1$ and $E_4$ is a carbon atom which may be substituted or a nitrogen atom which may be substituted; each of $E_2$ and $E_3$ is a carbon atom which may be substituted, a nitrogen atom which may be substituted, a sulfur atom which may be oxidized, or an oxygen atom; each of a and b is a single bond or a double bond; $X^2$ is a bivalent chain group whose straight chain moiety is constituted of 1 to 4 atoms; $Z^1$ is a bond or a bivalent cyclic group; $Z^2$ is a bond or a bivalent group; and $R^2$ is (1) an amino group which may be substituted and whose nitrogen atoms may be converted to quarternary ammonium or oxide, (2) a nitrogen-containing heterocyclic group which may be substituted, may contain a sulfur or oxygen atom as a ring constituent atom, and whose nitrogen atom may be converted to quarternary ammonium or oxide, (3) a group of the formula:

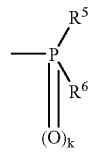

wherein k is 0 or 1; when k is 0, the phosphorus atom may form a phosphonium salt; each of $R^5$ and $R^6$ is a hydrocarbon group which may be substituted, a hydroxy group which may be substituted or an amino group which may be substituted; and $R^5$ and $R^6$ may form a ring with the adjacent phosphorus atom), (4) an amidino group which may be substituted, or (5) a guanidino group which may be substituted; or a salt thereof, provided that a compound of the formula:

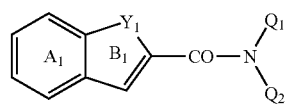

wherein ring $A_1$ is a benzene ring which may be substituted; $Y_1$ is a bivalent group so that ring $B_1$ forms a 8-membered ring; $Q_1$ is a group of the formula:

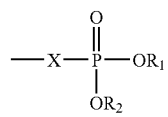

wherein X is a bond or a bivalent group; and $R^1$ and $R^2$ are the same or different and each is hydrogen, or a lower alkyl group, or may bind each other to form a ring; and $Q_2$ is hydrogen, a hydrocarbon group which may be substituted or a heterocyclic group which may be substituted, is excluded;

[2] A pro-drug of the compound of the above [I];

[3] The compound of the above [1], wherein $R^1$ is benzene, furan, thiophene, pyridine, cyclopentane, cyclohexane, pyrrolidine, piperidine, piperazine, morpholine, thiomorpholine, or tetrahydropyran, each of which may be substituted;

[4] The compound of the above [1], wherein $R^1$ is benzene which may be substituted;

[5] The compound of the above [1], wherein ring B is a 8-membered ring which may be substituted;

[6] The compound of the above [1], wherein $Z^1$ is phenylene which may be substituted with substituent(s) selected from the group consisting of (1) a halogen atom; (2) an alkyl group of 1 to 4 carbons which may be substituted with halogen atom(s); and (3) an alkoxy group of 1 to 4 carbons which may be substituted with halogen atom(s);

[7] The compound of the above [1], wherein $Z^1$ is phenylene which may be substituted with methyl or trifluoromethyl;

[8] The compound of the above [1], wherein $Z^2$ is $Z^{2a}$—$W^1$—$Z^{2b}$— wherein, each of $Z^{2a}$ and $Z^{2b}$ is O, $S(O)_m$ (wherein m is 0, 1, or 2), an imino group which may be substituted, or a bond; $W^1$ is an alkylene chain which may be substituted, an alkenylene chain, or a bond;

[9] The compound of the above [1], wherein $Z^2$ is —$CH_2$—, —CH(OH)—, or —$S(O)_m$—$CH_2$— (wherein m is 0, 1, or 2);

[10] The compound of the above [1], wherein $Z^2$ is —$S(O)_m$—$CH_2$— (wherein m is 0 or 1 or 2);

[11] The compound of the above [1], wherein $R^2$ is (1) an amino group which may be substituted and whose nitrogen atoms may be converted to quarternary ammonium or oxide, (2) a nitrogen-containing heterocyclic group which may be substituted, may contain a sulfur or oxygen atom as a ring constituent atom, and whose nitrogen atom may be converted to quarternary ammonium or oxide, (3) an amidino group which may be substituted, or (4) a guanidino group which may be substituted;

[12] The compound of the above [1], wherein $R^2$ is an amino group which may be substituted or a nitrogen-containing heterocyclic group which may be substituted and may contain a sulfur atom or an oxygen atom as a ring constituent atom;

[13] The compound of the above [1], wherein $R^2$ is a group of —NRR' (wherein each of R and R' is an aliphatic hydrocarbon group which may be substituted, or an alicyclic heterocyclic group which may be substituted);

[14] The compound of the above [1], wherein $R^2$ is a nitrogen-containing aromatic heterocylic group which may substituted;

[15] The compound of the above [1], wherein $R^2$ is imidazolyl group which may be substituted or triazolyl group which may be substituted;

[16] The compound according to the above [1], wherein $R^1$ is benzene, furan, thiophene, pyridine, cyclopentane, cyclohexane, pyrrolidine, piperidine, piperazine, morpholine, thiomorpholine or tetrahydropyran each or which may be substituted with halogen, nitro, cyano, $C_{1-6}$ alkyl, $C_{1-6}$ alkoxy, $C_{1-6}$ alkoxy-$C_{1-6}$ alkyl or $C_{1-6}$ alkoxy-$C_{1-6}$ alkoxy, Ring B is 8- to 10-membered ring which may contain oxygen atom, nitrogen atom or sulfur atom which may be oxidized as a ring constituent atom and may be substituted with alkyl which may be substituted, alkenyl which may be substituted, a heterocyclic group which may be substituted or formyl, $Z^1$ is benzene which may be substituted with substituent(s) selected from (1) halogen, (2) $C_{1-4}$ alkyl which may be halogenated and (3) $C_{1-4}$ alkoxy which may be halogenated, $Z^2$ is —$Z^{2a}$—$W^1$—$Z^{2b}$—, wherein $Z^{2a}$ and $Z^{2b}$ are O, S(O)m (m is 0, 1 or 2), imino which may be substituted with $C_{1-4}$ alkyl or a bond, respectively, $W^1$ is a bond or $C_{1-4}$ alkylene or $C_{2-4}$ alkenylene chain each of which may be subsitited with $C_{1-6}$ alkyl, hydorxy, hydroxyimino or $C_{1-6}$ alkoxyimino, and $R^2$ is an amino group which may be substituted with $C_{1-4}$ alkyl, or a nitrogen-containing heterocyclic group which may be substituted with $C_{1-4}$ alkyl, may contain a sulfur or oxygen atom as a ring constituent atom;

[17] A compound of the formula:

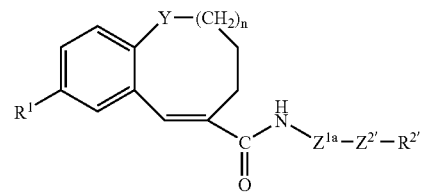

wherein $Z^{1a}$ is a 5- or 6-membered aromatic ring group; $Z^{2'}$ is a group of —$Z^{2a}$—$W^2$—$Z^{2b}$— (wherein each of $Z^{2a}$ and $Z^{2b}$ is O, $S(O)_m$ (wherein m is 0, 1, or 2), an imino group which may be substituted, or a bond; and $W^2$ is a alkylene chain which may be substituted); n is 1, 2, or 3; Y is O, S(O)p (wherein p is 0, 1, or 2), $CH_2$, or $NR^4$ ($R^4$ is hydrogen, a hydrocarbon group which may be substituted, a heterocyclic group which may be substituted or an acyl group which may be substituted); and $R^{2'}$ is (1) an amino group which may be substituted and whose nitrogen atom may be converted to quarternary ammonium or oxide; (2) a nitrogen-containing heterocyclic group which may be substituted and may contain a sulfur atom or an oxygen atom as a ring constituent atom, and whose nitrogen atom may be converted to quarternary ammonium or oxide; (3) an amidino group which may be substituted; (4) a guanidino group which may be substituted; and $R^1$ is as described in the above [1], or a salt thereof;

[18] A compound of the formula:

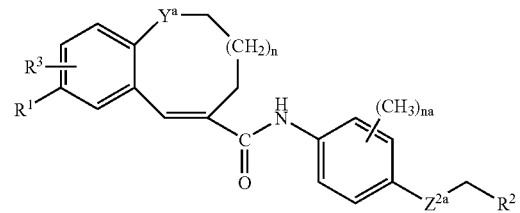

wherein
$R^1$ is ($C_{1-6}$ alkoxy-$C_{1-6}$ alkoxy)phenyl,
$R^2$ is (1) N—$C_{1-6}$ alkyl-N-tetrahydropyranylamino, (2) imidazolyl which may be substituted with $C_{1-6}$ alkyl which may be substituted, or (3) triazolyl which may be substituted with $C_{1-6}$ alkyl which may be substituted, R³ is hydrogen, a lower alkyl group which may be substituted or a lower alkoxy group which may be substituted, Yᵃ is (1) oxygen atom, (2) S(O)$_p$ (p is 0, 1 or 2), (3) CH$_2$ or (4) imono which may be substituted with formyl, C$_{1-6}$ alkyl which may be substituted, C$_{2-6}$ alkenyl which may be substituted, aryl which may be substituted, a heterocyclic group which may be substituted, arylmethyl which may be substituted or a heterocyclic methyl which may be substitued, n is 1, 2 or 3, na is 0 or 1, and Z²ᵃ is a bond, S, SO or SO$_2$, or a salt thereof;

[19] The compound of the above [18], wherein Z²ᵃ is SO;

[20] The compound of the above [18], wherein Z²ᵃ is SO whose configuration is (S);

[21] The compound of the above [18], wherein Yᵃ is imono which may be substituted with formyl, C$_{1-6}$ alkyl which may be substituted, C$_{2-6}$ alkenyl which may be substituted, aryl which may be substituted, a heterocyclic group which may be substituted, arylmethyl which may be substituted or a heterocyclic methyl which may be substitued;

[22] 8-[4-(2-butoxyethoxy)phenyl]-1-isobutyl-N-[4-[[N-methyl-N-(tetrahydropyran-4-yl)amino]methyl]phenyl]-1,2,3,4-tetrahydro-1-benzazocine-5-carboxamide;

[23] (S)-8-[4-(2-butoxyethoxy)phenyl]-1-isobutyl-N-[4-[[(1-propyl-1H-imidazol-5-yl)methyl]sulfinyl]phenyl]-1,2,3,4-tetrahydro-1-benzazocine-5-carboxamide methanesulfonate;

[24] (S)-8-[4-(2-butoxyethoxy)phenyl]-1-propyl-N-[4-[[(1-propyl-1H-imidazol-5-yl)methyl]sulfinyl]phenyl]-1,2,3,4-tetrahydro-1-benzazocine-5-carboxamaide methanesulfonate;

[25] (S)-1-isobutyl-8-[4-(2-propoxyethoxy)phenyl]-N-[4-[[(1-propyl-1H-imidazol-5-yl)methyl]sulfiyl]phenyl]-1,2,3,4-tetrahydro-1-benzazocine-5-carboxamide;

[26] (S)-8-[4-(2-butoxyethoxy)phenyl)-1-[(1-methyl-1H-pyrazol-4-yl)methyl]-N-[4-[[(1-propyl-1H-imidazol-5-yl]methyl]sulfinyl]phenyl]-1,2,3,4-tetrahydro-1-benzazocine-5-carboxamide;

[27] (S)-8-[4-(2-butoxyethoxy)phenyl]-1-isobutyl-N-[4-[[(4-propyl-4H-1,2,4-triazol-3-yl)methyl]sulfinyl]phenyl]-1,2,3,4-tetrahydro-1-benzazocine-5-carboxamide;

[28] A process for producing a compound of the formula

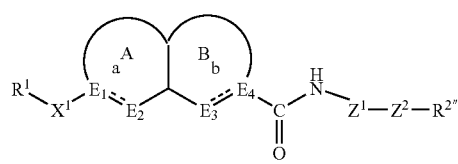

wherein R²‴ is (1) an amino group which may be substituted and whose nitrogen atom may be converted to quarternary ammonium or oxide, (2) a nitrogen-containing heterocyclic group which may be substitute and may contain a sulfur atom or an oxygen atom as a ring constituent atom, and whose nitrogen atom may be converted to quarternary ammonium or oxide, or (3) a compound represented by the formula:

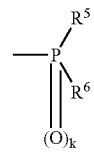

wherein k is 0, or 1, when k is 0, the phosphorus atom may form a phosphonium salt; each of R⁵ and R⁶ may be a hydrocarbon group which may be substituted, a hydroxy group which may be substituted, or an amino group which may be substituted; and R⁵ and R⁶ may bind each other with the adjacent phosphorus atom to form a cyclic group; and the other symbols are as defined in the above [1] or a salt thereof, provided that a compound of the formula:

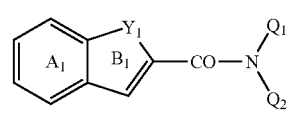

wherein each symbol is as defined in the above [1] is excluded, which comprises subjecting a compound represented the formula:

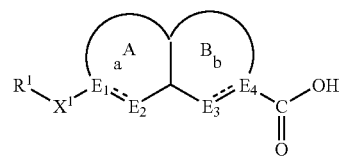

wherein each symbol is as defined in the above [1], provided that a compound represented by the formula:

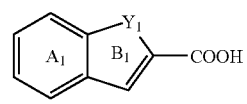

wherein each symbol is as defined in the above [1] is excluded, or a salt thereof or a derivative thereof, and a compound represented by the formula:

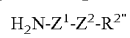

H$_2$N-Z¹-Z²-R²‴ wherein R²‴ is as defined above; Z¹ and Z² are as defined in the above [1], or salt thereof, provided that a compound represented by the formula:

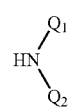

wherein each symbol is as defined in the above [1] is excluded, to a condensation reaction, and then optionally to deprotection, oxidation/reduction or quarternary ammonium formation reaction;

[29] A compound of the formula:

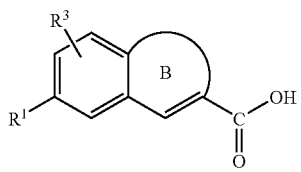

wherein R³ is hydrogen, a halogen atom, a lower alkyl group which may be substituted, or a lower alkoxy group which may be substituted; and the other symbols are as defined in claim 1, or a salt thereof, provided that a compound represented by the formula:

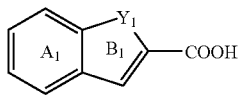

wherein each symbol is as defined in the above [1] is excluded;

[30] A CCR antagonist pharmaceutcial composition comprising a compound of the formula [I], or a salt or prodrug thereof;

[31] A pharmaceutical composition comprising the compound of the above [1], or a salt or prodrug thereof;

[32] The composition of the above [31] which is a CCR antagonist;

[33] The compoisiton of the above [30], wherein CCR is CCR 5 and/or CCR 2;

[34] The composition of the above [30], wherein CCR is CCR5;

[35] The composition of the above [30] which is a medicine for preventing or treating HIV infectious diseases, chronic rheumatoid arthritis, autoimmune disease, allergic diseases, ischemic brain cell disorder, cradiac infarction, chronic nephritis or arteriosckerisus;

[36] The composition of the above [30] which is a medicine for preventing or treating HIV infectious diseases;

[37] The composition of the above [30] which is a medicine for preventing or treating AIDS;

[38] The composition of the above [30] which is a medicine for suppression on disease progression of AIDS;

[39] The composition of the above [30] which is blood for transfusion or blood derivatives;

[40] The composition of the above [30] which is a medicine for preventing or treating graft versus host disease and/or rejection in case of organ or bone marrow transplantation;

[41] The composition of the above [30] in combination with a protease inhibitor and/or a reverse transcriptase inhibitor;

[42] The composition of the above [41], wherein the reverse transcriptase inhibitor is zidovudine, didanosine, zaicitabine, lamivudine, stavudine, nevirapine, delavirdine, efavirenz, or abacavir;

[43] The composition of the above [41], wherein the protease inhibitor is saquinavir, ritonavir, indinavir, amprenavir, or nelfinavir;

[44] A method for antagonizing CCR5 which comprises administering an effective amount of a compound of the formula [I], or a salt or prodrug thereof, to a mammal in need thereof;

[45] The method of the above [44], wherein a protease inhibitor and/or a reverse transcriptase inhibitor is further administered;

[46] A method for preventing or terating HIV infectious disease, chronic rheumatoid, autoimmune disease, allergic disease, ischemic brain cell disorder, cardiac infarction, chronic nephrotis or arteriosclerosis which comprises administering an effective amount of a compound of the formula [I], or a salt or prodrug thereof, to a mammal in need thereof;

[47] A method for preventing or treating graft versus host disease and/or rejection in case of organ or bone marrow transplantation which comprises administering an effective amount of a compound of the formula [I], or a salt or prodrug thereof, to a mammal in need thereof;

[48] A method for preventing HIV infectious disease in case of transfusion or using blood derivatives which comprises administering an effective amount of a compound of the formula [I], or a salt or prodrug thereof;

[49] The method of the above [48], wherein the compound is administered at the same time of or within 1 hour after transfusion or use of blood derivatives;

[50] A process for producing blood for transfusion or blood derivatives prevented or inhibited from infection of HIV virous and proliferation thereof which comprises compounding the blood for transfusion or blood derivatives with a compound of the formula [I], or a salt thereof;

[51] A method for preventing or inhibiting infection of HIV virus and proliferation thereof in blood for transfusion or blood derivatives which comprises compounding the blood for transfusion or blood derivatives with a compound of the formula [I], or a salt thereof;

[52] Use of a compound of the formula [I], or a salt or prodrug thereof for manufacturing a CCT5 antagonist;

[53] Use of a compound of the formula [I], or a salt or prodrug thereof, for manufacturing a medicine for preventing or treating graft versus host disease and/or rejection in case of organ or bone marrow transplantation;

[54] Use of a compound of the formula [I], or a salt or prodrug thereof, for manufacturing a medicine for preventing or treating HIV infectious disease, chronic rheumatoid, autoimmune disease, allergic disease, ischemic brain cell disorder, cardiac infarction, chronic nephrotis or arteriosclerosis;

[55] Use of a compound of the formula [I], or a salt or prodrug thereof, for manufacturing blood for transfusion or blood derivatives;

[56] Use of a compound of the formula [I], or a salt or prodrug thereof, for manufacturing a medicine for preventing or treating HIV infectious disease containing a protease inhibitor and/or a reverse transcriptase inhibitor; and the like.

DETAILED DESCRIPTION OF THE INVENTION

Examples of the "5- to 6-membered ring" in the "5- to 6-membered ring which may be substituted" represented by $R^1$ in the formula [I] include a group which is formed by subtracting a hydrogen atom from 6-membered aromatic hydrocarbon such as benzene, etc.; 5- to 6-membered aliphatic hydrocarbon such as cyclopentane, cyclohexane, cyclopentene, cylcohexene, cyclobutadiene, cyclohexadiene, etc.; 5- to 6-membered aromatic heterocyclic group containing 1 to 4 hetero atoms of one or two kinds selected from the group consisting of nitrogen, sulfur and oxygen, such as furan, thiophene, pyrrole, imidazole, pyrazole, thiazole, oxazole, isothiazole, isoxazole, tetrazole, pyridine, pyrazine, pyrimidine, pyridazine, triazole, etc.; 5- to 6-membered non-aromatic heterocyclic group containing 1 to 4 hetero atoms of one or two kinds selected from the group consisting of nitrogen, sulfur and oxygen, such as tetrahydrofuran, tetrahydrothiophene, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, tetrahydrothiopyran, etc.; and the like. Among them, the "5- to 6-membered ring" (preferably a 6-membered ring) is preferably benzene, furan, thiophene, pyridine, cyclopentane, cyclohexane, pyrrolidine, piperidine, piperazine, morpholine, thiomorpholine, tetrahydropyran, etc., in particular, benzene.

Examples of the "substituent" of the "5- to 6-membered ring" of the "5- to 6-membered ring which may be substituted" represented by $R^1$ include, for example; halogen, nitro, cyano, alkyl which may be substituted, cycloalkyl which may be substituted, hydroxy which may be substituted, thiol which may be substituted (wherein the sulfur atom may be oxidized to form sulfinyl which may be substituted or sulfonyl which may be substituted), amino which may be substituted, acyl which may be substituted, carboxyl which may be esterified, an aromatic group which may be substituted, and the like.

Examples of the "halogen" as the substituent of $R^1$ include fluorine, chlorine, bromine, iodine, and the like, preferably, fluorine and chlorine.

Examples of the "alkyl" of the "alkyl which may be substituted" as the substituent of $R^1$ include straight or branched alkyl of 1 to 10 carbons, for example, alkyl of 1 to 10 carbons, such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably, lower ($C_{1-6}$) alkyl. Examples of the substituent of said "alkyl which may be substituted" include halogen (for example, fluorine, chlorine, bromine, iodine, etc.), nitro, cyano, hydroxy, thiol which may be substituted (for example, thiol, $C_{1-4}$ alkylthio, etc.), amino which may be substituted (for example, amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc.), carboxyl which may be esterified or amidated (for example, carboxyl, $C_{1-4}$ alkoxy-carbonyl, carbamoyl, $C_{1-4}$ monoalkyl-carbamoyl, di-$C_{1-4}$ alkyl-carbamoyl, etc.), $C_{1-4}$ alkoxy which may be halogenated (for example, methoxy, ethoxy, propoxy, butoxy, trifluoromethoxy, trifluoroethoxy, etc.), $C_{1-4}$ alkoxy-$C_{1-4}$ alkoxy which may halogenated (for example, methoxymethoxy, methoxyethoxy, ethoxyethoxy, trifluoromethoxyethoxy, trifluoroethoxyethoxy, etc.), formyl, $C_{2-4}$ alkanoyl (for example, acetyl, propionyl, etc.), $C_{1-4}$ alkylsulfonyl (for example, methanesulfonyl, ethanesulfonyl, etc.), and the like, and the number of the substituents is preferably 1 to 3.

Examples of the "cycloalkyl" of the "cycloalkyl which may be substituted" as the substituent of $R^1$ include $C_{3-7}$ cycloalkyl such as cyclopropyl, cyclobutyl, cyclopentyl, cyclohexyl, cycloheptyl, etc. Examples of the substituent in the "cycloalkyl which may be substituted" include halogen (for example, fluorine, chlorine, bromine, iodine, etc.), nitro, cyano, hydroxy, thiol which may be substituted (for example, thiol, $C_{1-4}$ alkylthio, etc.), amino which may be substituted (for example, amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc.), carboxyl which may be esterified or amidated (for example, carboxyl, $C_{1-4}$ alkoxycarbonyl, carbamoyl, mono-$C_{1-4}$ alkyl-carbamoyl, di-$C_{1-4}$ alkyl-carbamoyl, etc.), $C_{1-4}$ alkoxy which may be halogenated (for example, methoxy, ethoxy, propoxy, butoxy, trifluoromethoxy, trifluoroethoxy, etc.), $C_{1-4}$ alkoxy-$C_{1-4}$ alkoxy which may be halogenated (for example, methoxymethoxy, methoxyethoxy, ethoxyethoxy, trifluoromethoxyethoxy, trifluoroethoxyethoxy, etc.), formyl, $C_{2-4}$ alkanoyl (for example, acetyl, propionyl, etc.), $C_{1-4}$ alkylsulfonyl (for example, methanesulfonyl, ethanesulfonyl, etc.), and the like, and the number of the substituents is preferably 1 to 3.

Examples of the substituent of the "hydroxy which may be substituted" as the substituent of $R^1$ include:

(1) alkyl which may be substituted (for example, $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl; and the like);

(2) cycloalkyl which may be substituted and may contain hetero atom(s) (for example, $C_{3-7}$ cycloalkyl such as cyclopropyl, cyclobutyl, cyclopentyl, cyclohexyl, cycloheptyl, etc.; 5- to 6-membered saturated heterocyclic group containing 1 to 2 hetero atoms such as tetrahydrofuranyl, tetrahydrothienyl, pyrrolidinyl, pyrazolidinyl, piperidinyl, piperazinyl, morpholinyl, thiomorpholinyl, tetrahydropyranyl, tetrahydrothiopyranyl, etc., perferably tetrahydropyranyl, etc.; and the like);

(3) alkenyl which may be substituted (for example, $C_{2-10}$ alkenyl such as allyl, crotyl, 2-pentenyl, 3-hexenyl, etc., preferably lower ($C_{2-6}$) alkenyl; and the like);

(4) cycloalkenyl which may be substituted (for example, $C_{3-7}$ cycloalkenyl such as 2-cyclopentenyl, 2-cyclohexenyl, 2-cyclopentenylmethyl, 2-cyclohexenylmethyl, etc.; and the like);

(5) aralkyl which may be substituted (for example, phenyl $C_{1-4}$ alkyl such as benzyl, phenethyl, etc.; and the like);

(6) formyl or acyl which may be substituted (for example, $C_{2-4}$ alkanoyl such as acetyl, propionyl, butyryl, isobutyryl, etc.), $C_{1-4}$ alkylsulfonyl (for example, methanesulfonyl, ethanesulfonyl, etc.), and the like);

(7) aryl which may be substituted (for example, phenyl, naphthyl, etc.; and the like); and the like.

Examples of the substituent of the above-described (1) alkyl which may be substituted, (2) cycloalkyl which may be substituted, (3) alkenyl which may be substituted, (4) cycloalkenyl which may be substituted, (5) aralkyl which may be substituted, (6) acyl which may be substituted, and (7) aryl which may be substituted, include halogen (for example, fluorine, chlorine, bromine, iodine, etc.), nitro, cyano, hydroxy, thiol which may be substituted (for example, thiol, $C_{1-4}$ alkylthio, etc.), amino which may be substituted (for example, amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc.), carboxyl which may be esterified or amidated (for example, carboxyl, $C_{1-4}$ alkoxy-carbonyl, carbamoyl, mono-$C_{1-4}$ alkyl-carbamoyl, di-$C_{1-4}$ alkyl-carbamoyl, etc.), $C_{1-4}$ alkyl which may be halogenated (for example, trifluoromethyl, methyl, ethyl, etc.), $C_{1-6}$ alkoxy which may be halogenated (for example, methoxy, ethoxy, propoxy, butoxy, trifluoromethoxy, trifluoroethoxy, etc., preferably, $C_{1-4}$ alkoxy which may be halogenated), formyl, $C_{2-4}$ alkanoyl (for example, acetyl, propionyl, etc.), $C_{1-4}$ alkylsulfonyl (for example, methanesulfonyl, ethanesulfonyl, etc.), 5- to 6-membered aromatic heterocyclic group which may be substituted [for example, 5- to 6-membered aromatic heterocyclic group containing 1 to 4 hetero atoms of one to two kinds selected from the group consisting of nitrogen, sulfur and oxygen atoms such as furan, thiophene, pyrrole, imidazole, pyrazole, thiazole, oxazole, isothiazole, isoxazole, tetrazole, pyridine, pyrazine, pyrimidine, pyridazine, triazole, etc.; examples of the substituent of said heterocyclic ring include halogen (for example, fluorine, chlorine, bromine, iodine, etc.), nitro, cyano, hydroxy, thiol, amino, carboxyl, $C_{1-4}$ alkyl which may be halogenated (for example, trifluoromethyl, methyl, ethyl, etc.), $C_{1-4}$ alkoxy which may be halogenated (for example, methoxy, ethoxy, propoxy, butoxy, trifluoromethoxy, trifluoroethoxy. etc.), formyl, $C_{2-4}$ alkanoyl (for example, acetyl, propionyl, etc.), $C_{1-4}$ alkylsulfonyl (for example, methanesulfonyl, ethanesulfonyl, etc.), and the like; and the number of the substituents is preferably 1 to 3], and the like; and the number of the substituents is preferably 1 to 3.

Examples of the substituent of the "thiol which may be substituted" as the substituent of $R^1$ include the same substituent as that described above with respect to the "hydroxy which may be substituted as the substituent of $R^1$", and, among them, preferably, (1) alkyl which may be substituted (for example, $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower $C_{1-6}$ alkyl; and the like);

(2) cycloalkyl which may be substituted (for example, $C_{3-7}$ cycloalkyl such as cyclopropyl, cyclobutyl, cyclopentyl, cyclohexyl, cycloheptyl, etc.);

(3) aralkyl which may be substituted (for example, phenyl-$C_{1-4}$ alkyl such as benzyl, phenethyl, etc.);

(4) aryl which may be substituted (for example, phenyl, naphthyl, etc.); and the like.

Examples of the "substituent" of the above-described (1) alkyl which may be substituted, (2) cycloalkyl which may be substituted, (3) aralkyl which may be substituted and (4) aryl which may be substituted include halogen (for example, fluorine, chlorine, bromine, iodine, etc.), nitro, cyano, hydroxy, thiol which may be substituted (for example, thiol, $C_{1-4}$ alkylthio, etc.), amino which may be substituted (for example, amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc.), carboxyl which may be esterified or amidated (for example, carboxyl, $C_{1-4}$ alkoxy-carbonyl, carbamoyl, mono-$C_{1-4}$ alkyl-carbamoyl, di-$C_{1-4}$ alkyl-carbamoyl, etc.), $C_{1-4}$ alkoxy which may be halogenated (for example, methoxy, ethoxy, propoxy, butoxy, trifluoromethoxy, trifluoroethoxy, etc.), $C_{1-4}$ alkoxy-$C_{1-4}$ alkoxy which may be halogenated (for example, methoxymethoxy, methoxyethoxy, ethoxyethoxy, trifluoromethoxyethoxy, trifluoroethoxyethoxy, etc.), formyl, $C_{2-4}$ alkanoyl (for example, acetyl, propionyl, etc.), $C_{1-4}$ alkylsulfonyl (for example, methanesulfonyl, ethanesulfonyl, etc.), and the like, and the number of the substituents is preferably 1 to 3.

Examples of the substituent in the "amino which may be substituted" as the substituent of $R^1$ include the same substituent as that described above with respect to the "hydroxy which may be substituted as the substituent of $R^1$", and the number of substituents on the amino group may be 1 or 2. Among them, the substituent is preferably:

(1) alkyl which may be substituted (for example, $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-10}$) alkyl; and the like);

(2) cycloalkyl which may be substituted (for example, $C_{3-7}$ cycloalkyl groups, such as cyclopropyl, cyclobutyl, cyclopentyl, cyclohexyl, cycloheptyl, etc.);

(3) alkenyl which may be substituted (for example, alkenyl of 2 to 10 carbons such as allyl, crotyl, 2-pentenyl, 3-hexenyl, etc., preferably lower ($C_{2-6}$) alkenyl; and the like);

(4) cycloalkenyl which may be substituted (for example, cycloalkenyl of 3 to 7 carbons such as 2-cyclopentenyl, 2-cyclohexenyl, 2-cyclopentenylmethyl, 2-cyclohexenylmethyl, etc.; and the like);

(5) formyl or acyl which may be substituted (for example, alkanoyl of 2 to 4 carbons (for example, acetyl, propionyl, butyryl, isobutyryl, etc.), alkylsulfonyl of 1 to 4 carbons (for example, methanesulfonyl, ethanesulfonyl, etc.) and the like);

(6) aryl which may be substituted (for example, phenyl, naphthyl, etc.); and the like.

Examples of the substituent of the above-described (1) alkyl which may be substituted, (2) cycloalkyl which may be substituted, (3) alkenyl which may be substituted, (4) cycloalkenyl which may be substituted, (5) acyl which may be substituted, (6) aryl which may be substituted include halogen (for example, fluorine, chlorine, bromine, iodine, etc.), nitro, cyano, hydroxy, thiol which may be substituted (for example, thiol, $C_{1-4}$ alkylthio, etc.), amino which may be substituted (for example, amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc.), carboxyl which may be esterified or amidated (for example, carboxyl, $C_{1-4}$ alkoxy-carbonyl, carbamoyl, mono-$C_{1-4}$ alkyl-carbamoyl, di-$C_{1-4}$ alkyl-carbamoyl, etc.); $C_{1-4}$ alkoxy which may be halogenated (for example, methoxy, ethoxy, propoxy, butoxy, trifluoromethoxy, trifluoroethoxy, etc.), $C_{1-4}$ alkoxy-$C_{1-4}$ alkoxy which may be halogenated (for example, methoxymethoxy, methoxyethoxy, ethoxyethoxy, trifluoromethoxyethoxy, trifluoroethoxyethoxy, etc.), formyl, $C_{2-4}$ alkanoyl (for example, acetyl, propionyl, etc.), $C_{1-4}$ alkylsulfonyl (for example, methanesulfonyl, ethanesulfonyl, etc.), and the like, and the number of the substituents is preferably 1 to 3.

Further, the substituents of the "amino which may be substituted" as the substituent of $R^1$ may bind each other to form a cyclic amino group (for example, a group which is formed by subtracting a hydrogen atom from the ring constituting nitrogen atom of a 5- to 6-membered ring such as tetrahydropyrrole, piperazine, piperidine, morpholine, thiomorpholine, pyrrole, imidazole, etc. so that a substituent can be attached to the nitrogen atom, or the like). The cyclic amino group may be substituted and examples of the substituent include halogen (for example, fluorine, chlorine, bromine, iodine, etc.), nitro, cyano, hydroxy, thiol which may be substituted (for example, thiol, $C_{1-4}$ alkylthio, etc.), amino which may be substituted (for example, amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc.), carboxyl which may be esterified or amidated (for example, carboxyl, $C_{1-4}$ alkoxy-carbonyl, carbamoyl, mono-$C_{1-4}$ alkyl-carbamoyl, di-$C_{1-4}$ alkyl-carbamoyl, etc.), $C_{1-4}$ alkoxy which may be halogenated (for example, methoxy, ethoxy, propoxy, butoxy, trifluoromethoxy, trifluoroethoxy, etc.), $C_{1-4}$ alkoxy-$C_{1-4}$ alkoxy which may halogenated (for example, methoxymethoxy, methoxyethoxy, ethoxyethoxy, trifluoromethoxyethoxy, trifluoroethoxyethoxy, etc.), formyl, $C_{2-4}$ alkanoyl (for example, acetyl, propionyl, etc.), $C_{1-4}$ alkylsulfonyl (for example, methanesulfonyl, ethanesulfonyl), and the like, and the number of the substituents is preferably 1 to 3.

Examples of the "acyl which may be substituted" as the substituent of $R^1$ include a group formed by binding (1) hydrogen;

(2) alkyl which may be substituted (for example, $C_{1-10}$ alkyl groups, such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, and the like);

(3) cycloalkyl which may be substituted (for example, $C_{3-7}$ cycloalkyl such as cyclopropyl, cyclobutyl, cyclopentyl, cyclohexyl, cycloheptyl, etc.);

(4) alkenyl which may be substituted (for example, alkenyl of 2 to 10 carbons such as allyl, crotyl, 2-pentenyl, 3-hexenyl, etc., preferably lower ($C_{2-6}$) alkenyl, and the like);

(5) cycloalkenyl which may be substituted (for example, cycloalkenyl of 3 to 7 carbons such as 2-cyclopentenyl, 2-cyclohexenyl, 2-cyclopentenylmethyl, 2-cyclohexenylmethyl, etc.); and (6) 5- to 6-membered monocyclic aromatic group which may be substituted (for example, phenyl, pyridyl, etc.) or the like;

to carbonyl or sulfonyl group, (for example, formyl, acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexane carbonyl, cycloheptane carbonyl, crotonyl, 2-cyclohexenecarbonyl, benzoyl, nicotinoyl, methanesulfonyl, ethanesulfonyl, etc.). Examples of the substituent of the above-described (2) alkyl which may be substituted, (3) cycloalkyl which may be substituted, (4) alkenyl which may be substituted, (5) cycloalkenyl which may be substituted, and (6) 5- to 6-membered monocyclic aromatic group which may be substituted include halogen (for example, fluorine, chlorine, bromine, iodine, etc.), nitro, cyano, hydroxy, thiol which may be substituted (for example, thiol, $C_{1-4}$ alkylthio, etc.), amino which may be substituted (for example, amino, mono-$C_{1-4}$ alkylamino, di-$C_{1-4}$ alkylamino, 5-to 6-membered cyclic amino such as tetrahydropyrrole, piperazine, piperidine, morpholine, thiomorpholine, pyrrole, imidazole, etc.), carboxyl which may be esterified or amidated (for example, carboxyl, $C_{1-4}$ alkoxycarbonyl, carbamoyl, mono-$C_{1-4}$ alkyl-carbamoyl, di-$C_{1-4}$ alkyl-carbamoyl, etc.), $C_{1-4}$ alkoxy which may be halogenated (for example, methoxy, ethoxy, propoxy, butoxy, trifluoromethoxy, trifluoroethoxy, etc.); $C_{1-4}$ alkoxy-$C_{1-4}$ alkoxy which may be halogenated (for example, methoxymethoxy, methoxyethoxy, ethoxyethoxy, trifluoromethoxyethoxy, trifluoroethoxyethoxy, etc.), formyl, $C_{2-4}$ alkanoyl (for example, acetyl, propionyl, etc.), $C_{1-4}$ alkylsulfonyl (for example, methanesulfonyl, ethanesulfonyl, etc.), and the like and the number of the substituents is preferably 1 to 3.

Examples of the "carboxyl which may be esterified" as the substituent of $R^1$ include a group formed by binding (1) hydrogen;

(2) alkyl which may be substituted (for example, $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl; and the like);

(3) cycloalkyl which may be substituted (for example, $C_{3-7}$ cycloalkyl such as cyclopropyl, cyclobutyl, cyclopentyl, cyclohexyl, cycloheptyl, etc.);

(4) alkenyl which may be substituted (for example, alkenyl of 2 to 10 carbons such as allyl, crotyl, 2-pentenyl, 3-hexenyl, etc., preferably lower ($C_{2-6}$) alkenyl and the like);

(5) cycloalkenyl which may be substituted (for example, cycloalkenyl of 3 to 7 carbons such as 2-cyclopentenyl, 2-cyclohexenyl, 2-cyclopentenylmethyl, 2-cyclohexenylmethyl, etc.);

(6) aryl which may be substituted (for example, phenyl, naphthyl, etc.) to carbonyloxy group, preferably carboxyl, lower ($C_{1-6}$) alkoxy-carbonyl, aryloxycarbonyl (for example, methoxycarbonyl, ethoxycarbonyl, propoxycarbonyl, phenoxycarbonyl and naphthoxycarbonyl, etc.), or the like.

The "substituent" of the above-described (2) alkyl which may be substituted, (3) cycloalkyl which may be substituted, (4) alkenyl which may be substituted, (5) cycloalkenyl which may be substituted, and (6) aryl which may be substituted include halogen (for example, fluorine, chlorine, bromine, iodine, etc.), nitro, cyano, hydroxy, thiol which may be substituted (for example, thiol, $C_{1-4}$ alkylthio, etc.), amino which may be substituted (for example, amino, mono-$C_{1-4}$ alkylamino, di-$C_{1-4}$ alkylamino groups, 5- to 6-membered cyclic amino such as tetrahydropyrrole, piperazine, piperidine, morpholine, thiomorpholine, pyrrole, imidazole, etc.), carboxyl which may be esterified or amidated (for example, carboxyl, $C_{1-4}$ alkoxy-carbonyl, carbamoyl, mono-$C_{1-4}$ alkyl-carbamoyl, di-$C_{1-4}$ alkyl-carbamoyl, etc.), $C_{1-4}$ alkoxy which may be halogenated (for example, methoxy, ethoxy, propoxy, butoxy, trifluoromethoxy, trifluoroethoxy, etc.), $C_{1-4}$ alkoxy-$C_{1-4}$ alkoxy which may be halogenated (for example, methoxymethoxy, methoxyethoxy, ethoxyethoxy, trifluoromethoxyethoxy, trifluoroethoxyethoxy, etc.), formyl, $C_{2-4}$ alkanoyl (for example, acetyl, propionyl, etc.), $C_{1-4}$ alkylsulfonyl (for example, methanesulfonyl, ethanesulfonyl, etc.), and the like, and the number of the substituents is preferably 1 to 3.

Examples of the "aromatic group" of the "aromatic group which may be substituted" as the substituent of $R^1$ include a 5- to 6-membered homocyclic or heterocyclic aromatic group such as phenyl, pyridyl, furyl, thienyl, pyrrolyl, imidazolyl, pyrrazolyl, thiazolyl, oxazolyl, isothiazolyl, isoxazoyl, tetrazolyl, pyrazinyl, pyrimidinyl, pyridazinyl, triazolyl, etc., a fused-ring heterocyclic aromatic group such as groups of benzofuran, indole, benzothiophene, benzoxazole, benzthiazole, indazole, benzimidazole, quinoline, isoquinoline, quinoxaline, phthalazine, quinazoline, cinnoline, imidazopyridine, etc. and the like. Examples of the substituent of the aromatic group include halogen (for example, fluorine, chlorine, bromine, iodine, etc.), nitro, cyano, hydroxy, thiol which may be substituted (for example, thiol, $C_{1-4}$ alkylthio etc.), amino which may be substituted (for example, amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc.), carboxyl which may be esterified or amidated (for example, carboxyl, $C_{1-4}$ alkoxy-carbonyl, carbamoyl, mono-$C_{1-4}$ alkyl-carbamoyl, di-$C_{1-4}$ alkyl-carbamoyl, etc.); $C_{1-4}$ alkyl which may be halogenated (for example, trifluoromethyl, methyl, ethyl, etc.); $C_{1-4}$ alkoxy which may be halogenated (for example, methoxy, ethoxy, propoxy, butoxy, trifluoromethoxy, trifluoroethoxy, etc.), formyl, $C_{2-4}$ alkanoyl (for example, acetyl, propionyl, etc.), $C_{1-4}$ alkylsulfonyl (for example, methanesulfonyl, ethanesulfonyl, etc.), and the like, and the number of the substituents is preferably 1 to 3.

The number of the above substituents of $R^1$ may be 1 to 4, preferably 1 to 2 and, the substituents may be the same or different and present at any possible positions of the ring. When the "5- to 6-membered ring group" of the "5- to 6-membered ring group which may be substituted" represented by $R^1$ has two or more substituents, two of the substituents may be bound each other to form; for example, a group selected from the group consisting of lower ($C_{1-6}$) alkylene (for example, trimethylene, tetramethylene, etc.); lower ($C_{1-6}$) alkyleneoxy (for example, —$CH_2$—O—$CH_2$—, —O—$CH_2$—$CH_2$—, —O—$CH_2$—$CH_2$—$CH_2$—, —O—$CH_2$—$CH_2$—$CH_2$—$CH_2$—, —O—$C(CH_3)(CH_3)$—$CH_2$—$CH_2$—, etc.); lower ($C_{1-6}$) alkylenethio (for example, —$CH_2$—S—$CH_2$—, —S—$CH_2$—$CH_2$—, —S—$CH_2$—$CH_2$—$CH_2$—, —S—$CH_2$—$CH_2$—$CH_2$—$CH_2$—, —S—C$(CH_3)(CH_3)$—$CH_2$—$CH_2$—, etc.); lower ($C_{1-6}$) alkylenedioxy (for example, —O—$CH_2$—O—, —O—$CH_2$—$CH_2$—O—, —O—$CH_2$—$CH_2$—$CH_2$—O—, etc.); lower ($C_{1-6}$) alkylenedithio (for example, —S—$CH_2$—S—, —S—$CH_2$—$CH_2$—S—, —S—$CH_2$—$CH_2$—$CH_2$—S—, etc.); oxy-lower ($C_{1-6}$) alkyleneamino (for example, —O—$CH_2$—NH—, —O—$CH_2$—$CH_2$—NH—, etc.); oxy-lower ($C_{1-6}$) alkylenethio (for example, —O—$CH_2$—S—, —O—$CH_2$—$CH_2$—S—, etc.); lower ($C_{1-6}$) alkyleneamino (for example, —NH—$CH_2$—$CH_2$—, —NH—$CH_2$—$CH_2$—$CH_2$—, etc. ); lower ($C_{1-6}$) alkylenediamino (for example, —NH—$CH_2$—NH—, —NH—$CH_2$—$CH_2$—NH—, etc.); thia-lower ($C_{1-6}$) alkyleneamino (for example, —S—$CH_2$—NH—, —S—$CH_2$—$CH_2$—NH—, etc.); lower ($C_{2-6}$) alkenylene (for example, —$CH_2$—CH═CH—, —$CH_2$—$CH_2$—CH═CH—, —$CH_2$—CH═CH—$CH_2$—, etc.); lower ($C_{4-6}$) alkadienylen (for example, —CH═CH—CH═CH—, etc.); and the like.

Further, the bivalent group formed by binding two substituents of $R^1$ each other may contain 1 to 3 substituents similar to those of the "5 to 6-membered ring" of the "5- to 6-membered ring which may be substituted" represented by $R^1$ (for example, halogen, nitro, cyano, alkyl which may be substituted, cycloalkyl which may be substituted, hydroxy which may be substituted, thiol which may be substituted (wherein the sulfur atom may be oxidized, or may form sulfinyl which may be substituted or sulfonyl which may be substituted), amino which may be substituted, acyl which may be substituted, carboxyl which may be esterified or amidated, an aromatic group which may be substituted, and the like).

In particular, the substituents of the "5- to 6-membered ring group" of the "5- to 6-membered ring group which may be substituted" represented by $R^1$ are lower ($C_{1-4}$) alkyl which may be halogenated, or lower ($C_{1-4}$) alkoxylated (for example, methyl, ethyl t-butyl, trifluoromethyl, methoxymethyl, ethoxymethyl, propoxymethyl, butoxymethyl, methoxyethyl, ethoxyethyl, propoxyethyl, butoxyethyl, etc.); lower ($C_{1-4}$) alkoxy which may be halogenated or lower ($C_{1-4}$) alkoxylated (for example, methoxy, ethoxy, propoxy, butoxy, t-butoxy, trifluoromethoxy, methoxymethoxy, ethoxymethoxy, propoxymethoxy, butoxymethoxy, methoxyethoxy, ethoxyethoxy, propoxyethoxy, butoxyethoxy, methoxypropoxy, ethoxypropoxy, propoxypropoxy, butoxypropoxy, etc.); halogen (for example, fluorine, chlorine, etc.); nitro; cyano; amino which may be substituted with 1 to 2 groups selected from the group consisting of lower ($C_{1-4}$) alkyl, formyl and lower ($C_{2-4}$) alkanoyl (for example, amino, methylamino, dimethylamino, formylamino, acetylamino, etc.); 5- to 6-membered cyclic amino (for example, 1-pyrrolidinyl, 1-piperazinyl, 1-piperidinyl, 4-morpholino, and 4-thiomorpholino, 1-imidazolyl, 4-tetrahydropyranyl, etc.); and the like.

Examples of the "bivalent chain group whose straight moiety is constituted of 1 to 4 carbons" represented by $X^1$ and $X^2$ include —$(CH_2)_{a'}$— [wherein a' is an integer of 1 to 4, preferably 1 or 2]; —$(CH_2)_{b'}$—$X^3$— [wherein b' is an integer of 0 to 3, preferably 0 or 1, $X^3$ is an imino group which may be substituted (for example, imino group which may be substituted with lower ($C_{1-6}$) alkyl, lower ($C_{3-7}$) cycloalkyl, formyl, lower ($C_{2-7}$) alkanoyl, lower ($C_{1-6}$) alkoxy-carbonyl, etc.), carbonyl, oxygen atom, sulfur atom which may be oxidized (for example, —$S(O)_m$— (wherein, m is an integer of 0 to 2), etc.); —CH═CH—; —C≡C—; —CO—NH—; —$SO_2$—NH—; and the like. These groups may be bound to ring A or ring B at either of the right and left sides thereof, but $X^1$ is preferably bound to ring A at the right side thereof and $X^2$ is preferably bound to ring B at the left side thereof.

$X^1$ is preferably, a bond, —$(CH_2)_{b'}$—O— (wherein, b' is an integer of 0, 1 or 2, preferably 0 or 1), —C≡C—, etc., and more preferably a bond.

$X^2$ is preferably —$(CH_2)_{a'}$— (wherein, a' is an integer of 1 or 2), —$(CH_2)_{b'}$—$X^3$— (wherein, b' is an integer of 0 or 1, and $X^3$ is imino group which may be substituted, carbonyl, oxygen atom or sulfur atom which may be oxidized), —CH═CH—, —CO—NH—, —$SO_2$—NH—, etc., and more preferably —CO—NH—.

The bivalent group represented by $X^1$ and $X^2$ may be substituted at any position (preferably on a carbon atom thereof) and the substitutent is not limited to a specific one in so far as it can be bound to a bivalent chain which constitutes a linear chain part. Examples thereof include lower ($C_{1-6}$) alkyl (e.g., methyl, ethyl, propyl, isopropyl, butyl, isobutyl, sec-butyl, tert-butyl, pentyl, isopentyl, neopentyl, hexyl, etc.), lower ($C_{3-7}$) cycloalkyl (e.g., cyclopropyl, cyclobutyl, cyclopentyl, cyclohexyle, cycloheptyl, etc.), formyl, lower ($C_{2-7}$) alkanoyl (e.g., acetyl, propionyl, butyryl, etc.), a phosphono group which may be esterified, a carboxyl group which may be esterified, hydroxy, oxo, and the like, preferably a lower alkyl group having 1 to 6 carbon atoms (more preferably, $C_{1-3}$ alkyl), hydroxy, oxo, etc.

Examples of the phosphono group which may be esterified include a group represented by the formula —P(O)(OR$^7$)(OR$^8$) (wherein $R^7$ and $R^8$ are independently hydrogen, $C_{1-6}$ alkyl or $C_{3-7}$ cycloalkyl, or $R^7$ and $R^8$ may be bound to each other to form a 5- to 7-membered ring).

Examples of the $C_{1-6}$ alkyl represented by $R^7$ and $R^8$ in the above formula include methyl, ethyl, propyl, isopropyl, butyl, isobutyl, sec-butyl, tert-butyl, pentyl, isopentyl, neopentyl, hexyl, and the like. Examples of the $C_{3-7}$ cycloalkyl include cyclopropyl, cyclobutyl, cyclopentyl, cyclohexyl, cycloheptyl, and the like. Preferably, $R^7$ and $R^8$ are a linear lower alkyl group having 1 to 6, more perferabl 1 to 3 carbon atoms. $R^7$ and $R^8$ may be the same or different, but preferably they are the same. When $R^7$ and $R^8$ are bound to each other to form a 5- to 7-membered ring, $R^7$ and $R^8$ are bound to each other to form a linear $C_{2-4}$ alkylene side chain represented by —$(CH_2)_2$—, —$(CH_2)_3$—, or —$(CH_2)_4$—. The side chain may be substituted and examples of the substituent include hydroxy, halogen, and the like.

Examples of the esterified carboxyl group of the carboxyl group which may be esterified include carboxyl bound to $C_{1-6}$ alkyl or $C_{3-7}$ cycloalkyl, e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl, etc.

In the above formula [I], examples of the "5- to 6-membered ring group" of the "5- to 6-membered ring group which may be substituted" represented by A include 5- to 6-membered saturated or unsaturated alicyclic hydrocarbon such as $C_{5-6}$ cycloalkane (for example, cylcopentane, cyclohexane, etc.), $C_{5-6}$ cycloalkenes (for example, 1-cyclopentene, 2-cyclopentene, 3-cyclopentene, 2-cyclohexene, 3-cyclohexene, etc.), $C_{5-6}$ cycloalkadienes (for example, 2,4-cyclopentadiene, 2,4-cyclohexadiene, 2,5-cyclohexadiene, etc.), and the like; 6-membered aromatic hydrocarbon such as benzene, etc.; 5- to 6-membered aromatic heterocyclic ring containing at least one, preferably 1 to 4, more preferably 1 to 2 hetero atoms of 1 to 3 kinds (preferably 1 to 2 kinds) selected from oxygen, sulfur and nitrogen; saturated or unsaturated non-aromatic heterocyclic ring (aliphatic heterocyclic rings); and the like.

Examples of the "aromatic heterocyclic ring" include 5- to 6-membered aromatic monocyclic heterocyclic ring (for example, furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazane, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine, etc.), and the like. Examples of the "non-aromatic heterocyclic ring" include saturated and unsaturated non-aromatic (aliphatic) heterocyclic 5- to 6-membered ring such as pyrrolidine, tetrahydrofuran, thiolane, piperidine, tetrahydropyran, morpholine, thiomorpholine, piperazine, pyran, oxepine, thiepine, azepine, etc., 5- to 6-membered non-aromatic heterocyclic ring all or part of whose double bonds in said aromatic monocyclic heterocyclic rings are saturated, and the like.

The "5- to 6-membered ring group" of the "5- to 6-membered ring group which may be substituted" represented by A is preferably a 5- to 6-membered aromatic ring group, and more preferably a 6-membered ring group selected from benzene, furan, thiophene, pyrrole, pyridine, etc., and most preferably benzene.

Examples of the substituent of the "5- to 6-membered ring group" of the "5- to 6-membered ring group which may be substituted" represented by A include the same "substituent" as that of the "5- to 6-membered ring group" of the "5- to 6-membered ring group which may be substituted" represented by $R^1$. The number of the substituents of A is 1 to 4, preferably 1 to 2 and the substituents may be the same or different and present at any possible positions of the ring. Such positions include those represented by $E_1$, $E_2$ or others, as far as the substitution is possible.

Examples of the lower alkyl of the "lower alkyl which may be substituted" represented by the above $R^3$ include $C_{1-6}$ alkyl such as methyl, ethyl, propyl, isopropyl, butyl, isobutyl, sec-butyl, tert-butyl, pentyl, isopentyl, neopentyl, hexyl, etc.

Examples of the lower alkoxy of the "lower alkoxy group which may be substituted" represented by the above $R^3$ include $C_{1-6}$ alkoxy such as methoxy, ethoxy, propoxy, butoxy, etc.

Examples of the substituent of the "lower alkyl which may be substituted", and the "lower alkoxy which may be substituted" include halogen (for example, fluorine, chlorine, bromine, iodine, etc.), hydroxy, amino, mono-(lower alkyl) amino, di-(lower alkyl)amino, lower alkanoyl, etc.

Examples of the lower alkyl group of said mono-(lower alkyl) amino and di-(lower alkyl) amino group are similar to those of the lower alkyl group of the "lower alkyl which may be substituted" represented by the above $R^3$.

Examples of the lower alkanoyl are $C_{2-6}$ alkanoyl such as acetyl, propionyl butyryl, isobutyryl, etc.

Examples of the "halogen" represented by the above $R^3$ are fluorine, chlorine, bromine, iodine, etc.

$R^3$ is preferably a lower $C_{1-6}$ alkyl which may be substituted or halogen, and more preferably methyl which may be substituted or halogen.

In the above formula [I}, the "8- to 10-membered ring group" of the "8- to 10-membered ring group which may be substituted" represented by B includes, for example, a 8- to 10-membered ring of the following formula which may have substituent(s) at any positions of the ring as far as the substitution is possible:

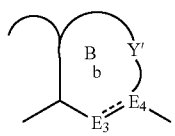

wherein Y' is a bivalent group and the other symbols are as defined above.

In the above formula, the bivalent group represented by Y' is a bivalent group so that ring B forms a 8- to 10-membered ring which may be substituted, and example thereof include:

(1) —$Alk_{a1}$—O—$Alk_{a2}$— (wherein $Alk_{a1}$ are $Alk_{a2}$ are either a bond or a divalent straight chain hydrocarbon group of 1 to 5 carbons, respectively, and the total number of carbons of $Alk_{a1}$ and $Alk_{a2}$ is 5 or below);

(2) —$Alk_{b1}$—S(O)$_m$—$Alk_{b2}$— (wherein m is an integer of 0 to 2, $Alk_{b1}$ and $Alk_{b2}$ are, respectively, either a bond or a bivalent straight chain hydrocarbon group of 1 to 5 carbons, and the total number of carbons of $Alk_{b1}$ and $Alk_{b2}$ is 5 or below);

(3) —$Alk_{d1}$— (wherein $Alk_{d1}$ is a bivalent straight chain hydrocarbon group of 4 to 6 carbons);

(4) —$Alk_{e1}$—NH—$Alk_{e2}$—

(wherein $Alk_{e1}$ and $Alk_{e2}$ are, respectively, a bond or a bivalent straight chain hydrocarbon group of 1 to 5 carbons, and the total number of carbons of $Alk_{e1}$ and $Alk_{e2}$ is 5 or below), —$Alk_{e6}$—N=CH—$Alk_{e7}$—, —$Alk_{e7}$—CH=N—$Alk_{e6}$—, or —$Alk_{e6}$—N=N—$Alk_{e7}$— (wherein $Alk_{e6}$ and $Alk_{e7}$ are either a bond or a bivalent straight chain hydrocarbon group of 1 to 4 carbons, respectively, and the total number of carbons of $Alk_{e6}$ and $Alk_{e7}$ is 4 and below); and the like.

Examples of the bivalent straight chain hydrocarbon group include —$CH_2$—, —$(CH_2)_2$—, —$(CH_2)_3$—, —$(CH_2)_4$—, —$(CH_2)_5$—, —$(CH_2)_6$—, —CH=, —CH=CH—, —CH=CH—$CH_2$—, —$CH_2$CH=CH—, —CH=CH—CH=CH—, =CH—CH=CH—, —$CH_2$—CH=CH—$CH_2$—, —CH=CH—$(CH_2)_2$—, —CH=CH—$(CH_2)_3$—, —CH=CH—$(CH_2)_4$—, etc.

More specifically, examples of Y' are a bivalent group such as —O—$(CH_2)_3$—, —O—$(CH_2)_4$—, —O—$(CH_2)_5$—, —$CH_2$—O—$(CH_2)_2$—, —O—CH=CH—$CH_2$—, —S(O)$_m$—$(CH_2)_3$— (wherein m is an integer of 0 to 2), —S(O)$_m$—$(CH_2)_4$— (wherein m is an integer of 0 to 2), —S(O)$_m$—$(CH_2)_5$— (wherein m is an integer of 0 to 2), —$CH_2$—S(O)$_m$—$(CH_2)_2$— (wherein m is an integer of 0 to 2), —S(O)$_m$—CH=CH—$CH_2$— (wherein m is an integer of 0 to 2), —$(CH_2)_4$—, —$(CH_2)_5$—, —$(CH_2)_6$—, —CH=CH—CH=CH—, —CH=CH—(CH$_2$)$_2$—, —NH—(CH$_2$)$_3$—, —NH—(CH$_2$)$_4$—, —NH—(CH$_2$)$_5$—, —CH$_2$—NH—(CH$_2$)$_2$—, —NH—CH=CH—CH$_2$—, —N=CH—CH=CH—, —CH=N—(CH$_2$)$_2$—, —CH=N—CH=CH—, —N=N—(CH$_2$)$_2$—, —N=N—CH=CH—, —CH=N—N=CH— (expressed from a starting position on ring A, respectively). Preferably, ring B is a 8-membered ring.

Further, said bivalent group may have substituent(s), and the substituents may be similar to those of the "5- to 6-membered ring group" of the "5- to 6-membered ring group which may be substituted" represented by R$^1$, and preferred examples of the substituent(s) include lower (C$_{1-3}$) alkyl (for example, methyl, ethyl, propyl, etc.), phenyl, oxo, hydroxy, etc. The bivalent group may have 1 to 6, preferably 1 to 2, the same or different substituents. Substitution may be at any positions of the bivalent group as far as the substitution is possible.

The "substituent" of the "8- to 10-membered ring" of the "8- to 10-membered ring which may be substituted" represented by B may be similar to those of the "5- to 6-membered ring group" of the "5- to 6-membered ring group which may be substituted" represented by R$^1$, and oxo. Preferred examples of the bivalent group represented by Y include a bivalent group such as —O—(CH$_2$)$_3$—, —O—(CH$_2$)$_4$—, —O—(CH$_2$)$_5$—, —S(O)$_m$—(CH$_2$)$_3$— (wherein m is an integer of 0 to 2), —S(O)$_m$—(CH$_2$)$_4$— (wherein m is an integer of 0 to 2), —S(O)$_m$—(CH$_2$)$_5$— (wherein m is an integer of 0 to 2), —(CH$_2$)$_4$—, —(CH$_2$)$_5$—, —(CH$_2$)$_6$—, and a bivalent group having —N(R$^O$)— group in the main chain [wherein R$^O$ is hydrogen or a substituent] such as —NH—(CH$_2$)$_3$—, —NH—(CH$_2$)$_4$— and —NH—(CH$_2$)$_5$—, etc, most preferably a bivalent group having —N(R$^O$)— groups in the main chain [wherein, R$^O$ is hydrogen or a substituent].

Preferred examples of R$^O$ are hydrogen atom; hydrocarbon group which may be substituted; heterocyclic group which may be substituted; hydroxy group which may be substituted; thiol group which may be substituted (the sulfur atom may be oxidized, or may form sulfinyl group which may be substituted, or sulfonyl group which may be substituted; amino group which may be substituted; carboxyl group which may be esterified or amidated; acyl group which may be substituted; and the like. R$^O$ is more preferably hydrogen atom, hydrocarbon group which may be substituted, heterocyclic ring group which may be substituted, acyl group which may be substituted, and the like.

Preferred embodiments of R$^O$ are hydrogen atom, hydrocarbon group which may be substituted, acyl group which may be substituted, and the like. As the hydrocarbon group which may be substituted, C$_{1-6}$ alkyl which may be halogenated or hydroxylated and C$_{2-6}$ alkenyl which may be halogenated or hydroxylated are more preferred. As the acyl group which may be substituted, C$_{1-6}$ alkylsulfonyl which may be halogenated or hydroxylated, formyl, C$_{2-5}$ alkanoyl which may be halogenated or hydroxylated, etc. are more preferred. R$^O$ is further more preferably C$_{1-4}$ alkyl which may be halogenated or hydroxylated, formyl, C$_{2-5}$ alkanoyl which may be halogenated or hydroxylated, and the like, in particular, propyl, isobutyl, isobutenyl or 3-hydroxy-2-methylpropyl are most preferred.

Other preferred embodiments of R$^O$ include the group of formula —(CH$_2$)$_s$—R$^x$ [wherein S is an integer of 0 or 1, R$^x$ is a monocyclic aromatic 5- to 6-membered group which may be substituted (for example, substituted by the same substituent as that exemplified with respect to the monocyclic aromatic 5- to 6-membered group of ring A; preferably phenyl, pyridyl, piperazolyl, thiazolyl, oxazolyl and tetrazolyl which may be substituted with halogen, C$_{1-4}$ alkyl which may be halogenated or hydroxylated, C$_{1-4}$ alkoxy which may be halogenated or hydroxylated, etc., respectively)], and the like.

Examples of the "hydrocarbon group" of said "hydrocarbon group which may be substituted" include:

(1) alkyl (for example, C$_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower (C$_{1-6}$) alkyl, more preferably lower (C$_{1-4}$) alkyl, and the like);

(2) cycloalkyl (for example, C$_{3-7}$ cycloalkyl such as cyclopropyl, cyclobutyl, cyclopentyl, cyclohexyl, cycloheptyl, etc.);

(3) alkenyl (for example, alkenyl of 2 to 10 carbons such as allyl, crotyl, 2-pentenyl, 3-hexenyl, etc. preferably lower (C$_{2-6}$) alkenyl, and the like);

(4) cycloalkenyl (for example, cycloalkenyl of 3 to 7 carbons such as 2-cyclopentenyl, 2-cyclohexenyl, 2-cyclopentenylmethyl, 2-cylcohexenylmethyl, etc.);

(5) alkynyl (for example, alkynyl of 2 to 10 carbons such as ethynyl, 1-propynyl, 2-propynyl, 1-butynyl, 2-pentynyl, 3-hexynyl, etc., preferably lower (C$_{2-6}$) alkynyl, and the like);

(6) aralkyl (for example, phenyl C$_{1-4}$ alkyl (for example, benzyl, phenethyl, etc.);

(7) aryl (for example, phenyl, naphthyl, etc.);

(8) cycloalkyl-alkyl (for example, C$_{3-7}$ cycloalkyl-C$_{1-4}$-alkyl such as cyclopropylmethyl, cyclobutylmethyl, cyclopentylmethyl, cyclohexylmethyl, cycloheptylmethyl, etc.); and the like. Examples of the substituents of the above-described (1) alkyl, (2) cycloalkyl, (3) alkenyl, (4) cycloalkenyl, (5) alkynyl, (6) aralkyl, (7) aryl and (8) cycloalkyl-alkyl include halogen (for example, fluorine, chlorine, bromine, iodine, etc.); nitro; cyano; hydroxy; thiol which may be substituted (for example, thiol, C$_{1-4}$ alkylthio, etc.); amino which may be substituted (for example, amino, mono-C$_{1-4}$ alkylamino, di-C$_{1-4}$ alkylamino, 5-to-6 membered cyclic amino such as tetrahydropyrrole, piperazine, piperidine, morpholine, thiomorpholine, pyrrole, and imidazole, etc.); carboxyl which may be esterified or amidated (for example, carboxyl, C$_{1-4}$ alkoxy-carbonyl, carbamoyl, mono-C$_{1-4}$ alkyl-carbamoyl, di-C$_{1-4}$ alkyl-carbamoyl, etc.); C$_{1-4}$ alkyl which may be halogenated (for example, trifluoromethyl, methyl, ethyl, etc.); C$_{1-4}$ alkoxy which may be halogenated (for example, methoxy, ethoxy, propoxy, butoxy, trifluoromethoxy, trifluoroethoxy, etc.); C$_{1-4}$ alkylenedioxy (for example, —O—CH$_2$—O—, —O—CH$_2$—CH$_2$—O—, etc.); sulfonamide which may be substituted [for example, a group formed by binding amino which may be substituted (for example, amino, mono-C$_{1-4}$ alkylamino, di-C$_{1-4}$ alkylamino, 5- to 6-membered cyclic amino such as tetrahydropyrrole, piperazine, piperidine, morpholine, thiomorpholine, pyrrole, imidazole, etc.) to —SO$_2$—, and the like]; formyl; C$_{2-4}$ alkanoyl (for example, acetyl, propionyl, etc.); C$_{1-4}$ alkylsulfonyl (for example, methanesulfonyl, ethanesulfonyl, etc.); heterocyclic group which may be substituted; and the like, and the number of the substituents is preferably 1 to 3.

Examples of the "heterocyclic group" of the "heterocyclic group which may be substituted" and of the heterocyclic group which may be substituted represented by R$^O$ include a group formed by subtracting a hydrogen atom from an aromatic heterocyclic ring or a non-aromatic heterocyclic ring.

The aromatic heterocyclic ring include, for example, 5- to 6-membered aromatic heterocyclic ring containing 1 to 4 hetero atoms of one or two kinds selected from the group consisting of nitrogen, sulfur and oxygen atoms such as furan, thiophene, pyrrole, imidazole, pyrazole, thiazole, oxazole, isothiazole, isoxazole, tetrazole, pyridine, pyrazine, pyrimidine, pyridazine, triazole, oxadiazole, thiadiazole, etc.; and the non-aromatic heterocyclic ring include, for example, 5- to 6-membered non-aromatic heterocyclic ring containing 1 to 4 hetero atoms of one to two kinds selected from the group consisting of nitrogen, sulfur and oxygen atom, such as tetrahydrofuran, tetrahydrothiophene, dioxolane, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, etc.; non-aromatic heterocyclic ring all or part of whose bonds are saturated; and the like (preferably, aromatic heterocyclic ring such as pyrazole, thiazole, oxazole, tetrazole, etc.).

Examples of the "hydroxy which may be substituted", "thiol which may be substituted", "amino which may be substituted", "carboxyl which may be esterified" and "acyl group which may be substituted" represented by $R^0$ include the same "hydroxy which may be substituted", "thiol which may be substituted", "amino which may be substituted", "carboxyl which may be esterified" and "acyl which may be substituted" as the substituents of the "5- to 6-membered ring group" of the "5- to 6-membered ring group which may be substituted" represented by $R^1$. Examples of the "carboxyl which may be amidated" include a group formed by binding the "amino group which may be substituted" and the like to a carbonyl group, and preferably carbamoyl, mono-$C_{1-6}$ alkyl-carbamoyl, di-$C_{1-6}$ alkyl-carbamoyl, etc.

The imino which may be substituted with formyl, $C_{1-6}$ alkyl which may be substituted, $C_{2-6}$ alkenyl which may be substituted, aryl which may be substituted, a heterocyclic group which may be substituted, arylmethyl which may be substituted or a heterocyclic methyl group which may be substituted represented by $Y^a$ are the corresponding same groups as those exemplified with respect to the ($R^0$)— of Y. Among them, preferred are those where $R^0$ are 1) $C_{1-6}$ alkyl, 2) $C_{2-6}$ alkenyl, 3) $C_{6-10}$ aryl, 4) $C_{6-10}$ aryl-methyl, 5) heterocyclic group and 6) heterocyclic methyl group (the above 1) and 2) may be substituted with halogen or hydroxy and the above 3), 4), 5) and 6) may be substituted with halogen, $C_{1-6}$ alkyl which may be substituted with halogen or hydroxy or $C_{1-6}$ alkoxy which may be substituted with halogen or hydroxy).

The number of the substituents of ring B may 1 to 7, preferably 1 to 2, and the substituents may be the same and different and present at any possible positions of the ring (including $E_3$ and $E_4$), but preferably $E_3$ position of the ring is unsubstituted.

In the above formula [I], preferably, $E_3$ and $E_4$ are carbon atoms which may be substituted (preferably unsubstituted carbon atoms), respectively, and b is a double bond.

In the above formula [I], examples of the "bivalent cyclic group" represented by $Z^1$ include the same group as those of the "5- to 6-membered ring group" of "the 5- to 6-membered ring group which may be substituted" represented by $R^1$, or a group formed by subtracting two hydrogen atoms from aromatic heterocycle fused ring such as benzofuran, indole, benzothiophene, benzoxazole, benzthiazole, indazole, benzimidazole, quinoline, isoquinoline, quinoxaline, phthalazine, quinazoline, cinnoline, imidazopyridine, etc. Among them, preferred is the bivalent cyclic group formed by subtracting two hydrogen atoms from benzene, furan, thiophene, pyridine, pyridazine, pyrimidine, benzimidazole, cyclopentane, cyclohexane, pyrrolidine, piperidine, piperazine, morpholine, thiomorpholine, tetrahydropyran, etc.

The "bivalent cyclic group" represented by $Z^1$ may have the same substituent as that of the "5- to 6-membered rings" of the "5- to 6-membered rings which may be substituted" represented by $R^1$. Among them, preferred examples of the substituent include halogen (for example, fluorine, chlorine, bromine, etc.), $C_{1-4}$ alkyl which may be halogenated (for example, methyl, ethyl, trifluoromethyl, trifluoroethyl, etc.), $C_{1-4}$ alkoxy which may be halogenated (for example, methoxy, ethoxy, propoxy, trifluoromethoxy, trifluoroethoxy, etc.), and the like. The bivalent cyclic group represented by $Z^1$ has preferably no substituent other than $X^2$ and $Z^2$, and when $Z^1$ is a bivalent 6-membered ring group, (preferably phenylene), $Z^2$ is preferably located at the para position to $X^2$. Further, $Z^1$ is preferably phenylene which may be substituted with 1) halogen, 2) $C_{1-4}$ alkyl which may be substituted with halogen or 3) $C_{1-4}$ alkoxy which may be substituted with halogen, in particular, phenylene which may be substituted with methyl or trifluoromethyl.

In the above formula [I], the bivalent group represented by $Z^2$ can be represented by the formula —$Z^{2a}$—$W^1$—$Z^{2b}$— (wherein $Z^{2a}$ and $X^{2b}$ are, respectively, O, $S(O)_m$ (wherein, m is an integer of 0, 1, or 2), an imino group which may be substituted (—$N(R_a)$—), or a bond, and $W^1$ is alkylene which may be substituted, an alkenylene group which may be substituted, or a bond). When $Z^1$ is benzene ring, $Z^2$ may be present at any positions of the benzene ring, but preferably at para position.

Examples of the substituent $R^a$ of the imino group which may be substituted represented by $Z^{2a}$ or $Z^{2b}$ include hydrogen atoms; lower ($C_{1-6}$) alkyl (for example, methyl, ethyl, propyl, isopropyl, butyl, isobutyl, sec-butyl, tert-butyl, pentyl, isopentyl, neopentyl, hexyl, etc.); hydroxy $C_{1-6}$ alkyl (for example, hydroxyethyl, hydroxypropyl, hydroxybutyl, etc.); halogenated $C_{1-6}$ alkyl (for example, trifluoromethyl, trifluoroethyl, etc.); cyano $C_{1-6}$ alkyl (for example, cyanoethyl, cyanopropyl, etc.); carboxyl $C_{1-6}$ alkyl which may be esterified or amidated; formyl; lower ($C_{2-5}$) alkanoyl (for example, acetyl, propionyl, butyryl, etc.); lower ($C_{1-5}$) alkylsulfonyl (for example, methylsulfonyl, ethylsulfonyl, etc.); and the like.

Examples of the alkylene of the "alkylene which may be substituted" represented by $W^1$ include an alkylene chain of the formula —$(CH_2)_{k1}$— (wherein, k1 is an integer of 1 to 4), and the like.

Examples of the alkenylene of the "alkenylene which may be substituted" represented by $W^1$ include alkenylene of the formula —$(CH_2)_{k2}$—(CH=CH)—$(CH_2)_{k3}$— (wherein k2 and k3 are the same or different and each integers of 0, 1, or 2, but the sum of k2 and k3 is 2 or below).

The alkylene and alkenylene represented by $W^1$ may have substituent(s) at any possible positions (preferably on carbon atoms), and the substituent may be any group as far as the group can bind to the alkylene or alkenylene chain constituting the straight chain moiety, and suitable examples thereof include lower ($C_{1-6}$) alkyl (for example, methyl, ethyl, propyl, isopropyl, butyl, isobutyl, sec-butyl, tert-butyl, pentyl, isopentyl, neopentyl, hexyl, etc.); lower ($C_{3-7}$) cycloalkyl (for example, cyclopropyl, cyclobutyl, cyclopentyl, cyclohexyl, cycloheptyl, etc.); formyl; lower ($C_{2-7}$) alkanoyl (for example, acetyl, propionyl, butyryl, etc.); phosphono which may be esterified; carboxyl which may be esterified or amidated; hydroxy; oxo; hydroxyimino; lower ($C_{1-6}$) alkoxyimino which may be substituted; and the like. Preferably, it is lower alkyl of 1 to 6 carbons (preferably, $C_{1-3}$ alkyl), hydroxy, oxo, hydroxyimino, lower ($C_{1-6}$) alkoxyimino which may be substituted by a polar group such as hydroxy, cyano, carboxyl which may be esterified or amidated (for example, carboxyl, $C_{1-4}$ alkoxy-carbonyl, carbamoyl, mono-$C_{1-4}$ alkyl-carbamoyl, di-$C_{1-4}$ alkyl-carbamoyl groups, etc.) and the like.

The phosphono which may be esterified is, for example, a group of the formula, P(O)(O R$^9$)(OR$^{10}$) [wherein, R$^9$ and R$^{10}$ are respectively hydrogen, alkyl of 1 to 6 carbons, or cycloalkyl of 3 to 7 carbons, and R$^9$ and R$^{10}$ may bind to each other to form a 5- to 7-membered ring].

In the above formula, the alkyl of 1 to 6 carbons represented by R$^9$ or R$^{10}$ may be methyl, ethyl, propyl, isopropyl, butyl, isobutyl, sec-butyl, tert-butyl, pentyl, isopentyl, neopentyl, hexyl, etc., and suitable examples of the cycloalkyl of 3 to 7 carbons include cyclopropyl, cyclobutyl, cyclopentyl, cyclohexyl, cycloheptyl, etc. R$^9$ and R$^{10}$ are preferably straight chain lower alkyl of 1 to 6 carbons, more preferably lower alkyl of 1 to 3 carbons. R$^9$ and R$^{10}$ may be the same or different, but are preferably the same. When R$^9$ and R$^{10}$ form a 5- to 7-membered ring by binding each other, R$^9$ and R$^{10}$ form a straight chain $C_{2-4}$ alkylene group of the formula, —(CH$_2$)$_2$—, —(CH$_2$)$_3$—, or —(CH$_2$)$_4$—. The chain may have substituent(s), and suitable examples of the substituent include hydroxy, halogen, etc.

Examples of the ester of carboxyl which may be esterified are that formed by binding carboxyl to alkyl of 1 to 6 carbons or cycloalkyl of 3 to 7 carbons such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl, cyclopentyloxycarbonyl, cyclohexyloxycarbonyl, etc.

Examples of the amide of carboxyl which may be amidated include that formed by binding carboxyl to alkylamino of 1 to 6 carbons, cycloalkylamino of 3 to 7 carbons or 5- to 8-membered cyclic amine (for example, pyrrolidine, piperidine, morpholine, etc.) such as carbamoyl, mono $C_{1-6}$ alkylcarbamoyl groups, di $C_{1-6}$ alkylcarbamoyl groups, cyclopentylaminocarbamoyl, cyclohexylaminocarbamoyl, pyrrolidinocarbonyl, piperidinocarbony, morpholinocarbonyl, thiomorpholinocarbonyl, etc.

In a preferred embodiment of Z$^2$ one of Z$^{2a}$ and Z$^{2b}$ is O, S(O)$_m$ (m is an integer of 0, 1 or 2), or —N(R$^a$)— (wherein R$^a$ is hydrogen or lower $C_{1-4}$ alkyl which may be substituted), the other is a bond, and W is —(CH$_2$)$_p$— (wherein p is an integer of 1 to 3), or Z$^2$ is a bivalent group of the formula —CH(OH)—. More preferably, Z$^2$ is a bivalent group wherein one of Z$^{2a}$ and Z$^{2b}$ is O, or S(O)$_m$ (m is an integer of 0, 1 or 2) or —N(R$^a$)— (R$^a$ is a hydrogen or $C_{1-4}$ alkyl which may be substituted), and the other is a bond, and W is —(CH$_2$)$_p$— (wherein p is an integer of 1 to 3) or Z$^2$ is a bivalent group of the formula —CH(OH)—. Further, particularly preferred Z$^2$ is —CH$_2$—, —CH(OH)—, —S(O)$_m$—CH$_2$— (wherein m is 0, 1 or 2), with —S(O)$_m$—CH$_2$— being more preferred. In particular, most preferably, Z$^2$ is a group of —SOCH$_2$— when Z$^{2a}$ is bound to Z$^1$.

Z$^{2a}$ is a bond, S, SO or SO$_2$, with SO being preferred. In this case, the configuration of SO is preferably (S).

In the above formula [I], examples of the "amino which may be substituted, or converted to quarternary ammonium or oxide" represented by R$^2$ include amino which may have 1 to 2 substituents, amino having three substituents whose nitrogen atom is converted to quarternary ammonium, and the like.

When the amino group has two or more substituents on its nitrogen atom, the substituents may be the same or different, and when the nitrogen atom has 3 substituents, the ammonium group may be in any type of the following formulas, —N$^+$R$^p$R$^p$R$^p$, —N$^+$R$^p$R$^p$R$^q$, and —N$^+$R$^p$R$^q$R$^r$ (wherein R$^p$, R$^q$, and R$^r$ are different and each is hydrogen or substituents). Examples of a counter anion of the amino group which is converted to quarternary ammonium include, in addition to a halogen anion (for example, Cl$^-$, Br$^-$, I$^-$, etc.), anions derived from inorganic acids such as hydrochloric acid, hydrobromic acid, nitric acid, sulfuric acid, phosphoric acid, etc.; anions derived from organic acids such as formate, acetate, trifluoroacetate, fumarate, oxalate, tartrate, maleate, citrate, succinate, malate, methanesulfonate, benzenesulfonate, p-toluenesulfonate; and anions derived from acidic amino acids such as aspartate, glutamate, etc., and preferably Cl$^-$, Br$^-$, and I$^-$.

Examples of the substituent of said amino group include:

(1) alkyl which may be substituted (for example, $C_{1-10}$ alkyl groups such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, and the like); and (2) cycloalkyl which may be substituted (for example, $C_{3-8}$ cycloalkyl such as cyclopropyl, cyclobutyl, cyclopentyl, cyclohexyl, cycloheptyl, cyclooctyl, etc., and the like);

(2-1) the cycloalkyl may contain a hetero atom selected from the group consisting of sulfur, oxygen and nitrogen, forming a heterocyclic ring such as oxirane, thiolane, aziridine, tetrahydrofuran, tetrahydrothiophene, pyrrolidine, tetrahydropyran, tetrahydrothiopyran, tetrahydrothiopyran-1-oxide, piperidine, etc., (preferably, a 6-membered ring such as tetrahydropyran, tetrahydrothiopyran, piperidine, etc.), wherein the hetero atom may be present at the 3 or 4 position (preferably at the 4 position) relative to the amino group;

(2-2) the cycloalkyl may be fused to a benzene ring forming a fused-ring group, such as indane (for example, indan-1-yl, indan-2-yl, etc.), tetrahydronaphthalene (for example, tetrahydronaphthalen-5-yl, tetrahydronaphthalen-6-yl, etc.), (and preferably fused to form an indane group, etc.);

(2-3) further, the cycloalkyl may be crosslinked via a straight chain group of 1 to 2 carbons, forming a crosslinked cyclic hydrocarbon group such as bicyclo[2.2.1]heptyl, bicyclo[2.2.2]octyl, bicyclo[3.2.1]octyl, bicyclo[3.2.2]nonyl, etc., (preferably cyclohexyl crosslinked via a straight chain group of 1 to 2 carbons, more preferably, bicyclo [2.2.1]heptyl, etc.);

(3) alkenyl which may be substituted (for example, alkenyl of 2 to 10 carbon atoms such as allyl, crotyl, 2-pentenyl, 3-hexenyl, etc., preferably lower ($C_{2-6}$) alkenyl, and the like);

(4) cycloalkenyl which may be substituted (for example, cycloalkenyl of 3 to 7 carbons such as 2-cyclopentenyl, 2-cyclohexenyl, 2-cyclopentenylmethyl, 2-cylcohexenylmethyl, etc.);

(5) aralkyl which may be substituted (for example, phenyl $C_{1-4}$ alkyl (for example, benzyl, phenethyl, etc.), and the like);

(6) formyl or acyl which may be substituted (for example, alkanoyl of 2 to 4 carbons (for example, acetyl, propionyl, butyryl, isobutyryl, etc.), alkylsulfonyl of 1 to 4 carbons (for example, methanesulfonyl, ethanesulfonyl, etc.), alkoxycarbonyl of 1 to 4 carbons (for example, methoxycarbonyl, ethoxycarbonyl, tert-butoxycarbonyl, etc.), aralkyloxycarbonyl of 7 to 10 carbons (for example, benzyloxycarbonyl, etc.), and the like);

(7) aryl which may be substituted (for example, phenyl, naphthyl, etc.);

(8) heterocyclic group which may be substituted (for example, a group formed by subtracting a hydrogen atom from an aromatic heterocyclic 5- to 6-membered ring containing 1 to 4 atoms of one or two kinds selected from the group consisting of nitrogen, sulfur and oxygen such as furan, thiophene, pyrrole, imidazole, pyrazole, thiazole, oxazole, isothiazole, isoxazole, tetrazole, pyridine, pyrazine, pyrimidine, pyridazine, triazole, oxadiazole, thiadiazole, etc., a group formed by subtracting a hydrogen atom from a fused-ring heterocyclic aromatic ring such as benzofuran, indole, benzothiophene, benzoxazole, benzthiazole, indazole, benzimidazole, quinoline, isoquinoline, quinoxaline, phthalazine, quinazoline, cinnoline, imidazopyridine, etc.; a group formed by subtracting a hydrogen atom from a non-aromatic heterocyclic ring containing 1 to 4 hetero atoms of one or two kinds selected from the group consisting of nitrogen, sulfur and oxygen such as tetrahydrofuran, tetrahydrothiophene, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, etc.; and the like; preferably, a group formed by subtracting a hydrogen atom from a 5- to 6-membered non-aromatic heterocyclic ring, more preferably, groups which are formed by subtracting a hydrogen atom from a non-aromatic heterocyclic 5- to 6-membered ring containing a hetero atom such as tetrahydrofuran, piperidine, tetrahydropyran, tetrahydrothiopyran, etc.); and the like. The substituents on the amino group may be bound to each other to form a 5- to 7-membered cyclic amino such as piperidine, piperazine, morpholine, thiomorpholine, etc.

Examples of the substituent of the above-described (1) alkyl which may be substituted, (2) cycloalkyl which may be substituted, (3) alkenyl which may be substituted, (4) cycloalkenyl which may be substituted, (5) aralkyl which may be substituted, (6) acyl which may be substituted, (7) aryl which may be substituted, and (8) heterocyclic group which may be substituted include halogen (for example, fluorine, chlorine, bromine, iodine, etc.); lower ($C_{1-4}$) alkyl which may be halogenated; lower ($C_{1-4}$) alkyl which may be substituted by a polar group such as hydroxy, cyano, carboxyl which may be esterified or amidated, etc. (for example, hydroxy $C_{1-4}$ alkyl, cyano $C_{1-4}$ alkyl, carboxyl $C_{1-4}$ alkyl, $C_{1-4}$ alkoxy-carbonyl $C_{1-4}$ alkyl, carbamoyl $C_{1-4}$ alkyl, mono-$C_{1-4}$ alkyl-carbamoyl $C_{1-4}$ alkyl, di-$C_{1-4}$ alkyl-carbamoyl, di-$C_{1-4}$ alkyl-carbamoyl $C_{1-4}$ alkyl, pyrrolidinocarbonyl $C_{1-4}$ alkyl, piperidinocarbony $C_{1-4}$ alkyl, morpholinocarbonyl $C_{1-4}$ alkyl, thiomorpholinocarbonyl $C_{1-4}$ alkyl, etc.); $C_{1-4}$ alkoxy may be halogenated (for example, methoxy, ethoxy, propoxy, butoxy, trifluoromethoxy, trifluoroethoxy, etc.); $C_{1-4}$ alkylenedioxy (for example, —O—CH$_2$—O—, —O—CH$_2$—CH$_2$—O—, etc.); formyl; $C_{2-4}$ alkanoyl (for example, acetyl, propionyl, etc.); $C_{1-4}$ alkylsulfonyl (for example, methanesulfonyl, ethanesulfonyl, etc.); phenyl-lower ($C_{1-4}$) alkyl; $C_{3-7}$ cycloalkyl; cyano; nitro; hydroxy; thiol which may be substituted (for example, thiol, $C_{1-4}$ alkylthio, etc.); amino which may be substituted (for example, amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc.); carboxyl which may be esterified or amidated (for example, carboxyl, $C_{1-4}$ alkoxy-carbonyl, carbamoyl, mono-$C_{1-4}$ alkylcarbamoyl, di-$C_{1-4}$ alkylcarbamoyl, etc.); lower ($C_{1-4}$) alkoxy-carbonyl; lower ($C_{7-10}$) aralkyloxy-carbonyl; oxo; and the like (preferably, halogen, lower ($C_{1-4}$) alkyl which may be halogenated, lower ($C_{1-4}$) alkoxy which may be halogenated, phenyl-lower ($C_{1-4}$) alkyl, $C_{3-7}$ cycloalkyl, cyano, hydroxy, etc). The number of the substituents is preferably 1 to 3.

In the above formula [I], the "amino which may be substituted or converted to quaternary ammonium or oxide" represented by $R^2$ is preferably an amino group which has 1 to 3 substituents selected from:

(1) straight or branched chain lower ($C_{1-6}$) alkyl which may be substituted with 1 to 3 groups selected from halogen, cyano, hydroxy, and $C_{3-7}$ cycloalkyl;

(2) $C_{5-8}$ cycloalkyl which may be substituted by 1 to 3 groups selected from halogen, lower ($C_{1-4}$) alkyl which may be halogenated, and phenyl-lower ($C_{1-4}$) alkyl, which may contain a hetero atom selected from the group consisting of sulfur, oxygen and nitrogen, which may be fused to a benzene ring and which may be crosslinked via a straight chain of 1 to 2 carbons (for example, cyclopentyl, cyclohexyl, cycloheptyl, cyclooctyl, tetrahydropyranyl, tetrahydrothiopyranyl, piperidinyl, indanyl, tetrahydronaphthalenyl, bicyclo[2,2,1]heptyl, etc.);

(3) phenyl-lower ($C_{1-4}$) alkyl which may contain 1 to 3 groups selected from halogen, lower ($C_{1-4}$) alkyl which may be halogenated, and lower ($C_{1-4}$) alkoxy which may be halogenated;

(4) phenyl which may containing 1 to 3 groups selected from halogen, lower ($C_{1-4}$) alkyl which may be halogenated, and lower ($C_{1-4}$) alkoxy which may be halogenated; and (5) 5- to 6-membered aromatic heterocyclic group which may contain 1 to 3 substituents selected from halogen, lower ($C_{1-4}$) alkyl which may be halogenated, lower ($C_{1-4}$) alkoxy groups which may be halogenated, lower ($C_{1-4}$) alkoxy-lower ($C_{1-4}$) alkoxy, phenyl-lower ($C_{1-4}$) alkyl, cyano, and hydroxy (for example, furan, thiophene, pyrrole, pyridine, etc.)

In the above formula [I], examples of the "nitrogen-containing heterocyclic ring group" of the "nitrogen-containing heterocyclic ring group which may be substituted, which may contain sulfur atom or oxygen atom as the ring constituting atom, and whose nitrogen atom can be converted to quaternary ammonium or oxide" represented by $R^2$ includes 5- to 6-membered aromatic heterocyclic ring containing 1 to 4 hetero atoms of one or two kinds selected from nitrogen, sulfur and oxygen such as pyrrole, imidazole, pyrazole, thiazole, oxazole, isothiazole, isoxazole, tetrazole, pyridine, pyrazine, pyrimidine, pyridazine, triazole, oxadiazole, thiadiazole, etc.; fused aromatic heterocyclic ring such as benzofuran, indole, benzothiophene, benzoxazole, benzthiazole, indazole, benzimidazole, quinoline, isoquinoline, quinoxaline, phthalazine, quinazoline, cinnoline, imidazopyridine, etc.; non-aromatic heterocyclic 5- to 8-membered ring containing a nitrogen atom and additionally 1 to 3 hetero atoms of one or two kinds selected from nitrogen, sulfur and oxygen such as pyrrolidine, pyrroline, imidazolidine, imidazoline, pyrazolidine, pyrazoline, piperidine, piperazine, oxazine, oxadiazine, thiazine, thiadiazine, morpholine, thiomorpholine, azacycloheptane, azacyclooctane (azocane), etc.; and the like, and these nitrogen-containing heterocyclic rings may form a crosslinked nitrogen-containing heterocyclic ring via a straight chain of 1 to 2 carbons, such as azabicyclo[2.2.1]heptane, azabicyclo[2.2.2]octane (quinuclidine), etc. (preferably piperidine crosslinked via a straight chain of 1 to 2 carbons, etc.).

Preferred examples of the above-described nitrogen-containing heterocyclic ring include pyridine, pyridazine, pyrazole, imidazole, triazole, tetrazole, imidazopyridine, pyrrolidine, piperidine, piperazine, morpholine, thiomorpholine, azabicyclo[2.2.2]octane, etc. (preferably, pyridine, imidazole, triazole, imidazopyridine, pyrrolidine, piperidine, morpholine).

The nitrogen atom in the "nitrogen-containing heterocyclic ring group" may be converted to quarternary ammonium or oxidized. When the "nitrogen atom" of the "nitrogen-containing heterocyclic ring group" is converted to quarternary ammonium, the counter anion may be, in addition to an anion of halogen (for example, Cl⁻, Br⁻, I⁻, etc.); an anion derived from inorganic acids such as hydrochloric acid, hydrobromic acid, nitric acid, sulfuric acid, phosphoric acid, etc.; an anion derived from organic acids such as formate, acetate, trifluoroacetate fumarate, oxalate, tartrate, maleate, citrate, succinate, malate, methanesulfonate, benzenesulfonate, p-toluenesulfonate, etc.; and an anion from acidic amino acids such as aspartate, glutamate, etc.; and preferably Cl⁻, Br⁻, and I⁻.

The nitrogen-containing heterocyclic ring group may be bound via a carbon or nitrogen atom to the bivalent group represented by $Z^2$, and may be bound via a ring constituting carbon atom such as 2-pyridyl, 3-pyridyl, 2-piperidyl, etc., or via a ring constituting nitrogen atom as represented by the formula:

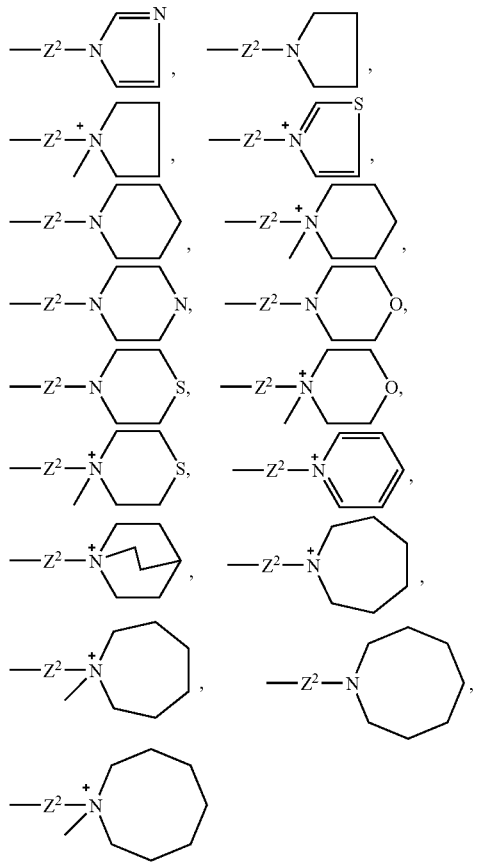

Examples of the substituent of the "nitrogen-containing heterocyclic group" include halogen (for example, fluorine, chlorine, bromine, iodine, etc.); lower ($C_{1-4}$) alkyl which may be substituted; lower ($C_{1-4}$) alkoxy which may be substituted; phenyl which may be substituted; mono- or di-phenyl-lower ($C_{1-4}$) alkyl which may be substituted; $C_{3-7}$ cycloalkyl which may be substituted; cyano; nitro; hydroxy; thiol which may be substituted (for example, thio, $C_{1-4}$ alkylthio, etc.); amino which may be substituted (for example, amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc.); carboxyl which may be esterified or amidated (for example, carboxyl, $C_{1-4}$ alkoxy-carbonyl, carbamoyl, mono-$C_{1-4}$ alkylcarbamoyl, di-$C_{1-4}$ alkylcarbamoyl, etc.); lower ($C_{1-4}$) alkoxycarbonyl; formyl; lower ($C_{2-4}$) alkanoyl; lower ($C_{1-4}$) alkylsulfonyl; heterocyclic group which may be substituted (for example, 5- to 6-membered aromatic heterocyclic ring containing 1 to 4 hetero atoms of one or two kinds selected from nitrogen, sulfur and oxygen such as furan, thiophene, pyrrole, imidazole, pyrazole, thiazole, oxazole, isothiazole, isoxazole, tetrazole, pyridine, pyrazine, pyrimidine, pyridazine, triazole, oxadiazole, thiadiazole, etc.); a group formed by subtracting a hydrogen atom form a fused aromatic heterocyclic ring containing 1 to 4 hetero atoms of one or two kinds selected from nitrogen, sulfur and oxygen such as benzofuran, indole, benzothiophene, benzoxazole, benzthiazole, indazole, benzimidazole, quinoline, isoquinoline, quinoxaline, phthalazine, quinazoline, cinnoline, imidazopyridine, etc.; a group formed by subtracting a hydrogen atom from a 5- to 6-membered non-aromatic heterocyclic ring containing 1 to 4 hetero atoms of one or two kinds selected from nitrogen, sulfur and oxygen such as tetrahydrofuran, tetrahydrothiophene, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, tetrahydrothiopyran, etc.; and the like, and the number of the substituents is preferably 1 to 3. The nitrogen atom in the nitrogen-containing heterocyclic rings may be oxidized.

Examples of the substituent of the "lower ($C_{1-4}$) alkyl which may be substituted", the "lower ($C_{1-4}$) alkoxy which may be substituted", the "phenyl which may be substituted", the "mono- or di-lower ($C_{1-4}$) alkyl which may be substituted", the "$C_{3-7}$ cycloalkyl which may be substituted", and the "heterocyclic group which may be substituted", all of which are the substituents of the "nitrogen-containing heterocyclic ring group", include halogen (for example, fluorine, chlorine, bromine, iodine, etc.); lower ($C_{1-4}$) alkyl which may be halogenated; lower ($C_{1-4}$) alkyl which may be substituted by a polar group such as hydroxy, cyano, carboxyl which may be esterified or amidated, etc. (for example, hydroxy $C_{1-4}$ alkyl, cyano $C_{1-4}$ alkyl, carboxyl $C_{1-4}$ alkyl, $C_{1-4}$ alkoxy-carbonyl $C_{1-4}$ alkyl, carbamoyl $C_{1-4}$ alkyl, mono-$C_{1-4}$ alkyl-carbamoyl $C_{1-4}$ $C_{1-4}$alkyl, di-$C_{1-4}$ alkyl-carbamoyl $C_{1-4}$ alkyl, pyrrolidinocarbonyl $C_{1-4}$ alkyl, piperidinocarbony $C_{1-4}$ alkyl, morpholinocarbonyl $C_{1-4}$ alkyl, thiomorpholinocarbonyl $C_{1-4}$ alkyl, etc.); lower ($C_{3-10}$) cycloalkyl; lower ($C_{3-10}$) cycloalkenyl; $C_{1-4}$ alkoxy which may be halogenated (for example, methoxy, ethoxy, trifluoromethoxy, trifluoroethoxy, etc.); formyl; $C_{2-4}$ alkanoyl (for example, acetyl, propionyl, etc.); $C_{1-4}$ alkylsulfonyl (for example, methanesulfonyl, ethanesulfonyl, etc.); $C_{1-3}$ alkylenedioxy (for example, methylenedioxy, ethylenedioxy, etc.); cyano; nitro; hydroxy; thiol which may be substituted (for example, thiol, $C_{1-4}$ alkylthio groups, etc.); amino which may be substituted (for example, amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc.); carboxyl which may be esterified or amidated (for example, carboxyl, $C_{1-4}$ alkoxy-carbonyl, carbamoyl, mono-$C_{1-4}$ alkyl-carbamoyl, di-$C_{1-4}$ alkyl-carbamoyl, etc.); lower ($C_{1-4}$) alkoxy-carbonyl; and the like, and the number of the substituents is preferably 1 to 3.

In the above formula [I], examples of the substituent of the "nitrogen-containing heterocyclic ring group" of the "nitrogen containing heterocyclic ring group of the heterocyclic ring which may be substituted, which may contain additional sulfur or oxygen atoms as ring constituting atoms, and whose nitrogen atom may be converted to ammonium or oxide" include (1) halogen, (2) cyano, (3) hydroxy, (4) carboxyl, (5) carbamoyl, (6) lower ($C_{1-4}$)alkyl-carbonyl, (7) lower ($C_{1-4}$)alkyl-carbamoyl or 5- to 6-membered cyclic amino (e.g., piperidino, morpholino, etc.)-carbonyl, (8) lower ($C_{1-4}$) alkyl which may be substituted with halogen, hydroxy, cyano, lower ($C_{1-4}$) alkoxy, or carboxyl which may be esterified or amidated, (9) lower ($C_{1-4}$) alkoxy which may be substituted by halogen, hydroxy, or lower ($C_{1-4}$) alkoxy, (10) phenyl which may be substituted by halogen, lower ($C_{1-4}$)alkyl, hydroxy, lower ($C_{1-4}$)alkoxy or $C_{1-3}$ alkylenedioxy, (11) monophenyl- or diphenyl-lower ($C_{1-4}$) alkyl which may be substituted with halogen, lower ($C_{1-4}$) alkyl, hydroxy, lower ($C_{1-4}$) alkoxy or $C_{1-3}$ alkylenedioxy, (12) a group formed by subtracting a hydrogen atom form a 5- to 6-membered aromatic heterocyclic ring such as furan, thiophene, pyrrole, pyridine, etc., and the like.

In the group represented by the following formula:

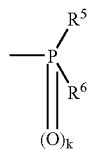

wherein k is integer 0 or 1; when k is 0, the phosphorus atom may form a phosphonium salt; and $R^5$ and $R^6$ are, respectively, a hydrocarbon group which may be substituted, a hydroxy group which may be substituted, or an amino group which may be substituted (preferably, a hydrocarbon group which may be substituted or an amino group which may be substituted, more preferably, a hydrocarbon group which may be substituted, and $R^5$ and $R^6$ may be bound to each other to form a ring together with the adjacent phosphorus atom) of $R^2$ in the above formula [I], examples of the "hydrocarbon group which may be substituted" represented by $R^5$ and $R^6$ include:

(1) alkyl which may be substituted (for example, $C_{1-10}$ alkyl groups such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, and the like);

(2) cycloalkyl which may be substituted (for example, $C_{3-7}$ cycloalkyl groups such as cyclopropyl, cyclobutyl, cyclopentyl, cyclohexyl, cycloheptyl etc.);

(3) alkenyl which may be substituted (for example, alkenyl of 2 to 10 carbons such as allyl, crotyl, 2-pentenyl, 3-hexenyl, etc., preferably lower ($C_{2-6}$) alkenyl, and the like);

(4) cycloalkenyl which may be substituted (for example, cycloalkenyl of 3 to 7 carbons such as 2-cyclopentenyl, 2-cyclohexenyl, 2-cyclopentenylmethyl, 2-cyclohexenylmethyl, etc.);

(5) alkynyl which may be substituted (for example, alkynyl groups of 2 to 10 carbons such as ethynyl, 1-propynyl, 2-propynyl, 1-butynyl, 2-pentynyl, 3-hexynyl, etc., preferably lower ($C_{2-6}$) alkynyl, and the like);

(6) aralkyl which may be substituted (for example, phenyl-$C_{1-4}$ alkyl (for example, benzyl, phenethyl, etc.), and the like);

(7) aryl which may be substituted (for example, phenyl, naphthyl, etc.); and the like.

Examples of the substituent of the above-described (1) alkyl which may be substituted, (2) cycloalkyl which may be substituted, (3) alkenyl which may be substituted, (4) cycloalkenyl which may be substituted, (5) alkynyl which may be substituted, (6) aralkyl which may be substituted, and (7) aryl which may be substituted include halogen (for example, fluorine, chlorine, bromine, iodine, etc.); nitro; cyano; hydroxy; thiol which may be substituted (for example, thiol, $C_{1-4}$ alkylthio, etc.); amino which may be substituted (for example, amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc.); carboxyl which may be esterified or amidated (for example, carboxyl, $C_{1-4}$ alkoxy-carbonyl, carbamoyl, mono-$C_{1-4}$ alkyl-carbamoyl, di-$C_{1-4}$ alkyl-carbamoyl, etc,); $C_{1-4}$ alkyl which may be halogenated (for example, trifluoromethyl, methyl, ethyl, etc.); $C_{1-4}$ alkoxy which may be halogenated (for example, methoxy, ethoxy, trifluoromethoxy, trifluoroethoxy, etc.); formyl; $C_{2-4}$ alkanoyl (for example, acetyl, propionyl, etc.); $C_{1-4}$ alkylsulfonyl (for example, methanesulfonyl, ethanesulfonyl, etc.); and the like, and the number of the substituents is preferably 1 to 3.

Examples of the "hydroxy group which may be substituted" represented by $R^5$ and $R^6$ include hydroxy having a substituent selected from:

(1) alkyl which may be substituted (for example, $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, and the like);

(2) cycloalkyl which may be substituted (for example, $C_{3-7}$ cycloalkyl such as cyclopropyl, cyclobutyl, cyclopentyl, cyclohexyl, cycloheptyl etc.);

(3) alkenyl which may be substituted (for example, alkenyl groups of 2 to 10 carbons such as allyl, crotyl, 2-pentenyl, 3-hexenyl, etc., preferably lower ($C_{2-6}$) alkenyl, and the like);

(4) cycloalkenyl which may be substituted (for example, cycloalkenyl of 3 to 7 carbons such as 2-cyclopentenyl, 2-cyclohexenyl, 2-cyclopentenylmethyl, 2-cyclohexenylmethyl, etc.);

(5) aralkyl which may be substituted (for example, phenyl $C_{1-4}$ alkyl (for example, benzyl, phenethyl, etc.));

(6) formyl or acyl which may be substituted (for example, alkanoyl of 2 to 4 carbons (for example, acetyl, propionyl, butyryl, isobutyryl, etc.), and alkylsulfonyl of 1 to 4 carbons (for example, methanesulfonyl, ethanesulfonyl, etc.), and the like);

(7) aryl which may be substituted (for example, phenyl, naphthyl, etc.); and the like.

Examples of the substituent of the above-described (1) alkyl which may be substituted, (2) cycloalkyl which may be substituted, (3) alkenyl which may be substituted, (4) cycloalkenyl which may be substituted, (5) aralkyl which may be substituted, (6) acyl which may be substituted, and (7) aryl which may be substituted include halogen (for example, fluorine, chlorine, bromine, iodine, etc.); nitro; cyano; hydroxy; thiol which may be substituted (for example, thiol, $C_{1-4}$ alkylthio, etc.); amino which may be substituted (for example, amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc.); carboxyl which may be esterified or amidated (for example, carboxyl, $C_{1-4}$ alkoxy-carbonyl, carbamoyl, mono-$C_{1-4}$ alkyl-carbamoyl, di-$C_{1-4}$ alkyl-carbamoyl, etc,); $C_{1-4}$ alkyl which may be halogenated (for example, trifluoromethyl, methyl, ethyl, etc.); $C_{1-4}$ alkoxy which may be halogenated (for example, methoxy, ethoxy, trifluoromethoxy, trifluoroethoxy, etc.); formyl; $C_{2-4}$ alkanoyl (for example, acetyl, propionyl, etc.); $C_{1-4}$ alkylsulfonyl (for example, methanesulfonyl, ethanesulfonyl, etc.); and the like, and the number of the substituents is preferably 1 to 3.

In the above formula, $R^5$ and $R^6$ may bind each other to form a ring together with the adjacent phosphorus atom (preferably, a 5- to 7-membered ring). Such a cyclic group may be substituted and examples of the substituent include halogen (for example, fluorine, chlorine, bromine, iodine, etc.); nitro; cyano; hydroxy; thiol which may be substituted (for example, thiol, $C_{1-4}$ alkylthio, etc.); amino which may be substituted (for example, amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc.); carboxyl which may be esterified or amidated (for example, carboxyl, $C_{1-4}$ alkoxy-carbonyl, carbamoyl, mono-$C_{1-4}$ alkyl-carbamoyl, di-$C_{1-4}$ alkyl-carbamoyl, etc,); $C_{1-4}$ alkyl which may be halogenated (for example, trifluoromethyl, methyl, ethyl, etc.); $C_{1-4}$ alkoxy which may be halogenated (for example, methoxy, ethoxy, trifluoromethoxy, trifluoroethoxy, etc.); formyl; $C_{2-4}$ alkanoyl (for example, acetyl, propionyl, etc.); $C_{1-4}$ alkylsulfonyl (for example, methanesulfonyl, ethanesulfonyl, etc.); and the like, and the number of the substituents is preferably 1 to 3.

In the above formula [I], when the phosphorus atom forms phosphonium salt, examples of the counter anion include an anion of halogen (for example, Cl⁻, Br⁻, I⁻, etc.); as well as anions of inorganic acids such as hydrochloric acid, hydrobromic acid, nitric acid, sulfuric acid, phosphoric acid, etc.; anions of organic acids such as formate, acetate, trifluoroacetate, fumarate, oxalate, tartrate, maleate, citrate, succinate, malate, methanesulfonate, benzenesulfonate, p-toluenesulfonate, etc.; anions of acidic amino acids such as aspartate, glutamate, etc.; and the like, and preferably Cl⁻, Br⁻, I⁻, etc.

Examples of amino which may be substituted represented by $R^5$ and $R^6$ include amino having 1 or 2 substituents selected from:

(1) alkyl which may be substituted (for example, $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, and the like);

(2) cycloalkyl which may be substituted (for example, $C_{3-7}$ cycloalkyl groups such as cyclopropyl, cyclobutyl, cyclopentyl, cyclohexyl, cycloheptyl etc.);

(3) alkenyl which may be substituted (for example, alkenyl groups of 2 to 10 carbons such as allyl, crotyl, 2-pentenyl, 3-hexenyl, etc., preferably lower ($C_{2-6}$) alkenyl and the like);

(4) cycloalkenyl which may be substituted (for example, cycloalkenyl groups of 3 to 7 carbons such as 2-cyclopentenyl, 2-cyclohexenyl, 2-cyclopentenylmethyl, 2-cyclohexenylmethyl, etc.);

(5) formyl or acyl which may be substituted (for example, alkanoyl of 2 to 4 carbons (for example, acetyl, propionyl, butyryl, isobutyryl, etc.), and alkylsulfonyl of 1 to 4 carbons (for example, methanesulfonyl, ethanesulfonyl, etc.), and the like);

(6) aryl which may be substituted (for example, phenyl, naphthyl, etc.); and the like.

Examples of the substituent of the above-described (1) alkyl which may be substituted, (2) cycloalkyl which may be substituted, (3) alkenyl which may be substituted, (4) cycloalkenyl which may be substituted, (5) acyl which may be substituted, and (6) aryl which may be substituted include halogen (for example, fluorine, chlorine, bromine, iodine, etc.); nitro; cyano; hydroxy; thiol which may be substituted (for example, thiol, $C_{1-4}$ alkylthio, etc.); amino which may be substituted (for example, amino, mono-$C_{1-4}$ alkylamino, di-$C_{1-4}$ alkylamino, 5- to 6-membered cyclic amino such as tetrahydropyrrole, piperazine, piperidine, morpholine, thiomorpholine, pyrrole, imidazole, etc.); carboxyl which may be esterified or amidated (for example, carboxyl, $C_{1-4}$ alkoxycarbonyl, carbamoyl, mono-$C_{1-4}$ alkyl-carbamoyl, di-$C_{1-4}$ alkyl-carbamoyl, etc,); $C_{1-4}$ alkyl which may be halogenated (for example, trifluoromethyl, methyl, ethyl, etc.); $C_{1-4}$ alkoxy which may be halogenated (for example, methoxy, ethoxy, trifluoromethoxy, trifluoroethoxy, etc.); formyl; $C_{2-4}$ alkanoyl (for example, acetyl, propionyl, etc.); $C_{1-4}$ alkylsulfonyl groups (for example, methanesulfonyl, ethanesulfonyl, etc.); and the like, and the number of the substituents is preferably 1 to 3.

The substituent of the "amidino which may be substituted" and the "guanidino which may be substituted" represented by $R^2$ may be the same substituent as that of the "amino group which may be substituted and whose nitrogen atom may be converted to quarternary ammonium or oxide" represented by $R^2$ above.

$R^2$ is preferably (1) amino which may be substituted and whose nitrogen atom is converted to quarternary ammonium or oxide; (2) nitrogen-containing heterocyclic ring group which may be substituted, which may contain additional sulfur or oxygen atoms as the ring constituting atom and whose nitrogen atom may be converted to quarternary ammonium or oxide; (3) amidino which may be substituted; or (4) guanidino which may be substituted; and more preferably amino which may be substituted and whose nitrogen atom is converted to quarternary ammonium; and nitrogen-containing heterocyclic ring groups which may be substituted, which may contain additional sulfur or oxygen atoms as the ring constituting atom and whose nitrogen atom may be converted to oxide. In particular, amino which may be substituted, nitorgen-containing heterocyclic ring which may be substituted, which may contain additional sulfur or oxygen atoms as the ring constituting atom, etc. are preferred.

$R^2$ is further more preferably a group of the formula —NRR'' or —N⁺RR'R'' (wherein, R, R' and R'' are, respectively, an aliphatic hydrocarbon group (an aliphatic straight chain hydrocarbon group or an aliphatic cyclic hydrocarbon group) or an alicyclic (non-aromatic) heterocyclic ring group which may be substituted), or a nitrogen-containing aromatic heterocyclic ring group which may be substituted and whose nitrogen atom may be converted to oxide.

The "aliphatic hydrocarbon group which may be substituted" and "the alicyclic heterocyclic ring group which may be substituted" represented by R, R' and R'' in the above formula may be the same "aliphatic hydrocarbon group which may be substituted (for example, alkyl, cycloalkyl, alkenyl, cycloalkenyl, etc., all of which may be substituted)" and "alicyclic heterocyclic ring groups which may be substituted (for example, 5- to 6-membered non-aromatic heterocyclic ring which may be substituted, etc.)" as those exemplified with respect to the substituent of the "amino which may be substituted" represented by $R^2$.

Among them, each of R and R' is preferably a straight chain hydrocarbon group which may be substituted (for example, alkyl and alkenyl both of which may be substituted, etc.), more preferably $C_{1-6}$ alkyl which may be substituted, and most preferably methyl which may be substituted.

R" is preferably an alicyclic hydrocarbon group which may be substituted (preferably, $C_{3-8}$ cycloalkyl which may be substituted, more preferably cyclohexyl which may be substituted), or an alicyclic heterocyclic ring group which may be substituted (preferably, a saturated alicyclic heterocyclic group (preferably, a 6-membered ring) which may be substituted; more preferably, tetrahydropyranyl which may be substituted, or tetrahydrothiopyranyl which may be substituted, or piperidyl which may be substituted; and most preferably tetrahydropyranyl which may be substituted).

The "nitrogen-containing aromatic heterocyclic ring group" of the "nitrogen-containing aromatic heterocyclic ring group which may be substituted or whose nitrogen atom my be converted to oxide" represented by $R^2$ is preferably pyridine, imidazole, triazole, or imidazopyridine, in particular, imidazole and triazole being preferred.

Examples of "a nitrogen-containing heterocyclic group which may be substituted, may contain a sulfur or oxygen atom as a ring constituent atom, and whose nitrogen atom may be converted to quarternary ammonium or oxide", etc. represented by $R^{2'}$ and $R^{2''}$ include the corresponding same groups as those exemplified with respect to the above $R^2$.

Examples of "a hydrocarbon group which may be substituted", "a $C_{1-6}$ alkyl group which may be substituted", etc. of the substituent represented by $R^4$ of imino group represented by Y and the subsituent of imino group represented by Y' include the corresponding same groups as those exemplified with respect to the above $R^0$.

Examples of "an alkylene chain which may be subsituted represented by $W^2$ include the corresponding same groups as those exemplified with respect to the above $W^1$.

The following compounds are preferred examples of the compound of the formula [I]:

8-[4-(2-butoxyethoxy)phenyl]-N-[4-[[N-methyl-N-(tetrahydropyran-4-yl)amino]methyl]phenyl]-3,4-dihydro-2H-1-benzoxocine-5-carboxamide;

8-[4-(2-butoxyethoxy)phenyl]-N-[4-[[N-methyl-N-(tetrahydropyran-4-yl)amino]methyl]phenyl]-1,2,3,4-tetrahydro-1-benzazocine-5-carboxamide;

8-[4-(2-butoxyethoxy)phenyl]-1-propyl-N-[4-[[[1-propylimidazol-5-yl]methyl]sulfanyl]phenyl]-1,2,3,4-tetrahydro-1-benzazocine-5-carboxamaide;

8-[4-(2-butoxyethoxy)phenyl]-1-propyl-N-[4-[[[1-propylimidazol-5-yl]methyl]sulfinyl]phenyl]-1,2,3,4-tetrahydro-1-benzazocine-5-carboxamide;

8-[4-(2-butoxyethoxy)phenyl]-1-propyl-N-[4-[[1-propylimidazol-5-yl]methyl]sulfanyl]phenyl]-1,2,3,4-tetrahydro-1-benzazocine-5-carboxamide;

8-[4-(2-butoxyethoxy)phenyl]-1-isobutyl-N-[4-[[[1-propylimidazol-5-yl]methyl]sulfanyl]phenyl]-1,2,3,4-tetrahydro-1-benzazocine-5-carboxamide;

8-[4-(2-butoxyethoxy)phenyl]-1-isobutyl-N-[4-[[[1-propylimidazol-5-yl]methyl]sulfinyl]phenyl]-1,2,3,4-tetrahydro-1-benzazocine-5-carboxamide;

8-[4-(2-butoxyethoxy)phenyl]-1-isobutyl-N-[4-[[[1-propylimidazol-5-yl]methyl]sulfonyl]phenyl]-1,2,3,4-tetrahydro-1-benzazocine-5-carboxamide;

8-[4-(2-butoxyethoxy)phenyl]-1-isobutyl-N-[4-[[N-methyl-N-(tetrahydropyran-4-yl)amino]methyl]phenyl]-1,2,3,4-tetrahydro-1-benzazocine-5-carboxamide;

(S)-8-[4-(2-butoxyethoxy)phenyl]-1-isobutyl-N-[4-[[(1-propyl-1H-imidazol-5-yl)methyl]sulfinyl]phenyl]-1,2,3,4-tetrahydro-1-benzazocine-5-carboxamide methanesulfonate;

(S)-8-[4-(2-butoxyethoxy)phenyl]-1-propyl-N-[4-[[(1-propyl-1H-imidazol-5-yl)methyl]sulfinyl]phenyl]-1,2,3,4-tetrahydro-1-benzazocine-5-carboxamaide methanesulfonate;

(S)-1-isobutyl-8-[4-(2-propoxyethoxy)phenyl]-N-[4-[[(1-propyl-1H-imidazol-5-yl)methyl]sulfiyl]phenyl]-1,2,3,4-tetrahydro-1-benzazocine-5-carboxamide;

(S)-8-[4-(2-butoxyethoxy)phenyl]-1-[(1-methyl-1H-pyrazol-4-yl)methyl]-N-[4-[[(1-propyl-1H-imidazol-5-yl]methyl]sulfinyl]phenyl]-1,2,3,4-tetrahydro-1-benzazocine-5-carboxamide;

(S)-8-[4-(2-butoxyethoxy)phenyl]-1-isobutyl-N-[4-[[(4-propyl-4H-1,2,4-triazol-3-yl)methyl]sulfinyl]phenyl]-1,2,3,4-tetrahydro-1-benzazocine-5-carboxamide;

and the like.

A salt of the compound of the formula [I] of the present invention is preferably a pharmaceutically acceptable salt. Examples of the salt include salts with inorganic bases, salts with organic bases, salts with inorganic acids, salts with organic acids, salts with basic or acidic amino acids; and the like. Suitable examples of the salt with inorganic base include alkali metal salts such as sodium salt, potassium salt, etc.; alkali earth metal salts such as calcium salt, magnesium salt, etc.; aluminum salt; ammonium salt; etc. Suitable examples of the salt with organic base include salts with trimethylamine, triethylamine, pyridine, picoline, ethanolamine, diethanolamine, triethanolamine, dicyclohexylamine, N,N'-dibenzylethylenediamine, etc. Suitable examples of the salt with inorganic acid include salts with hydrochloric acid, hydrobromic acid, nitric acid, sulfuric acid, phosphoric acid, etc. Suitable examples of the salt with organic acid include salts such as formate, acetate, trifluoroacetate, fumarate, oxalate, tartrate, maleate, citrate, succinate, malate, methanesulfonate, benzenesulfonate, p-toluenesulfonate, etc. Suitable examples of the salt with basic amino acid include salts with arginine, lysine, and ornithine. Suitable examples of the salts with acidic amino acids include salts with aspartic acid, glutamic acid, etc. The compound of the formula [I] of the present invention may be either hydrate or non-hydrate. When the compound of the formula [I] of the present invention is present as a mixture of configurational isomers, diastereomers, or conformers, the compound may be isolated by separation and purification methods known in the art. When the compound of the formula [I] is present as a racemic mixture, each of (S) and (R) isomer may be isolated by common means for optical resolution. Each of the optical isomers as well as the racemic mixture is included in the scope of the present invention.

A pro-drug of the compound of the formula [I] of the present invention or a salt thereof [hereinafter, referred to as the compound [I]] is defined as a compound which may be converted to the compound [I] by enzymes, gastric acid, etc, in a physiological condition within the living body, in other words, by enzymatic oxidation, reduction, hydrolysis, etc., or by hydrolysis by gastric acid, etc. Examples of a pro-drug of the compound [I] include compounds which are formed by acylation, alkylation or phosphorylation of an amino group in the compound [I], (for example, compounds wherein amino group of the compound [I] is substituted by eicosanoyl, alanyl, pentylaminocarbony, (5-methyl-2-oxo-1, 3-dioxolen-4-yl) methoxycarbonyl, tetrahydrofuranyl, pyrrolidylmethyl, pivaloyloxymethyl, tert-butyl, etc.); compounds which are formed by acylation, alkylation, phosphorylation, or borate formation of hydroxy group in the compound [I], (for example, compounds wherein hydroxy group of the compound [I] is substituted by acetyl, palmitoyl, propanoyl, pivaloyl, succinoyl, fumaroyl, alanyl, dimethylaminomethylcarbonyl, etc.); compounds which are formed by esterification or amidation of carboxyl group in the compound [I] (for example, compounds wherein carboxyl group of the compound [I] is converted to ethyl ester, phenyl ester, carboxymethyl ester, dimethylaminomethyl ester, pivaloyloxymethyl ester, ethoxycarbonyloxydiethyl ester, phthalidyl ester, (5-methyl-2-oxo-1,3-dioxolen-4-yl) methyl ester, cyclohexyloxycarbonylethyl ester, methylamide, etc.), and the like. These compounds may be produced from the compound [I] by methods known in the art.

A pro-drug of the compound [I] may be a compound which may be converted to the compound [I] under physiological conditions as described in "Development of Medicines", Vol. 7, Molecular Design, p163-198, Hirokawa Shoten, 1990.

In addition, the compound [I] may be labeled by isotopes (for example, $^3$H, $^{14}$C, $^{35}$S, $^{125}$I, etc.)

Hereinafter, a process for producing the compound of the formula [I] or a salt thereof will be explained.

The compound of the formula [I] or the salt thereof may be produced by a per se known process. For example, it may be produced by the following processes. In addition, the compound of formula [I] or a salt thereof may be produced by the process described in JP 8-73476 A or modification thereof.

Compounds which will be used in each of the following processes may form salts similar to that of the compound [I] as far as the salt does not interfere with reactions.

Further, amino, carboxyl and hydroxy groups which may be present in starting compounds used in the following reactions, may be protected by protective groups which are commonly used in peptide chemistry and the protective groups may be removed after the reactions to obtain desired compounds, if necessary.

Examples of the protective group of amino group include $C_{1-6}$ alkylcarbonyl which may be substituted (for example, acetyl, propionyl, etc); formyl; phenylcarbonyl; $C_{1-6}$ alkyloxycarbonyl (for example, methoxycarbonyl, ethoxycarbonyl, t-butoxycarbonyl, etc.); phenyloxycarbonyl (for example, benzoxycarbonyl, etc.); $C_{7-10}$ aralkyloxycarbonyl (for example, benzyloxycarbonyl, etc.); trityl; phthaloyl; etc. Examples of the substituent of the above protective groups include halogen (for example, fluorine, chlorine, bromine, iodine, etc.); $C_{1-6}$ alkylcarbonyl (for example, acetyl, propionyl, butyryl, etc.); nitro; and the like, and the number of the substituents is about 1 to 3.

Examples of the protective group of carboxyl group include $C_{1-6}$ alkyl which may be substituted (for example, methyl, ethyl, propyl, isopropyl, butyl, tert-butyl, etc.), phenyl, trityl, silyl, etc. Examples of these substituents include halogen (for example fluorine, chlorine, bromine, iodine, etc.), $C_{1-6}$ alkylcarbonyl (for example, acetyl, propionyl, butyryl, etc.), formyl, nitro, and the like, and the number of the substituents is about 1 to 3.

Examples of the protective groups of hydroxy group include $C_{1-6}$ alkyl which may be substituted (for example, methyl, ethyl, propyl, isopropyl, butyl, tert-butyl, etc.), phenyl, $C_{7-10}$ aralkyl (for example, benzyl, etc.), $C_{1-6}$ alkylcarbonyl (for example, acetyl, propionyl, etc.), formyl, phenyloxycarbonyl, $C_{7-10}$ aralkyloxycarbonyl (for example, benzyloxycarbonyl, etc.), pyranyl, furanyl, silyl, etc. The substituents of these protective groups include halogen (for example, fluorine, chlorine, bromine, iodine, etc.), $C_{1-6}$ alkyl, phenyl, $C_{7-10}$ aralkyl, nitro, and the like, and the number of the substituents is about 1 to 4.

Protection and deprotection of the protective groups are carried out according to a per se known method or modification thereof [for example, the method described in "Protective Groups in Organic Chemistry", (J. F. W. McOmie et al., Plenum Press)], and the deprotection methods include, for example, methods by treatment with an acid, a base, a reducing agent, ultraviolet light, hydrazine, phenylhydrazine, sodium N-methydithiocarbamate, tetrabutylammonium fluoride, palladium acetate, etc.

In the following description, sometimes, compounds represented by the formulas [I], [I-1], [I-2], [I'], [I''], [I'''], [II], [II-1], [II'], [IIa'], [IIb'], [IIc'], [IId], [IIe'], [IIf'], [III], [III-1], [IV], [V], [VI], [VII], [VIII], [IX], [X], [XI], [XII] and [XIII] including their salts are simply referred to as compound [I], compound [I-1], compound [I-2], compound [I'], compound [I''], compound [I'''], compound [II], compound [II-1], compound [II'], compound [IIa'], compound [IIb'], compound [IIc'], compound [IId'], compound [IIe'], compound [IIf'], compound [III], compound [III-1], compound [IV], compound [V], compound [VI], compound [VII], compound [VIII], compound [IX], compound [X], compound [XI], compound [XII] and compound [XIII], respectively.

[Process A]

The compound [I] can be prepared by reacting a compound [II] and a compound [III], according to the following reaction.

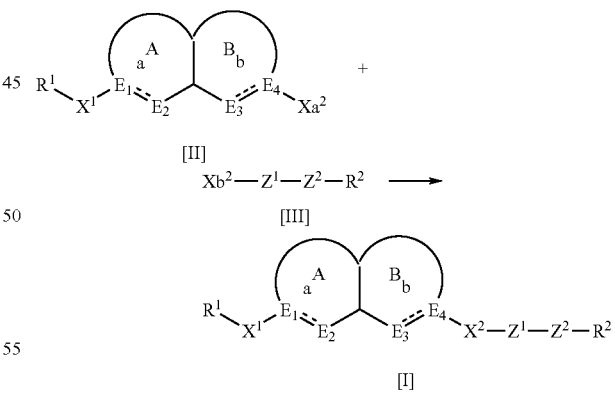

wherein $X^{a2}$ represents a group which reacts with a substituent $X^{b2}$ of the compound [III] to form a group $X^2$ (for example, carboxyl, etc.), and $X_{b2}$ represents a group which reacts with the substituent $X^{a2}$ of the compound [II] to form the group $X^2$ (for example, amino, etc.), and the other symbols are as defined above.

The following scheme shows the above process wherein $X^{a2}$ is carboxyl, $X^{b2}$ is amino, and $X^2$ is —CO—NH—.

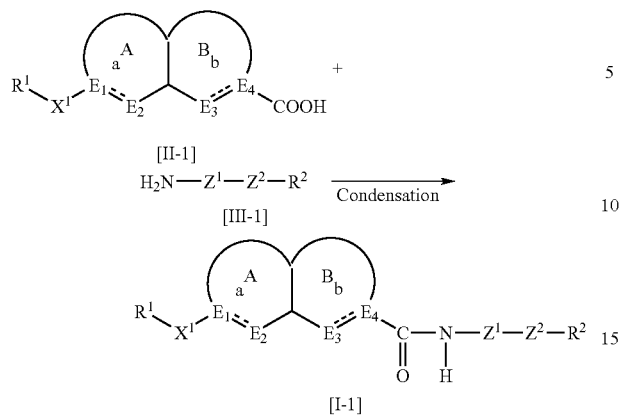

wherein each symbol is as defined above.

In this reaction, a carboxylic acid derivative [II-1] and an amine derivative [III-1] are reacted to give compound [I-1].

Condensation of compound [II-1] and compound [III-1] may be conducted by any means commonly practiced in peptide synthesis. The peptide synthesis means may be any of the methods known in the art, for example, the methods described in M. Bodansky and M. A. Ondetti Ed., Peptide Synthesis, Interscience, New York, 1996; F. M. Finn and K. Hofmann, The Proteins, Vol. 2; H. Nenrath and R. L. Hill Ed., Academic Press Inc., New York, 1976; and N. Izuo, Basics and Experiments in Organic Chemistry, Maruzen, 1985, which include, for example, azide method, chloride method, acid anhydride method, mixed acid anhydride method, DCC method, activated ester method, method using Woodward Reagent K, carbonyldiimidazole method, oxidation/reduction method, DCC/HONB method, as well as WSC method, and cyanodiethylphosphate (DEPC) method. In other words, examples of the reactive derivatives that may be used include acid halides (for example, acid chloride, acid bromide, etc.); acid azides; acid anhydrides; mixed acid anhydrides (for example, mono $C_{1-6}$ alkylcarbonate mixed acid anhydrides, (for example, mixed acid anhydrides between a free acid, and monomethylcarbonate, monoethylcarbonate, monoisopropylcarbonate, monoisobutylcarbonate, monotert-butylcarbonate, monobenzylcarbonate, mono(p-nitrobenzyl)carbonate, or monoallylcarbonate, etc.); $C_{1-6}$ aliphatic carboxylic acid mixed acid anhydrides (for example, mixed acid anhydrides between a free acid, and acetic acid, trichloroacetic acid, cyanoacetic acid, propionic acid, butyric acid, isobutyric acid, valeric acid, isovaleric acid, pivalic acid, trifluoroacetic acid, trichloroacetic acid, acetoacetic acid, etc.); $C_{7-12}$ aromatic carboxylic acid mixed acid anhydrides (for example, mixed acid anhydrides between a free acid, and benzoic acid, p-toluic acid, p-chlorobenzoic acid, etc.); organic sulfonic acid mixed acid anhydrides (for example, mixed acid anhydrides between a free acid and methanesulfonic acid, ethanesulfonic acid, benzenesulfonic acid, p-toluenesulfonic acid, etc.); activated amides; activated esters (for example, diethoxyphosphate ester, diphenoxyphosphate ester, p-nitrophenyl ester, 2,4-dinitrophenyl ester, etc.); and activated thioesters (for example, 2-pyridylthiol ester, 2-benzothiazolylthiol ester, etc.). The condensation reaction may be carried out in a solvent. The solvent may be dehydrated or hydrated. Suitable examples of the solvent include N,N-dimethylformamide, dimethylsulfoxide, pyridine, chloroform, dichloromethane, tetrahydrofuran, dioxane, acetonitrile, or an appropriate mixture of the solvents above. The reaction temperature is commonly about −20 to about 50° C., and preferably about −10 to about 30° C. The reaction is usually carried out for about 1 to about 100 hours, preferably about 2 to about 40 hours. The compound [I-1] thus prepared can be purified from the reaction mixture by known isolation/purification means, including, for example, concentration, vacuum concentration, solvent extraction, crystallization, recrystallization, resolubilization, chromatography, etc.

[Process B]

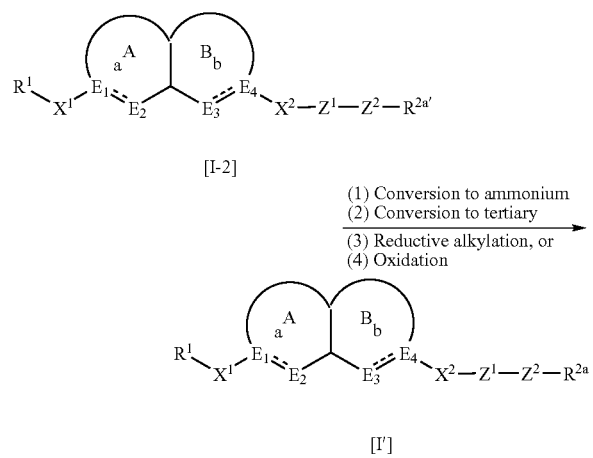

(1) When $R^{2a'}$ of the compound [I-2] is, for example, a tertiary amino group, a quarternary ammonium compound [I'] can be prepared by a reaction of the compound [I-2] and an alkyl halide or an aralkyl halide. Herein, examples of the halogen atom include chlorine, bromine, iodine, etc, and the alkyl halide (for example, lower ($C_{1-6}$) alkyl halides, etc.), or the aralkyl halide (for example, lower ($C_{1-4}$) alkylphenyl halides, etc.) is used in excess, about 1 to 5 moles per 1 mole of the compound [I-2]. The reaction may be carried out in an inert solvent, for example toluene, benzene, xylene, dichloromethane, chloroform, 1,2-dichloroethane, dimethylformamide (DMF), dimethylacetamide, etc., or a mixture of the solvents above. The reaction temperature is in a range of about 10° C. and about 160° C., preferably about 20° C. and about 120° C. The reaction time is about 1 to about 100 hours, preferably about 2 to about 40 hours. The reaction is preferably carried out under an inert gas atmosphere (for example, nitrogen, argon, etc.).

(2) When $R^{2a'}$ of the compound [I-2] is for example a secondary amino group, a ternary ammonium compound [I'] can be prepared by a reaction of the compound [I-2] and an alkyl halide or an aralkyl halide. Herein, examples of the halogen atom include chlorine, bromine, iodine, etc., and the alkyl halide or aralkyl halide is used in excess, usually about 1 to 2 moles per mole of compound [I-2]. The reaction can be carried out more smoothly by addition of about 1 to about 3 moles of a base, such as triethylamine, diisopropylethylamine, pyridine, lithium hydride, sodium hydride, sodium methoxide, sodium ethoxide, sodium carbonate, potassium carbonate, sodium bicarbonate or the like, and by further addition of sodium iodide, potassium iodide, or the like.

The reaction to form the tertiary amino compound may be carried out in an inert solvent such as methanol, ethanol, propanol, isopropanol, n-butanol, tetrahydrofuran, diethylether, dimethoxyethane, 1,4-dioxane, toluene, benzene, xylene, dichloromethane, chloroform, 1,2-dichloroethane, dimethylformamide (DMF), dimethylsulfoxide (DMSO), pyridine, or a mixture of the solvents above.

The reaction is carried out at a temperature of about 0° C. to about 180° C. for about 1 to about 40 hours. The reaction is preferably carried out under an inert gas atmosphere (for example, nitrogen, argon).

(3) When $R^{2a'}$ of the compound [I-2] is for example secondary amino group, a tertiary amino compound [I'] can be prepared by a reaction of the compound [I-2] and an aldehyde compound in the presence of a reductive amino reagent such as sodium triacetoxyborohydride, sodium cyanoborohydride, sodium borohydride. The reaction condition for the reductive alkylation of the amino group is preferably changed according to the reagent used. For example, when sodium triacetoxyborohydride is used, the reaction is preferably conducted in an inert solvent, for example, dichloromethane, chloroform, 1,2-dichloroethane, tetrahydrofuran (THF), diethylether, dioxane, acetonitrile, dimethylformamide (DMF), etc., or a mixture of the solvents above. About 1 to 2 moles of the reagent is used per 1 mole of the compound [I-2]. The reaction is usually carried out at a temperature of about 0° C. to about 80° C. for about 1 to about 40 hours. The reaction is preferably carried out under an inert gas atmosphere (for example, nitrogen, argon, etc.).

(4) When $R^{2a'}$ of the compound [I-2] is, for example, sulfide residue, or a tertiary amino group, or $Z^2$ is, for example, sulfide residue, the compound [I-2] can be oxidized by an oxidizing agent, for example, m-chloroperbenzoic acid, perbenzoic acid, p-nitroperbenzoic acid, magnesium monoperoxyphthalate, peracetic acid, hydrogen peroxide, sodium periodate, potassium periodate, to give a compound [I'] having a sulfinyl, sulfonyl or amine oxide group. The reaction condition for the oxidation reaction is preferably changed according to the oxidizing agent used. For example, when m-chloroperbenzoic acid is used, the reaction may be carried out in an inert solvent, for example, dichloromethane, chloroform, 1,2-dichloroethane, diethylether, tetrahydrofuran, acetone, ethyl acetate, or a mixture of the solvents above. The oxidizing agent is used in excess, usually about 1 to 3 moles per 1 mole of the compound [I-2]. The reaction is usually carried out at a temperature of about −78° C. to about 80° C. (preferably −50 to 25° C.) for about 1 to about 40 hours. When $Z^2$ of compound [I-2] is, for example, sulfide group, the compound [I'-1] having an optically-active sulfinyl group can be prepared according to the methods known in the art, for example, the method described in Ojima, I., ed., Catalytic Asymmetric Synthesis, 2000, Wiley-VCH (New York), or the modification thereof.

[Process C]

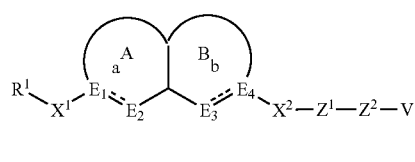

[IV]

(1) Conversion to ammonium
(2) Conversion to phosphonium or
(3) Substitution

-continued

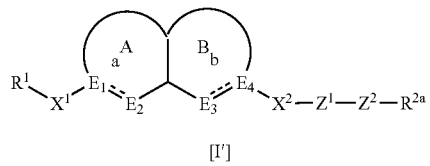

[I']

Group V of the compound [IV] is a halogen atom (chlorine, bromine, iodine, etc.), or a sulfonyloxy group (for example, methanesulfonyloxy, trifluoromethanesulfonyloxy, benzenesulfonyloxy, toluenesulfonyloxy, etc.), and the other symbols are as defined above.

(1) A quarternary ammonium derivative of the compound [I'] can be prepared by a reaction of the compound [IV] and a tertiary amine. The reaction can be carried out in an inert solvent, for example, toluene, benzene, xylene, chloromethane, chloroform, 1,2-dichloromethane, dimethylformamide (DMF), dimethylacetamide, etc., or a mixture of the solvents above. The tertiary amine is used in an amount of about 1 to 5 moles per 1 mole of the compound [IV]. The reaction is carried out at a temperature of about 10° C. to about 120° C. for about 1 to about 40 hours. The reaction is preferably carried out under an inert gas atmosphere (for example, nitrogen, argon, etc.).

(2) A quarternary ammonium derivative of the compound [I'] can be prepared in a reaction of the compound [IV] and a tertiary phosphine. The reaction may be carried out in an inert solvent, for example, toluene, benzene, xylene, dichloromethane, chloroform, 1,2-dichloromethane, acetonitrile, dimethylformamide (DMF), etc., or a mixture of the solvents above. The tertiary phosphine is used in an amount of about 1 to 2 moles per 1 mole of compound [IV]. The reaction is carried out at a temperature of about 20° C. to about 150° C. for about 1 to about 50 hours. The reaction is preferably carried out under an inert gas atmosphere (for example, nitrogen, argon, etc.).

(3) A compound [I'] having a secondary or tertiary amino group, or a thio group can be prepared in a reaction of the compound [IV] and a primary or secondary amine compound or a thiol compound. The primary or secondary amine compound or the thiol compound is usually used in an amount of about 1 to 3 moles per 1 mole of the compound [IV]. The reaction can be carried out more smoothly by adding about 1 to 3 moles of triethylamine, diisopropylethylamine, pyridine, lithium hydride, sodium hydride, sodium methoxide, sodium ethoxide, sodium carbonate, potassium carbonate, or sodium bicarbonate as a base, and by further adding sodium iodide, potassium iodide or the like. The substitution reaction can be carried out in an inert solvent, for example, methanol, ethanol, propanol, isopropanol, n-butanol, tetrahydrofuran, diethylether, dimethoxyethane, 1,4-dioxane, toluene, benzene, xylene, dichloromethane, chloroform, 1,2-dichloroethane, dimethylformamide (DMF), dimethylsulfoxide (DMSO), pyridine, etc., or a mixture of the solvents above. The reaction is carried out at a temperature of about −10° C. to about 180° C. for about 1 to about 40 hours. The reaction is preferably carried out under an inert gas atmosphere (for example, nitrogen, argon, etc.).

[Process D]

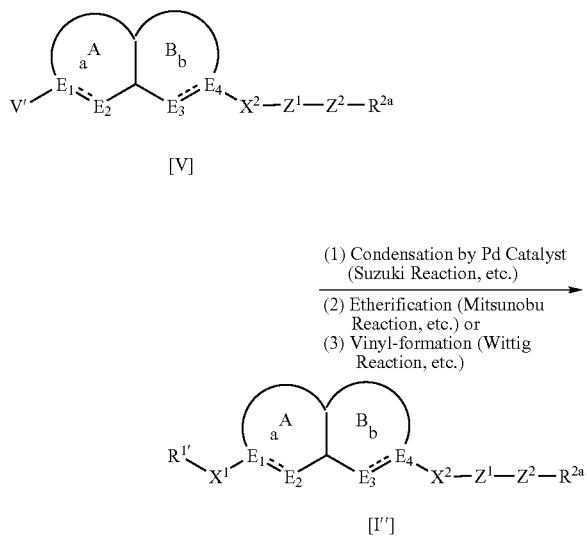

[Formula 38]

(1) Compound [I″] (wherein $X^1$ is a bond; and $R^{1'}$ is a 5- to 6-membered aromatic ring group) can be prepared by subjecting the compound [IV] (wherein V' is a halogen atom (bromine, iodine, etc.), or a sulfonyloxy group (trifluoromethanesulfonyloxy; etc); and the other symbols are as described above), to the Suzuki reaction (i.e., a cross-condensation reaction catalyzed by a palladium catalyst between, for example, an aryl borate, and an aryl halide or an aryloxytrifluoromethanesulfonate). The aryl halide is used in an amount of about 1 to 1.5 moles per 1 mole of the compound [V] to obtain the compound [I″].

Further, compound [I″] having an acetylene bonding, (i.e., —C≡C— as $X^1$ can be prepared in a cross condensation reaction between the compound [V] and a arylacetylene compound in the presence of, for example, a palladium catalyst (dichlorobis-triphenylphosphine palladium, etc.), [K. S. Y. Lau et al., J. Org. Chem., 1981, 46, 2280; J. W. Tilley, S. Zawoisky et al., J. Org. Chem., 1988, 53, 386]. The arylacetylene compound is usually used in an amount of about 1 to 2 moles per 1 mole of the compound [V] to obtain the compound [I″].

(2) Compound [I″] having an ether group can be prepared by subjecting the compound [V] (wherein, V' is a hydroxy group; and the other symbols are the same as described above) to the Mitsunobu reaction (i.e., an etherification reaction using, for example, triphenylphosphine and diethylazodicarboxylate; O. Mitsunobu et al., Synthesis, 1981, 1). The compound [I″] can be obtained by reacting the corresponding alcohol or phenol compound in an amount of about 1 to 3 moles per mole of the compound [V].

The compound [I″] having an ether group can also be prepared by an etherification reaction of the compound [V] with a reactive compound, for example halide (chloride, bromide, iodide, etc.), tosylate, mesylate, etc. The reactive compound is usually used in an amount of about 1 to 2 moles per 1 mole of the compound [V]. The reaction can be carried out more smoothly by adding about 1 to 3 moles of a base, such as triethylamine, diisopropylethylamine, pyridine, lithium hydride, sodium hydride, sodium hydroxide, potassium hydroxide, sodium methoxide, sodium ethoxide, sodium carbonate, potassium carbonate, sodium bicarbonate, etc., and by further addition of sodium iodide or potassium iodide. The reaction may be carried out in an inert solvent such as tetrahydrofuran, diethylether, dimethoxyethane, 1,4-dioxane, toluene, benzene, xylene, dichloromethane, chloroform, 1,2-dichloroethane, dimethylformamide (DMF), dimethylsulfoxide (DMSO), pyridine, etc., or a mixture of the solvent above. The reaction is carried out at a temperature of about −10° C. to 180° C. for about 1 to about 40 hours. The reaction is preferably carried out under an inert gas atmosphere (for example, nitrogen, argon, etc.).

(3) Compound [I″] having an vinyl group can be prepared by subjecting the compound [V] (wherein, V' is a carbonyl group, a phosphonium salt or a phosphonate ester group; and the other symbols are the same as described above) to, for example, the Wittig reaction (A. Maercker, Org.React., 14, 270 (1965)), and or the Wittig-Horner-Emmons reaction (J. Boutagy, R. Thomas, Chem. Rev., 74, 87 (1974)). The corresponding carbonyl, phosphonium salt, or phosphonate ester compound is used in an amount of 1 to 1.5 moles per 1 mole of compound [VI].

[Process E]

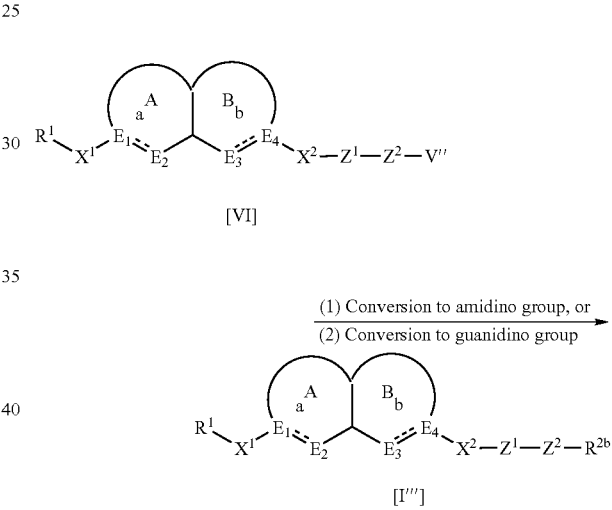

(1) First, the compound [VI] (wherein V″ is cyano group; and the other symbols are as described above) is reacted with a lower alcohol such as methanol, ethanol, propanol, etc., in the presence of an acid such as hydrochloric acid to obtain an imidate compound. The reaction is usually carried out in the presence of excess amount of said alcohol at a temperature of about −10° C. to 50° C. for about 1 hour to about 40 hours. The reaction may be conducted in an inert solvent such as diethylether, 1,4-dioxane, toluene, benzene, xylene, dichloromethane, chloroform, 1,2-dichloroethane, or a mixture of the solvents above.

Subsequently, the imidate compound is subjected to a substitution reaction by a primary or secondary amine compound to give an amidine compound [I‴]. The primary or secondary amine is usually used in an amount of about 1 to 5 moles per 1 mole of the imidate compound. The reaction can be made to proceed more smoothly by addition of about 1 to 3 moles of triethylamine, pyridine, sodium hydroxide, potassium hydroxide, sodium methoxide, sodium ethoxide, sodium carbonate, potassium carbonate, etc., as a demineralization agent. The substitution reaction may be conducted in an inert solvent, for example, methanol, ethanol, propanol, isopropanol, n-butanol, tetrahydrofuran, diethylether, dimethoxyethane, 1,4-dioxane, toluene, benzene, xylene, dichloromethane, chloroform, 1,2-dichloroethane, dimethylformamide (DMF), dimethylsulfoxide (DMSO), pyridine, or a mixture of the solvent above. The reaction is carried out at a temperature of about 0° C. to 150° C. for about 1 to about 50 hours. The reaction is preferably conducted under an inert gas atmosphere (for example, nitrogen, argon, etc.).

(2) A guanidine compound can be prepared in a substitution reaction of the compound [VI] (wherein, V" is amino; and the other symbols are as described above) by a S-alkyl (for example, methyl, ethyl, etc.)-isothiourea compound. The S-alkyl-isothiourea compound is usually used in an amount of about 1 to 2 moles per 1 mole of the compound [VI]. The reaction can be carried out if desired in the presence of about 1 to 3 moles of a demineralization agent such as triethylamine, pyridine, sodium hydroxide, potassium hydroxide, sodium methoxide, sodium ethoxide, sodium carbonate, potassium carbonate, etc., to promote the reaction more smoothly. The substitution reaction may be carried out in an inert solvent, for example, methanol, ethanol, propanol, isopropanol, n-butanol, tetrahydrofuran, diethylether, dimethoxyethane, 1,4-dioxane, toluene, benzene, xylene, dichloromethane, chloroform, 1,2-dichloroethane, dimethylformamide (DMF), dimethylsulfoxide (DMSO), pyridine, etc., or a mixture of the solvent above. The reaction is conducted at a temperature of about 0° C. to 150° C. for about 1 to about 50 hours. The reaction is preferably carried out under an inert gas atmosphere (for example, nitrogen, argon, etc.).

The compound [I] thus prepared can be isolated and purified by known isolation and purification means, for example, concentration, vacuum concentration, solvent extraction, crystallization, resolubilization, chromatography, etc.

The compound [II-1] uses as the starting material may be prepared by any of the known methods (for example, the methods described in Japanese Patent Publication 8-73476; and Japanese Patent Publication 2001-058988) or modification thereof, for example, the method of the scheme I, methods in Reference Examples described below and modified methods thereof.

Reaction Scheme I

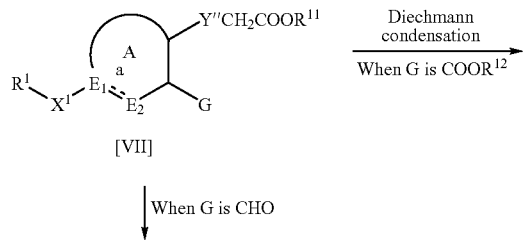

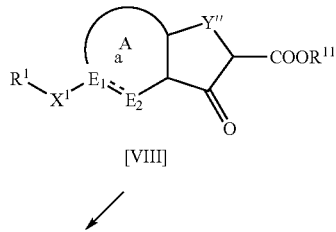

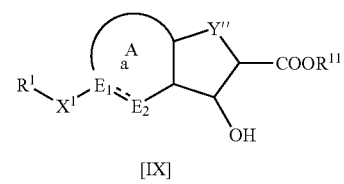

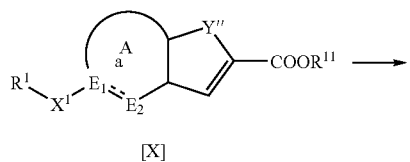

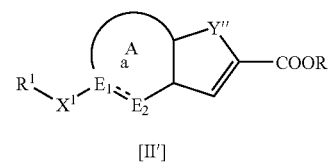

wherein $R^{11}$ and $R^{12}$ are $C_{1-4}$ alkyls; Y" is a bivalent group containing no unsaturated bonds which forms 8- to 10-membered ring B, and the other symbols are as defined above.

Compound [VIII] or compound [IX] can be prepared by subjecting the compound [VII] to the Dieckmann condensation reaction (J. P. Schaefer and J. J. Bloomfield, Org. Reactions, 1967, 15, 1). The compound [VIII] is reduced in a reduction reaction, for example, by catalytic hydrogenation, sodium borohydride, etc., to yield compound [IX]. The compound [IX] is dehydrated by a commonly-practiced method to give compound [X], which is subsequently subjected to an ester hydrolysis reaction to give unsaturated carboxylic acid compound [II'].

Compounds [II] which do not have a carboxyl group as $X^{a2}$ in the compound [II] used as the starting material (e.g. $X^{a2}$ is chlorosulfonyl, hydroxymethyl, halo(chloro or bromo) methyl, formyl, acetamide, etc.), can be prepared according to the methods shown in reaction scheme II, methods of Reference Examples described below, or modification thereof.

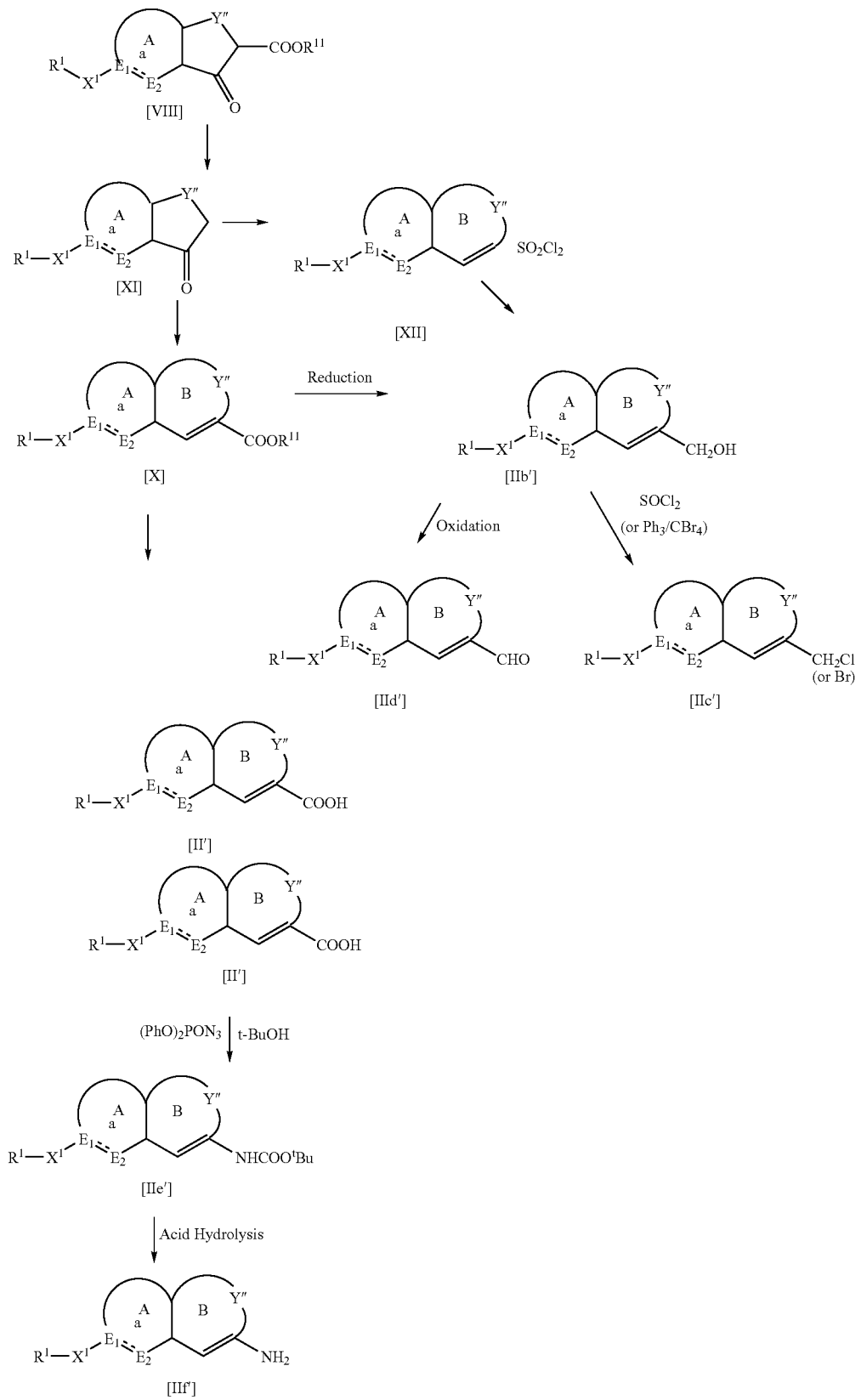

wherein each symbol is as defined above.

The chlorosulfonyl compound [IIa'] can be prepared from the compound [VIII] by the steps of; ester hydrolysis of the compound [VIII] by a commonly-practiced method; decarboxylation, and subsequent reduction of ketone [XI] formed by decarboxylation, by a commonly used method (reduction by sodium borohydride or catalytic hydrogenation, etc.); subsequent dehydration to give the compound [XII]; and subsequent reaction with sulfuryl chloride.

Hydroxymethyl compound [IIb'] can be prepared from the ester compound [X] in a reduction reaction by a commonly-used method (reduction by sodium borohydride, lithium aluminum hydride, diisobutylaluminum hydride (DIBAL), etc,). The resulting hydroxymethyl compound [IIb'] may be subjected to a chlorination reaction by thionylchloride and the like, or to a bromination reaction by triphenylphosphine/tetrachlorocarbon, to yield halomethyl compound [IIc'].

The hydroxymethyl compound [IIb'] may be oxidized in an oxidation reaction by activated manganese dioxide and the like to yield formyl compound [IId'].

Amine compound [IIf'] can be prepared from the carboxylic acid compound [II'] by the steps of; a transfer reaction by diphenylphosphoramide (DPPA)/t-butanol; and subsequent acid hydrolysis of the resulting urethane compound [IIe'].

By subjecting each of the compound thus obtained, [IIa'], [IIb'], [IIc'], [IIc'], [IIe'], or [IIf'], and the compound [III] to the various reactions described above, including amide formation, tertiary amino formation, reductive amination, vinyl-formation, etherification, alkylation (aralkylation), etc., the compound [I] which do not have a carbonylamide group as $X^2$ can be obtained.

The compound [III-1] can also be prepared by known methods (for example, the method described in Japanese Patent Publication 8-73476, etc.) or the modification thereof, for example, by the method shown in reaction scheme III, and methods of Reference Examples described below, or the modification thereof.

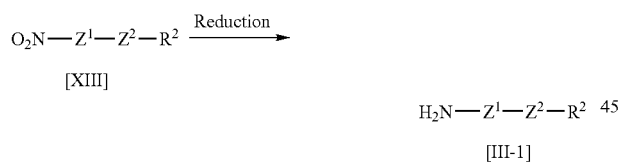

Reaction Scheme III wherein, each symbol is as defined above.

Reduction of the compound [XIII] may be carried out by methods known in the art. These methods include, for example, reduction by metal, metal hydride, metal hydrogen complex compound, diborane and substituted borane, catalytic hydrogenation, etc. That is, the reaction is carried out by reducing the compound [XIII] by a reducing agent. Suitable examples of the reducing agent include; metals such as reduced iron, zinc powder, etc.; metal hydrogen complex compounds such as alkali metal borohydrides (for example, sodium borohydride, lithium borohydride, etc.), aluminum lithium hydride, etc.; metal hydrides such as sodium hydride, etc.; organic tin compounds (triphenyltin hydride, etc.); metals and metal salts such as nickel compounds, zinc compounds, etc.; catalytic reducing agents using hydrogen and transition metal catalysts such as palladium, platinum, rhodium, etc.; diborane, etc. The catalytic reduction using hydrogen and transition a metal such as palladium, platinum, rhodium, etc., and the reduction by a metal such as reduced iron are more preferably employed. The reaction may be carried out in an organic solvent which does not interfere with the reaction.

According to a reducing agent to be used, a suitable solvent is selected from solvents including benzene, toluene, xylene, chloroform, carbon tetrachloride, dichloromethane, 1,2-dichloroethane, 1,1,2,2-tetrachloroethane, diethylether, tetrahydrofuran, dioxane, methanol, ethanol, propanol, isopropanol, 2-methoxyethanol, N,N-dimethylformamide, acetic acid, or a mixture of the solvents above. The reaction is usually carried out at a temperature of about −20° C. to about 150° C., preferably about 0° C. to about 100° C., for about 1 to about 24 hours.

The compound [III-1] thus obtained may be isolated and purified by any of the known methods such as concentration, vacuum concentration, solvent extraction, crystallization, recrystallization, resolubilization, chromatography, etc.

The compound of the formula [I] of the present invention or the salt thereof including the above compound [I-1], compound [I-2], compound [I'], compound [I"] and compound [II'''] (hereinafter, the compound of the formula [I] includes the compound of formula [I] and a salt thereof) may be administered orally or parenterally alone or by formulating it together with a pharmaceutically acceptable carrier in the form of a solid preparation such as tablet, capsule, granule, etc. or powder, or a liquid preparation such as syrup, injectable solution, etc.

Examples of a dosage form for parenteral administration include injectable solution, infusion, suppository, vaginal suppository, etc., and a vaginal suppository is especially effective for prevention of HIV infection.

As the pharmaceutically acceptable carriers, a variety of organic or inorganic carriers commonly used as pharmaceutical materials may be used, and such carriers include, for solid preparations, diluents, lubricants, binders, and disintegrants, and for liquid preparations, solvents, solubilizing agents, suspending agents, isotonic agents, buffer agents, soothing agents, etc. Other pharmaceutical additives such as antiseptic substances, antioxidants, coloring agents, and sweeteners may also be added if necessary. Suitable examples of the diluent include lactose, sucrose, D-mannitol, starch, crystalline cellulose, light silica anhydrate, etc. Suitable examples of the lubricant include magnesium stearate, calcium stearate, talc, colloidal silica, etc. Suitable examples of the binder include crystalline cellulose, sucrose, D-mannitol, dextrin, hydroxypropylcellulose, hydroxypropylmethylcellulose, polyvinylpyrrolidone, etc. Suitable examples of the disintegrant include starch, carboxymethylcellulose, calcium carboxymethylcellulose, sodium croscarmellose, sodium carboxymethylstarch, etc. Suitable examples of the solvent include injectable water, alcohol, propylene glycol, macrogol, sesame oil, corn oil, etc. Suitable examples of the solubilizing agent include polyethylene glycol, propylene glycol, D-mannitol, benzylbenzoate, ethanol, trisaminomethane, cholesterol, triethanolamine, sodium carbonate, sodium citrate, etc. Suitable examples of the suspending agent include surfactants such as stearyltriethanolamine, sodium laurylsulfate, laurylaminopropionic acid, lecithin, benzalkonium chloride, benzethonium chloride, glycerin monostearate, etc.; and hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose, etc. Suitable examples of the isotonic agent include sodium chloride, glycerin, D-mannose, etc. Suitable examples of the buffer agent include buffer solutions of salts, such as phosphate, acetates, carbonates, and citrates. Suitable examples of the soothing agent include benzyl alcohol, etc. Suitable examples of the antiseptic substance include para-oxybenzoic acid esters, chlorobutanol, benzyl alcohol, phenethyl alcohol, dehydroacetic acid, sorbic acid, etc. Suitable examples of the antioxidant include sulfite salts, ascorbic acid, etc.

The compound of the formula [I] of the present invention has excellent CCR antagonistic action, in particular, CCR5 and/or CCR2 antagonistic action, especially, a strong CCR5 antagonistic action, and may be used, for example, for prevention and treatment of a variety of human HIV infectious diseases, for example, AIDS, and other various diseases. The compound of the formula [I] of the present invention has low toxicity and can be used safely.

For example, a pharmaceutical composition containing the compound of the formula [I] can be used as a CCR5 antagonist, for example, as a preventive and therapeutic medicine for AIDS and for suppression on disease progression of AIDS. Further, a pharmaceutical composition containing the compound of the formula [I] can be used as a preventive and therapeutic medicine for a variety of disorders, that is, as a preventive and therapeutic drug for graft versus host disease and/or rejection, or as a preventive and therapeutic drug for chronic rheumatoid arthritis, autoimmune disease, allergic diseases, ischemic brain cell disorder, cardiac infarction, chronic nephritis, arteriosclerosis and so on.

Examples of the diseases for which the preventive and therapeutic medicine of the present invention is used including, graft rejection (posttransplantational rejection, posttransplantational polycythaemia, hypertension, organ disorder, vascular hypertrophy, graft versus host disease, etc.,); arthritic osteopathy diseases such as periostitis, meningitis, etc., (chronic rheumatoid arthritis, osteoarthritis, rheumatoid myelitis, osteoporosis, abnormal growth of cell, fracture, refracture, osteomalacia, osseous Behchet's disease, rigorous myelitis, articular tissue destruction by gonarthrosis and similar diseases thereto, etc.); autoimmune diseases (collagen disease, SLE (systemic lupus erythematosus), pachyderms, polyarteritis, myasthenia gravis, multiple sclerosis, etc.); allergic diseases (allergic nasal catarrh, conjunctivitis, gastrointestinal allergy, pollinosis, anaphylaxis, atopic dermatitis, bronchial asthma, etc.); inflammatory enteropathy diseases (ulcerative colitis, Crohn disease, gastritis, gastric ulcer, gastric cancer, postgastrotomy disorder, dyspepsia, esophageal ulcer, pancreatitis, polyp of the colon, cholelithiasis, hemorrhoids, peptic ulcer, situational ileitis, etc.); inflammatory diseases (retinopathy, postoperative and posttraumatic inflammation, remission of puffiness, pharyngitis, cystitis, meningitides, inflammatory ophthalmic diseases, etc.); respiratory diseases (cold syndrome, pneumonia, asthma, pulmonary hypertension, pulmonary thrombi/pulmonary obliteration, pulmonary sarcoidosis, pulmonary tuberculosis, interstitial pneumonia, silicosis, adult tachypnea syndrome, chronic obliterative pulmonary diseases, etc.); infectious diseases (virus infection diseases by cytomegalovirus, influenzavirus, herpesvirus and the like, rickettsia infection diseases, bacterial infectious diseases, sexually transmitted diseases, carinii pneumonia, helicobacter pylori infectious disease, systemic fungal infection disease, tuberculosis, invasive staphylococcal infection disease, acute viral encephalitis, acute bacteria meningitides, AIDS encephalopathia, septicemia, sepsis, sepsis gravis, septic shock, endotoxin shock, toxin shock syndromes, et.); cancers and accompanying cachexia, cancer metastases (bladder cancer, breast cancer, cervical cancer, ovarian cancer, chronic lymphoblastic leukemia, chronic myeloid leukemia, colon cancer, rectal cancer, colic cancer, multiple myeloma, malignant myeloma, prostatic cancer, lung cancer, gastric cancer, Hodgkin disease, malignant melanoma, malignant lymphoma, etc.); non-Hodgkin's lymphoma; non-small cell lung cancer; malignant melanoma, neurodegenerative diseases (Alzheimer disease, Parkinson disease, amyotrophic lateral sclerosis (ALS), Huntington chorea, diabetic neural disorder, Creutzfeldt-Jakob disease, etc.); mental diseases (depression, epilepsy, alcoholism etc.); schizophrenia; venous dysfunction; central nerve disorders (disorder and aftereffect/complication from intracerebral breeding, brain infarction and the like, cephalic trauma, spine damage, brain edema, sensory function disorder, sensory function disorder, autonomic nervous function disorder, autonomic nervous function disorder, etc.); centralis damage (cephalic trauma, spiral damage, whiplash injury, etc.); vascular dementia (multiinfarct dementia, Binswanger's disease, etc.); cerebro-vascular accident (asymptomatic cerebro-vascular accident, transient cerebral ischemic attack, stroke, multiinfarct dementia, hypertensive encephalopathia, etc.); recurrence and aftereffect of cerebro-vascular accident (neural sympton, mental symptom, subjective sympton, operational disorder in daily life, etc.); multiinfarct dementia; post-cerebrovascular obliteration central hypofunction; disorder or abnormality of cerebral circulation and autoregulation of renal; blood brain barrier damage; anxiety symptom; acute coronary artery syndromes including unstable angina, etc.; anxious mental state; amnesia; prosopalgia; otolaryngological disease (Menuel syndrome, buzzing, gustation disorder, dizziness, dysequilibrium, dysphagia, etc.); migraine; chronic pain; dermatoses (keloid, angioma, psoriasis, etc.); arteriosclerosis obliterans; thromboangiitis obliterans; peripheral obstruction; postischemic reperfusion injury; Raynaud disease; Buerger disease; myocarditis; cardiac ischemia; cardiac infarction; progress of cardiac failure after cardiac infarction; cardiomyopathy; cardiac hypertrophy; acute cardiac failure and chronic (including estatic) cardiac failure; angina pectoris; arrhythmia; tachycardia; circadian rhythm disorder of blood pressure; abnormality in characteristic of blood haemocyte components (enhancement in platelet aggregation, abnormality of erythrocyte deformability, enhancement in leucocyte adhesiveness, increase in blood viscosity, polycythaemia, vascular peliosis, autoimmune hemolytic anemia, disseminated intravascular coagulation syndrome, multiple myelopathy, etc.); arteriosclerosis including atherosclerosis (aneurysm, coronary arteriosclerosis, cerebro arteriosclerosis, peripheral arteriosclerosis, etc.); vascular reocclusion and restenosis after bypass operation; vascular hyperplasy or occlusion and organ malfunction after intervention (transdermal coronary arterioplasty, stent detention, coronary autoscope, vascular ultrasound therapy, coronary injection thrombolytic therapy, etc.); production and enhancement of vasoactive materials and thrombi inducing materials (endothelin, thromboxan A2, etc.); arterialization (including abnormal vasculogenesis in abnormal capillary vasoganglion formation of pultaceous arteriosclerosis outer membrane); thrombosis; fat storage disease acceleration; ophthalmic diseases (glaucoma, hyper-ocular-tension disease, etc.); hypertension; hypertensive buzzing; dialysis hypotension; endothelial cell and organ disorders; endocrinopathy (Addison disease, Cushing syndrome, melanocytoma, primary aldosteronism, etc.); nephritis; renal diseases (nephritis, glomerulonephritis, glomerulosclerosis, renal failure, thrombotic microangiopathy, dialysis complications, organ disorders including nephropathia by radiation, diabetic nephropathia, etc.); diabetic diseases (insulin-dependent diabetes, diabetic complications, diabetic retinopathy, diabetic microangiopathy, diabetic neuropathy, etc.); glucose torlerance abnormality; hepatic diseases (hepatitis (including chronic hepatitis), cirrhosis, etc.); interstitial hepatic diseases; chronic pancreatitis; portal blood pressure enhancement; obesity; male sterility; gynecologic diseases (climacteric disorder, gestational toxicosis, endometriosis, hysteromyoma, ovarian disease, mammary disease, etc.); dropsy; chronic fatigue syndromes; prostatomegaly; Behcet's disease; Hodgkin disease; lacunar infarction; consciousness disorder; psoriasis; diseases due to environmental or occupational factors (radiational disorder, disorders by ultraviolet ray/infrared ray/laser ray, altitude sickness, etc.); and intermittent claudication.

A pharmaceutical composition containing a compound of the formula {I}, although they are different by a kind of the object disease, may be used in combination with other medicines. Examples of the other medicines include, HDL-increasing drugs [squalene synthase inhibitor, CETP inhibitor, LPL activator, etc.]; preventive and therapeutic drug for HIV infectious disease [nucleic acid reverse transcriptase inhibitors such as zidovudine, didanosine, zalcitabine, lamivudine, stavudine, abacavir, adefovir, adefovir dipivoxil, fozivudine tidoxil, etc., non-nucleic acid reverse transcriptase inhibitors such as nevirapine, delavirdine, efavirenz, loviride, immuncal, oltipraz, etc., protease inhibitors such as saquinavir, ritonavir, indinavir, nelfinavir, amprenavir, palinavir, lasinavir, lopinavir, etc.]; HMG-CoA reductase inhibitors [cerivastatin, atorvastatin, pravastatin, simvastatin, Itavastatin, lovastatin, lvastatin, (+)-3R,5S-7-[4-[4-fluorophenyl]-6-isopropyl-2-(N-methyl-N-methane-sulfonylamino]pyrimidin-5-yl]-3,5-dihydroxy-6(E)-peptenoic acid, etc.]; atopic dermatitis drugs [sodium cromoglicate, etc.]; allergic nasal catarrh drugs [sodium cromoglicate, chlorpheniramine maleate, alimemazine tartrate, clemastine fumarate, homochlorcyclizine hydrochloride, terfenadine, mequitazine, etc.]; imipenem•cilastatin sodium; endotoxin antagonists or antibodies; oxidosqualene-lanosterol cyclase [e.g., decalin derivatives, azadecalin derivatives and indan derivatives]; calcium antagonists (diltiazem, etc.); glycerol; cholinesterase inhibitors (e.g., Aricept (donepezil), etc.); compounds suppressing cholesterol uptake [e.g., sitosterol, neomycin, etc.]; compounds inhibiting cholesterol biosyntheses [e.g., HMG-CoA reductase inhibitors such as lovastatin, simvastatin, pravastatin, etc.]; cyclooxygenase depressants [Cox-I, Cox-II depressants such as celecoxib, rofecoxib, salicylic acid derivatives such as aspirin and the like, diclofenac, indometacin, loxoprofen, etc.]; sigal transduction inhibitors, squalene epoxidase inhibitors [e.g., NB-598 and the analogous compounds, etc.]; steroidal drugs [dexamethasone, hexestrol, methimazole, betamethasone, triamcinolone, triamcinolone acetonide, fluocinonide, fluocinolone acetonide, prednisolone, methylprednisolone, cortisone acetate, hydrocortisone, fluorometholone, beclomethasone dipropionate, estriol, etc.]; diacerin; nicotinic acid and derivatives and analogues thereof [e.g., acipimox and probucol]; nicergoline, nephrotic syndrome drugs: prednisolone (Predonine), prednisolone sodium succinate (Predonine), methylprednisolone sodium succinate (Solu medrol), betamethasone (Rinderon), dipyridamole (Persantine), dilazep dihydrochloride (Comelian), ticlopidine, clopidogrel, antiplatelet drugs and anticoagulants such as FXa inhibitors, etc.; barbital-based anticonulsants or anaesthetic drugs (phenobarbital, mephobarbital, metharbital, etc.); Parkinson disease drugs (e.g., L-DOPA, etc.); histamine receptor blockers (cimetidine, famotidine, etc.); hidantoin-based anticonvulsant drugs (phenytoin, mephenytoin, ethotoin, etc.); hydroxicam, fibrates [e.g., clofibrate, benzafibrate, gemfibrozil, etc.]; prostaglandins; megestrol acetate; gastric and intraduodenal ulcer drugs: antacids [e.g., histamine H2 antagonists (cimetidine, etc.), proton pump inhibitors (lansoprazole etc.,), etc.]; inflammatory mediator depressants; coronary vasodilators: nifedipine, diltiazem, nicorandil, nitrite drugs, etc.; infectious disease drugs: [e.g., antibiotic formulations (cefotiam hydrochloride, cefozopran hydrochloride, ampicillin, etc.), chemotherapeutic agents (sulfa drugs, synthetic antibacterial agents, antiviral agents, etc.), biologic formulations (vaccines, blood preparations including immunoglobulins) etc.] etc.; hepatic disease drugs: glycyrrhizin formulations [e.g., Stronger Minophagen, etc.]; liver hydrolysate; SH compounds [e.g., glutathione, etc.]; special amino acid formulations [e.g., aminoleban, etc.]; phospholipids [e.g., polyene-phosphatidyl choline, etc.]; vitamins [e.g., vitamin $B_1$, $B_2$, $B_6$, $B_{12}$, C, etc.]; adrenocortical hormones [e.g., dexamethasone, betamethasone, etc.]; interferons [e.g., interferon α, β, etc.]; hepatic encephalopathy drugs [e.g., lactulose, etc.]; hemostats used in cases of rapture of esophageal or gastricvenous cancer [e.g., vasopressin, somatostatin, etc] etc.; arthritis drugs; muscle relaxants [pridinol, tubocurarine, pancuronium, tolperisone hydrochloride, chlorphenesin carbamate, baclofen, chlormezanone, mephenesin, chlorzoxazone, eperisone, tizanidine, etc.]; vasodilators [oxyfedrine, diltiazem, tolazoline, hexobendine, bamethan, clonidine, methyldopa, guanabenz, etc.]; vasoconstrictors [dopamine, dobutamine denopamine, etc.]; antiplatelet drugs (ozagrel, etc.); thrombogenesis preventive and therapeutic drugs: anticoagulant drugs [e.g., heparin sodium, heparin calcium, warfarin calcium (Warfarin), Xa inhibitor]; thrombolytic drugs [e.g., tPA, urokinase]; antiplatelet drugs [e.g., aspirin, sulfinpyrazone (Anturan), dipyridamole (Persantine), ticlopidine (Panaldine), cilostazol (Pletaal), GPIIb/IIIa antagonist (ReoPro)]; antidepressants [imipramine, clomipramine, noxiptiline, feneridine, amitriptyline hydrochloride, nortriptyline hydrochloride, amoxapine, mianserin hydrochloride, maprotiline hydrochloride, sulpiride, fluvoxamine maleate, trazodone hydrochloride, etc.]; antiepileptic drugs [gavapentin, phenytoin, ethosuximide, acetazolamide, chlordiazepoxide, trimethadione, carbamazepine, phenobarbital, primidone, sultiame, sodium valproate, clonazepam, diazepam, nitrazepam, etc.]; antiallergic drugs [diphenhydramine, chlorpheniramine, tripelennamine, metodiramine, clemizole, diphenylpyraline, methoxyphenamine, sodium cromoglicate, tranilast, repininast, amlexanox, ibudilast, ketotifen, terfenadine, mequitazine, azlastin, epinastine, ozagrel hydrochloride, pranlukast hydrate, seratrodast, fexofenadine, ebastine, bucillamine, oxatomide, Stronger Neo-Minophagen C, tranexamic acid, ketotifen fumarate, etc.]; anticholinergic drugs (e.g., ipratropium bromide, flutropium bromide, oxitropium bromide, etc.); anti-Parkinson drugs (dopamine, levodopa, etc.); antirheumatic drugs; anti-inflammatory drugs (e.g., aspirin, acetaminophen, diclofenac sodium, ibuprofen, indometacin, loxoprofen sodium, dexamethasone, etc.); anticoagulant and antiplatelet drugs [sodium citrate, activated protein C, tissue factor pathway inhibitors, antithrombin III, dalteparin sodium, argatroban, gabexate, ozagrel sodium, ethyl icosapentate, beraprost sodium, alprostadil, pentoxifylline, tisokinase, streptokinase, heparin, etc.]; anticoagulant therapeutic drugs [dipyridamole (Persantine), dilazep hydrochloride (Comelian), ticlopidine, clopidogrel, Xa inhibitors]; antibacterial drugs [(1) sulfa drugs [sulfamethizole, sulfisoxazole, sulfamonomethoxine, sulfamethizole, salazosulfapyridine, sulfadiazine silver, etc.], (2) quinolone-based antibacterial drugs [nalidixic acid, pipemidic acid trihydrate, enoxacin, norfloxacin, ofloxacin, tosufloxacin tosilate, ciprofloxacin hydrochloride, lomefloxacin hydrochloride, sparfloxacin, fleroxacin, etc.], (3) antituberculous drugs [isoniazid, ethambutol (ethambutol hydrochloric acid), p-aminosalicyclic acid (calcium p-aminosalicylate), pyrazinamide, ethionamide, prothionamide, rifampicin, streptomycin sulfate, kanamycin sulfate, cycloserine, etc.], (4) anti-acid fast bacteria drugs [diaphenylsulfone, rifampicin, etc.], (5) antiviral drugs [idoxuridine, aciclovir, vidarabine, ganciclovir, etc.], (6) anti-HIV drugs [zidovudine, didanosine, zalcitabine, indinavir sulfate ethanolate, ritonavir, etc.], (7) spirocheticide, (8) antibiotics [tetracycline hydrochloride, ampicillin, piperacillin, gentamicin, dibekacin, kanendomycin, rokitamycin, tobramycin, amikacin, fradiomycin, sisomicin, tetracycline, oxytetracycline, rolitetracycline, doxycycline, ampicillin, piperacillin, ticarcillin, cephalothin, cephapirin, cephaloridine, cefaclor, cefalexin, cefroxadine, cefadroxil, cefamandole, cefotiam, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmetazole, cefminox, cefoxitin, cefbuperazone, latamoxef, flomoxef, cefazolin, cefotaxime, cefoperazone, ceftizoxime, moxalactam, thienamycin, sufazecin, aztreonam or salts thereof, griseofulvin, lankacidins [J. Antibiotics, 38, 877-885 (1985)], etc., cefixime, levofloxacin]; antithrombotic drugs (argatroban, etc.); antiprotozoal drugs [metronidazole, tinidazole, diethylcarbamazine citrate, quinine hydrochloride, quinine sulfate, etc.]; antitumor drugs [6-O-(N-chloroacetylcarbamoyl]fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, busulfan, thiotepa, procarbazine hydrochloride, cisplatin, azathiopurine, mercaptopurine, tegafur, carmofur, cytarabine, methyltestosterone, testosterone propionate, testosterone enanthate, mepitiostane, fosfestrol, chlormadinone acetate, leuproline acetate, buserelin acetate, etc.]; antifungal drugs [(1) polyethylene-based antibiotics (e.g., amphotericin B, nystatin, trichomycin), (2) griseofulvin, pyrrolnitrin, etc., (3) cytosine metabolism antagonists (e.g., flucytosine), (4) imidazole derivatives (e.g., econazole, clotrimazole, miconazole nitrate, bifonazole, croconazole), (5) triazole derivatives (e.g., fluconazole, itoraconazole, azole compounds [2-[(1R,2R)-2-[2,4-difluorophenyl)-2-hydroxy-1-methyl-3-(1H-1,2,4-triazole-1-yl)propyl]-4-[4-(2,2,3,3-tetrafluoropropoxy)phenyl-3-(2H,4H)-1,2,4-triazolone], (6) thiocarbamate derivatives [e.g., trinaphthol], (7) echinocandin-based derivatives (e.g., caspofungin, FK-463, V-echinocandin), etc.]; antipsychotic drugs [chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine, etc.]; antiulcer drugs [metoclopramide, histidine hydrochloride, lansoprazole, metoclopramide, pirenzepine, cimetidine, ranitidine, famotidine, urogastron, oxethazaine, proglumide, omeprazole, sucralfate, sulpiride, cetraxate, gefarnate, aldioxa, teprenone, prostaglandins etc.]; anti diabetic drugs [e.g., pioglitazone, nateglinide, voglibose, acarbose, etc.]; antiobese drugs [mazindol, etc.]; antirheumatic drugs; antianxiety drugs [diazepam, lorazepam, oxazepam, chlordiazepoxide, medazepam, oxazolam, cloxazolam, clotiazepam, bromazepam, etizolam, fludiazepam, hydroxyzine, etc.]; antiarrhythmic drugs [disopyramide, lidocaine, quinidine sulfate, flecainide acetate, mexiletine hydrochloride, amiodarone hydrochloride, and β blockers, Ca antagonists, etc.; antiasthmatic drugs [isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranlukast hydrate, seratrodast, dexamethasone, prednisolone, hydrocortisone, beclomethasone propionate, fluticasone propionate, beclomethasone propionate, procaterol, etc.]; anti-hypothyroidism drugs [dried thyroid (Thyreoid), levothyroxine sodium (Tyradin S), liothyronine sodium (thyronine, tyronamine)]; nephrotic syndrome drugs [prednisolone (Predonine), prednisolone sodium succinate (Predonine), methylprednisolone sodium succinate (Solu medrol), betamethasone (Rinderon)]; antihypertensive drugs {(1) sympathetic nerve depressants [α2 stimulating drugs (e.g., clonidine, guanabenz, guanfacine, methyldopa, etc.), ganglionic blockers (e.g., hexamethonium, trimethaphan, etc.), presynaptic blockers (e.g., Alusa-Oxylone, dimethylamino reseru pinate, rescinnamine, reserpine syrosingopine, etc.), neuronal blockers (e.g., betanidine, guanethidine, etc.), α1 blockers (e.g., bunazosin, doxazosin, prazosin, terazosin, urapidil, etc.), β blockers (e.g., propranolol, nadolol, timolol, nipladilol, bunitrolol, indenolol, penbutolol, carteolol, carvedilol, pindolol, acebutolol, atenolol, bisoprolol, metoprolol, labetalol, amosulalol, arotinolol, etc.), etc], (2) vasodilators [calcium channel antagonists (e.g., manidipine, nicardipine, nilvadipine, nisoldipine, nitrendipine, benidipine, amlodipine, aranidipine, etc.), phthalazine derivatives (e.g., budralazine, cadralazine, ecarazine, hydralazine, todralazine, etc.), etc.], (3) ACE inhibitors [alacepril, captopril, cilazapril, delapril, enalapril, lisinopril, temocapril, trandolapril, quinapril, imidapril, benazepril, perindopril, etc.)], (4) AII antagonists [losartan, candesartan, valsartan, telmisartan, irbesartan, forasartan, etc.], (5) diuretic drugs [e.g., diuretic drugs described above, etc.]}; antihypertensive drugs {diuretic drugs [e.g., furosemide (Lasix), bumetanide (Lunetoron), azosemide (DIART)], antihypertensive drugs [e.g., ACE inhibitors, (enalapril maleate (RENIVACE) etc.,) and Ca antagonists (manidipine, amlodipine. etc.), α or β receptor blockers, etc.], antihyperlipemia drugs [HMG-COA reductase inhibitors (e.g., lvastatin, cerivastatin, atorvastatin, etc.), fibrates [e.g., simfibrate, aluminum clofibrate, clinofibrate, fenofibrate, etc.], anion exchange resin [e.g., cholestyramine, etc.], nicotinic acid drugs [e.g., nicomol, niceritrol, tocopherol nicotinate etc.], polyvalent unsaturated fatty acid derivatives [e.g., ethyl icosapentaenoic acid, polyene phosphatidyl choline, melinamide, etc.], phytosterols [e.g., .gamma.-oryzanol, soy sterol, etc.], elastase, sodium dextran sulfate, squalene synthase inhibitors, CETP inhibitors, 2-chloro-3-[4-(2-methyl-2-phenylpropoxy)phenyl] ethyl propionate [Chem. Pharm. Bull., 38, 2792-2796 (1990)], etc.}; osseous disease drugs {calcium formulations [e.g., calcium carbonate, etc.], calcitonin formulations, activated vitamin $D_3$ formulations [e.g., alfacalcidol (Alfarol etc.), calcitriol (ROCALTROL), etc.], sex hormones [e.g., estrogen, estradiol, etc.], hormone formulations [e.g., conjugated estrogen (Premarin), etc.], ipriflavone formulations [osten, etc.], vitamin $K_2$, vitamin $K_2$ formulations [e.g., menatetrenone (Glakay), etc.], bis-phosphonate-based formulations [etidronate, etc.], prostaglandin E2, fluorine compounds [e.g., sodium fluoride, etc.], bone morphogenetic protein (BMP), fibroblast growth factor (FGF), platelet derived growth factor (PDGF), transforming growth factor (TGF-β), insulin-like growth factor-1 and -2 (IGF-1,-2), parathyroid adrenal hormones (PTH), and compounds described in EP-A1-376197, EP-A1-460488, and EP-A1-719782 [e.g., (2R,4S)-(−)-N-[4-(diethoxyphosphorylmethyl)phenyl]-1,2,4,5-tetrahydro-4-methyl-7,8-methylenedioxy-5-oxo-3-bemzothiepin-2-carboxamide, etc.], etc.}, lipid-soluble vitamin drugs [(1) vitamin A family (vitamin $A_1$, vitamin $A_2$, and retinol palmitate), (2) vitamin D family (vitamin $D_1$, $D_2$, $D_3$, $D_4$ and $D_5$), (3) vitamin E family (α-tocopherol, β-tocopherol, γ-tocopherol, δ-tocopherol, dl-α-tocopherol nicotinate.), (4) vitamin K family (vitamin $K_1$, $K_2$, $K_3$ and $K_4$), (5) folic acids (vitamin M), etc.]; vitamin derivatives [various vitamin derivatives, e.g., vitamin $D_3$ derivatives such as 5,6-trans-cholecalciferol, 2,5-hydroxycholecalciferol, 1-α-hydroxycholecalciferol, vitamin $D_2$ derivatives such as 5,6-trans-ergocalciferol, and the like]; disease-modifying anti-rheumatic and immunosuppressive drugs [e.g., methotrexate, leflunomide, prograf, sulfasalazine, D-penicillamine, the oral gold salts]; hypertensors [dopamine, dobutamine, denopamine, digitoxin, digoxin, methyldigoxin, lanatoside C, G-strophanthin, etc.]; myocardial protective drugs: heart ATP-K opener (Na—H exchange inhibitors, endothelin antagonists, urotensin antagonist, etc.), cardiac failure drugs [cardiac stimulants (e.g., digitoxin, digoxin, methyldigoxin, lanatoside C, proscillaridin, etc.), α, β stimulating drugs (e.g., epinephrine, norepinephrine, isoproterenol, dopamine, docarpamine, dobutamine, denopamine, etc.), phosphodiesterase inhibitors (e.g., amrinone, milrinone, olprinone hydrochloride, etc.), calcium channel sensibility improvers (e.g., pimobendan, etc.), nitrate drugs (e.g., nitroglycerin, isosorbide nitrate, etc.), ACE inhibitors (e.g., the ACE inhibitor described above, etc.), diuretic drugs (e.g., diuretic drugs described above, etc.), calperitide, ubidecarenone, vesnarinone, aminophylline, etc.]; neurotrophic factors; renal failure and nephropathia drugs; biologic formulations [e.g., monoclonal antibodies (e.g., anti-TNF-α antibodies, anti-IL-12 antibodies, anti-IL-6 antibodies, anti-ICAM-I antibodies, anti-CD4 antibodies, etc.), soluble receptors (e.g., soluble TNF-α receptors, etc.), protein ligands (IL-I receptor antagonist, etc.)]; bile acid binding resins [e.g., cholestyramine, cholestipol, etc.]; biliary tract disease drugs:cholepoietic drugs [e.g., dehydrocholic acid, etc.], cholekinetic drugs [e.g., magnesium sulfate, etc.], etc.; central nervous system agonists: antianxiety drugs, hypnotic and sedative drugs, anesthetic drugs, spasmolytic drugs, autonomic drugs, anti-Parkinson drugs and other psychoneuro drugs, etc.; antitiussive and expectorants [ephedrine hydrochloride, noscapine hydrochloride, codeine phosphate, dihydrocodeine phosphate, isoproterenol hydrochloride, ephedrine hydrochloride, methylephedrine hydrochloride, noscapin hydrochloride, arocloramide, chlfedanol, picoperidamine, cloperastine, protoxlol, isoproterenol, salbutamol, terbutaline, oxymetebanol, morphine hydrochloride, dextromethorphan hydrobromide, oxycodone hydrochloride, dimemorfan phosphate, tipepidine hibenzate, pentoxyverine citrate, clofedanol hydrochloride, benzonatate, guaifenesin, bromhexine hydrochloride, ambroxol hydrochloride, acetylcysteine, ethylcysteine hydrochloride, carbocisteine, etc.], sedative drug [chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium, etc.], analgesic and antiphlogistic drugs [e.g., central analgesic drugs (e.g., morphine, codeine, pentazocine etc.), steroid drugs (e.g., prednisolone, dexamethasone, betamethasone), etc., antiphlogistic enzymic drugs (e.g., bromersine, lysozymes, protease, etc.)], diabetic drugs [sulfonylurea drugs (e.g., tolbutamide, chlorpropamide, glyclopyramide, acetohexamide, tolazamide, glibenclamide, glybuzole, etc.), biguanide drugs (e.g., metformin hydrochloride, buformin hydrochloride, etc.), α-glucosidase inhibitors (e.g., voglibose, acarbose, etc.), insulin resistance improvers (e.g., pioglitazone, troglytazone, etc.), insulin, glucagon, diabetic complication drugs (e.g., epalrestat, thioctic acid, etc.), actos, rosiglatazone, kinedak, penfill, humulin, euglucon, glimicron, daonil, novolin, monotard, insulin family, glucobay, dimelin, rastinone, bacilcon, deamelin S, Iszilin family, etc.]; brain function diluting agents (e.g., idebenone, vinpocetin, etc.); urinary and mele genital disease drugs [e.g., prostatomegaly drugs (tamsulosin hydrochloride, prazosin hydrochloride, chlormadinone acetate, etc.), prostate cancer drugs (leuprorelin acetate, goserelin acetate, chlormadinone acetate, etc.)], etc; nonsteroidal antiinflammatory drugs [acetaminophen, phenacetin, ethenzamide, sulpyrine, antipyrine, migrenin, aspirin, mefenamic acid, fulfenamic acid, diclofenac sodium, loxoprofen sodium, phenylbutazone, indomethacin, ibuprofenn, ketoprofen, naproxen, oxaoprozin, flurbiprofen, fenbufen, pranoprofen, floctafenine, epirizole, tiaramide hydrochloride, zaltoprofen, gabexate mesilate, camostat mesilate, urinastatin, colchicine, probenecid, sulfinpyrazone, benzbromarone, allopurinol, sodium aurothiomalate, sodium hyaluronate, sodium salicylate, morphine hydrochloride, salicyclic acid, atropine, scopolamine, morphine, pethidine, levorphanol, ketoprofen, naproxen, oxymorphine or the salts thereof, etc.]; frequent urination and anischuria drugs [flavoxate hydrochloride, etc.]; unstable plaque stablizers [MMP inhibitors, chymase inhibitors, etc.]; arrhythmic drugs [sodium channel blockers (e.g., quinidine, procainamide, disopyramide, ajmaline, cibenzoline, lidocaine, diphenylhydantoin, mexiletine, propafenone, flecainide, pilsicainide, phenytoin, etc.), β blockers (e.g., propranolol, alprenolol, bufetolol, oxprenolol, atenolol, acebutolol, metoprolol, bisoprolol, pindolol, carteolol, arotinolol, etc.), potassium channel blockers (e.g., amiodarone, etc.), calcium channel blockers (e.g., verapamil, diltiazem, etc.), etc.]; gynecologic disease drugs [e.g., climacteric disorder drugs (conjugated estrogen, estradiol, testosterone enanthate, valerate estradilo, etc.), breast cancer drugs (tamoxifen citrate, etc.), endometriosis and hysteromyoma drugs (leuprorelin acetate, danazol, etc.)], etc.; anesthetic drugs [a. local anaesthetic drugs [cocaine hydrochloride, procaine hydrochloride, lidocaine, dibucaine hydrochloride, tetracaine hydrochloride, mepivacaine hydrochloride, bupivacaine hydrochloride, ocybuprocaine hydrochloride, ethyl aminobenzoate, oxethazaine], etc.]; b. general anesthetic drugs [(1) inhalation anesthetic drugs (e.g., ether, halothane, nitrous oxide, influrane, enflurane), (2) intravenous anesthetic drugs (e.g., ketamine hydrochloride, droperidol, thiopental sodium, thiamylal sodium, pentobarbital), etc.]]; anesthetic antagonists [levallorphan, nalorphine, naloxone, or the salts thereof, etc.]; chronic cardiac failure drugs: cardiac stimulants [e.g., cardiac glycoside (digoxin), etc., β receptor stimulating drugs (catecholamine preparations such as denopamine, dobutamine.), PDE inhibitors, etc.]; diuretic drugs [e.g., furosemide (Lasix), spironolactone (Aldactone), bumetanide (Lunetoron), azosemide (Diart), etc.]; ACE inhibitors [e.g., enalapril maleate (Renivace), etc.]; Ca antagonists [e.g., amlodipine, manidipine, etc.] and β receptor blockers, etc.; immunomodulators [cyclosporin, tacrolimus, gusperimus, azathioprine, antilymphocyte sera, dried sulfonated immunoglobulins, erythropoietins, colony stimulating factors, interleukins, interferons, etc.]; diuretic drugs [thiazide-based diuretic drugs (benzylhydrochlorothiazide, cyclopenthiazide, ethiazide, hydrochlorothiazide, hydroflumethiazide, methylclothiazide, penflutiazide, polythiazide, trichlormethiazide, etc.), loop diuretic drugs (chlortalidone, clofenamide, indapamide, mefruside, meticrane, sotrazone, tripamide, quinethazone, metolazone, furosemide, mefruside, etc.), potassium-sparing diuretic drugs (spironolactone, triamterene, etc.)]; and erectile dysfunction drugs (Viagra, apomorphine, etc.).

These drugs, separately or simultaneously may be prepared by mixing with pharmaceutically carriers, excipients, binders, diluents or the like which can be accepted pharmacologically, and can be administered either orally or parenterally. When the drug is prepared separately, the drugs which is prepared separately may be mixed with a diluent or the like before using and then administered, or each of the preparations separately prepared may be administered, simultaneously or separately at an interval, to an identical person. Kit products used for mixing the separately-prepared preparations with a diluent and the like before using and administering, (for example, an injectable kit including ampoules for containing each powdery drug, and a diluent for mixing and solving with 2 or more drugs before using, and the like), kit products used for administering each of the separately-prepared preparation, formulation, simultaneously or separately at an interval, to an identical person, (for example, a tablet kit for 2 or more tablets, simultaneously or separately at an interval, put the tablet which is contained each drugs into the same or the separate bags, if necessary, a column provided on the bags wherein the drug administration date is to be indicated, and the like), or the like are also included in the pharmaceutical composition of the present invention.

A dosage of the pharmaceutical composition of the present invention can be appropriately selected by taking into consideration of subject, age and weight of subject, disease conditions, administration time, administration route, dosage form, etc.

A dosage of a particular subject can be determined according to the subject's age, weight, general health conditions, sex, meal, administration time, administration route, excretion rate and the degree of particular disease conditions to be treated by taking into consideration of these and other factors.

When the pharmaceutical composition described above is used as a preventive and therapeutic medicine for AIDS and a medicine for suppression on disease progression of AIDS, a dosage of the composition varies according to the patient's condition and body weight. However, usually, in the case of oral administration, a daily dosage is in a range of about 5 to 1000 mg, preferably about 10 to 600 mg, and more preferably about 10 to 300 mg, most preferably about 15 to 150 mg as the active ingredient (i.e. as the compound of the formula [I]) per an adult of body weight of 50 kg, and the medicine may be administered once or in 2 to 3 divided doses a day.

When the pharmaceutical composition described above is used as a preventive and therapeutic medicine for graft versus host disease and/or rejection associated with transplantation of organs such as heart, kidney, liver, bone marrow, etc., administration of the composition starts 3 days before the transplantation, and continues after the transplantation. A daily dosage of the pharmaceutical composition may be varied according to the patient's condition, weight, and route of administration, but is usually, in the case of oral administration, about 5 to 1000 mg as an active ingredient (i.e., as the compound of the formula [I]), per adult patient of 50 kg, preferably about 10 to 600 mg, more preferably about 10 to 300 mg, and most preferably about 15 to 150 mg, and the composition may be administered, once a day, or separately 2 or 3 times a day. In this case, the composition may be used in combination with other drugs to repress graft versus host disease and/or rejection at the time of other organ transplantation. Specific examples of the suppression of graft versus host disease and/or rejection at the time of organ transplantation which are used in combination with the compound represented by the compound of the formula [I] include cyclosporin, tacrolimus, rapamycin, steroids, azatguioprine, mycophenolate mophetil, mizoribine, etc. When a drug interferes with metabolism of other drugs in the case where these drugs are used in combination, dosage of each drugs is properly adjusted, but in most cases dosage of each of the drugs used in combination is that of each drugs when it is used independently.

When the compound of the formula [I] described above is used for the object disease except for suppression of the graft versus host disease and/or rejection at the time of organ transplantation, a daily dosage thereof may be varied according to the patient's condition, weight, and route of administration but is usually, in the oral administration, about 5 to 1000 mg as an active ingredient (i.e., as the free compound of the formula [I]), per adult patient of 50 kg, preferably about 10 to 600 mg, more preferably about 10 to 300 mg, and most preferably about 15 to 150 mg, and the composition may be administered, once a day, or separately 2 or 3 times a day. When the compound is used in combination with other drugs, dosage of the other drugs is properly selected in a range of about $1/200$ to $1/2$ or more to about 2 to 3 times less of usual dosage. Further, when the compound is used in combination with 2 or more drugs and one of the other drugs interferes with metabolism of other drugs, dosage of each of the drugs are properly adjusted, but in most cases dosage of each of the drugs used in combination is that of each drug when it used independently.

Further, the compound of the formula [I] can be included or used in combination with blood for transfusion or blood derivatives. Usually, blood for transfusion or blood derivatives are produced by mixing blood obtained form plural persons and, in some cases, uninfected cells are contaminated with cells infected with HIV virus. In such a case, uninfected cells are likely to be infected with HIV virus. When the compound of the formula [I] of the present invention is added to blood for transfusion or blood derivatives, infection and proliferation of the virus can be prevented or controlled. Especially, when blood derivatives are stored, infection and proliferation of the virus is effectively prevented or controlled by addition of the compound of the formula [I] of the present invention. In addition, when blood for transfusion or blood derivatives contaminated with HIV virus are administered to a person, infection and proliferation of the virus in the person's body can be prevented by adding the compound of the formula [I] to the blood or blood derivatives. For example, usually, for preventing HIV infectious disease upon using blood or blood derivatives by oral administration, a dosage is in a range of about 0.02 to 50 mg/kg, preferably about 0.05 to 30 mg/kg, and more preferably about 0.1 to 10 mg/kg as the CCR antagonist per an adult of body weight of about 60 kg, and the medicine may be administered once or 2 to 3 doses a day. As a matter of course, although the dosage range can be controlled on the basis of unit dosages necessary for dividing the daily dosage, as described above, a dosage of a particular subject can be determined according to the subject's age, weight, general health conditions, sex, meal, administration time, administration route, excretion rate and the degree of particular disease conditions to be treated by taking into consideration of these and other factors. In this case, the administration route is also appropriately selected and, the medicine for preventing HIV infectious disease of the present invention may be added directly to blood for transfusion or blood derivatives before transfusion or using blood derivatives. In such a case, desirably, the medicine of the present invention is mixed with blood or blood derivatives immediately to 24 hours before, preferably immediately to 12 hours before, more preferably immediately to 6 hours before transfusion or using blood derivatives.

Aside from blood for transfusion or blood derivatives, when the medicine for preventing HIV infectious disease of the present invention is administered together with the blood for transfusion or blood derivatives, the medicine is administered preferably at the same time of, to 1 hour before transfusion or using the blood derivatives. More preferably, the medicine is administered once to 3 times per day and the administration is continued 4 weeks.

Furthermore, when the compound of formula [I] is used in combination with a reverse transcriptase inhibitor and/or a protease inhibitor, the dosage of the reverse transcriptase or the protease is properly selected in a range of about 1/200 to 1/2, to about 2 to 3 times of the usual dosage. When two or more medicines are used in combination, dosage of each medicine is commonly identical to the dosage of the medicine when used independently, but when a medicine interferes with metabolism of other medicines, the dosage of each medicine is properly adjusted.

The usual dosages of the representative reverse transcriptases and proteases are as follows; zidovudine: 100 mg, didanosine: 125-200 mg, zalcitabine: 0.75 mg, lamivudine: 150 mg, stavudine: 30-40 mg, saquinavir: 600 mg, ritonavir: 600 mg, indinavir: 800 mg, and nelfinavir: 750 mg.

A typical embodiment of combined use of the compound of the formula [I], and a reverse transcriptase and/or a protease inhibitor will be described below.

(1) About 10 to 300 mg of the compound of formula [I] or the salt thereof and about 50 to 200 mg of zidovudine, per an adult of body weight of 50 kg, are administered in combination to the same object. Each medicine may be administered simultaneously or separately in a time interval of less than 12 hours.

(2) About 10 to 300 mg of the compound of formula [I] or the salt thereof and about 300 to 1200 mg of saquinavir, per an adult of body weight of 50 kg, are administered in combination to the same object. Each medicine may be administered simultaneously or separately in a time interval of less than 12 hours.

The following Examples, Reference Examples, Experimental Example and Formulation Examples further illustrate the present invention in detail but are not to be construed to limit the scope thereof.

EXAMPLE 1

(Preparation of Compound 1)

To a solution of 8-[4-(2-butoxyethoxy)phenyl]-3, 4-dihydro-2H-1-benzoxocin-5-carboxylic acid (80 mg) in THF (10 ml) were added a drop of DMF and then thionylchloride (0.02 ml) at 0° C. After stirring at room temperature for 30 minutes under a nitrogen atmosphere, the mixture was added to a solution of 4-[[N-methyl-N-(tetrahydropyran-4-yl) amino]methyl]aniline (57 mg) and triethylamine (526 mg) in tetrahydrofuran (20 ml) at 0° C. The mixture was stirred at room temperature for 1.5 hours under a nitrogen atmosphere. Water was added and the mixture was extracted with ethyl acetate. The organic layer was washed with saturated saline and dried over magnesium sulfate. After distilling off the solvent under reduced pressure, the residue was separated and purified by silica gel column chromatography (ethyl acetate). Recrystallization from hexane/ethyl acetate gave colorless crystals of 8-[4-(2-butoxyethoxy)phenyl]-N-[4-[[N-methyl-N-(tetrahydropyran-4-yl)amino]methyl]phenyl]-3,4-dihydro-2H-1-benzoxocin-5-carboxamide (Compound 1, 66 mg).

$^1$H-NMR (200 MHz, CDCl$_3$) δ 0.93 (3H,t, J=7.2 Hz), 1.34-1.44 (2H,m), 1.57-1.77 (6H, m), 1.88 (2H, br), 2.21 (3H, s), 2.50-2.78 (3H,m), 3.37 (2H, dt, J=10.4, 3.2 Hz), 3.52-3.59 (m, 4H), 3.81 (2H, t, J=4.8 Hz), 4.04 (2H, d, J=12.2 Hz), 4.16 (2H, t, J=5.0 Hz), 4.36 (2H, t, J=4.8 Hz), 6.99 (2H, d, J=8.8 Hz), 7.06 (IH, d, J=8.6 Hz), 7.29-7.36 (4H, m), 7.43-7.49 (3H, m), 7.56 (2H, d, J=8.4 Hz), 7.66(IH, s). Elementary Analysis: $C_{37}H_{46}N_2O_5$, Calcd. C, 74.22; H, 7.74; N, 4.68; Found. C, 74.05; H, 7.77; N, 4.66.

EXAMPLE 2

(Preparation of Compound 2)

To a solution of 8-[4-(2-butoxyethoxy)phenyl]-1-propyl-1,2,3,4-tetrahydro-1-benzazocine-5-carboxylic acid (180 mg) in THF (10 ml) were added a drop of DMF and then thionylchloride (0.04 ml) at 0° C. After stirring at room temperature for 30 minutes under a nitrogen atmosphere, the mixture was added to a solution of 4-[[N-methyl-N-(tetrahydropyran-4-yl)amino]methyl]aniline (118 mg), and triethylamine (1.08 g) in tetrahydrofuran (15 ml) at 0° C. After stirring at room temperature for 1.5 hours under a nitrogen atmosphere, water was added and the mixture was extracted with ethyl acetate. The organic layer was washed with saturated salt solutions, and dried over magnesium sulfate. After distilling off the solvent under reduced pressure, the residue was separated and purified by silica gel column chromatography (ethyl acetate:methanol=8:1) to obtain yellowish amorphous 8-[4-(2-butoxyethoxy)phenyl]-1-propyl-N-[4-[[N-methyl-N-(tetrahydropyran-4-yl)amino]methyl] phenyl]-1,2,3,4-tetrahydro-1-benzazocine-5-carboxamide (Compound 2, 64 mg).

$^1$H-NMR (200 MHz, CDCl$_3$) 60.93 (3H, t, J=7.2 Hz), 0.99 (3H, t, J=6.0 Hz), 1.30-1.85 (12H, m), 2.21 (3H, s), 2.50-2.70 (3H, m), 3.10-3.25(2H, m), 3.30-3.45 (2H, m), 3.50-3.60 (6H, m), 3.80 (2H,t, J=4.4 Hz), 4.04 (2H, d, J=11.2 Hz), 4.14 (2H, t, J=7.0 Hz), 6.82 (1H, d, J=8.4 Hz), 6.96 (2H, d, J=8.8 Hz), 7.28-7.61 (10H, m).

EXAMPLE 3

(Preparation of Compound 3)

To a solution of 8-[4-(2-butoxyethoxy)phenyl]-1-propyl-1,2,3,4-tetrahydro-1-benzazocine-5-carboxylic acid (900 mg) in tetrahydrofuran (15 ml) were added a drop of DMF and then thionylchloride (0.2 ml). The mixture was stirred for 1 hour under a nitrogen atmosphere. After distilling off the solvent and the excess thionylchloride under reduced pressure, the residue was redissolved in THF (15 ml). The solution was added dropwise to a solution of S-(4-aminophenyl)O-benzylcarbonothioate (534 mg) and triethylamine (1.4 ml) in THF (15 ml) at 0° C. under an argon atmosphere. After the dropwise addition, the solution was allowed to warm to room temperature and stirred overnight under an argon atmosphere. After addition of methanol (30 ml) and further 1N sodium hydroxide (10.3 ml), the solution was stirred for 30 minutes under an argon atmosphere. Then, 5-chloromethyl-1-propylimidazole hydrochloride (482 mg) was added to the solution, and the mixture was stirred under an argon atmosphere for 1.5 hours. After addition of water and extraction with ethyl acetate, the organic layer was washed with saturated saline and dried over magnesium sulfate. After distilling off the solvent under reduced pressure, the residue was separated and purified by silica gel column chromatography to obtain yellowish amorphous 8-[4-(2-butoxyethoxy)phenyl]-1-propyl-N-[4-[[[1-propylimidazol-5-yl]methyl]sulfanyl]phenyl]-1,2,3,4-tetrahydro-1-benzazocine-5-carboxamide (Compound 3, 633 mg).

$^1$H-NMR (300 MHz, CDCl$_3$) 60.91-1.01 (9H, m), 1.36-1.43 (2H, m), 1.56-1.75 (6H, m), 1.80-1.90 (2H, m), 2.57-2.61 (2H, m), 3.16-3.22 (2H, m), 3.50-3.57 (4H, m), 3.80 (2H, t, J=5.1 Hz), 3.92 (2H, t, J=7.5 Hz), 3.99 (2H, s), 4.14 (2H, t, J=5.1 Hz), 6.70 (IH, s), 6.79 (1H,d, J=9.3 Hz), 6.96 (2H, d, J=8.7 Hz), 7.25-7.30 (3H, m), 7.37-7.44(4H, m), 7.52-7.56 (3H, m), 7.82 (1H, s). Elemental Analysis; C$_{40}$H$_{50}$N$_4$O$_3$S-0.25H$_2$O, Calcd. C, 71.55; H, 7.58; N, 8.34; Found, C, 71.26; H, 7.49; N, 8.37.

EXAMPLE 4

(Preparation of Compounds 4 and 5)

A solution of 70% 3-chloroperbenzoic acid (316 mg) in dichloromethane (15 ml) was added dropwise to a solution of 8-[4-(2-butoxylethoxy)phenyl]-1-propyl-N-[4-[[[1-propylimidazol-5-yl]methyl]sulfanyl]phenyl]-1,2,3,4-tetrahydro-1-benzazocine-5-carboxamide (570 mg) in dichloromethane (15 ml) at −78° C. After removal of the dry ice-acetone bath, an aqueous solution of sodium thiosulfate was added to the solution with a vigorous stirring. The resultant solution was allowed to warm to room temperature and stirred for 30 minutes. After extraction with ethylacetate, the organic layer was washed with saturated sodium bicarbonate solution and saturated saline, and dried over magnesium sulfate. After distilling off the solvent under reduced pressure, the residue was separated and purified by basic silica gel column chromatography (ethylacetate) to obtain yellowish amorphous 8-[4-(2-butoxyethoxy)phenyl]-1-propyl-N-[4-[[[1-propylimidazol-5-yl]methyl]sulfinyl] phenyl]-1,2,3,4-tetrahydro-1-benzazocine-5-carboxamide (Compound 4, 392 mg), and 8-[4-(2-butoxyethoxy)phenyl]-1-propyl-N-[4-[[[1-propylimidazol-5-yl]methyl]sulfonyl] phenyl]-1,2,3,4-tetrahydro-1-benzazocine-5-carboxamide (Compound 5, 45 mg).

Compound 4:

$^1$H-NMR, (300 MHz, CDCl$_3$) δ 0.87-1.03 (9H, m), 1.34-1.49 (2H, m), 1.50-1.85 (8H,m), 2.55-2.65 (2H, m), 3.15-3.25 (2H, m), 3.52-3.58 (4H, m), 3.75-3.83 (4H, m), 4.02 (1H, d, J=13.8 Hz), 4.08-4.17 (3H, m), 6.56 (1H, d, J=1.0 Hz), 6.80 (1H, d, J=8.8 Hz), 6.96 (2H, d, J=8.8 Hz), 7.31-7.46 (7H, m), 7.55 (1H, s), 7.76 (2H, d, J=8.8 Hz), 7.98 (1H, s). Elemental Analysis, C$_{40}$H$_{50}$N$_4$O$_4$S, Calcd. C, 70.35; H, 7.38; N, 8.20; Found. C,70.03; H, 7.24; N, 8.13.

Compound 5:

$^1$H-NMR(300 MHz, CDCl$_3$) δ 0.90-1.03 (9H, m), 1.34-1.82 (1OH, m), 2.55-2.65 (2H, m), 3.15-3.25 (2H, m), 3.52-3.59 (4H, m), 3.80 (2H, t, J=5.4 Hz), 3.96 (2H, t, J=7.2 Hz), 4.15 (2H, t, J=5.4 Hz), 4.33 (2H, s), 6.54 (IH, s), 6.80 (1H, d, J=8.8 Hz), 6.96 (2H, d, J=8.8 Hz), 7.29-7.63 (8H, m), 7.77 (2H, d, J=8.8 Hz), 8.09 (1H, s). Elemental Analysis, C$_{40}$H$_{50}$N$_4$O$_5$S-0.25H$_2$O, Calcd. C, 68.30; H, 7.24; N, 7.96; Found, C, 68.12; H, 7.21; N, 7.92.

EXAMPLE 5

(Preparation of Compound 6)

To a solution of 8-[4-(2-butoxyethoxy)phenyl]-1-isobutyl-1,2,3,4-tetrahydro-1-benzazocine-5-carboxylic acid (700 mg) in tetrahydrofuran (15 ml) were added a drop of DMF and then thionylchloride (0.15 ml), and the solution was stirred under a nitrogen atmosphere for 1 hour. After distilling off the solvent and excess thionyl chloride under reduced pressure, the residue was redissolved in THF (15 ml). The solution was added dropwise to a solution of S-(4-aminophenyl) O-benzyl carbonothioate (402 mg) and trimethylamine (1.1 ml) in THF (15 ml) at 0° C. under an argon atmosphere. After dropwise addition, the solution was allowed to warm to room temperature and stirred overnight under an argon atmosphere. After addition of methanol (30 ml) and further 1N sodium hydroxide solution (7.8 ml), the solution was stirred under an argon atmosphere for 30 minutes. To the solution, 5-(chloromethyl)-1-propyl-1H-imidazole hydrochloride (333 mg) was added, and the resulting solution was further stirred for 1.5 hours under an argon atmosphere. After addition of water and extraction with ethyl acetate, the organic layer was washed with saturated saline and dried over magnesium sulfate. After distilling off the solvent under reduced pressure, the residue was separated and purified by basic silica gel column chromatography (hexane:ethyl acetate=1:1 to ethyl acetate) to obtain yellowish amorphous 8-[4-(2-butoxyethoxy)phenyl]-1-isobutyl-N-[4-[[[1-propyl-1H-imidazol-5-yl]methyl] sufanyl]phenyl-1,2,3,4-tetrahydro-1-benzazocine-5-carboxamide (Compound 6, 846 mg).

$^1$H-NMR (200 MHz, CDCl$_3$) δ 0.89-1.01 (12H, m), 1.30-1.44 (2H, m), 1.50-1.70 (4H, m), 1.75-1.93 (2H, m), 2.05-2.25 (1H,m), 2.50-2.65 (2H, m), 3.06 (2H, d, J=7.6 Hz), 3.45-3.58 (4H, m), 3.80 (2H, t, J=5.0 Hz), 3.93(2H, t, J=7.4 Hz), 3.99 (2H, s), 4.15 (2H, t, J=5.0 Hz), 6.69 (IH, s), 6.85 (1H, d, J=8.4 Hz), 6.96 (2H, d, J=8.8 Hz), 7.26-7.56 (10H, m), 7.72 (1H, s). Elemental Analysis C$_{41}$H$_{52}$N$_4$OS, Calcd. C, 72.32; H, 7.70; N, 8.23; Found. C, 72.11; H, 7.99; N, 8.14.

EXAMPLE 6

(Preparation of Compounds 7 and 8)

A solution of 70% 3-chloroperbenzoic acid (217 mg) in dichloromethane (10 ml) was added dropwise to a solution of 8-[4-(2-butoxyethoxy)phenyl]-1-isobutyl-N-[4-[[[1-propyl-1H-imidazol-5-yl]methyl]sulfanyl]phenyl]-1,2,3,4-tetrahydro-1-benzazocine-5-carboxamide (400 mg) in dichloromethane (10 ml) at −78° C. After stirring at −15° C. for 1 hour, dimethylsulfide (0.1 ml) was added. The solution was allowed to warm to room temperature and stirred for 30 minutes. After addition of water and extraction with ethyl acetate, the organic layer was washed with saturated sodium bicarbonate solution and saturated saline and dried over magnesium sulfate. After distilled off the solvent under reduced pressure, the residue was separated and purified by basic silica gel column chromatography (hexane:ethyl acetate=1:4 to ethyl acetate), and recrystallization from hexane:ethyl acetate gave yellow crystals of 8-[4-(2-butoxyethoxy)phenyl]-1-isobutyl-N-[4-[[[1-propyl-1H-imidazol-5-yl]methyl]sulfinyl]phenyl]-1,2,3,4-tetrahydro-1-benzazocine-5-carboxamide (Compound 7, 182 mg), and recrystallization from hexane:ethyl acetate gave yellow crystals of 8-[4-(2-butoxyethoxy)phenyl]-1-isobutyl-N-[4-[[[1-propyl-1H-imidazol-5-yl]methyl]sulfanyl]phenyl]-1,2,3,4-tetrahydro-1-benzazocine-5-carboxamide (Compound 8, 58 mg).

Compound 7:
$^1$H-NMR (200 MHz, CDCl$_3$) δ 0.87-1.02 (12H, m), 1.30-1.80 (8H, m), 2.05-2.25 (1H, m), 2.55-2.65 (2H, m), 3.08 (2H, d, J=7.6 Hz), 3.52-3.59 (4H, m), 3.75-3.83 (4H, m), 4.02 (1H, d, J=14.4 Hz), 4.08-4.18 (3H, m), 6.57 (1H, s), 6.85 (1H, d, J=8.8 Hz), 6.96 (2H, d, J=8.8 Hz), 7.28-7.85 (8H, m), 7.75 (2H, d, J=8.8 Hz), 7.95 (1H, s). Elemental Analysis; $C_{41}H_{52}N_4O_4S \cdot 0.5H_2O$, Calcd. C, 69.76; H, 7.57; N, 7.94; Found. C, 69.67; H, 7.63; N, 7.81.

Compound 8:
$^1$H-NMR (300 MHz, CDCl$_3$) 60.91-1.01 (12H, m), 1.33-1.43(2H, m), 1.45-1.65 (4H, m), 1.70-1.85 (2H, m), 2.10-2.25 (1H, m), 2.55-2.65 (2H, m),3.08 (2H, d, J=7.5 Hz), 3.45-3.60 (4H, m), 3.81 (2H, t, J=4.8 Hz), 3.96 (2H, t, J=6.9 Hz), 4.15 (2H, t, J=4.8 Hz), 4.33 (2H, s), 6.54(1H, s), 6.85 (1H, d, J=9.3 Hz), 6.96 (2H, d, J=9.0 Hz), 7.30 (1H, d, J=2.1 Hz), 7.39-7.62 (7H, m), 7.77 (2H, d, J=8.7 Hz), 8.10 (1H, s). Elemental Analysis $C_{41}H_{52}N_4O_5S$-0.25H$_2$O, Calcd. C, 68.64; H, 7.38; N, 7.81; Found. C, 68.61; H, 7.51; N, 7.56.

EXAMPLE 7

(Preparation of Compounds 9 and 10)

8-[4-(2-Butoxyethoxy)phenyl]-1-propyl-N-[4-[[[1-propyl-1H-imidazol-5-yl]methyl]sulfinyl]phenyl]-1,2,3,4-tetrahydro-1-benzazocin-5-carboxamide (317 mg) was resolved by using CHIRAKCEL OJ 50 mm ID×500 mmL (hexane/ethanol) to give (−)-8-[4-(2-butoxyethoxy)phenyl]-1-propyl-N-[4-[[[1-propylimidazol-5-yl]methyl]sulfinyl]phenyl]-1,2,3,4-tetrahydro-1-benzoazocine-5-carboxamide (142 mg) (Compound 9) and (+)-8-[4-(2-butoxyethoxy)phenyl]-1-propyl-N-[4-[[[1-propylimidazol-5-yl]methyl]sulfinyl]phenyl]-1,2,3,4-tetrahydro-1-benzoazocine-5-carboxamide (143 mg) (Compound 10).

Compound 9
[α]$_D$=−127.4° (C=0.533% in ethanol).
Compound 10
[α]$_D$=+121.0° (C=0.437% in ethanol).

EXAMPLE 8

(Preparation of Compounds 11 and 12)

8-[4-(2-Butoxyethoxy)phenyl]-1-isobutyl-N-[4-[[[1-propyl-1H-imidazol-5-yl]methyl]sulfinyl]phenyl]-1,2,3,4-tetrahydro-1-benzazocin-5-carboxamide (165 mg) was resolved by using CHIRAKCEL OJ 50 mm ID×500 mmL (hexane/ethanol) to give (−)-8-[4-(2-butoxyethoxy)phenyl]-1-isobutyl-N-[4-[[[1-propyl-1H-imidazol-5-yl]methyl]sulfinyl]phenyl]-1,2,3,4-tetrahydro-1-benzoazocine-5-carboxamide (74 mg) (Compound 11) and (+)-8-[4-(2-butoxyethoxy)phenyl]-1-isobutyl-N-[4-[[[1-propy-1H-limidazol-5-yl]methyl]sulfinyl]phenyl]-1,2,3,4-tetrahydro-1-benzoazocine-5-carboxamide (61 mg) (Compound 12).

Compound 11
[α]$_D$=−130.4° (C=0.440% in ethanol)
Compound 12
[α]$_D$=+127.5° (C=0.467% in ethanol).

EXAMPLE 9

(Preparation of Compound 13)

To a solution of (−)-8-[4-(2-butoxyethoxy)phenyl]-1-isobutyl-N-[4-[[[1-propyl-1H-imidazol-5-yl]methyl]sulfinyl]phenyl]-1,2,3,4-tetrahydro-1-benzoazocine-5-carboxamide (100 mg) in ethyl acetate (4 ml) was added a solution of oxalic acid (6.46 mg) in ethanol (2 ml), after which the solvent was distilled off under reduced pressure. Ethyl acetate (5 ml) was added, and the solvent was again distilled off under reduced pressure, after which ethyl acetate (4 ml) was added, and the mixture was allowed to stand overnight under light shielding. The precipitated crystals were filtered, and further washed with ethyl acetate (5 ml), after which the resultant was dried under reduced pressure to give (−)-8-[4-(2-butoxyethoxy)phenyl]-1-isobutyl-N-[4-[[[1-propyl-1H-imidazol-5-yl]methyl]sulfinyl]phenyl]-1,2,3,4-tetrahydro-1-benzoazocine-5-carboxamide/oxalate (50 mg) as yellow crystals (Compound 13).

m.p. 139.5-141.5° C.
$^1$H-NMR (300 MHz, CDCl$_3$) δ 0.90-0.99 (12H, m), 1.32-1.45 (2H, m), 1.55-1.65 (4H, m), 1.73-1.83 (2H, m), 2.05-2.17 (1H, m), 2.55-2.61 (2H, m), 3.00-3.20 (2H, m), 3.50-3.60 (4H, m), 3.74-3.81 (3H, m), 3.86-4.06 (2H, m), 4.14 (2H, t, J=5.7 Hz), 4.25 (1H, d, J=14.7 Hz), 6.61 (1H, s), 6.84 (1H, d, J=9.0 Hz), 6.95 (2H, d, J=8.7 Hz), 7.20 (2H, d, J=8.7 Hz), 7.38-7.46 (4H, m), 7.63 (1H, s), 7.83 (2H, d, J=8.7 Hz), 8.43 (1H, s), 8.80 (1H, s). Elementary analysis $C_{43}H_{54}N_4O_8S$ Calcd. C, 65.63; H, 6.92; N, 7.12; Found. C, 65.41; H, 7.11; N, 6.90.

[α]$_D$=−158.9° (C=0.450% in ethanol).

EXAMPLE 10

Preparation of Compound 14

To a solution of (−)-8-(4-(2-butoxyethoxy)phenyl]-1-isobutyl-N-(4-[[[1-propyl-1H-imidazol-5-yl]methyl]sulfinyl]phenyl]-1,2,3,4-tetrahydro-1-benzoazocine-5-carboxamide (100 mg) in ethyl acetate (4 ml) was added dropwise to a solution of methanesulfonic acid (9.31 μl) in ethyl acetate (2 ml) with vigorous stirring, after which the mixture was stirred under light shielding overnight. The precipitated crystals were filtered, and further washed with ethyl acetate (5 ml), followed by drying under reduced pressure. The resulting crystals were recrystallized from 2-butanone (4 ml) to give (−)-8-[4-(2-butoxyethoxy)phenyl]-1-isobutyl-N-[4-[[[1-propyl-1H-imidazol-5-yl]methyl]sulfinyl]phenyl]-1,2,3,4-tetrahydro-1benzazocine-5-carboxamide methansulfonate (88.4 mg) as yellow crystals (Compound 14).

m.p. 145.5-147.5° C.

¹H-NMR (300 MHz, DMSO-d₆) δ 0.82-0.97 (12H, m), 1.29-1.39 (2H, m), 1.40-1.55 (4H, m), 1.65-1.85 (2H, m), 2.00-2.25 (1H, m), 2.29 (3H,s), 2.38-2.60 (2H, m), 3.10 (2H, d, J=7.8 Hz), 3.30-3.60 (4H, m), 3.70 (2H, t, J=4.8 Hz), 3.98 (2H, t, J=6.6 Hz), 4.10 (2H, t, J=4.8 Hz), 4.34 (1H, d, J=15.0 Hz), 4.68 (1H, d, J=15.0 Hz), 6.87 (1H, d, J=8.7 Hz), 6.99 (2H, d, J=8.7 Hz), 7.16 (1H, s), 7.42-7.60 (8H, m), 7.93 (2H, d, J=8.7 Hz), 9.05 (1H, s), 10.18 (1H, s). Elementary analysis $C_{42}H_{56}N_4O_7S_2$ Calcd. C, 63.61; H, 7.12; N, 7.06; Found. C, 63.21; H, 7.10; N, 6.96.

$[\alpha]_D$=−191.9° (C=0.512% in ethanol).

EXAMPLE 11

(Preparation of Compound 15)

To a solution of 8-[4-(2-butoxyethoxy)phenyl]-1-isobutyl-1,2,3,4-tetrahydro-1-benzoazocine-5-carboxylic acid (500 mg) in tetrahydrofuran (10 ml) was added a drop of DMF. Then, after addition of thionyl chloride (0.105 ml), the mixture was stirred under nitrogen atmosphere for 1 hour. After distilling off the solvent and excessive thionyl chloride under reduced pressure, the mixture was dissolved in THF (15 ml). The resulting solution was added dropwise to a THF (15 ml) solution of S-(4-aminophenyl)O-benzyl carbonothioate (287 mg), triethylamine (0.77 ml) at 0° under argon atmosphere. After completion of dropwise addition, the reactant mixture was set back to room temperature and stirred under argon atmosphere overnight, followed by adding methanol (30 ml). Further, an aqueous solution of 1N sodium hydroxide (5.53 ml) was added and the mixture was stirred under argon atmosphere for 30 minutes. Then, 2-chloromethyl-1-propylimidazole hydrochloride (238 mg) was added and stirring was made under argon atmosphere for 1.5 hours. Water was added and the mixture was extracted with ethyl acetate, after which the organic layer was washed with saturated brine, and the resultant was dried with magnesium sulfate. After distilling off the solvent under reduced pressure, the resultant was separated and purified by basic silica gel column chromatography (hexane:ethyl acetate=1:1) to give 8-[4-(2-butoxyethoxy)phenyl]-1-isobutyl-N-[4-[[[1-propylimidazol-5-yl]methyl]sulfanyl]phenyl]-1,2,3,4-tetrahydro-1-benzoazocine-5-carboxamide (460 mg) as a yellow amorphous material (Compound 15).

¹H-NMR (300 MHz, CDCl₃) δ 0.91-1.00 (12H, m), 1.33-1.46 (2H, m), 1.50-1.70 (4H, m), 1.73-1.85 (2H, m), 2.16-2.23 (1H, m), 2.55-2.59 (2H, m), 3.06 (2H, d, J=7.5 Hz), 3.46-3.53 (2H, m), 3.55 (2H, t, J=6.6 Hz), 3.79-3.87 (4H, m), 4.11-4.17 (4H, m), 6.83-6.86 (2H, m), 6.92-6.98 (3H, m), 7.32-7.55 (9H, m), 7.81 (1H, s). Elementary analysis $C_{41}H_{52}N_4O_3S\cdot 0.5H_2O$ Calcd. C, 71.37; H, 7.74; N, 8.12; Found. C, 71.41; H, 7.74; N, 8.15.

EXAMPLE 12

(Preparation of Compound 16)

To a solution of 8-[4-(2-butoxyethoxy)phenyl]-1-isobutyl-N-[4-[[[1-propylimidazol-2-yl]methyl]sulfanyl]phenyl]-1,2,3,4-tetrahydro-1-benzoazocine-5-carboxamide (400 mg) in dichloromethane (10 ml) was added dropwise a 70% solution of 3-chloro-perbenzoic acid (217 mg) in dichloromethane (10 ml) at −78° C. After stirring as such for 1 hour, dimethyl sulfide (0.1 ml) was added. The mixture was returned to room temperature and stirred for 30 minutes, after which water was added and the mixture was extracted with ethyl acetate. The organic layer was washed with saturated aqueous sodium bicarbonate solution and saturated aqueous brine, and was dried with magnesium sulfate. The solvent was distilled off under reduced pressure, and the resulting residue was separated and purified by basic silica gel column chromatography (hexane:ethyl acetate=1:4→ethyl acetate) and recrystallized from diisopropyl ether-ethyl acetate to give 8-[4-(2-butoxyethoxy)phenyl]-1-isobutyl-N-[4-[[[1-propylimidazol-2-yl]methyl]sulfinyl]phenyl]-1,2,3,4-tetrahydro-1-benzoazocine-5-carboxamide (245 mg) as yellow crystals (Compound 16).

¹H-NMR (200 MHz, CDCl₃) δ 0.85-1.02 (12H, m), 1.34-1.74 (8H, m), 2.10-2.25 (1H, m), 2.55-2.67 (2H, m), 3.07 (2H, d, J=7.0 Hz), 3.47-3.58 (4H, m), 3.68-3.83 (4H, m), 4.07-4.18 (3H, m), 4.27 (1H, d, J=13.2 Hz), 6.83-7.01 (5H, m), 7.37-7.51 (7H, m), 7.74 (2H, d, J=8.8Hz), 7.95 (1H, s). Elementary analysis $C_{41}H_{52}N_4O_4S$ Calcd. C, 70.66; H, 7.52; N, 8.04; Found. C, 70.60; H, 7.65; N, 8.18.

EXAMPLE 13

(Preparation of Compounds 17, 18)

8-[4-(2-Butoxyethoxy)phenyl]-1-propyl-N-[4-[[[1-propylimidazol-2-yl]methyl]sulfynyl]phenyl]-1,2,3,4-tetrahydro-1-benzoazocine-5-carboxamide (200 mg) was resolved by using CHIRAKPAK AD 50 mm ID×500 mmL (hexane/isopropanol) to give (+)-8-[4-(2-butoxyethoxy)phenyl]-1-isobutyl-N-[4-[[[1-propylimidazol-2-yl]methyl]sulfinyl]phenyl]-1,2,3,4-tetrahydro-1-benzoazocine-5-carboxamide (84 mg) (Compound 17), and (−)-8-[4-(2-butoxyethoxy)phenyl]-1-isobutyl-N-[4-[[[1-propylimidazol-2-yl]methyl]sulfinyl]phenyl]-1,2,3,4-tetrahydro-1-benzoazocine-5-carboxamide (81 mg) (Compound 18).

Compound 17
$[\alpha]_D$=+87.9° (C=0.404% in ethanol)
Compound 18
$[\alpha]_D$=−87.6° (C=0.435% in ethanol)

EXAMPLE 14

(Preparation of Compound 19)

To a solution of 8-[4-(2-butoxyethoxy)phenyl]-1-propyl-1,2,3,4-tetrahydro-1-benzoazocine-5-carboxylic acid (500 mg) in tetrahydrofuran (10 ml) was added a drop of DMF. Then, after adding thionyl chloride (0.108 ml), the mixture was stirred under nitrogen atmosphere for 1 hour. After distilling off the solvent and excessive thionyl chloride under reduced pressure, the mixture was dissolved in THF (15 ml). The resulting solution was added dropwise to a THF (15 ml) solution of S-(4-aminophenyl)O-benzyl carbonothioate (296 mg), triethylamine (0.8 ml) at 0° C. under argon atmosphere. After completion of dropwise addition, the reactant was set back to room temperature and stirred under argon atmosphere overnight, followed by adding methanol (30 ml). Further, an aqueous solution of 1N sodium hydroxide (5.7 ml) was added and the mixture was stirred under argon atmosphere for 30 minutes. Then, 2-chloromethyl-1-propylimidazole hydrochloride (245 mg) was added and stirring was made under argon atmosphere for 1.5 hours. Water was added and the mixture extracted with ethyl acetate, after which the organic layer was washed with saturated brine, and the resultant was dried with magnesium sulfate. After distilling off the solvent under reduced pressure, the resultant was separated and purified with basic silica gel column chromatography (hexane:ethyl acetate=1:1) to give 8-[4-(2-butoxyethoxy)phenyl]-1-propyl-N-[4-

[[[1-propylimidazol-2-yl]methyl]sulfanyl]phenyl]-1,2,3,4-tetrahydro-1-benzoazocine-5-carboxamide (481 mg) as a yellow amorphous material (Compound 19).

$^1$H-NMR (200 MHz, CDCl$_3$) δ 0.90-1.02 (9H, m), 1.30-1.50 (2H, m), 1.55-1.90 (8H, m), 2.55-2.65 (2H, m), 3.10-3.25 (2H, m), 3.50-3.60 (4H, m), 3.78-3.88 (4H, m), 4.10-4.18 (4H, m), 6.78 (1H, d, J=8.8 Hz), 6.84 (1H, d, J=1.0 Hz), 6.92 (1H, d, J=1.0 Hz), 6.96 (2H, d, J=8.8 Hz), 7.31-7.56 (9H, m), 7.84 (1H, s). Elementary analysis C$_{40}$H$_{50}$N$_4$O$_3$S.0.25H$_2$O Calcd. C, 71.55; H, 7.58; N, 8.34; Found. C, 71.60; H, 7.82; N, 8.58.

EXAMPLE 15

(Preparation of Compound 20)

To a solution of 8-[4-(2-butoxyethoxy)phenyl]-1-propyl-N-[4-[[[1-propylimidazol-2-yl]methyl]sulfanyl]phenyl]-1,2,3,4-tetrahydro-1-benzoazocine-5-carboxamide (430 mg) in dichloromethane (10 ml) was added dropwise a 70% solution of 3-chloro-perbenzoic acid (238 mg) in dichloromethane (10 ml) at −78° C. After stirring as such for 1 hour, the dry ice-acetone bath was removed, and an aqueous sodium thiosulfate solution was added with vigorous stirring. The mixture was returned to room temperature and stirred for 30 minutes, after which water was added and the mixture was extracted with ethyl acetate. The organic layer was washed with saturated aqueous sodium bicarbonate solution and saturated aqueous brine, and was dried with magnesium sulfate. The solvent was distilled off under reduced pressure, and the resulting residue was separated and purified with basic silica gel column chromatography (hexane:ethyl acetate=1:4→ethyl acetate) and re-crystallized from diisopropyl ether-ethyl acetate to give 8-[4-(2-butoxyethoxy)phenyl]-1-propyl-N-[4-[[[1-propylimidazol-2-yl]methyl]sulfinyl]phenyl]-1,2,3,4-tetrahydro-1-benzoazocine-5-carboxamide (288 mg) as yellow crystals (Compound 20).

$^1$H-NMR (300 MHz, CDCl$_3$) δ 0.86-1.02 (9H, m), 1.30-1.80 (10H, m), 2.55-2.65 (2H, m), 3.10-3.25 (2H, m), 3.45-3.60 (4H, m), 3.65-3.85 (4H, m), 4.08-4.17 (3H, m), 4.28 (1H, d, J=13.8 Hz), 6.80 (1H, d, J=9.3 Hz), 6.88 (1H, d, J=1.5 Hz), 6.95-7.01 (3H, m), 7.38-7.45 (6H, m), 7.52 (1H, s), 7.74 (2H, d, J=8.7 Hz), 7.90 (1H, s). Elementary analysis C$_{40}$H$_{50}$N$_4$O$_4$S Calcd. C, 70.35; H, 7.38; N, 8.20; Found. C, 70.12; H, 7.45; N, 8.28.

EXAMPLE 16

(Preparation of Compounds 21 and 22)

8-[4-(2-Butoxyethoxy)phenyl]-1-propyl-N-[4-[[[1-propylimidazol-2-yl]methyl]sulfinyl]phenyl]-1,2,3,4-tetrahydro-1-benzoazocine-5-carboxamide (220 mg) was resolved by using CHIRAKPAK AD 50 mm ID×500 mmL (hexane/ethanol) to give (+)-8-[4-(2-butoxyethoxy)phenyl]-1-propyl-N-[4-[[[1-propylimidazol-2-yl]methyl]sulfinyl]phenyl]-1,2,3,4-tetrahydro-1-benzoazocine-5-carboxamide (107 mg) (Compound 21), and (−)-8-[4-(2-butoxyethoxy)phenyl]-1-propyl-N-[4-[[[1-propylimidazol-2-yl]methyl]sulfinyl]phenyl]-1,2,3,4-tetrahydro-1-benzoazocine-5-carboxamide (105 mg) (Compound 22).

Compound 21
[α]$_D$=+90.7° (C=0.450% in ethanol)
Compound 22
[α]$_D$=−85.1° (C=0.407% in ethanol)

EXAMPLE 17

(Preparation of Compound 23)

(−)-(4-(((1-Propylimidazol-5-yl)methyl)sulfinyl)aniline di-p-toluoyl-D-tartarate monohydrate (770 mg) was dissolved in ethyl acetate (5 ml) and 1N hydrochloric acid (3.91 ml), followed by separation. To the aqueous layer was added an aqueous 25% potassium carbonate solution (3.92 ml), followed by extraction with 2-propanol-ethyl acetate (1:4) three times. The organic layers were combined and washed with saturated brine, dried with magnesium sulfate, and the solvent was distilled off under reduced pressure. To the resulting residue was added tetrahydrofuran, after which the solvent was distilled off again under reduced pressure to give (−)-(4-(((1-propylimidazol-5-yl)methyl)sulfinyl)aniline.

Then, to a solution of 8-(4-(2-butoxyethoxy)phenyl)-1-(2-methyl-2-propen-1-yl)-1,2,3,4-tetrahydro-1-benzoazocine-5-carboxylic acid (400 mg) in tetrahydrofuran (10 ml) were added a drop of DMF, and then thionyl chloride (0.084 ml), and the mixture was stirred under nitrogen atmosphere for 30 minutes. The resulting solution was added dropwise to a solution of (−)-(4-(((1-propylimidazol-5-yl)methyl)sulfinyl) aniline and triethylamine (1.61 ml) in tetrahydrofuran (10 ml) at 0° C. under nitrogen atmosphere. The mixture was returned to room temperature and stirred for 3 hours, after which water was added and the mixture was extracted with ethyl acetate. The organic layer was washed with 10% aqueous acetic acid solution twice, with aqueous saturated sodium bicarbonate solution twice, and with saturated brine once, after which the resultant was dried with magnesium sulfate. After distilling off the solvent under reduced pressure, the resultant was separated and purified with a basic silica gel column chromatography (hexane:ethyl acetate=1:1→ethyl acetate) to give (−)-8-[4-(2-butoxyethoxy)phenyl]-1-(2-methyl-2-propen-1-yl)-N-[4-[[[1-propylimidazol-5-yl]methyl]sulfinyl]phenyl]-1,2,3,4-tetrahydro-1-benzoazocine-5-carboxamide (316 mg) (Compound 23) as a yellow amorphous material.

$^1$H-NMR (200 MHz, CDCl$_3$) δ 0.87-0.97 (6H, m), 1.34-1.45 (2H, m), 1.50-1.85 (6H, m), 1.80 (3H, s), 2.55-2.65 (2H, m), 3.52-3.58 (4H, m), 3.73-3.82 (6H, m), 3.95-4.17 (4H, m), 4.78 (1H, s), 4.92 (1H, s), 6.57 (1H, s), 6.71 (1H, d, J=8.8 Hz), 6.96 (2H, d, J=8.4 Hz), 7.32-7.45 (7H, m), 7.57 (1H, s), 7.76 (2H, d, J=8.4 Hz), 7.97 (1H, s). Elementary analysis C$_{41}$H$_{50}$N$_4$O$_4$S.0.25H$_2$O Calcd. C, 70.41; H, 7.28; N, 8.01; Found. C, 70.28; H, 7.30; N, 7.75. [α]$_D$=−131.7° (C=0.495% in ethanol)

EXAMPLE 18

(Preparation of Compound 24)

(−)-4-(((1-Propylimidazol-5-yl)methyl)sulfinyl)aniline di-p-toluoyl-D-tartarate monohydrate (660 mg) was dissolved in ethyl acetate (5 ml) and 1N hydrochloric acid (2.87 ml), followed by separation. To the aqueous layer was added an aqueous 25% potassium carbonate solution (2.87 ml), followed by extraction with 2-propanol-ethyl acetate (1:4) three times. The organic layers were combined and washed with saturated brine, dried with magnesium sulfate, and the solvent was distilled off under reduced pressure. To the resulting residue was added tetrahydrofuran, after which the solvent was distilled off again under reduced pressure to give (−)-4-(((1-propylimidazol-5-yl)methyl)sulfinyl)aniline.

Then, to a solution of 8-(4-(2-butoxyethoxy)phenyl)-1-isobutyl-9-methyl-1,2,3,4-tetrahydro-1-benzoazocine-5-carboxylic acid (380 mg) in tetrahydrofuran (10 ml) was added a drop of DMF, and then thionyl chloride (0.071 ml) was added, and the mixture was stirred under nitrogen atmosphere for 30 minutes. The resulting solution was added dropwise to a solution of (−)-4-(((1-propylimidazol-5-yl)methyl)sulfinyl)aniline and triethylamine (1.35 ml) in tetrahydrofuran (10 ml) at 0° C. under nitrogen atmosphere. The mixture was returned to room temperature and stirred for 3 hours, after which water was added and the mixture was extracted with ethyl acetate. The organic layer was washed with 10% aqueous acetic acid solution twice, with aqueous saturated sodium bicarbonate solution twice, and with saturated brine once, after which the resultant was dried with magnesium sulfate. After distilling off the solvent under reduced pressure, the resultant was separated and purified with a basic silica gel column chromatography (hexane:ethyl acetate=4:1→ethyl acetate) to give (−)-8-[4-(2-butoxyethoxy)phenyl]-1-isobutyl-9-methyl-N-[4-[[[1-propylimidazol-5-yl]methyl]sulfinyl]phenyl]-1,2,3,4-tetrahydro-1-benzoazocine-5-carboxamide (266 mg) (Compound 24) as a yellow amorphous material.

$^1$H-NMR (200 MHz, CDCl$_3$) δ 0.86-1.03 (12H, m), 1.26-1.78 (8H, m), 2.10-2.25 (1H, m), 2.25 (3H, s), 2.50-2.65 (2H, m), 3.07 (2H, d, J=7.0 Hz), 3.47-3.60 (4H, m), 3.73-3.83 (4H, m), 3.95-4.18 (4H, m), 6.58 (1H, s), 6.67 (1H, s), 6.92-6.99 (3H, m), 7.21 (2H, d, J=8.8 Hz), 7.34 (2H, d, J=8.8 Hz), 7.45 (2H, s), 7.72 (2H, d, J=8.8 Hz), 7.83 (1H, s). Elementary analysis C$_{42}$H$_{54}$N$_4$O$_4$S.0.25H$_2$O Calcd. C, 70.51; H, 7.68; N, 7.83; Found. C, 70.51; H, 7.68; N, 7.97. [α]$_D$=−128.0° (C=0.478% in ethanol)

EXAMPLE 19

(Preparation of Compound 25)

(−)-4-(((1-Propylimidazol-5-yl)methyl)sulfinyl)aniline di-p-toluoyl-D-tartarate monohydrate (962 mg) was dissolved in ethyl acetate (6 ml) and 1N hydrochloric acid (5.04 ml), followed by separation. To the aqueous layer was added an aqueous 25% potassium carbonate solution (5.04 ml), followed by extraction with 2-propanol-ethyl acetate (1:4) three times. The organic layers were combined and washed with saturated brine, dried with magnesium sulfate, and the solvent was distilled off under reduced pressure. To the resulting residue tetrahydrofuran was added, after which the solvent was distilled off again under reduced pressure to give (−)-4-(((1-propylimidazol-5-yl)methyl)sulfinyl)aniline.

Then, to a solution of 9-(4-(2-butoxyethoxy)phenyl)-1-propyl-2,3,4,5-tetrahydro-1H-1-benzoazonin-6-carboxylic acid (500 mg) in tetrahydrofuran (10 ml) was added a drop of DMF and then thionyl chloride (0.105 ml) was added, and the mixture was stirred under nitrogen atmosphere for 30 minutes. The resulting solution was added dropwise to a solution of (−)-4-(((1-propylimidazol-5-yl)methyl)sulfinyl) aniline and triethylamine (0.77 ml) in tetrahydrofuran (10 ml) at 0° C. under nitrogen atmosphere. The mixture was returned to room temperature and stirred for 3 hours, after which water was added and the mixture was extracted with ethyl acetate. The organic layer was washed with 10% aqueous acetic acid solution twice, with aqueous saturated sodium bicarbonate solution twice and with saturated brine once, after which the resultant was dried with magnesium sulfate. After distilling off the solvent under reduced pressure, the resultant was separated and purified with a basic silica gel column chromatography (hexane:ethyl acetate=1:4→ethyl acetate) to give (−)-9-[4-(2-butoxyethoxy)phenyl]-1-propyl-N-[4-[[[1-propylimidazol-5-yl]methyl]sulfinyl]phenyl]-2,3,4,5-tetrahydro-1H-1-benzoazonin-6-carboxamide (302 mg) (Compound 25) as a yellow amorphous material.

$^1$H-NMR (200 MHz, CDCl$_3$) δ 0.88-0.98 (9H, m), 1.25-2.00 (12H, m), 2.38-2.50 (2H, m), 2.95-3.10 (2H, m), 3.15-3.25 (2H, m), 3.55 (2H, t, J=6.6 Hz), 3.78-3.85 (4H, m), 4.03 (1H, d, J=14.2 Hz), 4.09-4.18 (3H, m), 6.57 (1H, s), 6.98 (2H, d, J=9.2 Hz), 7.13 (1H, d, J=8.4 Hz), 7.34-7.52 (8H, m), 7.76 (2H, d, J=8.8 Hz), 7.84 (1H, s). Elementary analysis C$_{41}$H$_{52}$N$_4$O$_4$S Calcd. C, 70.66; H, 7.52; N, 8.04; Found. C, 70.54; H, 7.57; N, 7.96. [α]$_D$=−93.7° (C=0.460% in ethanol)

EXAMPLE 20

(Preparation of Compound 26)

(−)-4-(((1-Propylimidazol-5-yl)methyl)sulfinyl)aniline di-p-toluoyl-D-tartarate monohydrate (932 mg) was dissolved in ethyl acetate (5 ml) and 1N hydrochloric acid (4.89 ml), followed by separation. To the aqueous layer was added an aqueous 25% potassium carbonate solution (4.89 ml), followed by extraction with 2-propanol-ethyl acetate (1:4) three times. The organic layers were combined and washed with saturated brine, dried with magnesium sulfate, and the solvent was distilled off under reduced pressure. To the resulting residue was added tetrahydrofuran, after which the solvent was distilled off again under reduced pressure to give (−)-4-(((1-propylimidazol-5-yl)methyl)sulfinyl)aniline.

Then, to a solution of 9-(4-(2-butoxyethoxy)phenyl)-1-isobutyl-2,3,4,5-tetrahydro-1H-1-benzoazonin-6-carboxylic acid (500 mg) in tetrahydrofuran (10 ml) was added a drop of DMF and then thionyl chloride (0.102 ml) was added, and the mixture was stirred under nitrogen atmosphere for 30 minutes. The resulting solution was added dropwise to a solution of (−)-4-(((1-propylimidazol-5-yl)methyl)sulfinyl) aniline and triethylamine (0.75 ml) in tetrahydrofuran (10 ml) at 0° C. under nitrogen atmosphere. The mixture was returned to room temperature and stirred for 3 hours, after which water was added and the mixture was extracted with ethyl acetate. The organic layer was washed with 10% aqueous acetic acid solution twice, with aqueous saturated sodium bicarbonate solution twice and with saturated brine once, after which the resultant was dried with magnesium sulfate. After distilling off the solvent under reduced pressure, the resultant was separated and purified with a basic silica gel column chromatography (hexane:ethyl acetate=1:4→ethyl acetate) to give (−)-9-[4-(2-butoxyethoxy)phenyl]-1-isobutyl-N-[4-[[[1-propylimidazol-5-yl]methyl]sulfinyl]phenyl]-2,3,4,5-tetrahydro-1H-1-benzoazonin-6-carboxamide (265 mg) (Compound 26) as a yellow amorphous material.

$^1$H-NMR (200 MHz, CDCl$_3$) δ 0.89-0.95 (12H, m), 1.26-1.85 (11H, m), 2.30-2.42 (2H, m), 2.74 (2H, d, J=7.2 Hz), 3.05-3.18 (2H, m), 3.55 (2H, t, J=7.6 Hz), 3.81-3.85 (4H, m), 4.00-4.18 (4H, m), 6.59 (1H, s), 6.99 (2H, d, J=8.8 Hz), 7.30-7.51 (9H, m), 7.75 (2H, d, J=8.4 Hz), 7.82 (1H, s). [α]$_D$=−121.0° (C=0.486% in ethanol)

EXAMPLE 21

(Preparation of Compound 27)

(−)-4-(((1-Propylimidazol-5-yl)methyl)sulfinyl)aniline di-p-toluoyl-D-tartarate monohydrate (935 mg) was dissolved in ethyl acetate (10 ml) and 1N hydrochloric acid (4.89 ml), followed by separation. To the aqueous layer was added an aqueous 25% potassium carbonate solution (4.89 ml), followed by extraction with 2-propanol-ethyl acetate (1:4) three times. The organic layers were combined and washed with saturated brine, dried with magnesium sulfate, and the solvent was distilled off under reduced pressure. To the resulting residue was added, after which the solvent was distilled off again under reduced pressure to give (−)-4-(((1-propylimidazol-5-yl)methyl)sulfinyl)aniline. Then, to a solution of 10-(4-(2-butoxyethoxy)phenyl)-1-propyl-1,2,3,4,5,6-hexahydro-1-benzoazetin-7-carboxylic acid (500 mg) in tetrahydrofuran (10 ml) was added a drop of DMF, and then thionyl chloride (0.10 ml) was added, and the mixture was stirred under nitrogen atmosphere for 30 minutes. The resulting solution was added dropwise to a solution of (−)-4-(((1-propylimidazol-5-yl)methyl)sulfinyl)aniline and triethylamine (1.49 ml) in tetrahydrofuran (10 ml) at 0° C. under nitrogen atmosphere. The mixture was returned to room temperature and stirred for 3 hours, after which water was added and the mixture was extracted with ethyl acetate. The organic layer was washed with 10% aqueous acetic acid solution twice, with aqueous saturated sodium bicarbonate solution twice, and with saturated brine once, after which the resultant was dried with magnesium sulfate. After distilling off the solvent under reduced pressure, the resultant was separated and purified with a basic silica gel column chromatography (hexane:ethyl acetate=1:4→ethyl acetate) to give (−)-10-[4-(2-butoxyethoxy)phenyl]-1-propyl-N-[4-[[[1-propylimidazol-5-yl]methyl]sulfinyl]phenyl]-1,2,3,4,5,6-hexahydro-1-benzoazetin-7-carboxamide (302 mg) (Compound 27) as a yellow amorphous material.

$^1$H-NMR (200 MHz, CDCl$_3$) δ 0.85-0.97 (9H, m), 1.25-1.81 (14H, m), 2.25-2.40 (2H, m), 2.83 (2H, t, J=7.0 Hz), 2.90-3.10 (2H, m), 3.55 (2H, t, J=6.6 Hz), 3.75-3.85 (4H, m), 4.03 (1H, d, J=14.0 Hz), 4.08-4.19 (3H, m), 6.58 (1H, s), 6.99 (2H, d, J=8.8 Hz), 7.27-7.55 (9H, m), 7.77 (2H, d, J=8.8 Hz), 7.89 (1H, s). Elementary analysis C$_{42}$H$_{54}$N$_4$O$_4$S.0.25H$_2$O Calcd. C, 70.51; H, 7.68; N, 7.83; Found. C, 70.26; H, 7.62; N, 7.69.

[α]$_D$=−125.0° (C=0.488% in ethanol)

EXAMPLE 22

(Preparation of Compound 28)

(−)-4-(((1-Propylimidazol-5-yl)methyl)sulfinyl)aniline di-p-toluoyl-D-tartarate monohydrate (905 mg) was dissolved in ethyl acetate (10 ml) and 1N hydrochloric acid (4.76 ml), followed by separation. To the aqueous layer was added an aqueous 25% potassium carbonate solution (4.76 ml), followed by extraction with 2-propanol-ethyl acetate (1:4) three times. The organic layers were combined and washed with saturated brine, dried with magnesium sulfate, and the solvent was distilled off under reduced pressure. To the resulting residue was added tetrahydrofuran, after which the solvent was distilled off again under reduced pressure to give (−)-4-(((1-propylimidazol-5-yl)methyl)sulfinyl)aniline. Then, to a solution of 10-(4-(2-butoxyethoxy)phenyl)-1-isobutyl-1,2,3,4,5,6-hexahydro-1-benzoazetin-7-carboxylic acid (500 mg) in tetrahydrofuran (10 ml) was added a drop of DMF, and then thionyl chloride (0.099 ml) was added, and the mixture was stirred under nitrogen atmosphere for 30 minutes. The resulting solution was added dropwise to the tetrahydrofuran (10 ml) solution of (−)-4-(((1-propylimidazol-5-yl)methyl)sulfinyl)aniline and triethylamine (1.9 ml) at 0° C. under nitrogen atmosphere. The mixture was returned to room temperature and stirred for 3 hours, after which water was added and the mixture was extracted with ethyl acetate. The organic layer was washed with 10% aqueous acetic acid solution twice, with aqueous saturated sodium bicarbonate solution twice, and with saturated brine once, after which the resultant was dried with magnesium sulfate. After distilling off the solvent under reduced pressure, the resultant was separated and purified with a basic silica gel column chromatography (hexane:ethyl acetate=1:4→ethyl acetate) to give (−)-10-[4-(2-butoxyethoxy)phenyl]-1-isobutyl-N-[4-[[[1-propylimidazol-5-yl]methyl]sulfinyl]phenyl]-1,2,3,4,5,6-hexahydro-1-benzoazetin-7-carboxamide (135 mg) (Compound 28) as a yellow amorphous material.

$^1$H-NMR (200 MHz, CDCl$_3$) δ 0.89-0.99 (12H, m), 1.25-1.85 (13H, m), 2.30-2.40 (2H, m), 2.69 (2H, d, J=7.0 Hz), 2.90-3.00 (2H, m), 3.55 (2H, t, J=7.0 Hz), 3.78-3.85 (4H, m), 4.03 (1H, d, J=14.2 Hz), 4.08-4.19 (3H, m), 6.59 (1H, s), 6.99 (2H, d, J=8.8 Hz), 7.24-7.60 (9H, m), 7.74 (2H, d, J=8.8 Hz), 7.83 (1H, s). Elementary analysis C$_{43}$H$_{56}$N$_4$O$_4$S.0.25H$_2$O Calcd. C, 70.80; H, 7.81; N, 7.68; Found. C, 70.81; H, 7.77; N, 7.63.

[α]$_D$=−125.3° (C=0.472% in ethanol)

EXAMPLE 23

(Preparation of Compound 29)

(−)-4-(((1-Propylimidazol-5-yl)methyl)sulfinyl)aniline di-p-toluoyl-D-tartarate monohydrate (6.58 g) was dissolved in ethyl acetate (50 ml) and 1N hydrochloric acid (33.5 ml), followed by separation. To the aqueous layer was added an aqueous 25% potassium carbonate solution (33.5 ml), followed by extraction with 2-propanol-ethyl acetate (1:4) twice. The organic layers were combined and washed with saturated brine, dried with magnesium sulfate, and the solvent was distilled off under reduced pressure. To the resulting residue tetrahydrofuran was added, after which the solvent was distilled off again under reduced pressure to give (−)-4-(((1-propylimidazol-5-yl)methyl)sulfinyl)aniline. Then, to a solution of 8-(4-(2-butoxyethoxy)phenyl)-1-formyl-1,2,3,4-tetrahydro-1-benzoazocine-5-carboxylic acid (3.0 g) in tetrahydrofuran (30 ml) was added a drop of DMF, and then oxalyl chloride (0.86 ml) was added, and the mixture was stirred under nitrogen atmosphere for 1 hour. The resulting solution was added dropwise to a solution of (−)-4-(((1-propylimidazol-5-yl)methyl)sulfinyl)aniline and pyridine (16 ml) in tetrahydrofuran (70 ml) at 0° C. under nitrogen atmosphere. The mixture was returned to room temperature and stirred for 3 hours, after which water was added and extracted with ethyl acetate. The organic layer was washed with 10% aqueous acetic acid solution twice, with aqueous saturated sodium bicarbonate solution twice, and with saturated brine once, after which the resultant was dried with magnesium sulfate. After distilling off the solvent under reduced pressure, the resultant was separated and purified with a basic silica gel column chromatography (methanol:ethyl acetate=1:25) to give (−)-8-[4-(2-butoxyethoxy) phenyl]-1-formyl-N-[4-[[[1-propylimidazol-5-yl]methyl]sulfinyl]phenyl]-1,2,3,4-tetrahydro-1-benzoazocine-5-carboxamide (3.34 g) (Compound 29) as a yellow amorphous material.

$^1$H-NMR (300 MHz, CDCl$_3$) δ 0.87-0.96 (9H, m), 1.34-1.46 (2H, m), 1.57-1.90 (6H, m), 2.47-2.60 (2H, m), 3.56 (2H, t, J=6.6 Hz), 3.73-3.84 (6H, m), 4.01-4.19 (4H, m), 6.59 (1H, s), 7.03 (2H, d, J=9.0 Hz), 7.30-7.36 (4H, m), 7.47-7.61 (5H, m), 7.76 (2H, d, J=9.0 Hz), 7.94 (1H, s), 8.47 (1H, s). [α]$_D$=−128.0° (C=0.443% in ethanol)

EXAMPLE 24

(Preparation of Compound 30)

To a solution of (−)-8-[4-(2-butoxyethoxy)phenyl]-1-formyl-N-[4-[[[1-propylimidazol-5-yl]methyl]sulfinyl]phenyl]-1,2,3,4-tetrahydro-1-benzoazocine-5-carboxamide (2.92 g) in methanol (75 ml) was added 3N hydrochloric acid (29.1 ml), after which the mixture was stirred at 80° C. for 7 hours. After diluting with water at 0° C., the product was neutralized with potassium carbonate. After extracting with ethyl acetate, the reaction product was washed with aqueous saturated solution of sodium bicarbonate and saturated brine, and dried with magnesium sulfate. The solvent was distilled off under reduced pressure, and the resultant residue was purified with a basic silica gel column chromatography (methanol:ethyl acetate=1:67) to give (−)-8-[4-(2-butoxyethoxy)phenyl]-N-[4-[[[1-propylimidazol-5-yl]methyl]sulfinyl]phenyl]-1,2,3,4-tetrahydro-1-benzoazocine-5-carboxamide (1.97 g) (Compound 30) as a yellow amorphous material.

$^1$H-NMR (300 MHz, CDCl$_3$) δ 0.88-0.96 (6H, m), 1.36-1.43 (2H, m), 1.50-1.77 (6H, m), 2.80-2.90 (2H, m), 3.55 (2H, t, J=6.9 Hz), 3.60-3.65 (2H, m), 3.76-3.82 (4H, m), 4.03 (1H, d, J=14.1 Hz), 4.09-4.16 (3H, m), 6.54-6.57 (2H, m), 6.95 (2H, d, J=8.7 Hz), 7.21-7.54 (8H, m), 7.76 (2H, d, J=8.7 Hz), 8.00 (1H, s). $[α]_D$=−138.9° (C=0.526% in ethanol)

EXAMPLE 25

(Preparation of Compound 31)

To a solution of (−)-8-[4(2-butoxyethoxy)phenyl]-N-[4-[[[1-propylimidazol-5-yl]methyl]sulfinyl]phenyl]-1,2,3,4-tetrahydro1-benzoazocine-5-carboxamide (30 mg) in 1,2-dichloroethane (10 ml) were added 2-methyl-3-tetrahydropyran-2-yloxy)propan-1-arl (403 mg) and triacetoxy sodium borohydride (297 mg)1 after which the mixture was stirred overnight. Water was added and the reaction mixture was extracted with ethyl acetate, and washed with aqueous saturated sodium bicarbonate solution and saturated brine, and then dried with magnesium sulfate. The solvent was distilled off under reduced pressure, and the resulting residue was purified by basic silica gel column chromatography (ethyl acetate) to give (−)-8-[4- (2-butoxyethoxy)phenyl]-1-(2-methyl-3-(tetrahydropyran-2-yloxy))propyl-N-[4-[[[1-propylimidazol-5-yl]methyl]sulfinyl]phenyl]-1,2,3,4-tetrahydro-1-benzoazocine-5-carboxamide (256 mg) (Compound 31) as a yellow amorphous material.

$^1$H-NMR (200 MHz, CDCl$_3$) δ 0.88-1.05 (9H, m), 1.30-1.90 (14H, m), 2.05-2.25 (1H, m), 2.50-2.65 (1H, m), 3.00-3.59 (8H, m), 3.60-3.83 (6H, m), 4.00-4.18 (4H, m), 4.56-4.65 (1H, m), 6.59 (1H, s), 6.98 (2H, d, J=8.8 Hz), 7.00-7.15 (1H, m), 7.34-7.48 (8H, m), 7.75-7.83 (2H, m), 8.30-8.40 (1H, m).

EXAMPLE 26

(Preparation of Compound 32)

To a solution of 8-[4-(2-butoxyethoxy)phenyl]-1-(2-methyl-3-(tetrahydropyran-2-yloxy))propyl-N-[4-[[[1-propylimidazol-5-yl]methyl]sulfinyl]phenyl]-1,2,3,4-tetrahydro-1-benzoazocine-5-carboxamide (236 mg) in tetrahydrofuran (30 ml) was added 1N hydrochloric acid (5.92 ml), after which the mixture was stirred under light shielding at room temperature for 3 hours. After adding water at 0° C., the mixture was neutralized with potassium carbonate, and extracted with ethyl acetate. The organic layer was washed with saturated brine, and dried with magnesium sulfate. The solvent was distilled off under reduced pressure, and the resulting residue was purified with basic silica gel column chromatography (methanol:ethyl acetate=1:40) to give 8-[4-(2-butoxyethoxy)phenyl]-1-(2-methyl-3-hydroxy)propyl-N-[4-[[[1-propylimidazol-5-yl]methyl]sulfinyl]phenyl]-1,2,3,4-tetrahydro-1-benzoazocine-5-carboxamide (177 mg) (Compound 32) as a yellow amorphous material.

$^1$H-NMR (300 MHz, CDCl$_3$) δ 0.82 (3H, d, J=6.6 Hz), 0.89-0.96 (6H, m), 1.36-1.43 (2H, m), 1.56-1.77 (6H, m), 2.05-2.20 (1H, m), 2.55-3.25 (5H, m), 3.40-3.57 (4H, m), 3.73-3.82 (5H, m), 4.06 (2H, s), 4.16 (2H, t, J=4.5 Hz), 6.61 (1H, s), 6.81 (1H, s), 6.99 (2H, d, J=8.7 Hz), 7.25-7.26 (1H, m), 7.34 (2H, d, J=8.7 Hz), 7.41-7.55 (5H, m), 7.73 (2H, d, J=8.7 Hz), 9.15 (1H, s). Elementary analysis C$_{41}$H$_{52}$N$_4$O$_5$S.0.5H$_2$O Calcd. C, 68.21; H, 7.40; N, 7.76; Found. C, 68.06; H, 7.69; N, 7.66.

EXAMPLE 27

(Preparation of Compound 33)

To a solution of 8-[4-(2-butoxyethoxy)phenyl]-1-isobutyl-1,2,3,4-tetrahydro-1-benzoazocine-5-carboxylic acid (700 mg) in tetrahydrofuran (10 ml) was added a drop of DMF. Then, after adding thionyl chloride (0.147 ml), the mixture was stirred under nitrogen atmosphere for 1 hour. The resulting solution was slowly added dropwise to a solution of ethyl 4-(2-(((4-aminophenyl)sulfanyl)methyl)imidazol-1-yl)butanoate (544 mg) in pyridine (10 ml) at 0° C. under nitrogen atmosphere. After stirring overnight at room temperature and under nitrogen atmosphere, to the reaction mixture was added water and the mixture was extracted with ethyl acetate. The organic layer was washed twice with water and once with saturated brine, and dried with magnesium sulfate. The solvent was distilled off under reduced pressure, and the resulting residue was purified with basic silica gel column chromatography (hexane:ethyl acetate=1:1→ethyl acetate), and re-crystallized from hexane-ethyl acetate to give ethyl 4-(2-(((4-(((8-(4-(2-butoxyethoxy)phenyl)-1-isobutyl-1,2,3,4-tetrahydro-1-benzoazocine-5-yl)carbonyl)amino)phenyl)sulfanyl)-methyl)imidazol-1-yl)butanoate (1.03 g) (Compound 33) as yellow crystals.

m.p. 130-131° C.

$^1$H-NMR (300 MHz, CDCl$_3$) δ 0.93 (3H, t, J=7.2 Hz), 1.00 (6H, d, J=6.6 Hz), 1.26 (3H, t, J=7.2 Hz), 1.33-1.46 (2H, m), 1.50-1.70 (4H, m), 2.00-2.25 (3H, m), 2.32 (2H, t, J=6.9 Hz), 2.50-2.65 (2H, m), 3.06 (2H, d, J=7.5 Hz), 3.45-3.60 (4H, m), 3.80 (2H, t, J=5.1 Hz), 3.95 (2H, t, J=7.2 Hz), 4.11-4.18 (6H, m), 6.83-6.85 (2H, m), 6.93-6.99 (3H, m), 7.26-7.55 (9H, m), 7.81 (1H, s). Elementary analysis C$_{44}$H$_{56}$N$_4$O$_5$S Calcd. C, 70.18; H, 7.50; N, 7.44; Found. C, 70.03; H, 7.45; N, 7.28.

EXAMPLE 28

(Preparation of Compound 34)

(−)-4-(((1-Propylimidazol-5-yl)methyl)sulfinyl)aniline di-p-toluoyl-D-tartarate monohydrate (620 mg) was dissolved in ethyl acetate (10 ml) and 1N hydrochloric acid (3.16 ml), followed by separation. To the aqueous layer was added an aqueous 25% potassium carbonate solution (3.16 ml), followed by extraction with 2-propanol-ethyl acetate (1:4) twice. The organic layers were combined and washed with saturated brine, dried with magnesium sulfate, and the solvent was distilled off under reduced pressure. To the resulting residue was added tetrahydrofuran, after which the solvent was distilled off again under reduced pressure to give (−)-4-(((1-propylimidazol-5-yl)methyl)sulfinyl)aniline.

Then, to a solution of 8-(4-(2-butoxyethoxy)phenyl)-1-((1-methyl pyrazol-4-yl)methyl)-1,2,3,4-tetrahydro-1-benzoazocine-5-carboxylic acid (350 mg) in dichloromethane (10 ml) was added a drop of DMF, and then oxalyl chloride (0.081 ml) was added, and the mixture was stirred under nitrogen atmosphere for 1 hour. The resulting solution was added dropwise to a solution of (−)-4-(((1-propylimidazol-5-yl)methyl)sulfinyl)aniline and triethylamine (2.6 ml) in dichloromethane (10 ml) at 0° C. under nitrogen atmosphere. The mixture was returned to room temperature and stirred for 3 hours, after which water was added and the mixture was extracted with ethyl acetate. The organic layer was washed with 10% aqueous acetic acid solution twice, with aqueous saturated sodium bicarbonate solution twice, and with saturated brine once, after which the resultant was dried with magnesium sulfate. After distilling off the solvent under reduced pressure, the resultant was separated and purified with a basic silica gel column chromatography (ethyl acetate→methanol:ethyl acetate=1:9) to give (−)-8-[4-(2-butoxyethoxy)phenyl]-1-((1-methylpyrazol-4-yl)methyl)-N-[4-[[[1-propylimidazol-5-yl]methyl]sulfinyl]phenyl]-1,2,3,4-tetrahydro-1-benzoazocine-5-carboxamide (98.3 mg) (Compound 34) as a yellow amorphous material.

$^1$H-NMR (300 MHz, CDCl$_3$) δ 0.88-0.95 (6H, m), 1.35-1.43 (2H, m), 1.50-1.70 (6H, m), 2.60-2.65 (2H, m), 3.52-3.57 (4H, m), 3.76-3.81 (4H, m), 3.87 (3H, m), 4.01 (1H, d, J=14.1 Hz), 4.04-4.16 (3H, m), 4.35 (2H, s), 6.54 (1H, s), 6.89 (1H, d, J=8.7 Hz), 6.95 (2H, d, J=8.7 Hz), 7.33-7.45 (9H, m), 7.55 (1H, s), 7.75 (2H, d, J=8.7 Hz), 8.06 (1H, s). Elementary analysis C$_{42}$H$_{50}$N$_6$O$_4$S.0.5H$_2$O Calcd. C, 67.81; H, 6.91; N, 11.30; Found. C, 67.72; H, 7.29; N, 11.06. [α]$_D$=−123.2° (C=0.451% in ethanol)

EXAMPLE 29

(Preparation of Compound 35)

(−)-4-(((1-Propylimidazol-5-yl)methyl)sulfinyl)aniline di-p-toluoyl-D-tartarate monohydrate (368 mg) was dissolved in ethyl acetate (5 ml) and 1N hydrochloric acid (1.87 ml), followed by separation. To the aqueous layer was added an aqueous 25% potassium carbonate solution (1.87 ml) was added, followed by extraction with 2-propanol-ethyl acetate (1:4). The organic layers were washed with saturated brine, dried with magnesium sulfate, and the solvent was distilled off under reduced pressure. To the resulting residue was added tetrahydrofuran, after which the solvent was distilled off again under reduced pressure to give (−)-4-(((1-propylimidazol-5-yl)methyl)sulfinyl)aniline. Then, to a solution of 8-(4-(2-butoxyethoxy)phenyl)-1-phenyl1,2,3,4-tetrahydro-1-benzoazocine-5-carboxylic acid (200 mg) in tetrahydrofuran (10 ml) was added a drop of DMF, and then oxalyl chloride (0.04 ml) was added, and the mixture was stirred under nitrogen atmosphere for 1 hour. The resulting solution was added dropwise to a solution of (−)-4-(((1-propylimidazol-5-yl)methyl)sulfinyl)aniline and triethylamine (1.54 ml) in tetrahydrofuran (10 ml) at 0° C. under nitrogen atmosphere. The mixture was returned to room temperature and stirred for 3 hours, after which water was added and the mixture was extracted with ethyl acetate. The organic layer was washed with 10% aqueous acetic acid solution twice, with aqueous saturated sodium bicarbonate solution twice, and with saturated brine once, after which the resultant was dried with magnesium sulfate. After distilling off the solvent under reduced pressure, the resultant was separated and purified with a basic silica gel column chromatography (ethyl acetate→methanol: ethyl acetate=1:99) to give (−)-8-[4-(2-butoxyethoxy) phenyl]-1-phenyl-N-[4-[[[1-propylimidazol-5-yl]methyl]sulfinyl]phenyl]-1,2,3,4-tetrahydro-1-benzoazocine-5-carboxamide (14.6 mg) (Compound 35) as a yellow amorphous material.

$^1$H-NMR (300 MHz, CDCl$_3$) δ 0.89-0.96 (6H, m), 1.34-1.46 (2H, m), 1.57-1.90 (6H, m), 2.40-2.60 (2H, m), 3.56 (2H, t, J=6.6 Hz), 3.76-3.95 (6H, m), 3.99 (1H, d, J=14.4 Hz), 4.07 (1H, d, J=14.4 Hz), 4.18 (2H, t, J=4.5 Hz), 6.47 (2H, d, J=8.4 Hz), 6.56 (1H, s), 6.71-6.79 (2H, m), 6.93 (1H, s), 7.02 (2H, d, J=9.0 Hz), 7.18-7.63 (12H, m).

EXAMPLE 30

(Preparation of Compound 36)

To a solution of 8-[4-(2-butoxyethoxy)phenyl]-1-isobutyl-1,2,3,4-tetrahydro-1-benzoazocine-5-carboxylic acid (700 mg) in tetrahydrofuran (10 ml) was added a drop of DMF. Then, after adding thionyl chloride (0.15 ml), the mixture was stirred under nitrogen atmosphere for 1 hour. After distilling off the solvent and excessive thionyl chloride under reduced pressure, the mixture was dissolved in THF (10 ml). The resulting solution was added dropwise to a solution of S-(4-aminophenyl) O-benzyl carbonothioate (402 mg) and triethylamine (1.08 ml) in THF (10 ml) at 0° C. under argon atmosphere. After completion of dropwise addition, the reactant was returned to room temperature and stirred under argon atmosphere overnight, followed by adding methanol (20 ml). Further, an aqueous solution of 1N sodium hydroxide (7.75 ml) was added and the mixture was stirred under argon atmosphere for 30 minutes. Then, 5-chloromethyl-4-methyl-1-propylimidazole hydrochloride (421 mg) was added and stirring was made under argon atmosphere for 1.5 hours. Water was added and the mixture was extracted with ethyl acetate, after which the organic layer was washed with saturated brine, and the resultant was dried with magnesium sulfate. After distilling off the solvent under reduced pressure, the resultant was separated and purified with basic silica gel column chromatography (hexane:ethyl acetate=1:1→ethyl acetate) to give 8-[4-(2-butoxyethoxy)phenyl]-1-isobutyl-N-[4-[[[4-methyl-1-propylimidazol-5-yl]methyl]sulfanyl]phenyl]-1,2,3,4-tetrahydro-1-benzoazocine-5-carboxamide (355 mg) as a yellow amorphous material (Compound 36).

$^1$H-NMR (300 MHz, CDCl$_3$) δ 0.91-1.01 (12H, m), 1.35-1.45 (2H, m), 1.50-1.65 (4H, m), 1.70-1.90 (5H, m), 2.10-2.25 (1H, m), 2.55-2.62 (2H, m), 3.06 (2H, d, J=7.5 Hz), 3.50-3.60 (4H, m), 3.80 (2H, t, J=4.8 Hz), 3.87 (2H, t, J=7.8 Hz), 3.95 (2H, s), 4.15 (2H, t, J=4.8 Hz), 6.84 (1H, d, J=9.3 Hz), 6.95 (2H, d, J=9.0 Hz), 7.22-7.54 (10H, m), 7.67 (1H, s). Elementary analysis C$_{42}$H$_{54}$N$_4$O$_3$S.0.5H$_2$O Calcd. C, 71.66; H, 7.87; N, 7.96; Found. C, 71.67; H, 7.66; N, 8.13.

EXAMPLE 31

(Preparation of Compound 37)

To a solution of 8-[4-(2-butoxyethoxy)phenyl]-1-isobutyl-N-[4-[[[4-methyl-1-propylimidazol-5-yl]methyl]sulfanyl]phenyl]-1,2,3,4-tetrahydro-1-benzoazocine-5-carboxamide (300 mg) in dichloromethane (10 ml) was added dropwise a 70% solution of 3-chloro-perbenzoic acid (117 mg) in dichloromethane (10 ml) at −78° C. After stirring as such for 1 hour, the dry ice-acetone bath was removed, and an aqueous sodium thiosulfate solution was added with vigorous stirring. The mixture was returned to room temperature and stirred for 30 minutes, after which water was added and the mixture was extracted with ethyl acetate. The organic layer was washed with aqueous saturated sodium bicarbonate solution and saturated aqueous brine, and was dried with magnesium sulfate. The solvent was distilled off under reduced pressure, and the resulting residue was separated and purified with basic silica gel column chromatography (hexane:ethyl acetate=1:4→ethyl acetate) to give 8-[4-(2-butoxyethoxy)phenyl]-1-isobutyl-N-[4-[[[4-methyl-1-propylimidazol-5-yl]methyl]sulfinyl]phenyl]-1,2,3,4-tetrahydro-1-benzoazocine-5-carboxamide (230 mg) as a yellow amorphous material (Compound 37).

$^1$H-NMR (300 MHz, CDCl$_3$) δ 0.86-0.96 (6H, m), 1.00 (6H, d, J=6.6 Hz), 1.33-1.46 (2H, m), 1.56-1.65 (9H, m), 2.10-2.25 (1H, m), 2.55-2.65 (2H, m), 3.07 (2H, d, J=7.2 Hz), 3.50-3.60 (4H, m), 3.75 (2H, t, J=7.5 Hz), 3.81 (2H, t, J=4.8 Hz), 4.05 (2H, s), 4.15 (2H, t, J=4.8 Hz), 6.84 (1H, d, J=9.0 Hz), 6.96 (2H, d, J=8.7 Hz), 7.26-7.31 (3H, m), 7.37-7.44 (4H, m), 7.56 (1H, s); 7.75 (2H, d, J=8.7 Hz), 8.26 (1H, s). Elementary analysis C$_{42}$H$_{54}$N$_4$O$_4$S.0.5H$_2$O Calcd. C, 70.07; H, 7.70; N, 7.78; Found. C, 70.15; H, 7.65; N, 7.67.

EXAMPLE 32

(Preparation of Compound 38)

To a solution of 8-[4-(2-butoxyethoxy)phenyl]-1-isobutyl-1,2,3,4-tetrahydro-1-benzoazocine-5-carboxylic acid (350 mg) in tetrahydrofuran (10 ml) was added a drop of DMF. Then, after adding thionyl chloride (0.073 ml), the mixture was stirred under nitrogen atmosphere for 1 hour. The solution was slowly added dropwise to a solution of 3-methyl-4-[((1-propylimidazol-5-yl)methyl)sulfanyl] aniline (223 mg) in pyridine (10 ml) at 0° C. under nitrogen atmosphere. After stirring the mixture at room temperature under nitrogen atmosphere overnight, water was added and the reaction mixture was extracted with ethyl acetate. The organic layer was washed with water and saturated brine, and dried with magnesium sulfate. The solvent was distilled off under reduced pressure, and the resulting residue was purified by basic silica gel column chromatography (hexane:ethyl acetate=1:1→ethyl acetate) to give 8-[4-(2-butoxyethoxy)phenyl]-1-isobutyl-N-[3-methyl-4-[[[1-propylimidazol-5-yl]methyl]sulfanyl]phenyl]-1,2,3,4-tetrahydro-1-benzoazocine-5-carboxamide (444 mg) as a yellow amorphous material (Compound 38).

$^1$H-NMR (300 MHz, CDCl$_3$) δ 0.91-1.01 (12H, m), 1.33-1.46 (2H, m), 1.50-1.66 (4H, m), 1.80-1.92 (2H, m), 2.10-2.25 (1H, m), 2.31 (3H, s), 2.55-2.62 (2H, m), 3.07 (2H, d, J=7.5 Hz), 3.47-3.57 (4H, m), 3.80 (2H, t, J=4.5 Hz), 3.91-3.96 (4H, m), 4.15 (2H, t, J=4.5 Hz), 6.66 (1H, s), 6.85 (1H, d, J=8.7 Hz), 6.96 (2H, d, J=8.7 Hz), 7.25-7.51 (9H, m), 7.63 (1H, s). Elementary analysis C$_{42}$H$_{54}$N$_4$O$_3$S.0.25H$_2$O Calcd. C, 72.12; H, 7.85; N, 8.01; Found. C, 72.05; H, 7.91; N, 7.83.

EXAMPLE 33

(Preparation of Compound 39)

To a solution of 8-[4-(2-butoxyethoxy)phenyl]-1-isobutyl-N-[3-methyl-4-[[[1-propylimidazol-5-yl]methyl]sulfanyl]phenyl]-1,2,3,4-tetrahydro-1-benzoazocine-5-carboxamide (370 mg) in dichloromethane (10 ml) was added dropwise a 70% solution of 3-chloro-perbenzoic acid (144 mg) in dichloromethane (10 ml) at −78° C. After stirring as such for 1 hour, the dry ice-acetone bath was removed, and an aqueous sodium thiosulfate solution was added with vigorous stirring. The mixture was returned to room temperature and stirred for 30 minutes, after which water was added and the mixture was extracted with ethyl acetate. The organic layer was washed with aqueous saturated sodium bicarbonate solution and saturated brine, and was dried with magnesium sulfate. The solvent was distilled off under reduced pressure, and the resulting residue was separated and purified with basic silica gel column chromatography (ethyl acetate→methanol:ethyl acetate=1:40) and recrystallized from hexane-ethyl acetate to give 8-[4-(2-butoxyethoxy)phenyl]-1-isobutyl-N-[3-methyl-4-[[[1-propylimidazol-5-yl]methyl]sulfinyl]phenyl]-1,2,3,4-tetrahydro-1-benzoazocine-5-carboxamide (289 mg) as yellow crystals (Compound 39).

$^1$H-NMR (300 MHz, CDCl$_3$) δ 0.91-1.02 (12H, m), 1.33-1.45 (2H, m), 1.50-1.70 (4H, m), 1.73-1.80 (2H, m), 2.05-2.25 (4H, m), 2.55-2.65 (2H, m), 3.08 (2H, d, J=7.2 Hz), 3.50-3.57 (4H, m), 3.79-3.87 (4H, m), 4.03 (1H, d, J=14.4 Hz), 4.08-4.17 (3H, m), 6.51 (1H, s), 6.85 (1H, d, J=8.7 Hz), 6.97 (2H, d, J=8.7 Hz), 7.32-7.53 (7H, m), 7.63 (1H, d, J=8.7 Hz), 7.69 (1H, s), 7.79 (1H, s). Elementary analysis C$_{42}$H$_{54}$N$_4$O$_4$S Calcd. C, 70.95; H, 7.66; N, 7.88; Found. C, 70.65; H, 7.51; N, 7.74.

EXAMPLE 34

(Preparation of Compound 40)

To a solution of 8-[4-(2-butoxyethoxy)phenyl]-1-isobutyl-1,2,3,4-tetrahydro-1-benzoazocine-5-carboxylic acid (350 mg) in tetrahydrofuran (10 ml) was added a drop of DMF. Then, after adding thionyl chloride (0.073 ml), the mixture was stirred under nitrogen atmosphere for 1 hour. The solution was slowly added dropwise to a solution of 3-methyl-4-[((4-methyl-1-propylimidazol-5-yl)methyl)sulfanyl]aniline (235 mg) in pyridine (10 ml) at 0° C. under nitrogen atmosphere. After stirring the mixture at room temperature under nitrogen atmosphere overnight, water was added and the reaction mixture was extracted with ethyl acetate. The organic layer was washed with water and saturated brine, and dried with magnesium sulfate. The solvent was distilled off under reduced pressure, and the resulting residue was purified by basic silica gel column chromatography (hexane:ethyl acetate=1:1→ethyl acetate) to give 8-[4-(2-butoxyethoxy)phenyl]-1-isobutyl-N-[3-methyl-4-[[[4-methyl-1-propylimidazol-5-yl]methyl]sulfanyl]phenyl]-1,2,3,4-tetrahydro-1-benzoazocine-5-carboxamide (351 mg) as a yellow amorphous material (Compound 40).

$^1$H-NMR (300 MHz, CDCl$_3$) δ 0.91-1.01 (12H, m), 1.35-1.43 (2H, m), 1.56-1.65 (4H, m), 1.79-1.86 (5H, m), 2.10-2.25 (1H, m), 2.30 (3H, s), 3.06 (2H, d, J=7.2 Hz), 3.47-3.57 (4H, m), 3.80 (2H, t, J=4.5 Hz), 3.84-3.88 (4H, m), 4.15 (2H, t, J=4.5 Hz), 6.84 (1H, d, J=9.0 Hz), 6.96 (2H, d, J=9.0 Hz), 7.22-7.50 (9H, m), 7.61 (1H, s). Elementary analysis C$_{43}$H$_{56}$N$_4$O$_3$S Calcd. C, 72.84; H, 7.96; N, 7.90; Found. C, 72.64; H, 8.06; N, 7.87.

EXAMPLE 35

(Preparation of Compound 41)

To a solution of 8-[4-(2-butoxyethoxy)phenyl]-1-isobutyl-N-[3-methyl-4-[[[4-methyl-1-propylimidazol-5-yl]methyl]sulfanyl]phenyl]-1,2,3,4-tetrahydro-1-benzoazocine-5-carboxamide (290 mg) in dichloromethane (10 ml) was added dropwise a 70% solution of 3-chloro-perbenzoic acid (111 mg) in dichloromethane (10 ml) at −78° C. After stirring as such for 1 hour, the dry ice-acetone bath was removed, and an aqueous sodium thiosulfate solution was added under vigorous stirring. The mixture was returned to room temperature and stirred for 30 minutes, after which water was added and the mixture was extracted with ethyl acetate. The organic layer was washed with aqueous saturated sodium bicarbonate solution and saturated brine, and was dried with magnesium sulfate. The solvent was distilled off under reduced pressure, and the resulting residue was separated and purified with basic silica gel column chromatography (ethyl acetate→methanol:ethyl acetate=1:30) and recrystallized from hexane-ethyl acetate to give 8-[4-(2-butoxyethoxy)phenyl]-1-isobutyl-N-[3-methyl-4-[[[4-methyl-1-propylimidazol-5-yl]methyl]sulfinyl]phenyl]-1,2,3,4-tetrahydro-1-benzoazocine-5-carboxamide (232 mg) as yellow crystals (Compound 41).

m.p. 175.5-176.0° C.

$^1$H-NMR (300 MHz, CDCl$_3$) δ 0.89-1.01 (12H, m), 1.36-1.43 (2H, m), 1.50-1.80 (9H, m), 2.04 (3H, s), 2.08-2.25 (1H, m), 2.55-2.65 (2H, m), 3.07 (2H, d, J=7.2 Hz), 3.50-3.60 (4H, m), 3.79-3.83 (4H, m), 4.04 (1H, d, J=13.8 Hz), 4.09 (1H, d, J=13.8 Hz), 4.15 (2H, t, J=5.1 Hz), 6.85 (1H, d, J=8.7 Hz), 6.97 (2H, d, J=8.7 Hz), 7.31 (1H, d, J=1.8 Hz), 7.37-7.53 (6H, m), 7.65 (1H, d, J=2.1 Hz), 7.68 (1H, d, J=8.7 Hz), 7.89 (1H, s). Elementary analysis C$_{43}$H$_{56}$N$_4$O$_4$S Calcd. C, 71.24; H, 7.79; N, 7.73; Found. C, 70.97; H, 7.76; N, 7.43.

EXAMPLE 36

(Preparation of Compound 42)

To a solution of 8-[4-(2-butoxyethoxy)phenyl]-1-isobutyl-1,2,3,4-tetrahydro-1-benzoazocine-5-carboxylic acid (200 mg) in tetrahydrofuran (10 ml) was added a drop of DMF. Then, after adding thionyl chloride (0.042 ml), the mixture was stirred under nitrogen atmosphere for 1 hour. After the solvent and excessive thionyl chloride were distilled off under reduced pressure, the mixture was dissolved in tetrahydrofuran (15 ml). The solution was added dropwise to a solution of 4-[[N-methyl-N-(tetrahydropyran-4-yl)amino]methyl]anilin (127 mg) and triethylamine (1.6 ml) in tetrahydrofuran (10 ml) at 0° C. under nitrogen atmosphere. After stirring the mixture at room temperature under nitrogen atmosphere overnight, water was added and the reaction mixture was extracted with ethyl acetate. The organic layer was washed with water and saturated brine, and dried with magnesium sulfate. The solvent was distilled off under reduced pressure, and the resulting residue was purified by basic silica gel column chromatography (methanol:ethyl acetate=1:8) to give 8-(4-(2-butoxyethoxy)phenyl)-1-isobutyl-N-(4-((methyl(tetrahydro-2H-pyran-4-yl)amino)methyl)phenyl)-1,2,3,4-tetrahydro-1-benzoazocine-5-carboxamide (257 mg) as a yellow amorphous material (Compound 42).

$^1$H-NMR (200 MHz, CDCl$_3$) δ 0.90-1.01 (9H, m), 1.33-1.85 (10H, m), 2.00-2.25 (4H, m), 2.55-2.65 (2H, m), 3.06 (2H, d, J=7.4 Hz), 3.37 (2H, td, J=11.4, 3.2 Hz), 3.45-3.58 (6H, m), 3.80 (2H, t, J=4.4 Hz), 4.03 (2H, d, J=9.8 Hz), 4.15 (2H, t, 4.4 Hz), 6.85 (1H, d, 8.8 Hz), 6.96 (2H, d, 8.8 Hz), 7.28-7.59 (10H, m). Elementary analysis C$_{41}$H$_{55}$N$_3$O$_4$.0.25H$_2$O Calcd. C, 74.79; H, 8.50; N, 6.38; Found. C, 74.58; H, 8.28; N, 6.34.

EXAMPLE 37

(Preparation of Compound 43)

To (−)-4-[(1-propyl-1H-imidazol-5-yl)methyl)sulfinyl]aniline di-p-toluoyl-D-tartarate monohydrate (1.79 g) was added 1N hydrochloric acid (9 ml), and the mixture was extracted with ethyl acetate. To the aqueous layer was added an aqueous 25% potassium carbonate solution (9 ml), and the mixture was extracted with ethyl acetate-2-propanol (4:1). The organic layer was washed with saturated brine, and dried with magnesium sulfate. The resulting product was concentrated under reduced pressure to give (−)-4-[(1-propyl-1H-imidazol-5-yl)methyl]sulfinyl]aniline as a colorless amorphous material.

To a solution of 1-isobutyl-8-[4-(2-propoxyethoxy) phenyl]-1,2,3,4-tetrahydro-1-benzoazocine-5-carboxylic acid (0.90 g) in THF (10 ml) were added thionyl chloride (0.23 ml) and DMF (a drop), and the mixture was stirred at room temperature for 1.5 hours. After concentration under reduced pressure, the residual THF (35 ml) solution was added dropwise to a suspension of (−)-4-[(1-propyl-1H-imidazol-5-yl)methyl]sulfinyl]aniline and triethylamine (2.17 ml) in THF (10 ml) at room temperature. After stirring at room temperature for 18 hours, water was added and the mixture was extracted with ethyl acetate. The organic layer was washed with 5% aqueous acetic acid solution, with aqueous saturated sodium bicarbonate solution, and with saturated brine, and dried with magnesium sulfate. After concentration under reduced pressure, the residue was separated and purified with a column chromatography (basic silica gel, ethyl acetate:hexane 9:1) to give (−)-1-isobutyl-8-[4-(2-propoxyethoxy)phenyl]-N-[4-[[(1-propyl-1H-imidazol-5-yl]methyl]sulfinyl]phenyl]-1,2,3,4-tetrahydro-1-benzoazocine-5-carboxamide (677.7 mg) (Compound 43) as a yellow amorphous material.

[α]$_D$=−135.5° (c=0.503, in ethanol)

$^1$H-NMR (200 MHz, CDCl$_3$) δ 0.87-1.02 (12H, m), 1.54-1.82 (6H, m), 2.03-2.32 (1H, m), 2.53-2.66 (2H, m), 3.07 (2H, d, J=7.0 Hz), 3.48-3.54 (4H, m), 3.75-3.83 (4H, m), 4.01 (1H, d, J=13.8 Hz), 4.08-4.18 (3H, m), 6.56 (1H, s), 6.85 (1H, d, J=8.4 Hz), 6.96 (2H, d, J=8.8 Hz), 7.32-7.46 (7H, m), 7.54 (1H, s), 7.76 (2H, d, J=8.8 Hz), 7.99 (1H, s). IR (KBr) 3094, 1663, 1607, 1588, 1518, 1497, 1314, 1248, 1177, 1123, 1047, 831 cm$^{-1}$

Elementary analysis C$_{40}$H$_{50}$N$_4$O$_4$S.0.5H$_2$O Calcd. C, 69.43; H, 7.43; N, 8.10: Found. C, 69.46; H, 7.49; N, 7.91.

EXAMPLE 38

(Preparation of Compound 44)

To (−)-4-[(1-propyl-1H-imidazol-5-yl)methyl)sulfinyl]aniline di-p-toluoyl-D-tartarate monohydrate (1.77 g) was added 1N hydrochloric acid (9 ml), and the mixture was extracted with ethyl acetate. To the aqueous layer was added an aqueous 25% potassium carbonate solution (9 ml), and the mixture was extracted with ethyl acetate-2-propanol (4:1). The organic layer was washed with saturated brine, and dried with magnesium sulfate. The resulting product was concentrated under reduced pressure to give (−)-4-[(1-propyl-1H-imidazol-5-yl)methyl]sulfinyl]aniline as a colorless amorphous material.

To a solution of 8-[4-(2-propoxyethoxy)phenyl]-1-propyl-1,2,3,4-tetrahydro-1-benzoazocine-5-carboxylic acid (0.75 g) in THF (10 ml) were added thionyl chloride (0.19 ml) and DMF (a drop), and the mixture was stirred at room temperature for 1 hour. After concentration under reduced pressure, the residual THF (30 ml) solution was added dropwise to a suspension of (−)-4-[(1-propyl-1H-imidazol-5-yl)methyl]sulfinyl]aniline and triethylamine (1.48 ml) in THF (20 ml) at room temperature. After stirring at room temperature for 20 hours, water was added and the mixture was extracted with ethyl acetate. The organic layer was washed with 5% aqueous acetic acid solution, aqueous saturated sodium bicarbonate solution and saturated brine, and dried with magnesium sulfate. After concentration under reduced pressure, the residue was separated and purified with a column chromatography (basic silica gel, ethyl acetate:hexane 9:1) to give (−)-8-[4-(2-propoxyethoxy)phenyl]-1-propyl-N-[4-[[(1-propyl-1H-imidazol-5-yl)methyl]sulfinyl]phenyl]-1,2,3,4-tetrahydro-1-benzoazocine-5-carboxamide (650.3 mg) (Compound 44) as a yellow amorphous material.

$[\alpha]_D = -138.2°$ (C=0.499%, in ethanol solution)

$^1$H-NMR (200 MHz, CDCl$_3$) δ 0.87-1.03 (9H, m), 1.52-1.84 (8H, m), 2.53-2.66 (2H, m), 3.12-3.28 (2H, m), 3.48-3.59 (4H, m), 3.74-3.83 (4H, m), 4.01 (1H, d, J=14.0 Hz), 4.07-4.18 (3H, m), 6.56 (1H, s), 6.80 (1H, d, J=8.8 Hz), 6.96 (2H, d, J=8.8 Hz), 7.30-7.46 (7H, m), 7.55 (1H, s), 7.76 (2H, d, J=8.8 Hz), 8.00 (1H, s). IR (KBr) 3030, 1663, 1607, 1588, 1518, 1497, 1314, 1246, 1175, 1119, 1088, 1047, 831 cm$^{-1}$

Elementary analysis C$_{39}$H$_{48}$N$_4$O$_4$S.0.5H$_2$O Calcd. C, 69.10; H, 7.29; N, 8.26: Found. C, 69.04; H, 7.41; N, 7.96.

EXAMPLE 39

(Preparation of Compound 45)

To a solution of (−)-8-[4(2-butoxyethoxy)phenyl]-1-propyl-N-[4-[[(1-propyl-1H-imidazol5-yl]methyl]sulfinyl]phenyl[1,2,3,4-tetrahydro-1-benzoazocine-5-carboxamide (201.5 mg) in ethyl acetate (4 ml) was added methanesulfonic acid (28.9 mg) at room temperature, and the mixture was stirred at room temperature overnight. The resultant was concentrated under reduced pressure, and the precipitated crystals were collected by filtration. The crystals were washed with ethyl acetate to give (S)-(−)-8-[4-(2-butoxyethoxy) phenyl]-1-propyl-N-[4-[[(1-propyl-1H-imidazol-5-yl]methyl]sulfinyl]phenyl]-1,2,3,4-tetrahydro-1-benzoazocine-5-carboxamide/methanesulfonate (118.6 mg) (Compound 45) as yellow crystals.

mp 153-156° C.

$[\alpha]_D = -202.88°$ (C=0.520% in ethanol)

$^1$H-NMR (300 MHz, DMSO-d$_6$) δ 0.82-0.97 (9H, m), 1.29-1.36 (2H, m), 1.41-1.54 (4H, m), 1.56-1.79 (4H, m), 2.29 (3H, s), 2.40-2.54 (2H, m), 3.15-3.26 (2H, m), 3.43-3.55 (4H, m), 3.69-3.72 (2H, m), 3.96-4.01 (2H, m), 4.08-4.12 (2H, m), 4.35 (1H, d, J=14.6 Hz), 4.67 (1H,d, J=14.6 Hz), 6.82 (1H, d, J=8.7 Hz), 6.98 (2H, d, J=8.7 Hz), 7.15 (1H, s), 7.42-7.59 (8H, m), 7.92 (2H, d, J=8.4 Hz), 9.03 (1H, s). IR (KBr) 3275, 3108, 1655, 1603, 1586, 1518, 1497, 1314, 1236, 1177, 1036, 831 cm$^{-1}$

Elementary analysis C$_{41}$H$_{54}$N$_4$O$_7$S$_2$.0.5H$_2$O Calcd. C, 62.49; H, 7.03; N, 7.11: Found. C, 62.57; H, 7.14; N, 7.10.

EXAMPLE 40

(Preparation of Compound 46)

To a solution of 8-[4-(2-butoxyethoxy)phenyl]-1-isobutyl-1,2,3,4-tetrahydro-1-benzoazocine-5-carboxylic acid (0.8 g) in THF (10 ml) were added thionyl chloride (0.19 ml) and DMF (a drop), and the mixture was stirred at room temperature for 1.5 hour. After concentration under reduced pressure, the residual THF (30 ml) solution was added dropwise to a solution of S-(4-aminophenyl) O-benzylthiocarbonate (0.46 g) and triethylamine (1.48 ml) in THF (5 ml) at 0° C. After stirring at room temperature for 4 days, methanol (30 ml) and aqueous 1N sodium hydroxide solution (11 ml) were added, and the mixture was stirred for 0.5 hour. To the reaction system was added 3-chloromethyl-4-propyl-4H-1,2,4-triazol/hydrochloride (0.38 g), and the mixture was stirred for 2 hours. After concentration under reduced pressure, the contents were extracted with ethyl acetate. The organic layer was washed with saturated brine, and dried with magnesium sulfate. After concentration under reduced pressure, the residue was separated and purified with a column chromatography (basic silica gel, ethyl acetate), and further recrystallized (ethyl acetate-diisopropyl ether) to give 8-[4-(2-butoxyethoxy)phenyl]-1-isobutyl-N-[4-[[(4-propyl-4H-1,2,4-triazol-3-yl)methyl]thio]phenyl]-1,2,3,4-tetrahydro-1-benzazocine-5-carboxamide (871.2 mg) (Compound 46) as yellow crystals.

mp 122-126° C.

$^1$H-NMR (200 MHz, CDCl$_3$) δ 0.93 (3H, t, J=7.2 Hz), 0.96 (3H, t, J=7.4 Hz), 0.99 (6H, d, J=6.6 Hz), 1.34-1.49 (2H, m), 1.52-1.85 (6H, m), 2.02-2.29 (1H, m), 2.50-2.63 (2H, m), 3.06 (2H, d, J=7.4 Hz), 3.44-3.54 (2H, m), 3.55 (2H, t, J=6.6 Hz), 3.78-3.89 (4H, m), 4.11 (4H, m), 4.15 (2H, t, J=5.0 Hz), 6.83 (1H, d, J=8.8 Hz), 6.95 (2H, d, J=8.8 Hz), 7.16-7.17 (1H, m), 7.27-7.45 (6H, m), 7.58 (2H, d, J=8.8 Hz), 8.03 (1H, s), 8.18 (1H, s). IR (KBr) 3031, 1661, 1605, 1588, 1520, 1497, 1314, 1248, 1179, 1128, 829 cm$^{-1}$

Elementary analysis C$_{40}$H$_{51}$N$_5$O$_3$S.0.25H$_2$O Calcd. C, 69.99; H, 7.56; N, 10.20: Found. C, 69.93; H, 7.50; N, 10.28.

EXAMPLE 41

(Preparation of Compound 47)

To a solution of 8-[4-(2-butoxyethoxy)phenyl]-1-isobutyl-N-[4-[[(4-propyl-4H-1,2,4-triazol-3-yl)methyl]thio]phenyl]-1,2,3,4-tetrahydro-1-benzoazocine-5-carboxamide (0.70 g) in dichloromethane (20 ml) was added dropwise a solution of 3-chloro-perbenzoic acid (70%, 0.38 g) in dichloromethane (10 ml) and the mixture was stirred at −78° C. for 1 hour. To the reaction system was added an aqueous sodium thiosulfate solution, and the mixture was stirred at room temperature for 10 minutes. The mixture was extracted with ethyl acetate. The organic layer was washed with aqueous sodium bicarbonate solution and saturated brine, and was dried with magnesium sulfate. The resultant was concentrated under reduced pressure, the residue was separated and purified with column chromatography (basic silica gel, ethyl acetate→ethanol:ethyl acetate 1:19), followed by recrystallization (ethyl acetate-diisopropyl ether) to give 8-[4-(2-butoxyethoxy)phenyl]-1-isobutyl-N-[4-[[(4-propyl-4H-1,2,4-triazol-3-yl)methyl]sulfinyl]phenyl]-1,2,3,4-tetrahydro-1-benzazocin-5-carboxamide (490.1 mg) as yellow crystals (Compound 47).

mp 105-110° C.

¹H-NMR (300 MHz, CDCl$_3$) δ 0.91 (3H, t, J=7.4 Hz), 0.94 (3H, t, J=7.2 Hz), 1.00 (6H, d, J=6.6 Hz), 1.32-1.45 (2H, m), 1.50-1.73 (6H, m), 2.08-2.26 (1H, m), 2.52-2.62 (2H, m), 3.08 (2H, d, J=6.9 Hz), 3.46-3.58 (4H, m), 3.61-3.82 (4H, m), 3.96 (1H, d, J=13.8 Hz), 4.11-4.16 (3H, m), 6.83 (1H, d, J=9.0 Hz), 6.93-6.96 (3H, m), 7.32-7.39 (6H, m), 7.85 (2H, d, J=9.0 Hz), 8.07 (1H, s), 8.71 (1H, s). IR (KBr) 3034, 1665, 1607, 1590, 1516, 1497, 1316, 1248, 1179, 1125, 1088, 829 cm$^{-1}$

Elementary analysis C$_{40}$H$_{51}$N$_5$O$_4$S.0.25H$_2$O Calcd. C, 68.40; H, 7.39; N, 9.97: Found. C, 68.15; H, 7.33; N, 9.97.

EXAMPLE 42

(Preparation of Compound 48, Compound 49)

8-[4-(2-Butoxyethoxy)phenyl]-1-isobutyl-N-[4-[[(4-propyl-4H-1,2,4-triazol-3-yl)methyl]sulfinyl]phenyl]-1,2,3,4-tetrahydro-1-benzazocine-5-carboxamide (Compound 5) (350 mg) was optically resolved by using CHIRALPAK AD (50 mm ID×500 mmL) (elution solvent, ethanol). The fraction was concentrated into dry solid, and the residue was dissolved in ethanol, and was filtered with a 0.45 μm filter. The filtrate was concentrated to give (+)-8-[4-(2-butoxyethoxy)phenyl]-1-isobutyl-N-[4-[[[4-propyl-4H-1,2,4-triazol-3-yl)methyl]sulfinyl]phenyl]-1,2,3,4-tetrahydro-1-benzazocine-5-carboxamide (Compound 48) (161 mg, >99.9% ee), and (−)-8-[4-(2-butoxyethoxy)phenyl]-1-isobutyl-N-[4-[[[4-propyl-4H-1,2,4-triazol-3-yl)methyl]sulfinyl]phenyl]-1,2,3,4-tetrahydro-1-benzazocine-5-carboxamide (Compound 49) (167 mg, >99.9% ee).

Compound 48: [α]$_D$=+131.2° (C=0.4985%, in ethanol)
Compound 49: [α]$_D$=−131.1° (C=0.518%, in ethanol)

EXAMPLE 43

(Preparation of Compound 50)

To a solution of 8-[4-(2-butoxyethoxy)phenyl]-1-propyl-1,2,3,4-tetrahydro-1-benzoazocine-5-carboxylic acid (0.8 g) in THF (10 ml) were added thionyl chloride (0.20 ml) and DMF (a drop), and the mixture was stirred at room temperature for 1.5 hours. After concentration under reduced pressure, the residual THF (30 ml) solution was added dropwise to a solution of S-(4-aminophenyl)O-benzyl thiocarbonate (0.47 g) and triethylamine (1.5 ml) in THF (5 ml) at 0° C. After stirring at room temperature for 20 hours, methanol (30 ml) and aqueous 1N sodium hydroxide solution (12 ml) were added, and the mixture was stirred for 0.5 hour. To the reaction system was added 3-chloromethyl-4-propyl-4H-1,2,4-triazol/hydrochloride (0.39 g), and the mixture was stirred for 2 hours. After concentration under reduced pressure, the reaction mixture was extracted with ethyl acetate. The organic layer was washed with saturated brine, and dried with magnesium sulfate. After concentration under reduced pressure, the residue was separated and purified with column chromatography (basic silica gel, ethyl acetate), and further recrystallized (with ethyl acetate-diisopropyl ether) to give 8-[4-(2-butoxyethoxy)phenyl]-1-propyl-N-[4-[[(4-propyl-4H-1,2,4-triazol-3-yl)methyl]thio]phenyl]-1,2,3,4-tetrahydro-1-benzazocine-5-carboxamide (894.4 mg) (Compound 50) as yellow crystals.

mp 166-169° C.
¹H-NMR (300 MHz, CDCl$_3$) δ 0.91-1.01 (9H, m), 1.36-1.43 (2H, m), 1.46-1.87 (8H, m), 2.53-2.62 (2H, m), 3.12-3.24 (2H, m), 3.48-3.57 (4H, m), 3.80 (2H, t, J=4.9 Hz), 3.91 (2H, t, J=7.1 Hz), 4.15 (2H, t, J=4.9 Hz), 4.17 (2H, s), 6.78 (1H, d, J=8.7 Hz), 6.96 (2H, d, J=8.7 Hz), 7.23-7.44 (6H, m), 7.48 (1H, s), 7.56 (2H, d, J=9.0 Hz), 7.87 (1H, s), 8.05 (1H, s). IR (KBr) 3031, 1638, 1607, 1590, 1520, 1497, 1319, 1248, 1190, 1165, 1123, 826 cm$^{-1}$

Elementary analysis C$_{39}$H$_{49}$N$_5$O$_3$S Calcd. C, 70.13; H, 7.39; N, 10.49: Found. C, 70.01; H, 7.25; N, 10.64.

EXAMPLE 44

(Preparation of Compound 51)

To a solution of 8-[4-(2-butoxyethoxy)phenyl]-1-propyl-N-[4-[[(4-propyl-4H-1,2,4-triazol-3-yl)methyl]thio]phenyl]-1,2,3,4-tetrahydro-1-benzazocine-5-carboxamide (0.70 g) in dichloromethane (20 ml) was added dropwise a solution of 3-chloro-perbenzoic acid (70%, 0.39 g) in dichloromethane (10 ml) and the mixture was stirred at −78° C. for 1 hour. To a reaction system was added an aqueous sodium thiosulfate solution, and the mixture was stirred at room temperature for several minutes. The mixture was extracted with ethyl acetate, the organic layer was washed with aqueous sodium bicarbonate solution and saturated brine, and was dried with magnesium sulfate. The resultant was concentrated under reduced pressure, after which the residue was separated and purified with column chromatography (basic silica gel, ethyl acetate→ethanol:ethyl acetate 1:19), followed by recrystallization (ethyl acetate-diisopropyl ether) to give 8-[4-(2-butoxyethoxy)phenyl]-1-propyl-N-[4-[[(4-propyl-4H-1,2,4-triazol-3-yl)methyl]sulfinyl] phenyl]-1,2,3,4-tetrahydro-1-benzazocine-5-carboxamide (579.7 mg) as yellow crystals (Compound 51).

mp 167-170° C.
¹H-NMR (300 MHz, CDCl$_3$) δ 0.88-1.02 (9H, m), 1.34-1.46 (2H, m), 1.52-1.76 (8H, m), 2.53-2.63 (2H, m), 3.15-3.24 (2H, m), 3.47-3.58 (4H, m), 3.62-3.82 (4H, m), 3.98 (1H, d, J=14.1 Hz), 4.12-4.16 (3H, m), 6.78 (1H, d, J=9.0 Hz), 6.93-6.96 (3H, m), 7.33-7.39 (6H, m), 7.85 (2H, d, J=9.0 Hz), 8.07 (1H, s), 8.67 (1H, s). IR (KBr) 3104, 1638, 1588, 1518, 1497, 1318, 1250, 1181, 1165, 1123, 1090, 1040, 837 cm$^{-1}$

Elementary analysis C$_{39}$H$_{49}$N$_5$O$_4$S.0.25H$_2$O Calcd. C, 68.04; H, 7.25; N, 10.17: Found. C, 68.01; H, 7.14; N, 10.21.

EXAMPLE 45

(Preparation of Compound 52, Compound 53)

8-[4-(2-Butoxyethoxy)phenyl]-1-propyl-N-[4-[[(4-propyl-4H-1,2,4-triazol-3-yl)methyl]sulfinyl]phenyl]-1,2,3,4-tetrahydro-1-benzazocine-5-carboxamide (400 mg) was optically resolved by using CHIRALPAK AD (50 mm ID×500 mmL) (elution solvent, ethanol). The fraction was concentrated into dry solid, and the residue was dissolved in ethanol, and was filtered with a 0.45 μm filter. The filtrate was concentrated to give (+)-8-[4-(2-butoxyethoxy) phenyl]-1-propyl-N-[4-[[(4-propyl-4H-1,2,4-triazol-3-yl)methyl]sulfinyl]phenyl]-1,2,3,4-tetrahydro-1-benzazocin-5-carboxamide (Compound 53) (185 mg, >99% ee), and (−)-8-[4-(2-butoxyethoxy)phenyl]-1-propyl-N-[4-[[[4-propyl-4H-1,2,4-triazol-3-yl)methyl]sulfinyl]phenyl]-1,2,3,4-tetrahydro-1-benzazocine-5-carboxamide (Compound 52) (196 mg, >99.9% ee).

Compound 52: [α]$_D$=+127.5° (C=0.498%, in ethanol)
Compound 53: [α]$_D$=−126.1° (C=0.537%, in ethanol)

EXAMPLE 46

(Preparation of Compound 54)

To a solution of ethyl 4-(2-(((4-(((8-(4-(2-butoxyethoxy)phenyl)-1-isobutyl-1,2,3,4-tetrahydro-1-benzazocine-5-1)carbonyl)amino)phenyl)sulfanyl)methyl)imidazol-1-yl)butanoate (400 mg) in dichloromethane (10 ml) was added dropwise a 70% solution of 3-chloroperbenzoic acid (144 mg) in dichloromethane (10 ml) at −78° C. As such, the mixture was stirred for 1 hour. Then, dry ice-acetone bath was removed and an aqueous sodium thiosulfate solution was added with vigorous stirring. After stirring the mixture at room temperature for 30 minutes, water was added and the mixture was extracted with ethyl acetate. The organic layer was washed with aqueous saturated sodium bicarbonate solution and saturated brine, and was dried with magnesium sulfate. The solvent was distilled off under reduced pressure, and the resulting residue was separated and purified with basic silica gel column chromatography (hexane:ethyl acetate=1:1→ethyl acetate), and recrystallized from hexane-ethyl acetate to give ethyl 4-(2-(((4-(((8-(4-(2-butoxyethoxy)phenyl)-1-isobutyl-1,2,3,4-tetrahydro-1-benzoazocine-5-yl)carbonyl)amino)phenyl)sulfinyl)methyl)imidazol-1-yl)butanoate (317 mg) as yellow crystals (Compound 54).

m.p. 133.5-134.5° C.

$^1$H-NMR (300 MHz, CDCl$_3$) δ 0.93 (3H, t, J=7.5 Hz), 1.00 (6H, d, J=6.6 Hz), 1.25 (3H, t, J=7.5 Hz), 1.30-1.50 (2H, m), 1.55-1.70 (4H, m), 1.90-2.05 (2H, m), 2.10-2.24 (1H, m), 2.27 (2H, t, J=7.2 Hz), 2.55-2.61 (2H, m), 3.07 (2H, d, J=6.9 Hz), 3.50-3.78 (4H, m), 3.78-3.98 (4H, m), 4.09-4.16 (5H, m), 4.28 (1H, d, J=11.1 Hz), 6.85 (1H, d, J=9.0 Hz), 6.88 (1H, d, J=1.2 Hz), 6.95 (2H, d, J=8.7 Hz), 7.02 (1H, d, J=1.2 Hz), 7.29 (1H, d, J=2.1 Hz), 7.37-7.52 (6H, m), 7.73 (2H, d, J=8.7 Hz), 7.85 (1H, s). Elementary analysis C$_{44}$H$_{56}$N$_4$O$_6$S Calcd. C, 68.72; H, 7.34; N, 7.29; Found. C, 68.49; H, 7.37; N, 7.16.

EXAMPLE 47

(Preparation of Compound 55)

To a solution of ethyl 4-(2-(((4-(((8-(4-(2-butoxyethoxy)phenyl)-1-isobutyl-1,2,3,4-tetrahydro-1-benzoazocine-5-yl)carbonyl)amino)phenyl)sulfanyl)methyl)imidazol-1-yl)butanoate (500 mg) in tetrahydrofuran (5 ml) and methanol (5 ml) was added an aqueous 1N sodium hydroxide solution (1.33 ml), and the mixture was stirred for 3 hours. 1N Hydrochloric acid (1.33 ml) was added thereto at 0° C. and then the solvent was distilled off under reduced pressure. As such, DMF (20 ml), methylamine hydrochloride (56 mg), 1-hydroxybenzotriazol monohydrate (132 mg), triethylamine (0.12 ml) and a catalytic amount of 4-(N,N-dimethylamino)pyridine were added, and then 1-ethyl-3-(3-dimethylaminopropyl)carbodiimide hydrochloride (165 mg) was added. The mixture was stirred overnight under nitrogen atmosphere. Water was added and the mixture was extracted with ethyl acetate. The organic layer was washed with saturated brine, followed by drying over magnesium sulfate. The solvent was distilled off under reduced pressure, and the resulting residue was purified by basic silica gel column chromatography (ethyl acetate→methanol:ethyl acetate=1:9) to give 8-(4-(2-butoxyethoxy) phenyl)-1-isobutyl-N-(4-(((1-(4-(methylamino)-4-oxobutyl)imidazol-2-yl)methyl)sulfanyl)phenyl)-1,2,3,4-tetrahydro-1-benzoazocine-5-carboxamide (411 mg) as yellow amorphous material (Compound 55).

$^1$H-NMR (300 MHz, CDCl$_3$) δ 0.93 (3H, t, J=7.2 Hz), 0.99 (6H, d, J=6.9 Hz), 1.30-1.46 (2H, m), 1.56-1.65 (4H, m), 1.95-2.08 (4H, m), 2.10-2.25 (1H, m), 2.50-2.60 (2H, m), 2.77 (3H, d, J=4.8 Hz), 3.06 (2H, d, J=6.9 Hz), 3.45-3.60 (4H, m), 3.78-3.84 (4H, m), 4.10-4.16 (4H, m), 5.71 (1H, br), 6.82-6.84 (2H, m), 6.93-6.96 (3H, m), 7.24-7.50 (9H, m), 7.96 (1H, s). Elementary analysis C$_{43}$H$_{55}$N$_5$O$_4$S.0.5H$_2$O Calcd. C, 69.13; H, 7.55; N, 9.38; Found. C, 69.17; H, 7.64; N, 9.31.

EXAMPLE 48

(Preparation of Compound 56)

To a solution of 8-(4-(2-butoxyethoxy)phenyl)-1-isobutyl-N-(4-(((1-(4-(methylamino)-4-oxobutyl)imidazol-2-yl)methyl)sulfanyl)phenyl)-1,2,3,4-tetrahydro-1-benzoazocine-5-carboxamide (338 mg) in dichloromethane (10 ml) was added dropwise a 70% solution of 3-chloroperbenzoic acid (124 mg) in dichloromethane (10 ml) at −78° C. As such, the mixture was stirred for 1 hour. Then, dry ice-acetone bath was removed and an aqueous sodium thiosulfate solution was added with vigorous stirring. After stirring the mixture at room temperature for 30 minutes, water was added and the mixture was extracted with ethyl acetate. The organic layer was washed with aqueous saturated sodium bicarbonate solution and saturated brine, and was dried with magnesium sulfate. The solvent was distilled off under reduced pressure, and the resulting residue was separated and purified with basic silica gel column chromatography (methanol:ethyl acetate=1:50→methanol:ethyl acetate=1:10), and re-crystallization was effected from diisopropylether-ethyl acetate to give 8-(4-(2-butoxyethoxy)phenyl)-1-isobutyl-N-(4-(((1-(4-(methylamino)-4-oxobutyl)imidazol-2-yl)methyl)sulfanyl)phenyl)-1,2,3,4-tetrahydro-1-benzoazocine-5-carboxamide (257 mg) as yellow crystals (Compound 56).

$^1$H-NMR (300 MHz, CDCl$_3$) δ 0.93 (3H, t, J=7.2 Hz), 1.00 (6H, d, J=6.6 Hz), 1.33-1.43 (2H, m), 1.50-1.70 (4H, m), 1.90-2.25 (5H, m), 2.55-2.62 (2H, m), 2.76 (3H, d, J=4.8 Hz), 3.07 (2H, d, J=7.2 Hz), 3.47-3.60 (4H, m), 3.77-3.82 (4H, m), 4.08-4.16 (3H, m), 4.25 (1H, d, 13.8 Hz), 6.05 (1H, br), 6.84 (1H, d, 9.0 Hz), 6.89 (1H, d, 1.2 Hz), 6.95 (2H, d, 9.0 Hz), 7.04 (1H, d, 1.2 Hz), 7.25-7.28 (1H, m), 7.36-7.54 (6H, m), 7.73 (2H, d, 8.4 Hz), 8.00 (1H, s). Elementary analysis C$_{43}$H$_{55}$N$_5$O$_5$S.0.5H$_2$O Calcd. C, 67.69; H, 7.40; N, 9.18; Found. C, 67.37; H, 7.58; N, 8.89.

EXAMPLE 49

(Preparation of Compound 57)

To a solution of (−)-8-(4-(2-butoxyethoxy)phenyl)-N-(4-(((1-propylimidazol-5-yl)methyl)sulfinyl)phenyl)-1,2,3,4-tetrahydro-1-benzoazocine-5-carboxamide (120 mg) in 1,2-dichloroethane (10 ml), cyclopropanecarboxaldehyde (65.6 mg) and sodium triacetoxyborohydride (119 mg) were added. The mixture was stirred at room temperature for overnight. The reaction mixture was poured into water and extracted with ethyl acetate. The organic layer was washed with saturated NaHCO$_3$, brine, and dried over MgSO$_4$. The volatile materials were removed in vacuo and the residue was purified by column chromatography (basic silicagel, ethyl acetate) to give (−)-8-(4-(2-butoxyethoxy)phenyl)-1-(cyclopropylmethyl)-N-(4-(((1-propylimidazol-5-yl)methyl)sulfinyl)phenyl)-1,2,3,4-tetrahydro-1-benzazocine-5-carboxamide (55 mg)(compound 57) as a yellow amorphous.

$^1$H-NMR (300 MHz, CDCl$_3$) δ 0.25-0.31 (2H, m), 0.59-0.65 (2H, m), 0.88-1.00 (6H, m), 1.10-1.22 (1H, m), 1.34-1.50 (2H, m), 1.55-1.85 (6H, m), 2.58-2.63 (2H, m), 3.16 (2H, d, J=6.3 Hz), 3.55 (2H, t, J=6.9 Hz), 3.60-3.67 (2H, m), 3.76-4.00 (4H, m), 4.07 (1H, d, J=10.5 Hz), 4.14-4.17 (3H, m), 6.56 (1H, s), 6.95-6.99 (3H, m), 7.33-7.48 (7H, m), 7.55 (1H, s), 7.76 (1H, d, J=8.7 Hz), 8.02 (1H, s). Anal. C$_{41}$H$_{50}$N$_4$O$_4$S.2H$_2$O Calcd. C, 67.37; H, 7.45; N, 7.66; Found. C, 67.56; H, 7.33; N, 7.56.

EXAMPLE 50

(Preparation of Compounds 58 and 59)

A diastereomer mixture of 8-(4-(2-butoxyethoxy)phenyl)-1-(2-methyl-3-hydroxy)propyl-N-(4-(((1-propylimidazol-5-yl)methyl)sulfinyl)phenyl)-1,2,3,4-tetrahydro-1-benzazocine-5-carboxamide (compound 32: 140 mg) was separated by CHIRALPAK AD 50 mmID×500 mmL [hexane/ethanol (55/45)] to give compound 58 (67 mg; short retention time) and compound 59 (63 mg; long retention time).

REFERENCE EXAMPLE 1

Ethyl 5-bromopentanoate (28.6 g) was added to a suspension of 4-bromo-2-formylphenol (25.0 g) and potassium carbonate (18.9 g) in DMF (100 ml), and the resulting solution was stirred at 50° C. overnight under a nitrogen atmosphere. The solution was allowed to cool. Water was added and the resultant mixture was extracted with ethyl acetate. The organic layer was washed with saturated saline and dried over magnesium sulfate. The solvent was distilled off under reduced pressure to obtain yellow oil of ethyl 5-(4-bromo-2-formylphenoxy)pentanoate (40.9 g).

$^1$H-NMR (200 MHz, CDCl$_3$) δ1.26 (3H, t, J=7.2 Hz), 1.88 (4H, br), 2.40 (2H, t, J=6.6 Hz), 4.05-4.19 (4H, m), 6.87 (1H, d, J=9.2 Hz), 7.61 (1H, dd, J=8.8, 2.6 Hz), 7.92 (1H, d, J=2.6 Hz), 10.41 (1H, s).

REFERENCE EXAMPLE 2

A suspension of ethyl 5-(4-bromo-2-formylphenoxy)pentanoate (9.0 g) and 4-(2-butoxyethoxy)phenylboric acid (7.8 g) and potassium carbonate (9.1 g) in toluene (100 ml), ethanol (10 ml) and water (10 ml) was stirred under an argon atmosphere for 30 minutes. After addition of tetrakis(triphenyl)phosphine palladium (1.6 g), the solution was heated at 100° C. for 12 hours under an argon atmosphere. The solution was allowed to cool. Water was added and the mixture was extracted with ethyl acetate. The organic layer was washed with saturated saline and dried over magnesium sulfate. The solvent was distilled off under reduced pressure to obtain brown amorphous ethyl 5-[[4'-(2-butoxyethoxy)-3-formyl [1,1'-biphenyl]-4-yl]oxy]pentanoate (12.0 g).

$^1$H-NMR (200 MHz, CDCl$_3$) δ 0.93 (3H, t, J=7.4 Hz), 1.26 (3H, t, J=6.8 Hz), 1.30-1.48 (2H, m), 1.54-1.68 (2H, m), 1.82-2.00 (4H, m), 2.42 (2H, t, J=6.6 Hz), 3.55 (2H, t, J=8.6 Hz), 3.80 (2H, t, J=4.8 Hz), 4.09-4.19 (6H, m), 6.95-7.04 (3H, m), 7.49 (2H, dd, J=8.8, 2.0 Hz), 7.73 (1H, dd, J=8.8, 2.6 Hz), 8.22 (1H, d, J=2.6 Hz).

REFERENCE EXAMPLE 3

To a solution of ethyl 5-[[4'-(2-butoxyethoxy)-3-formyl [1,1'-biphenyl]-4-yl]oxy]pentanoate (6.00 g) in diethyl carbonate (60 ml) was added a solution of 20% sodium ethoxide in ethanol (5.55 g). The mixture was stirred at 50° C. for 2 hours under a nitrogen atmosphere. The solution was allowed to cool. Water was added and the mixture was extracted with ethyl acetate. The organic layer was washed with saturated saline and dried over magnesium sulfate. After distilling off the solvent under reduced pressure, the residue was purified by silica gel column chromatography (hexane:ethyl acetate=5:1) to obtain yellowish oil of ethyl 8-[4-(2-butoxyethoxy)phenyl]-3,4-dihydro-2H-1-benzoxocin-4-carboxylate (527 mg).

$^1$H-NMR (200 MHz, CDCl$_3$) δ 0.93 (3H, t, J=7.4 Hz), 1.23-1.45 (5H, m), 1.5 7-1.64 (2H, m), 1.70-1.95 (2H, m), 2.67 (2H, t, J=6.4 Hz), 3.55 (2H, t, J=6.6 Hz), 3.80 (2H, t, J=4.8 Hz), 4.13-4.40 (6H, m), 6.95-7.03 (3H, m), 7.35-7.49 (3H, m), 7.76 (1H, s).

REFERENCE EXAMPLE 4

Ethyl 8-[4-(2-butoxyethoxy) phenyl]-3,4-dihydro-1-benzoxocin-5-carboxylate (527 mg) was dissolved in THF (40 ml) and methanol (40 ml). Aqueous 1N sodium hydroxide solution (12.4 ml) was added to the solution and the resulting solution was stirred overnight. After neutralization with 1N hydrochloric acid at 0° C., the solution was extracted with ethyl acetate. The organic layer was washed with saturated saline and dried over magnesium sulfate. The solvent was distilled off under reduced pressure and the residue was recrystallized from hexane-ethyl acetate to obtain colorless crystals of 8-[4-(2-butoxyethoxy)phenyl]-3,4-dihydro-2H-1-benzoxocin-5-carboxylic acid (160 mg).

$^1$H-NMR (200 MHz, CDCl$_3$) δ 0.93 (3H, t, J=7.4 Hz), 1.34-1.45 (2H, m), 1.55-1.65 (2H, m), 1.81 (2H, br), 2.70 (2H, br), 3.56 (2H, t, J=7.0 Hz), 3.81 (2H, t, J=5.2 Hz), 4.16 (2H, t, J=5.2 Hz), 4.36 (2H, t, J=5.4 Hz), 6.96-7.04 (3H, m), 7.36 (1H, d, J=2.2 Hz), 7.46 (2H, d, J=8.8 Hz), 7.90 (1H, s). Elemental Analysis C$_{24}$H$_{28}$O$_5$ Calcd. C, 72.70; H, 7.12; Found. C,72.30; H, 7.41.

REFERENCE EXAMPLE 5

A suspension of 85% potassium hydroxide (15.5 g), tetrabutylammonium bromide (4.1 g) in toluene (250 ml) was refluxed in a Dean Stalk apparatus overnight. Then, a solution of 2-piperidone (21.2 g) and 1-bromopropane (34.2 g) in toluene (50 ml) was added dropwise thereto at 115° C. After the dropwise addition, the mixture was further refluxed for 2.5 hours, and then filtered to remove undesired materials.

The filtrate was washed with water and saturated saline solution, and dried over magnesium sulfate. After distilling off the solvent under reduced pressure, the residue was distilled under reduced pressure (5 mmHg, 91° C.) to obtain colorless oil of 1-propyl-2-piperidone (7.7 g).

$^1$H-NMR (200 MHz, CDCl3) δ 0.91 (3H, t, J=7.8 Hz), 1.46-1.67 (2H, m), 1.71-1.84 (4H, m), 2.30-2.45 (2H, m), 3.24-3.36 (4H, m).

REFERENCE EXAMPLE 6

A mixture of 1-propyl-2-piperidone (7.5 g) and 4N sodium hydroxide (26.6 ml) was refluxed for 4 hours. The mixture was cooled to 0° C. and conc. hydrochloric acid (8.85 ml) was added thereto. To the mixture were added sodium carbonate (11.3 g), 5-bromo-2-fluorobenzaldehyde (5.4 g) and DMSO (70 ml), and the resulting mixture was heated at 135° C. for 6 hours. The mixture was allowed to cool. Water was added and the mixture was extracted with THF-ethyl acetate. The organic layer was washed with water and saturated saline, and dried over magnesium sulfate. After distilling off the solvent under reduced pressure, the residue was purified by silica gel column chromatography to obtain brown oil of 5-(4-bromo-2-formyl-N-propylanilino) pentanoic acid (8.8 g)

$^1$H-NMR (200 MHz, CDCl$_3$) δ 0.83 (3H, t, J=7.6 Hz), 1.26 (2H, t, J=7.0 Hz), 1.40-1.70 (4H, m), 2.32 (2H, t, J=7.0 Hz), 3.04-3.19 (4H, m), 7.04 (1H, d, J=8.8 Hz), 7.56 (1H, dd, J=8.4, 2.6 Hz), 7.90 (1H, d, J=2.6 Hz), 10.24 (1H, s).

REFERENCE EXAMPLE 7

To a suspension of 5-(4-bromo-2-formyl-N-propylanilino)pentanoic acid (8.00 g) and potassium carbonate (3.88 g) in DMF (25 ml) was added dropwise a solution of iodomethane (4.66 g) in DMF (5 ml) under a nitrogen atmosphere. The mixture was stirred overnight under a nitrogen atmosphere. Then, water was added and the mixture was extracted with ethyl acetate. The organic layer was washed with saturated saline and dried over magnesium sulfate. The solvent was distilled off under reduced pressure to obtain brown oil of methyl 5-(4-bromo-2-formyl-N-propylanilino)pentanoate (7.89 g).

$^1$H-NMR (200 MHz, CDCl$_3$) δ 0.83 (3H, t, J=7.2 Hz), 1.44-1.70 (6H, m), 2.28 (2H, t, J=7.0 Hz), 3.04-3.18 (4H, m), 3.64 (3H, s), 7.04 (1H, d, J=8.8 Hz), 7.56 (1H, dd, J=8.8, 2.6 Hz), 7.90 (1H, d, J=2.6 Hz), 10.23 (1H, s).

REFERENCE EXAMPLE 8

To a solution of ethyl 5-(4-bromo-2-formyl-N-propylanilino)pentanoate (5.0 g) in dimethylcarbonate (100 ml) was added a methanol solution of 28% sodium methoxide (3.5 g), and the mixture was heated at 50° C. for 2 hours under a nitrogen atmosphere. After cooling to 0° C. and neutralization with 1N hydrochloric acid, to the solution was added water, followed by extraction with ethyl acetate. The organic layer was washed with saturated saline, and dried over magnesium sulfate. After distilling off the solvent under reduced pressure, the residue was purified by silica gel column chromatography (hexane:ethyl acetate=5:1) to obtain yellow oil of methyl 8-bromo-1-propyl-1,2,3,4-tetrahydro-1-benzazocine-5-carboxylate (3.5 g).

$^1$H-NMR (200 MHz, CDCl$_3$) δ 0.95 (3H, t, J=7.6 Hz), 1.30-1.50 (2H, m), 1.55-1.80 (2H, m), 2.51 (2H, t, J=6.2 Hz), 3.00-3.20 (2H, m), 3.42 (2H, t, J=6.2 Hz), 3.78 (3H, s), 6.56 (1H, d, J=9.6 Hz), 7.15-7.21 (2H, m), 7.68 (1H, s).

REFERENCE EXAMPLE 9

A suspension of methyl 8-bromo-1-propyl-1,2,3,4-tetrahydro-1-benzazocine-5-carboxylate (700 mg), 4-(2-butoxyethoxy)phenylboric acid (640 g), and potassium carbonate (744 mg) in toluene (15 ml), ethanol (1.5 ml) and water (1.5 ml) was stirred for 30 minutes under an argon atmosphere. After addition of tetrakis(triphenyl)phosphine palladium (120 mg), the solution was heated at 100° C. for 3 hours under an argon atmosphere. The solution was allowed to cool, followed by addition of water and extraction with ethyl acetate. The organic layer was washed with saturated saline and dried over magnesium sulfate. After distilling off the solvent under reduced pressure, the residue was purified by silica gel column chromatography (hexane:ethyl acetate=10:1) to obtain yellow oil of methyl 8-[4-(2-butoxyethoxy)phenyl]-1-propyl-1,2,3,4-tetrahydro-1-benzazocine-5-carboxylate (294 mg). The oil was redissolved in THF (21 ml) and methanol (21 ml), and after addition of 1N sodium hydroxide (7 ml), the mixture was heated at 70° C. for 2 hours. The mixture was cooled to 0° C., followed by addition of water, neutralized with 1N hydrochloric acid, and then extraction with ethyl acetate. The organic layer was washed with saturated saline, and dried over magnesium sulfate. After distilling off the solvent under reduced pressure, the residue was recrystallized from hexane-ethyl acetate to yield yellow crystals of 8-[4-(2-butoxyethoxy) phenyl]-1-propyl-1,2,3,4-tetrahydro-1-benzazocine-5-carboxylic acid (200 mg).

$^1$H-NMR (200 MHz, CDCl$_3$) δ 0.89-1.02 (6H, m), 1.30-1.80 (8H, m), 2.58 (2H, br), 3.19 (2H, br), 3.45-3.58 (4H, m), 3.80 (2H, t, J=4.8 Hz), 4.15 (2H, t, J=4.6 Hz), 6.77 (1H, d, J=9.0 Hz), 6.96 (2H, d, J=8.8 Hz), 7.32-7.46 (4H, m), 7.99 (1H, s), Elemental Analysis; C$_{27}$H$_{35}$NO$_4$, Calcd. C, 74.11; H, 8.06; N, 3.20; Found. C, 74.02; H, 7.92; N, 3.15.

REFERENCE EXAMPLE 10

A suspension of 85% potassium hydroxide (36.6 g), and tetrabutylammonium bromide (9.1 g) in toluene (400 ml) was refluxed overnight in a Dean Stalk apparatus. Then, a solution of 2-piperidone (50.0 g) and iodoisobutane (120.7 g) in toluene (150 ml) was added dropwise at 115° C. to the solution above. After the dropwise addition, the mixture was refluxed further for 2.5 hours, and then cooled, and filtered to remove insoluble matter. The filtrate was washed with water, and the aqueous layer was extracted with toluene. The organic layers were combined and dried over magnesium sulfate. After distilling off the solvent under reduced, the residue was separated and purified by silica gel column chromatography (ethyl acetate) to obtain yellow oil of 1-isobutyl-2-piperidone (9.3 g).

$^1$H-NMR (200 MHz, CDCl$_3$) δ 0.89 (6H, d, J=6.9 Hz), 1.75-1.82 (4H, m), 1.90-2.07 (1H, m), 2.37-2.42 (2H, m), 3.19 (2H, d, J=7.8 Hz), 3.24-3.28 (2H, m).

REFERENCE EXAMPLE 11

A mixture of 1-isobutyl-2-piperidone (8.8 g) and aqueous methanesulfonic acid solution (10.9 g/19 ml) was refluxed at 110° C. for 3 days. To the mixture which was previously cooled to room temperature, were added water (10 ml) and sodium carbonate (18.0 g) slowly. Then, after heating the mixture at 50° C. for 1 hour, DMSO (13 ml) was added. The resulting mixture was heated to 135° C., and then a solution of 5-bromo-2-fluorobenzaldehyde (11.5 g) in DMSO (15 ml) was added dropwise. After stirring at 135° C. for 6 hours, the mixture was cooled to 0° C., and the mixture was adjusted to pH 2.5 by using 6N hydrochloric acid. After ethyl acetate extraction, the organic layer was dried over magnesium sulfate. The solvent was distilled off under reduced pressure and the residue was purified by silica gel column chromatography (hexane:ethyl acetate=1:1 to ethyl acetate) to obtain brown oil of 5-(4-bromo-2-formyl-N-isobutylanilino) pentanoic acid (15.3 g).

$^1$H-NMR (200 MHz, CDCl$_3$) δ 0.86 (6H, d, J=6.6 Hz), 1.52-1.59 (4H, m), 1.77-1.90 (1H, m), 2.25-2.35 (2H, m), 2.95 (2H, d, J=7.2 Hz), 3.10-3.23 (2H, m), 7.04 (1H, d, J=8.8), 7.54 (1H, dd, J=8.8, 2.6 Hz), 7.88 (1H, d, J=2.6 Hz), 10.23 (1H, s)

REFERENCE EXAMPLE 12

To a suspension of 5-(4-bromo-2-formyl-N-isobutylanilino)pentanoic acid (15.0 g), potassium carbonate (7.0 g) in DMF (50 ml) was added dropwise a solution of iodomethane (8.4 g) in DMF (10 ml) at 0° C. under a nitrogen atmosphere. The mixture was warmed to room temperature, and stirred for 2 hours under a nitrogen atmosphere. After addition of water, the solution was extracted with ethyl acetate. The organic layer was washed with water and saturated saline, and dried over magnesium sulfate. After distilling off the solvent under reduced pressure, the resulting residue was purified by silica gel column chromatography (hexane:ethyl acetate=9:1 to hexane:ethyl acetate=1:1) to obtain brown oil of methyl 5-(4-bromo-2-formyl-N-isobutylanilino)pentanoate (13.1 g).

$^1$H-NMR (200 MHz, CDCl$_3$) δ 0.86 (6H, d, J=6.6 Hz), 1.52-1.55 (4H, m), 1.75-1.90 (1H, m), 2.21-2.29 (2H, m), 2.95 (2H, d, J=7.2 Hz), 3.10-3.20 (2H, m), 3.64 (3H, s), 7.04 (1H, d, J=8.7), 7.54 (1H, dd, J=8, 7, 2.4 Hz), 7.89 (1H, d, J=2.4 Hz), 10.22 (1H, s).

REFERENCE EXAMPLE 13

To a solution of methyl 5-(4-bromo-2-formyl-N-isobutylanilino)pentanoate (10.0 g) in dimethylcarbonate (250 ml) was added a methanol solution of 28% sodium methoxide (6.8 g) and the mixture was heated at 50° C. for 3 hours under a nitrogen atmosphere. The mixture was cooled to 0° C., neutralized with 1N hydrochloric acid and extracted with ethyl acetate. The organic layer was washed with saturated saline, and dried over magnesium sulfate. After distilling off the solvent under reduced pressure, the residue was purified by silica gel column chromatography (hexane:ethyl acetate=9:1) to obtain yellow oil of methyl 8-bromo-1-isobutyl-1,2,3,4-tetrahydro-1-benzazocine-5-carboxylate (8.6 g). A suspension of methyl 8-bromo-1-isobutyl-1,2,3,4-tetrahydro-1-benzazocine-5-carboxylate (5.0 g), 4-(2-butoxyethoxy)phenylboric acid (4.8 g) and potassium carbonate (5.6 g) in toluene (60 ml), ethanol (6.0 ml) and water (6.0 ml) was stirred for 30 minutes under an argon atmosphere. After addition of tetrakis(triphenyl)phosphine palladium (0.9 g), the mixture was heated at 105° C. for 3 hours under an argon atmosphere. The mixture was cooled, followed by addition of water, and extraction with ethyl acetate. The organic layer was washed with saturated saline, and dried over magnesium sulfate. After distilling off the solvent under reduced pressure, the residue was purified by silica gel column chromatography (hexane:ethyl acetate=9:1) to obtain yellow oil of methyl 8-[4-(2-butoxyethoxy)phenyl]-1-isobutyl-1,2,3,4-tetrahydro-1-benzazocine-5-carboxylate (5.43 g). The oil was redissolved in THF (50 ml) and methanol (50 ml). To the solution was added aqueous 2N sodium hydroxide solution (23 ml), and the resulting mixture was heated at 90° C. for 3.5 days. The mixture was cooled to 0° C., followed by addition of water, and neutralized with 1N hydrochloric acid. After extraction with ethyl acetate, the organic layer was washed with saturated saline and dried over magnesium sulfate. After distilling off the solvent under reduced pressure, the residue was recrystallized from diisopropylether-ethyl acetate to obtain yellow crystals of 8-[4-(2-butoxyethoxy)phenyl-1-isobutyl-1,2,3,4-tetrahydro-1-benzazocine-5-carboxylic acid (1.04 g).

$^1$H-NMR (200 MHz, CDCl$_3$) δ 0.89-1.01 (9H, m), 1.30-1.68 (6H, m), 2.10-2.20 (1H, m), 2.50-2.65 (2H, m), 3.07 (2H, d, J=7.2 Hz), 3.45-3.58 (4H, m), 3.80 (2H, t, J=4.8 Hz), 4.15 (2H, t, J=4.8 Hz), 6.82(1H, d, J=8.8 Hz), 6.96 (2H, d, J=8.8 Hz), 7.33-7.46 (4H, m), 8.01(1H, s). Elemental Analysis; C$_{28}$H$_{37}$NO$_4$, Calcd. C, 74.47; H, 8.26; N, 3.10; Found. C, 74.40; H, 8.45; N, 2.71.

REFERENCE EXAMPLE 14

A suspension of potassium hydroxide (85%, 18.6 g) and tetrabutylammonium bromide (4.88 g) in toluene (250 ml) was refluxed overnight under nitrogen atmosphere using Deenschtark device. The mixture was cooled to 80° C., to which a solution of 2-piperidone (25.0 g) and 4-methoxybenzylchloride (51.3 g) in toluene (50 ml) were added dropwise. After refluxing for 8 hours, the reaction mixture was returned to room temperature and washed with water and saturated brine. The resultant was dried with magnesium sulfate, after which the solvent was distilled off under reduced pressure, and the resulting residue was purified by silica gel column chromatography (hexane:ethyl acetate=1:1) to give 1-(4-methoxybenzyl)piperidin-2-one (28.8 g) as a colorless oily material.

$^1$H-NMR (200 MHz, CDCl$_3$) δ 1.70-1.85 (4H, m), 2.40-2.50 (2H, m), 3.15-3.25 (2H, m), 3.80 (3H, s), 4.53 (2H, s), 6.85 (2H, d, J=8.8 Hz), 7.19 (2H, d, J=8.8 Hz).

REFERENCE EXAMPLE 15

To 1-(4-methoxybenzyl)piperidin-2-one (50.0 g) was added aqueous 4N sodium hydroxide solution (228 ml) and then the mixture was refluxed for a day. The mixture was cooled to 0° C. and concentrated hydrochloric acid (76 ml) was added thereto. The mixture was neutralized. Then, after adding sodium carbonate (53.8 g) and dimethyl sulfoxide (600 ml), 5-bromo-2-fluorobenzaldehyde (38.6 g) was added dropwise at 135° C. to the mixture. After refluxing for 5 hours, the mixture was neutralized with 3N hydrochloric acid at 0° C., and extracted with ethyl acetate. The organic layer was washed with water and saturated brine, after which it was dried with magnesium sulfate. The solvent was distilled off under reduced pressure to give 5-((4-bromo-2-formylphenyl)(4-methoxybenzyl)amino)pentanoic acid (77.2 g) as a brown oily material.

$^1$H-NMR (300 MHz, CDCl$_3$) δ 1.50-1.65 (4H, m), 2.25-2.33 (2H, m), 3.00-3.10 (2H, m), 3.78 (3H, s), 4.21 (2H, s), 6.79 (2H, d, J=8.7 Hz), 6.97 (1H, d, J=8.7 Hz), 7.33 (2H, d, J=8.7 Hz), 7.53 (1H, dd, J=8.7, 2.4 Hz), 7.89 (1H, d, J=2.4 Hz), 10.30 (1H, s).

REFERENCE EXAMPLE 16

To a solution of 5-((4-bromo-2-formylphenyl)(4-methoxybenzyl)amino)pentanoic acid (77.2 g) and potassium carbonate (30.5 g) in DMF (500 ml) was added dropwise a solution of iodomethane (36.5 g) in DMF (100 ml) at 0° C. under nitrogen atmosphere. After stirring for 2 hours, water was added and the mixture was extracted with ethyl acetate. After washing the organic layer with water three times and with saturated brine once, the resultant was dried with magnesium sulfate. The solvent was distilled off under reduced pressure and the resulting residue was purified by silica gel column chromatography (hexane:ethyl acetate=9:1→hexane:ethyl acetate=4:1) to give methyl 5-((4-bromo-2-formylphenyl)(4-methoxybenzyl)amino)-pentanoate (45.7 g) as a brown oily material.

$^1$H-NMR (200 MHz, CDCl$_3$) δ 1.50-1.65 (4H, m), 2.20-2.30 (2H, m), 3.05-3.15 (2H, m), 3.64 (3H, s), 3.78 (3H, s), 4.22 (2H, s), 6.80 (2H, d, J=8.6 Hz), 6.98 (1H, d, J=8.4 Hz), 7.05 (2H, d, J=8.6 Hz), 7.54 (1H, dd, J=8.4, 2.6 Hz), 7.90 (1H, d, J=2.6 Hz), 10.32 (1H, s)

REFERENCE EXAMPLE 17

To a solution of methyl 5-((4-bromo-2-formylphenyl)(4-methoxybenzyl)amino)pentanoate (45.7 g) in dimethyl carbonate (900 ml) was added a methanol solution of sodium methoxide (28%, 26.4 g) and then the mixture was stirred at 50° C. under nitrogen atmosphere for 6 hours. The resultant was cooled to 0° C., followed by addition of water, neutralized with 1N hydrochloric acid, and extracted with ethyl acetate. The organic layer was washed with saturated brine, and dried with magnesium sulfate. The solvent was distilled off under reduced pressure, and the resulting residue was recrystallized from hexane-ethyl acetate to give methyl 8-bromo-1-(4-methoxybenzyl)-1,2,3,4-terahydro-1-benzoazocine-5-carboxylate (32.2 g) as yellow crystals.

m.p. 130.5-132.0° C.

$^1$H-NMR (200 MHz, CDCl$_3$) δ 1.40-1.50 (2H, m), 2.57 (2H, t, J=4.0 Hz), 3.47 (2H, t, J=3.8 Hz), 3.80 (3H, s), 4.39 (2H, s), 6.54 (1H, d, J=6.0 Hz), 6.88 (2H, d, J=5.6 Hz), 7.07-7.13 (3H, m), 7.26 (1H, d, J=1.6 Hz), 7.74 (1H, s).

REFERENCE EXAMPLE 18

To a solution of methyl 8-bromo-1-(4-methoxybenzyl)-1,2,3,4-terahydro-1-benzoazocine-5-carboxylate (10.0 g), in toluene (50 ml) was added trifluoroacetic acid (50 ml), and the mixture was stirred at 65° C. for 2 hours. After distilling off the solvent under reduced pressure, water was added at 0° C. and the reaction mixture was neutralized with potassium carbonate and extracted with ethyl acetate. The organic layer was washed with aqueous saturated sodium bicarbonate solution and saturated brine, after which it was dried with magnesium sulfate. The solvent was distilled off under reduced pressure, and the resulting residue was purified by basic silica gel column chromatography (hexane:ethyl acetate=9:1). The resulting solid was washed with hexane to give methyl 8-bromo-1,2,3,4-terahydro-1-benzoazocine-5-carboxylate (6.59 g) as yellow crystals.

$^1$H-NMR (200 MHz, CDCl$_3$) δ 1.38-1.50 (2H, m), 2.72 (2H, t, J=6.2 Hz), 3.49 (2H, t, J=5.8 Hz), 3.78 (3H, s), 6.34 (1H, d, J=8.4 Hz), 7.06-7.11 (2H, m), 7.63 (1H, s).

REFERENCE EXAMPLE 19

A suspension of methyl 8-bromo-1,2,3,4-terahydro-1-benzoazocine-5-carboxylate (6.0 g), 4-(2-butoxyethoxy) phenyl boric acid (6.26 g) and potassium carbonate (7.28 g) in toluene (100 ml), ethanol (10 ml) and water (10 ml) was stirred under argon atmosphere for 1 hour, after which tetrakis(triphenylphosphin)palladium (1.17 g) was added, and the mixture was refluxed for 6 hours. After returning to room temperature, water was added and the reaction mixture was extracted with ethyl acetate. The organic layer was washed with saturated brine, and dried with magnesium sulfate. The solvent was distilled off under reduced pressure, and the resulting residue was purified by silica gel column chromatography (hexane:ethyl acetate=9:1→hexane:ethyl acetate=4:1), and recrystallized from hexane-ethyl acetate to give methyl 8-(4-(2-butoxyethoxy) phenyl)-1,2,3,4-terahydro-1-benzoazocine-5-carboxylate (3.33 g) as a yellow solid.

$^1$H-NMR (200 MHz, CDCl$_3$) δ 0.93 (3H, t, J=7.4 Hz), 1.30-1.70 (6H, m), 2.77 (2H, t, J=6.2 Hz), 3.51-3.58 (4H, m), 3.77-3.82 (5H, m), 3.93 (1H, br), 4.14 (2H, t, J=4.2 Hz), 6.52 (1H, d, J=8.0 Hz), 6.94 (2H, d, J=8.8 Hz), 7.21-7.29 (2H, m), 7.41 (2H, d, J=8.8 Hz), 7.81 (1H, s).

REFERENCE EXAMPLE 20

To a solution of sodium hydroxide (530 mg) in DMF (10 ml) was added dropwise a solution of methyl 8-(4-(2-butoxyethoxy)phenyl)-1,2,3,4-terahydro-1-benzoazocine-5-carboxylate (1.8 g) in DMF (20 ml) at 0° C. under nitrogen atmosphere. After returning to room temperature and stirring for 1 hour, 3-bromo-2-methylpropene (1.33 ml) and sodium iodide (1.98 g) were added, and the mixture was stirred at 100° C. overnight. After returning to room temperature, water and saturated brine were added and the reaction mixture was extracted with ethyl acetate. The organic layer was washed with water twice and with saturated brine once, and dried with magnesium sulfate. The solvent was distilled off under reduced pressure, and the resulting residue was purified by silica gel column chromatography (hexane:ethyl acetate=12:1→hexane:ethyl acetate=9:1). The resulting residue was recrystallized from hexane-ethyl acetate to give methyl 8-(4-(2-butoxyethoxy)phenyl)-1-(2-methyl-2-propen-1-yl)-1,2,3,4-tetrahydro-1-benzoazocine-5-carboxylate (1.64 g) as yellow crystals.

$^1$H-NMR (300 MHz, CDCl$_3$) δ 0.93 (3H, t, J=7.5 Hz), 1.35-1.50 (4H, m), 1.55-1.63 (2H, m), 1.78 (3H, s), 2.55 (2H, t, J=6.6 Hz), 3.46 (2H, t, J=5.7 Hz), 3.54 (2H, t, J=6.6 Hz), 3.70 (2H, s), 3.77-3.80 (5H, m), 4.14 (2H, t, J=5.1 Hz), 4.76 (1H, s), 4.89 (1H, s), 6.68 (1H, d, J=8.4 Hz), 6.93 (2H, d, J=8.7 Hz), 7.31-7.35 (2H, m), 7.42 (2H, d, J=8.7 Hz), 7.88 (1H, s). Elementary analysis C$_{29}$H$_{37}$NO$_4$ Calcd. C, 75.13; H, 8.04; N, 3.02: Found C, 74.88; H, 8.19; N, 3.00.

REFERENCE EXAMPLE 21

To methyl 8-(4-(2-butoxyethoxy)phenyl)-1-(2-methyl-2-propen-1-yl)-1,2,3,4-tetrahydro-1-benzoazocine-5-carboxylate (1.65 g) were added tetrahydrofuran (45 ml) and methanol (45 ml), followed by adding an aqueous 1N sodium hydroxide solution (15 ml), and the mixture was stirred at 60° C. overnight. After cooling down to 0° C., water was added and the mixture was neutralized with 1N hydrochloric acid. After extracting with ethyl acetate, the organic layer was washed with saturated water and dried with magnesium sulfate. The solvent was distilled off under reduced pressure, and the resulting residue was recrystallized from hexane-ethyl acetate to give 8-(4-(2-butoxyethoxy)phenyl)-1-(2-methyl-2-propen-1-yl)-1,2,3,4-tetrahydro-1-benzoazocine-5-carboxylic acid (0.97 g) as yellow crystals.

m.p. 132.5-134.5° C.

$^1$H-NMR (300 MHz, CDCl$_3$) δ 0.93 (3H, t, J=7.2 Hz), 1.30-1.65 (6H, m), 1.79 (3H, s), 2.57 (2H, t, J=6.6 Hz), 3.45-3.55 (2H, m), 3.54 (2H, t, J=6.6 Hz), 3.71 (2H, s), 3.79 (2H, t, J=4.5 Hz), 4.14 (2H, t, J=4.5 Hz), 4.76 (1H, s), 4.90 (1H, s), 6.68 (1H, d, J=8.4 Hz), 6.94 (2H, d, J=8.4 Hz), 7.33-7.37 (2H, m), 7.42 (2H, d, J=8.4 Hz), 8.01 (1H, s).

REFERENCE EXAMPLE 22

To a solution of 2-bromo-5-fluorotoluene (20 g) in dry tetrahydrofuran (200 ml) was added dropwise lithium diisopropylamide (2.0 M, heptan-tetrohydrofuran-ethylbenzene solution, 52.9 ml) under argon atmosphere at −78° C. After stirring as such for 2 hours, a solution of DMF (41 ml) in dry tetrahydrofuran (50 ml) was added dropwise. The mixture was returned to room temperature and stirred for 1 hour. Then, water was added and the mixture was neutralized with 1N hydrochloric acid. After extraction with ethyl acetate, the extract was washed with saturated brine and dried with magnesium sulfate. The solvent was distilled off under reduced pressure, and the resulting residue was purified by silica gel column chromatography (hexane:ethyl acetate=24: 1) and re-crystallized from hexane-ethyl acetate to give 5-bromo-2-fluoro-4-methylbenzaldehyde (9.39 g).

$^1$H-NMR (200 MHz, CDCl$_3$) δ 2.47 (3H, s), 7.09 (1H, d, J=8.6 Hz), 8.09 (1H, d, J=6.6 Hz), 10.25 (1H, s). Elementary analysis C$_8$H$_6$OBrF Calcd. C, 44.27; H, 2.79: Found C, 44.29; H, 2.79.

REFERENCE EXAMPLE 23

To a solution of 4-methoxybenzaldehyde (3.31 g) and 5-aminovaleric acid (2.85 g) in methanol (40 ml) were added an aqueous 1 N sodium hydroxide solution (24.3 ml) and palladium carbon (10%, 600 mg), after which the mixture was stirred under hydrogen atmosphere for a day. After filtering off insolubles, the reaction mixture was neutralized with 1N hydrochloric acid (24.3 ml) at 0° C., and solvent was distilled off under reduced pressure. To the resulting residue were added DMSO (50 ml), water (37.5 ml), and sodium carbonate (6.45 g), and then a solution of 5-bromo-2-fluoro-4-methylbenzaldehydr (4.4 g) in DMSO (25 ml) was added dropwise thereto at 135° C. After stirring as such overnight, the mixture was cooled to 0° C. and water was added. The mixture was neutralized with 1N hydrochloric acid, and extracted with ethyl acetate. After washing the organic layer with water and saturated brine, it was dried with magnesium sulfate. The solvent was distilled off under reduced pressure, and the resulting residue was purified by silica gel column chromatography (hexane:ethyl acetate=2: 1→hexane:ethyl acetate=1:1) to give 5-((4-bromo-2-formyl-5-methylphenyl)(4-methoxybenzyl)amino)-pentanoic acid (3.6 g) as a brown oily material.)

$^1$H-NMR (200 MHz, CDCl$_3$) δ 1.50-1.65 (4H, m), 2.25-2.35 (2H, m), 2.39 (3H, s), 2.99-3.06 (2H, m), 3.78 (3H, s), 4.20 (2H, s), 6.81 (2H, d, J=8.8 Hz), 6.96 (1H, s), 7.07 (2H, d, J=8.8 Hz), 7.93 (1H, s), 10.28 (1H, s).

REFERENCE EXAMPLE 24

To a solution of 5-((4-bromo-2-formyl-5-methylphenyl) (4-methoxybenzyl)amino)pentanoic acid (3.5 g) and potassium carbonate (1.34 g) DMF in (30 ml) was added dropwise a solution of iodomethane (1.6 g) in DMF (10 ml) under nitrogen atmosphere at 0° C. After returning to room temperature, the reaction mixture was stirred for 2 hours. Water was added and the mixture was extracted with ethyl acetate. The organic layer was washed with water five times and with saturated brine once, and dried with magnesium sulfate. The solvent was distilled off under reduced pressure to give methyl 5-((4-bromo-2-formyl-5-methylphenyl)(4-methoxybenzyl)amino)pentanoate (3.5 g) as a brown oily material.

$^1$H-NMR (200 MHz, CDCl$_3$) δ 1.45-1.65 (4H, m), 2.20-2.35 (2H, m), 2.39 (3H, s), 2.98-3.10 (2H, m), 3.63 (3H, s), 3.79 (3H, s), 4.20 (2H, s), 6.81 (2H, d, J=8.8 Hz), 6.96 (1H, s), 7.07 (2H, d, J=8.8 Hz), 7.93 (1H, s), 10.28 (1H, s).

REFERENCE EXAMPLE 25

A methanol solution of sodium methoxide (28%, 1.9 g) was added to a solution of methyl 5-((4-bromo-2-formyl-5-methylphenyl)(4-methoxybenzyl)amino)pentanoate (3.4 g) in dimethyl carbonate (50 ml), after which the mixture was stirred under nitrogen atmosphere at 50° C. for 3 hours. After cooling down to 0° C., water was added and the mixture was neutralized with 1N hydrochloric acid, and then extracted with ethyl acetate. The organic layer was washed with saturated brine and dried with magnesium sulfate. The solvent was distilled off under reduced pressure, and the resulting residue was purified by silica gel column chromatography (hexane:ethyl acetate=8:1) to give methyl 8-bromo-1-(4-methoxybenzyl)-9-methyl-1,2,3,4-tetrahydro-1-benzoazocine-5-carboxylate (2.42 g) as a brown oily material.

$^1$H-NMR (300 MHz, CDCl$_3$) δ 1.40-1.55 (2H, m), 2.20 (3H, s), 2.55 (2H, t, J=6.3 Hz), 3.43 (2H, t, J=5.7 Hz), 3.79 (3H, s), 3.80 (3H, s), 4.38 (2H, s), 6.53 (1H, s), 6.88 (2H, d, J=9.0 Hz), 7.08 (2H, d, J=9.0 Hz), 7.28 (1H, s), 7.72 (1H, s).

REFERENCE EXAMPLE 26

To a solution of methyl 8-bromo-1-(4-methoxybenzyl)-9-methyl-1,2,3,4-tetrahydro-1-benzoazocine-5-carboxylate (2.4 g) in toluene (12 ml) was added trifluoroacetic acid (12 ml), and the mixture was stirred under nitrogen atmosphere at 65° C. for 1.5 hours. After distilling off the solvent under reduced pressure, water was added at 0° C. and the mixture was neutralized with potassium carbonate, and extracted with ethyl acetate. After washing the organic layer with aqueous saturated sodium bicarbonate solution and saturated brine, the resultant was dried with magnesium sulfate. The solvent was distilled off under reduced pressure, and the resulting residue was purified by flash silica gel column chromatography (hexane-ethyl acetate 19:1→6:1) to give a yellow oily material. The resultant was as such dissolved in 1,2-dichloroethane (30 ml), to which isobutylaldehyde (2.01 g) and triacetoxy sodium borohydride (3.55 g) were added, and the mixture was stirred overnight. Water was added thereto and the mixture was extracted with ethyl acetate, after which it was washed with aqueous saturated sodium bicarbonate solution and saturated brine, and dried with magnesium sulfate. The solvent was distilled off under reduced pressure, and the resulting residue was purified by silica gel column chromatography (hexane:ethyl acetate=8:1) to give methyl 8-bromo-1-isobuthyl-9-methyl-1,2,3,4-tetrahydro-1-benzoazocine-5-carboxylate (920 mg) as a yellow oily material.

$^1$H-NMR (300 MHz, CDCl$_3$) δ 0.97 (6H, d, J=6.6 Hz), 2.05-2.20 (1H, m), 2.31 (3H, s), 2.45-2.55 (2H, m), 2.98 (2H, d, J=7.8 Hz), 3.38-3.42 (2H, m), 3.77 (3H, s), 6.59 (1H, s), 7.23 (1H, s), 7.67 (1H, s).

REFERENCE EXAMPLE 27

A suspension of methyl 8-bromo-1-isobutyl-9-methyl-1,2,3,4-tetrahydro-1-benzoazocine-5-carboxylate (900 mg) and 4-(2-butoxyethoxy)phenyl boric acid (759 mg) and potassium carbonate (883 mg) in toluene (20 ml), ethanol (2 ml) and water (2 ml) was stirred under argon atmosphere for 1 hour. Then, tetrakis(triphenylphosphine)palladium (142 mg) was added and the mixture was refluxed for 6 hours. After returning to room temperature, water was added and the reaction mixture was extracted with ethyl acetate. The organic layer was washed with saturated brine, and dried with magnesium sulfate. The solvent was distilled off under reduced pressure, and the resulting residue was purified by silica gel column chromatography (hexane:ethyl acetate=30: 1→6:1) to give methyl 8-(4-(2-butoxyethoxy)phenyl)-1-isobutyl-9-methyl-1,2,3,4-tetrahydro-1-benzoazocine-5-carboxylate (790 mg) as a yellow oily material.

¹H-NMR (200 MHz, CDCl₃) δ 0.90-1.02 (9H, m), 1.30-1.70 (6H, m), 2.10-2.25 (4H, m), 2.40-2.50 (2H, m), 3.06 (2H, d, J=7.4 Hz), 3.45-3.50 (2H, m), 3.55 (2H, t, J=7.0 Hz), 3.77 (3H, s), 3.80 (2H, t, J=6.6 Hz), 4.15 (2H, t, J=6.6 Hz), 6.63 (1H, s), 6.93 (2H, d, J=8.8 Hz), 7.00 (1H, s), 7.20 (2H, d, J=8.8 Hz), 7.81 (1H, s).

REFERENCE EXAMPLE 28

To methyl 8-(4-(2-butoxyethoxy)phenyl)-1-isobutyl-9-methyl-1,2,3,4-tetrahydro-1-benzoazocine-5-carboxylate (770 mg) were added tetrahydrofuran (15 ml) and methanol (15 ml), followed by adding aqueous 1N sodium hydroxide solution (4.8 ml), and the mixture was stirred at 90° C. overnight. After cooling to 0° C., water was added and the mixture was neutralized with 1N hydrochloric acid. After extracting with ethyl acetate, the organic layer was washed with saturated brine, and dried with magnesium sulfate. The solvent was distilled off under reduced pressure, and the resulting residue was recrystallized from hexane-ethyl acetate to give 8-(4-(2-butoxyethoxy)phenyl)-1-isobutyl-9-methyl-1,2,3,4-tetrahydro-1-benzoazocine-5-carboxylic acid (408 mg) as yellow crystals.

¹H-NMR (300 MHz, CDCl₃) δ 0.93 (3H, t, J=7.2 Hz), 1.01 (6H, d, J=6.6 Hz), 1.34-1.65 (6H, m), 2.10-2.25 (1H, m), 2.24 (3H, s), 2.55 (2H, t, J=6.6 Hz), 3.07 (2H, d, J=7.2 Hz), 3.45-3.50 (2H, m), 3.55 (2H, t, J=6.6 Hz), 3.81 (2H, t, J=5.1 Hz), 4.15 (2H, t, J=5.1 Hz), 6.63 (1H, s), 6.93 (2H, d, J=8.7 Hz), 7.01 (1H, s), 7.20 (2H, d, J=8.7 Hz), 7.92 (1H, s). Elementary analysis $C_{29}H_{40}NO_4$ Calcd. C, 74.64; H, 8.64; N, 3.00: Found C, 74.76; H, 8.45; N, 2.95.

REFERENCE EXAMPLE 29

To a solution of 4-methoxybenzaldehyde (20.8 g) and 6-aminohexanic acid (20.0 g) in methanol (240 ml) were added an aqueous 1N sodium hydroxide solution (152.5 ml) and palladium carbon (10%, 4.15 g), and then the mixture was stirred under hydrogen atmosphere for a day. After filtering off insolubles, the mixture was neutralized with 6N hydrochloric acid (25.4 ml) at 0° C. and the solvent was distilled off under reduced pressure. To the resulting residue were added DMSO (170 ml), water (114 ml), and sodium carbonate (40.4 g). Then, a solution of 5-bromo-2-fluoro benzaldehyde (25.8 g) in DMSO (52 ml) was added dropwise at 135° C. After stirring with heating as such overnight, the reaction mixture was cooled to 0° C., to which water was added, and it was neutralized with 6N hydrochloric acid and extracted with ethyl acetate. The organic layer was washed with water twice and with saturated brine once, and dried with magnesium sulfate. The solvent was distilled off under reduced pressure, and the resulting residue was purified by silica gel column chromatography (hexane:ethyl acetate=2:1→hexane:ethyl acetate=1:1) to give 6-((4-bromo-2-formylphenyl) (4-methoxybenzyl)amino)hexanoic acid (32.5 g) as a brown oily material.

¹H-NMR (200 MHz, CDCl₃) δ 1.20-1.70 (6H, m), 2.30 (2H, t, J=7.4 Hz), 3.06 (2H, t, J=7.4 Hz), 3.78 (3H, s), 4.22 (2H, s), 6.81 (2H, d, J=8.8 Hz), 6.98 (1H, d, J=8.8 Hz), 7.05 (2H, d, J=8.8 Hz), 7.54 (1H, dd, J=8.8, 2.6 Hz), 7.90 (1H, d, J=2.6 Hz), 10.31 (1H, s).

REFERENCE EXAMPLE 30

To a solution of 6-((4-bromo-2-formylphenyl)(4-methoxybenzyl)amino)hexanoic acid (32.0 g) and potassium carbonate (12.2 g) in DMF (300 ml) was added dropwise a solution of iodomethane (14.6 g) in DMF (100 ml) under nitrogen atmosphere at 0° C. After returning to room temperature, the reaction mixture was stirred for 2 hours, then water was added and the mixture was extracted with ethyl acetate. The organic layer was washed with water five times and with saturated brine once, and dried with magnesium sulfate. The solvent was distilled off under reduced pressure to give methyl 6-((4-bromo-2-formylphenyl)(4-methoxybenzyl)amino)hexanoate (30.5 g) as a brown oily material.

¹H-NMR (200 MHz, CDCl₃) δ 1.20-1.35 (2H, m), 1.40-1.65 (4H, m), 2.25 (2H, t, J=7.4 Hz), 3.06 (2H, t, J=7.8 Hz), 3.65 (3H, s), 3.78 (3H, s), 4.22 (2H, s), 6.81 (2H, d, J=8.4 Hz), 6.97 (1H, d, J=8.8 Hz), 7.06 (2H, d, J=8.4 Hz), 7.54 (1H, dd, J=8.8, 2.6 Hz), 7.90 (1H, d, J=2.6 Hz), 10.31 (1H, s).

REFERENCE EXAMPLE 31

A solution of sodium methoxide in methanol (28%, 16.5 g) was added to a solution of methyl 6-((4-bromo-2-formylphenyl) (4-methoxybenzyl)amino)hexanoate (29.4 g) in dimethyl carbonate (950 ml) and then the mixture was stirred under nitrogen atmosphere at 50° C. for 3 hours. After cooling down to 0° C., water was added and the mixture was neutralized with 1N hydrochloric acid, and then extracted with ethyl acetate. The organic layer was washed with saturated brine and dried with magnesium sulfate. The solvent was distilled off under reduced pressure, and the resulting residue was purified by silica gel column chromatography (hexane:ethyl acetate=12:1) to give methyl 9-bromo-1-(4-methoxybenzyl)-2,3,4-5-tetrahydro-1H-1-benzoazonin-6-carboxylate (12.8 g) as a yellow oily material.

¹H-NMR (300 MHz, CDCl₃) δ 1.50-1.68 (2H, m), 1.70-1.85 (2H, m), 2.25 (2H, t, J=6.3 Hz), 3.16 (2H, t, J=6.3 Hz), 3.80 (3H, s), 3.85 (3H, s), 4.14 (2H, s), 6.83 (2H, d, J=8.1 Hz), 6.91 (1H, d, J=7.8 Hz), 7.06 (2H, d, J=8.1 Hz), 7.24-7.27 (2H, m), 7.58 (1H, s).

REFERENCE EXAMPLE 32

To a solution of methyl 9-bromo-1-(4-methoxybenzyl)-2,3,4,5-tetrahydro-1H-1-benzoazonin-6-carboxylate (12.5 g) in toluene (62.5 ml) was added trifluoroacetic acid (62.5 ml) and the mixture was stirred under nitrogen atmosphere at 80° C. for 7 hours. After distilling off the solvent under reduced pressure, water was added at 0° C. and the mixture was neutralized with potassium carbonate, and extracted with ethyl acetate. After washing the organic layer with aqueous saturated sodium bicarbonate solution and saturated brine, the resultant was dried with magnesium sulfate. The solvent was distilled off under reduced pressure, and the resulting residue was purified by silica gel column chromatography (hexane-ethyl acetate=9:1) and recrystallized from hexane:ethyl acetate to give methyl 9-bromo-2,3,4,5-tetrahydro-1H-1-benzoazonin-6-carboxylate (7.4 g) as yellow crystals.

¹H-NMR (200 MHz, CDCl₃) δ 1.60-1.80 (4H, m), 2.15-2.25 (2H, m), 3.15-3.30 (2H, m), 3.65-3.80 (2H, m), 3.83 (3H, s), 6.88 (1H, d, J=8.8 Hz), 7.10 (1H, d, J=2.2 Hz), 7.28 (1H, dd, J=8.8, 2.2 Hz), 7.54 (1H, s).

REFERENCE EXAMPLE 33

To a solution of methyl 9-bromo-2,3,4,5-tetrahydro-1H-1-benzoazonin-6-carboxylate (2.0 g) in 1,2-dichloroethane (20 ml) were added propion aldehyde (1.87 g) and triacetoxy sodium borohydride (4.11 g) and the mixture was stirred overnight. Water was added and the mixture was extracted with ethyl acetate, after which it was washed with aqueous saturated sodium bicarbonate solution and saturated brine, and dried with magnesium sulfate. The solvent was distilled off under reduced pressure, and the resulting residue was purified by silica gel column chromatography (hexane:ethyl acetate=4:1) to give methyl 9-bromo-1-propyl-2,3,4,5-tetrahydro-1H-1-benzoazonin-6-carboxylate (2.15 g) as a yellow oily material.

$^1$H-NMR (200 MHz, CDCl$_3$) δ 0.89 (3H, t, J=7.2 Hz), 1.40-1.90 (6H, m), 2.25 (2H, t, J=6.6 Hz), 2.95 (2H, t, J=8.0 Hz), 3.13 (2H, t, J=6.6 Hz), 3.81 (3H, s), 6.88 (1H, d, J=8.8 Hz), 7.23-7.32 (2H, m), 7.60 (1H, s).

REFERENCE EXAMPLE 34

A suspension of methyl 9-bromo-1-propyl-2,3,4,5-tetrahydro-1H-1- benzoazocine-6-carboxylate (2.1 g) and 4-(2-butoxyethoxy) phenyl boric acid (1.84 g), and potassium carbonate (2.14 g) in toluene (25 ml), ethanol (2.5 ml) and water (2.5 ml) was stirred under argon atmosphere for 1 hour and then tetrakis(triphenylphosphine)palladium (343 mg) was added. The mixture was refluxed for 5 hours. After returning to room temperature, water was added and the reaction mixture was and extracted with ethyl acetate. The organic layer was washed with saturated brine, and dried with magnesium sulfate. The solvent was distilled off under reduced pressure, and the resulting residue was purified by silica gel column chromatography (hexane:ethyl acetate=19:1→hexane:ethyl acetate=9:1) to give methyl 9-(4-(2-butoxyethoxy)phenyl)-1-propyl-2,3,4,5-tetrahydro-1H-1-benzoazonin-6-carboxylate (2.18 g) as a yellow oily material.

$^1$H-NMR (200 MHz, CDCl$_3$) δ 0.89-0.97 (6H, m), 1.30-1.95 (10H, m), 2.33 (2H, t, J=6.2 Hz), 3.00-3.08 (2H, m), 3.21 (2H, t, J=6.2 Hz), 3.55 (2H, t, J=6.6 Hz), 3.77-3.83 (5H, m), 4.15 (2H, t, J=4.2 Hz), 6.96 (2H, d, J=8.8 Hz), 7.03 (1H, d, J=8.4 Hz), 7.32 (1H, d, J=2.2 Hz), 7.39-7.48 (3H, m), 7.77 (1H, s).

REFERENCE EXAMPLE 35

To methyl 9-(4-(2-butoxyethoxy)phenyl)-1-propyl-2,3,4,5-tetrahydro-1H-1-benzoazonin-6-carboxylate (2.1 g) was incorporated with tetrahydrofuran (27 ml) and methanol (27 ml), followed by adding aqueous 1N sodium hydroxide solution (9 ml), and the mixture was stirred at 90° C. for 7 hours. After cooling to 0° C., water was added and the mixture was neutralized with 1N hydrochloric acid. After extracting with ethyl acetate, the organic layer was washed with saturated brine, and dried with magnesium sulfate. The solvent was distilled off under reduced pressure, and the resulting residue was recrystallized from hexane-ethyl acetate to give 9-(4-(2-butoxyethoxy)phenyl)-1-propyl-2,3,4,5-tetrahydro-1H-1-benzoazonin-6-carboxylic acid (1.07 g) as yellow crystals.

$^1$H-NMR (300 MHz, CDCl$_3$) δ 0.91-0.97 (6H, m), 1.33-1.93 (10H, m), 2.36 (2H, t, J=6.3 Hz), 3.05-3.10 (2H, m), 3.24 (2H, t, J=6.3 Hz), 3.55 (2H, t, J=6.6 Hz), 3.80 (2H, t, J=5.1 Hz), 4.16 (2H, t, J=5.1 Hz), 6.97 (2H, d, J=8.7 Hz), 7.04 (1H, d, J=9.0 Hz), 7.35 (1H, d, J=2.1 Hz), 7.42-7.49 (3H, m), 7.92 (1H, s). Elementary analysis C$_{28}$H$_{37}$NO$_4$ Calcd. C, 74.47; H, 8.26; N, 3.10: Found C, 74.44; H, 8.18; N, 2.82.

REFERENCE EXAMPLE 36

To a solution of methyl 9-bromo-2,3,4,5-tetrahydro-1H-1-benzoazonin-6-carboxylate (2.0 g) in 1,2-dichloroethane (20 ml) were added isobutyl aldehyde (2.32 g) and triacetoxy sodium borohydride (4.11 g) and the mixture was stirred overnight. Water was added and the mixture was extracted with ethyl acetate, after which it was washed with aqueous saturated sodium bicarbonate solution and saturated brine, and dried with magnesium sulfate. The solvent was distilled off under reduced pressure, and the resulting residue was purified by silica gel column chromatography (hexane:ethyl acetate=4:1) to give methyl 9-bromo-1-isobutyl-2,3,4,5-tetrahydro-1H-1-benzoazonin-6-carboxylate (2.14 g) as a yellow oily material.

$^1$H-NMR (300 MHz, CDCl$_3$) δ 0.84 (6H, d, J=6.6 Hz), 1.50-1.75 (5H, m), 2.19 (2H, t, J=5.7 Hz), 2.64 (2H, d, J=7.2 Hz), 3.06 (2H, t, J=5.7 Hz), 3.81 (3H, s), 7.05 (1H, d, J=8.4 Hz), 7.21 (1H, d, J=2.1 Hz), 7.34 (1H, dd, J=8.4, 2.1 Hz), 7.57 (1H, s).

REFERENCE EXAMPLE 37

A suspension of methyl 9-bromo-1-isobutyl-2,3,4,5-tetrahydro-1H-1-benzoazonin-6-carboxylate (2.1 g) and 4-(2-butoxyethoxy)phenyl boric acid (1.77 g) and potassium carbonate (2.06 g) in toluene (25 ml), ethanol (2.5 ml) and water (2.5 ml) was stirred under argon atmosphere for 1 hour, and then tetrakis(triphenylphosphine)palladium (332 mg) was added. The mixture was refluxed for 5 hours. After returning to room temperature, water was added and the mixture was extracted with ethyl acetate. The organic layer was washed with saturated brine, and dried with magnesium sulfate. The solvent was distilled off under reduced pressure, and the resulting residue was purified by silica gel column chromatography (hexane:ethyl acetate=19:1→hexane:ethyl acetate=9:1) to give methyl 9-(4-(2-butoxyethoxy)phenyl)-1-isobutyl-2,3,4,5-tetrahydro-1H-1-benzoazonin-6-carboxylate (2.7 g) as a yellow oily material.

$^1$H-NMR (200 MHz, CDCl$_3$) δ 0.86-0.97 (9H, m), 1.30-1.80 (9H, m), 2.20-2.30 (2H, m), 2.73 (2H, d, J=7.4 Hz), 3.09-3.15 (2H, m), 3.55 (2H, t, J=6.6 Hz), 3.78-3.82 (5H, m), 4.16 (2H, t, J=4.8 Hz), 6.97 (2H, d, J=8.8 Hz), 7.19 (1H, d, J=8.6 Hz), 7.26-7.29 (1H, m), 7.42-7.50 (3H, m), 7.72 (1H, s).

REFERENCE EXAMPLE 38

To methyl 9-(4-(2-butoxyethoxy)phenyl)-1-isobutyl-2,3,4,5-tetrahydro-1H-1-benzoazonin-6-carboxylate (2.65 g) were added tetrahydrofuran (35 ml) and methanol (35 ml), followed by adding aqueous 1N sodium hydroxide solution (11.4 ml), and the mixture was stirred at 90° C. for 7 hours. After cooling to 0° C., water was added and the mixture was neutralized with 1N hydrochloric acid. After extracting with ethyl acetate, the organic layer was washed with saturated brine, and dried with magnesium sulfate. The solvent was distilled off under reduced pressure to give 9-(4-(2-butoxyethoxy)phenyl)-1-isobutyl-2,3,4,5-tetrahydro-1H-1-benzoazonin-6-carboxylic acid (2.5 g) as a yellow oily material.

$^1$H-NMR (300 MHz, CDCl$_3$) δ 0.86-0.96 (9H, m), 1.30-1.85 (9H, m), 2.25-2.35 (2H, m), 2.75 (2H, d, J=7.2 Hz), 3.14 (2H, t, J=5.7 Hz), 3.55 (2H, t, J=6.6 Hz), 3.81 (2H, t, J=4.8 Hz), 4.16 (2H, t, J=4.8 Hz), 6.98 (2H, d, J=8.7 Hz), 7.20 (1H, d, J=8.4 Hz), 7.31 (1H, d, J=2.4 Hz), 7.45-7.50 (3H, m), 7.86 (1H, s).

REFERENCE EXAMPLE 39

To a solution of 4-methoxybenzaldehyde (20.0 g) and 7-aminoheptanoic acid (18.8 g) in methanol (240 ml) were added an aqueous 1N sodium hydroxide solution (138 ml) and palladium carbon (10%, 4.0 g) and then the mixture was stirred under hydrogen atmosphere for a day. After filtering off insolubles, the mixture was neutralized with 6N hydrochloric acid (23 ml) at 0° C. and the solvent was distilled off under reduced pressure. To the resulting residue were added DMSO (160 ml), water (107 ml) and sodium carbonate (36.5 g), after which a solution of 5-bromo-2-fluorobenzaldehyde (23.3 g) in DMSO (50 ml) was added dropwise at 135° C. under nitrogen atmosphere. After stirring with heating as such overnight, the reaction mixture was cooled to 0° C., to which water was added, and it was neutralized with 6N hydrochloric acid and extracted with ethyl acetate. The organic layer was washed with water twice and with saturated brine once, and dried with magnesium sulfate. The solvent was distilled off under reduced pressure, and the resulting residue was purified by silica gel column chromatography (hexane:ethyl acetate=4:1→ethyl acetate) to give 7-((4-bromo-2-formylphenyl)(4-methoxybenzyl)amino)heptanoic acid (41.5 g) as a brown oily material.

$^1$H-NMR (200 MHz, CDCl$_3$) δ 1.15-1.65 (8H, m), 2.31 (2H, t, J=7.8 Hz), 3.05 (2H, t, J=7.4 Hz), 3.78 (3H, s), 4.22 (2H, s), 6.81 (2H, d, J=8.8 Hz), 6.98 (1H, d, J=8.8 Hz), 7.06 (2H, d, J=8.8 Hz), 7.54 (1H, dd, J=8.8, 2.2 Hz), 7.89 (1H, d, J=2.2 Hz), 10.30 (1H, s).

REFERENCE EXAMPLE 40

To a solution of 7-((4-bromo-2-formylphenyl)(4-methoxybenzyl)amino)heptanoic acid (41.0 g) and potassium carbonate (15.2 g) in DMF (400 ml) was added dropwise a DMF (100 ml) solution of iodomethane (18.2 g) under nitrogen atmosphere at 0° C. After returning to room temperature, the reaction mixture was stirred for 2 hours, water was added thereto and the mixture was extracted with ethyl acetate. The organic layer was washed with water five times and with saturated brine once, and dried with magnesium sulfate. The solvent was distilled off under reduced pressure to give methyl 7-((4-bromo-2-formylphenyl)(4-methoxybenzyl)amino)heptanoate (40.8 g) as a brown oily material.

$^1$H-NMR (200 MHz, CDCl$_3$) δ 1.20-1.35 (4H, m), 1.40-1.65 (4H, m), 2.26 (2H, t, J=7.6 Hz), 3.05 (2H, t, J=7.2 Hz), 3.65 (3H, s), 3.78 (3H, s), 4.22 (2H, s), 6.81 (2H, d, J=8.4 Hz), 6.97 (1H, d, J=8.8 Hz), 7.06 (2H, d, J=8.4 Hz), 7.53 (1H, dd, J=8.8, 2.4 Hz), 7.89 (1H, d, J=2.4 Hz), 10.30 (1H, s).

REFERENCE EXAMPLE 41

A sodium methoxide methanol solution (28%, 21.4 g) was added to a solution of methyl 7-((4-bromo-2-formylphenyl)(4-methoxybenzyl)amino)heptanoate (39.5 g) in dimethyl carbonate (1000 ml) and then the mixture was stirred under nitrogen atmosphere at 50° C. overnight. After cooling down to 0° C., water was added and the mixture was neutralized with 1N hydrochloric acid, and then extracted with ethyl acetate. The organic layer was washed with saturated brine and dried with magnesium sulfate. The solvent was distilled off under reduced pressure, and the resulting residue was purified by silica gel column chromatography (hexane:ethyl acetate=12:1) to give methyl 10-bromo-1-(4-methoxybenzyl)-1,2,3,4,5,6-hexahydro-1-benzoazetin-7-carboxylate (9.85 g) as a yellow oily material.

$^1$H-NMR (200 MHz, CDCl$_3$) δ 1.20-1.35 (2H, m), 1.40-1.65 (4H, m), 2.11 (2H, t, J=6.4 Hz), 2.87 (2H, t, J=6.2 Hz), 3.78 (3H, s), 3.82 (2H, s), 3.84 (3H, s), 6.77 (2H, d, J=8.8 Hz), 6.98-7.02 (3H, m), 7.17 (1H, d, J=2.2 Hz), 7.36 (1H, dd, J=8.8, 2.2 Hz), 7.45 (1H, s).

REFERENCE EXAMPLE 42

To a solution of methyl 10-bromo-1-(4-methoxybenzyl)-1,2,3,4,5,6-hexahydro-1-benzoazonin-7-carboxylate (9.5 g) in toluene (50 ml) was added trifluoroacetic acid (50 ml) and the mixture was stirred under nitrogen atmosphere at 80° C. for 6 hours. After distilling off the solvent under reduced pressure, water was added at 0° C. and the mixture was neutralized with potassium carbonate, and extracted with ethyl acetate. After washing the organic layer with aqueous saturated sodium bicarbonate solution and saturated brine, the resultant was dried with magnesium sulfate. The solvent was distilled off under reduced pressure, and the resulting residue was purified by silica gel column chromatography (hexane:ethyl acetate=9:1) to give methyl 10-bromo-1,2,3,4,5,6-hexahydro-1-benzoazetin-7-carboxylate (6.9 g) as a yellow oily material.

$^1$H-NMR (200 MHz, CDCl$_3$) δ 1.45-1.85 (6H, m), 2.10-2.25 (2H, m), 3.25-3.40 (2H, m), 3.68 (1H, br), 3.82 (3H, s), 6.76 (1H, d, J=8.8 Hz), 7.10 (1H, d, J=2.0 Hz), 7.29 (1H, dd, J=8.8, 2.0 Hz), 7.46 (1H, s).

REFERENCE EXAMPLE 43

To a solution of methyl 10-bromo-1,2,3,4,5,6-hexahydro-1-benzoazetin-7-carboxylate (2.0 g) in 1,2-dichloroethane (30 ml) were added propion aldehyde (1.79 g) and triacetoxy sodium borohydride (3.92 g) and the mixture was stirred overnight. Water was added and the mixture was extracted with ethyl acetate, after which it was washed with aqueous saturated sodium bicarbonate solution and saturated brine, and dried with magnesium sulfate. The solvent was distilled off under reduced pressure, and the resulting residue was purified by silica gel column chromatography (hexane:ethyl acetate=4:1) to give methyl 10-bromo-1-propyl-1,2,3,4,5,6-hexahydro-1-benzoazetin-7-carboxylate (1.95 g) as a yellow oily material.

$^1$H-NMR (200 MHz, CDCl$_3$) δ 0.78 (3H, t, J=7.2 Hz), 1.20-1.65 (8H, m), 2.09 (2H, t, J=6.4 Hz), 2.69-2.76 (2H, m), 2.97 (2H, t, J=4.8 Hz), 3.80 (3H, s), 7.08 (1H, d, J=8.4 Hz), 7.17 (1H, d, J=2.2 Hz), 7.38 (1H, dd, J=8.4, 2.2 Hz), 7.55 (1H, s).

REFERENCE EXAMPLE 44

A suspension of methyl 10-bromo-1-propyl-2,3,4,5,6-hexahydro-1-benzoazetin-7-carboxylate (1.86 g) and 4-(2-butoxyethoxy)phenyl boric acid (1.57 g), and potassium carbonate (1.82 g) in toluene (20 ml), ethanol (2.0 ml) and water (2.0 ml) was stirred under argon atmosphere for 1 hour. Then, tetrakis(triphenylphosphine)palladium (294 mg) was added and the mixture was refluxed for 5 hours. After returning to room temperature, water was added and the mixture was extracted with ethyl acetate. The organic layer was washed with saturated brine, and dried with magnesium sulfate. The solvent was distilled off under reduced pressure, and the resulting residue was purified by silica gel column chromatography (hexane:ethyl acetate=19:1→hexane:ethyl acetate=9:1) to give methyl 10-(4-(2-butoxyethoxy)phenyl)-1-propyl-1,2,3,4,5,6-hexahydro-1-benzoazetin-7-carboxylate (2.21 g) as a yellow oily material.

¹H-NMR (200 MHz, CDCl₃) δ 0.80 (3H, t, J=7.4 Hz), 0.93 (3H, t, J=7.2 Hz), 1.20-1.67 (12H, m), 2.10-2.20 (2H, m), 2.74-2.82 (2H, m), 2.95-3.05 (2H, m), 3.55 (2H, t, J=6.6 Hz), 3.78-3.83 (5H, m), 4.16 (2H, t, J=4.6 Hz), 6.97 (2H, d, J=9.2 Hz), 7.22-7.26 (2H, m), 7.45-7.51 (3H, m), 7.71 (1H, s).

REFERENCE EXAMPLE 45

To methyl 10-(4-(2-butoxyethoxy)phenyl)-1-propyl-1,2,3,4,5,6-hexahydro-1-benzoazetin-7-carboxylate (2.09 g) were added tetrahydrofuran (30 ml) and methanol (30 ml), followed by adding aqueous 1N sodium hydroxide solution (9 ml), and the mixture was stirred at 90° C. for 18 hours. After cooling to 0° C., water was added and the mixture was neutralized with 1N hydrochloric acid. After extracting with ethyl acetate, the organic layer was washed with saturated brine, and dried with magnesium sulfate. The solvent was distilled off under reduced pressure to give 10-(4-(2-butoxyethoxy)phenyl)-1-propyl-1,2,3,4,5,6-hexahydro-1-benzoazetin-7-carboxylic acid (2.03 g) as a yellow oily material.

¹H-NMR (200 MHz, CDCl₃) δ 0.81 (3H, t, J=7.4 Hz), 0.93 (3H, t, J=6.8 Hz), 1.23-1.80 (12H, m), 2.10-2.22 (2H, m), 2.75-2.83 (2H, m), 3.00-3.10 (2H, m), 3.55 (2H, t, J=6.6 Hz), 3.81 (2H, t, J=4.8 Hz), 4.16 (2H, t, J=4.8 Hz), 6.98 (2H, d, J=8.8 Hz), 7.24-7.28 (2H, m), 7.46-7.51 (3H, m), 7.84 (1H, s).

REFERENCE EXAMPLE 46

To a solution of methyl 10-bromo-1,2,3,4,5,6-hexahydro-1-benzoazetin-7-carboxylate (2.0 g) in 1,2-dichloroethane (30 ml) were added isobutyl aldehyde (2.22 g) and triacetoxy sodium borohydride (3.92 g), and the mixture was stirred overnight. Water was added and the mixture was extracted with ethyl acetate, after which it was washed with aqueous saturated sodium bicarbonate solution and saturated brine, and dried with magnesium sulfate. The solvent was distilled off under reduced pressure, and the resulting residue was purified by silica gel column chromatography (hexane:ethyl acetate=4:1) to give methyl 10-bromo-1-isobutyl-1,2,3,4,5,6-hexahydro-1-benzoazetin-7-carboxylate (2.2 g) as a yellow oily material.

¹H-NMR (200 MHz, CDCl₃) δ 0.82 (6H, d, J=6.6 Hz), 1.10-1.75 (7H, m), 2.12 (2H, t, J=6.2 Hz), 2.60 (2H, d, J=7.0 Hz), 2.93 (2H, t, J=5.6 Hz), 3.79 (3H, s), 7.09-7.14 (2H, m), 7.38 (1H, dd, J=8.8, 2.4 Hz), 7.60 (1H, s).

REFERENCE EXAMPLE 47

A suspension of methyl 10-bromo-1-isobutyl-1,2,3,4,5,6-hexahydro-1-benzoazetin-7-carboxylate (2.1 g), 4-(2-butoxyethoxy)phenyl boric acid (1.71 g) and potassium carbonate (1.99 g) in toluene (25 ml), ethanol (2.5 ml) and water (2.5 ml) was stirred under argon atmosphere for 1 hour. Then, tetrakis(triphenylphosphine)palladium (319 mg) was added and the mixture was refluxed for 5 hours. After returning to room temperature, water was added and the mixture was extracted with ethyl acetate. The organic layer was washed with saturated brine, and dried with magnesium sulfate. The solvent was distilled off under reduced pressure, and the resulting residue was purified by silica gel column chromatography (hexane:ethyl acetate=19:1→hexane:ethyl acetate=9:1) to give methyl 10-(4-(2-butoxyethoxy)phenyl)-1-isobutyl-1,2,3,4,5,6-hexahydro-1-benzoazetin-7-carboxylate (2.44 g) as a yellow oily material.

¹H-NMR (200 MHz, CDCl₃) δ 0.84-0.97 (9H, m), 1.15-1.80 (11H, m), 2.10-2.25 (2H, m), 2.65 (2H, d, J=7.0 Hz), 2.90-3.05 (2H, m), 3.55 (2H, t, J=6.6 Hz), 3.78-3.83 (5H, m), 4.16 (2H, t, J=4.6 Hz), 6.97 (2H, d, J=8.8 Hz), 7.18 (1H, d, J=1.8 Hz), 7.28 (1H, d, J=8.8 Hz), 7.45-7.51 (3H, m), 7.76 (1H, s).

REFERENCE EXAMPLE 48

To methyl 10-(4-(2-butoxyethoxy)phenyl)-1-isobutyl-1,2,3,4,5,6-hexahydro-1-benzoazetin-7-carboxylate (2.33 g) were added tetrahydrofuran (30 ml) and methanol (30 ml), followed by adding aqueous 1N sodium hydroxide solution (9.4 ml), and the mixture was stirred at 90° C. for 17 hours. After cooling to 0° C., water was added and the mixture was neutralized with 1N hydrochloric acid. After extracting with ethyl acetate, the organic layer was washed with saturated brine, and dried with magnesium sulfate. The solvent was distilled off under reduced pressure to give 10-(4-(2-butoxyethoxy)phenyl)-1-isobutyl-1,2,3,4,5,6-hexahydro-1-benzoazetin-7-carboxylic acid (2.21 g) as yellow crystals.

¹H-NMR (200 MHz, CDCl₃) δ 0.85-0.97 (9H, m), 1.20-1.80 (11H, m), 2.15-2.27 (2H, m), 2.67 (2H, d, J=7.0 Hz), 2.90-3.05 (2H, m), 3.55 (2H, t, J=6.6 Hz), 3.81 (2H, t, J=4.8 Hz), 4.16 (2H, t, J=4.8 Hz), 6.98 (2H, d, J=8.8 Hz), 7.20 (1H, d, J=2.2 Hz), 7.29 (1H, d, J=8.4 Hz), 7.47-7.51 (3H, m), 7.91 (1H, s). Elementary analysis $C_{30}H_{41}NO_4$ Calcd. C, 75.12; H, 8.62; N, 2.92: Found C, 75.25; H, 8.59; N, 2.79.

REFERENCE EXAMPLE 49

Formic acid (5.96 ml) was added to acetic anhydride (12.2 ml) at 0° C. and then the mixture was stirred under nitrogen atmosphere at 55° C. for 2 hours. After cooling to 0° C., THF (150 ml) was added, and further a solution of methyl 8-bromo-1,2,3,4-tetrahydro-1-benzoazocine-5-carboxylate (8.5 g) in THF (100 ml) was added dropwise under nitrogen atmosphere. The mixture was returned to room temperature and stirred for 5 hours, after which the solvent was distilled off under reduced pressure. The reaction material was diluted with ethyl acetate, followed by washing with saturated sodium bicarbonate, water and saturated brine. The resultant was dried with magnesium sulfate, after which the solvent was distilled off under reduced pressure, and the resulting residue was washed with hexane to give methyl 8-bromo-1-formyl-1,2,3,4-tetrahydro-1-benzoazocine-5-carboxylate (8.3 g) as colorless crystals.

¹H-NMR (300 MHz, CDCl₃) δ 1.73-1.78 (3H, m), 2.36 (2H, t, J=5.4 Hz), 3.70 (2H, t, J=5.7 Hz), 3.81 (3H, s), 7.15 (1H, d, J=5.2 Hz), 7.52-7.55 (3H, m), 7.87 (1H, s).

REFERENCE EXAMPLE 50

A suspension of methyl 8-bromo-1-formyl-1,2,3,4-tetrahydro-1-benzoazetin-5-carboxylate (8.25 g), 4-(2-butoxyethoxy)phenyl boric acid (7.88 g) and potassium carbonate (9.15 g) in toluene (120 ml), ethanol (12 ml) and water (12 ml) was stirred under argon atmosphere for 1 hour. Then, tetrakis(triphenylphosphine)palladium (1.47 g) was added, and the mixture was refluxed for 5 hours. After returning to room temperature, water was added and the reaction mixture was extracted with ethyl acetate. The organic layer was washed with saturated brine, and dried with magnesium sulfate. The solvent was distilled off under reduced pressure, and the resulting residue was purified by silica gel column chromatography (hexane:ethyl acetate=3:1→hexane:ethyl acetate=1:1) and recrystallized from ethyl acetate-diisopropyl ether to give methyl 8-(4-(2-butoxyethoxy)phenyl)-1-formyl-1,2,3,4-tetrahydro-1-benzoazocine-5-carboxylate (5.83 g) as colorless crystals.

$^1$H-NMR (300 MHz, CDCl$_3$) δ 0.94 (3H, t, J=7.5 Hz), 1.34-1.46 (2H, m), 1.55-1.66 (2H, m), 1.70-1.85 (2H, m), 2.39-2.43 (2H, m), 3.56 (2H, t, J=6.6 Hz), 3.76 (2H, t, J=5.4 Hz), 3.80-3.83 (5H, m), 4.18 (2H, t, J=5.1 Hz), 7.02 (2H, d, J=8.7 Hz), 7.31 (1H, d, J=8.4 Hz), 7.59 (1H, dd, J=8.4, 2.1 Hz), 7.48-7.53 (3H, m), 7.71 (1H, s), 7.97 (1H, s).

REFERENCE EXAMPLE 51

To methyl 8-(4-(2-butoxyethoxy)phenyl)-1-formyl-1,2,3,4-tetrahydro-1-benzoazocine-5-carboxylate (4.5 g) were added tetrahydrofuran (66 ml) and methanol (66 ml), followed by adding aqueous 1N sodium hydroxide solution (22 ml). The mixture was stirred at 90° C. for 19 hours. After cooling to 0° C., water was added and the mixture was neutralized with 1N hydrochloric acid. After extracting with ethyl acetate, the organic layer was washed with saturated brine, and dried with magnesium sulfate. The solvent was distilled off under reduced pressure, and the reaction material was re-crystallized from hexane-ethyl acetate to give 8-(4-(2-butoxyethoxy)phenyl)-1-formyl-1,2,3,4-tetrahydro-1-benzoazocine-5-carboxylic acid (2.21 g) as yellow crystals.

$^1$H-NMR (300 MHz, CDCl$_3$) δ 0.94 (3H, t, J=7.5 Hz), 1.34-1.46 (2H, m), 1.57-1.66 (2H, m), 1.75-1.90 (2H, m), 2.41-2.44 (2H, m), 3.56 (2H, t, J=6.6 Hz), 3.76-3.84 (4H, m), 4.18 (2H, t, J=4.8 Hz), 7.03 (2H, d, J=8.7 Hz), 7.32 (1H, d, J=8.4 Hz), 7.49-7.56 (3H, m), 7.60 (1H, dd, J=8.4, 2.4 Hz), 7.83 (1H, s), 8.01 (1H, s).

REFERENCE EXAMPLE 52

To a solution of methyl 8-(4-(2-butoxyethoxy)phenyl)-1,2,3,4-tetrahydro-1-benzoazocine-5-carboxylate (500 mg) in 1,2-dichloroethane (20 ml) were added 1-methylpyrazol-4-carboxyaldehyde (672 mg) and triacetoxy sodium borohydride (776 mg) and acetic acid (0.35 ml), and the mixture was stirred overnight. Water was added and the mixture was extracted with ethyl acetate, after which it was washed with aqueous saturated sodium bicarbonate solution and saturated brine, and dried with magnesium sulfate. The solvent was distilled off under reduced pressure, and the resulting residue was purified by silica gel column chromatography (hexane:ethyl acetate=1:1→hexane:ethyl acetate=1:3) to give a yellow oily material. The resultant was as such dissolved in terahydrofuran (36 ml) and methanol (36 ml), to which an aqueous 1N sodium hydroxide solution (12 ml) was added, and the mixture was stirred overnight. Water was added at 0° C., and the mixture was neutralized with 1N hydrochloric acid, and extracted with ethyl acetate. The organic layer was washed with saturated brine, and dried with magnesium sulfate. The solvent was distilled off under reduced pressure, the resulting residue was washed with hexane to give 8-(4-(2-butoxyethoxy)phenyl)-1-((1-methylpyrazol-4-yl)methyl)-1,2,3,4-tetrahydro-1-benzoazocine-5-carboxylic acid (495 mg) as yellow crystals.

m.p. 162.0-164.0° C.

$^1$H-NMR (300 MHz, CDCl$_3$) δ 0.93 (3H, t, J=7.2 Hz), 1.24-1.70 (6H, m), 2.55-2.65 (2H, m), 3.50-3.60 (4H, m), 3.80 (2H, t, J=4.8 Hz), 3.87 (3H, s), 4.14 (2H, t, J=4.8 Hz), 4.34 (2H, s), 6.87 (1H, d, J=9.9 Hz), 6.95 (2H, d, J=9.3 Hz), 7.24 (1H, s), 7.35-7.44 (5H, m), 7.98 (1H, s).

REFERENCE EXAMPLE 53

To a solution of methyl 8-(4-(2-butoxyethoxy)phenyl)-1,2,3,4-tetrahydro-1-benzoazocine-5-carboxylate (500 mg) and copper pivalate (108 mg) in dichloromethane (10 ml) was added triphenyl bismuth diacetate (1.36 g), and the mixture was stirred for 2 days. 3N Hydrochloric acid (10 ml) was added, and the mixture was stirred for 30 minutes, after which aqueous 1N sodium hydroxide solution (30 ml) was added at 0° C. The mixture was extracted with ethyl acetate, and the organic layer was washed with saturated brine, and dried with magnesium sulfate. The solvent was distilled off under reduced pressure, and the resulting residue was purified by silica gel column chromatography (hexane:ethyl acetate=9:1→ethyl acetate) to give methyl 8-(4-(2-butoxyethoxy)phenyl)-1-phenyl-1,2,3,4-tetrahydro-1-benzoazocine-5-carboxylate (238 mg) as a yellow oily material.

$^1$H-NMR (300 MHz, CDCl$_3$) δ 0.93 (3H, t, J=7.2 Hz), 1.34-1.46 (2H, m), 1.50-1.70 (4H, m), 2.42-2.52 (2H, m), 3.56 (2H, t, J=6.6 Hz), 3.77 (3H, s), 3.80-3.87 (4H, m), 4.17 (2H, t, J=4.2 Hz), 6.81-6.86 (3H, m), 6.99 (2H, d, J=8.4 Hz), 7.14-7.25 (3H, m), 7.42 (1H, dd, J=8.7, 2.4 Hz), 7.49-7.52 (3H, m), 7.74 (1H, s).

REFERENCE EXAMPLE 54

Methyl 8-(4-(2-butoxyethoxy)phenyl)-1-phenyl-1,2,3,4-tetrahydro-1-benzoazocine-5-carboxylate (230 mg) was dissolved in tetrahydrofuran (15 ml) and methanol (15 ml), after which an aqueous 1N sodium hydroxide solution (5 ml) was added. The mixture was stirred for 3 hours at 90° C. After adding water at 0° C., the reaction mixture was neutralized with 1N hydrochloric acid, and extracted with ethyl acetate. The organic layer was washed with saturated brine, and dried with magnesium sulfate. The solvent was distilled off under reduced pressure to give methyl 8-(4-(2-butoxyethoxy)phenyl)-1-phenyl-1,2,3,4-tetrahydro-1-benzoazocine-5-carboxylic acid (220 mg) as a yellow amorphous material.

$^1$H-NMR (300 MHz, CDCl$_3$) δ 0.93 (3H, t, J=7.2 Hz), 1.34-1.70 (6H, m), 2.45-2.55 (2H, m), 3.55 (2H, t, J=6.9 Hz), 3.81 (2H, t, J=4.8 Hz), 3.85-3.90 (2H, m), 4.16 (2H, t, J=4.8 Hz), 6.80-6.85 (3H, m), 6.98 (2H, d, J=8.7 Hz), 7.13-7.26 (3H, m), 7.42 (1H, dd, J=8.4, 2.4 Hz), 7.47-7.50 (3H, m), 7.84 (1H, s).

REFERENCE EXAMPLE 55

To a solution of 4-amino-2-methylthiophenol (500 mg) and triethylamine (3.0 ml) in tetrahydrofuran (15 ml) was added dropwise a solution of 5-chloromethyl-1-propylimidazole hydrochloride (847 mg) in methanol (5 ml) at 0° C. under argon atmosphere, after which the mixture was returned to room temperature and stirred for 3 hours. Water was added and the mixture was extracted with ethyl acetate, and organic layer was washed with saturated brine and dried with magnesium sulfate. The solvent was distilled off under reduced pressure, and the resulting residue was purified by basic silica gel column chromatography (hexane:ethyl acetate 1:1→ethyl acetate) and was recrystallized from hexane-ethyl acetate to give 3-methyl-4-[((1-propylimidazol-5-yl)methyl)sulfanyl]aniline (601 mg) as colorless crystals.

$^1$H-NMR (300 MHz, CDCl$_3$) δ 0.96 (3H, t, J=7.2 Hz), 1.77-1.89 (2H, m), 2.21 (3H, s), 3.69 (2H, br), 3.80 (2H, s), 3.90 (2H, t, J=7.2 Hz), 6.43 (1H, dd, J=8.1, 2.4 Hz), 6.52 (1H, d, J=2.4 Hz), 6.58 (1H, s), 7.09 (1H, d, J=8.1 Hz), 7.41 (1H, s).

REFERENCE EXAMPLE 56

To a solution of 4-amino-2-methylthiophenol (500 mg) and triethylamine (3.0 ml) in tetrahydrofuran (15 ml) was added dropwise a solution of 5-chloromethyl-4-methyl-1-propylimidazole hydrochloride (908 mg) in methanol (5 ml) at 0° C. under argon atmosphere, after which the mixture was returned to room temperature and stirred for 3 hours. Water was added and the mixture was extracted with ethyl acetate. The organic layer was washed with saturated brine and dried with magnesium sulfate. The solvent was distilled off under reduced pressure, and the resulting residue was purified by basic silica gel column chromatography (hexane:ethyl acetate=1:1→ethyl acetate) to give 3-methyl-4-[((4-methyl-1-propylimidazol-5-yl)methyl)sulfanyl]aniline (301 mg) as a brown powder.

$^1$H-NMR (300 MHz, CDCl$_3$) δ 0.96 (3H, t, J=7.2 Hz), 1.74 (3H, s), 1.76-1.88 (2H, m), 2.18 (3H, s), 3.69 (2H, br), 3.75 (2H, s), 3.84 (2H, t, J=7.2 Hz), 6.42 (1H, dd, J=8.4, 2.4 Hz), 6.52 (1H, d, J=2.4 Hz), 7.06 (1H, d, J=8.4 Hz), 7.34 (1H, s).

REFERENCE EXAMPLE 57

Under argon atmosphere, a mixture of methyl 8-bromo-1-isobutyl-1,2,3,4-tetrahydro-1-benzazocine-5-carboxylate (1.3 g), 4-(2-butoxyethoxy)phenyl boric acid (1.07 g) and potassium carbonate (1.02 g) in toluene-ethanol-water (40-4-4 ml) was stirred at room temperature for 1 hour. To the reaction system was added tetrakis(triphenylphosphine)-palladium (0.21 g), and the mixture was refluxed for 5 hours. After cooling to room temperature, water was added and the mixture was extracted with ethyl acetate. The organic layer was washed with saturated brine, and dried with magnesium sulfate. After concentration under reduced pressure, the residue was separated to purify by column chromatography (ethyl acetate:hexane=1:49→1:19→1:9) to give methyl 1-isobutyl-8-[4-(2-propoxyethoxy)phenyl]-1,2,3,4-tetrahydro-1-benzazocine-5-carboxylate (1.20 g) as a yellow oily material.

$^1$H-NMR (200 MHz, CDCl$_3$) δ 0.94 (3H, t, J=7.4 Hz), 0.99 (6H, d, J=6.4 Hz), 1.40-1.51 (2H, m), 1.55-1.70 (2H, m), 2.06-2.26 (1H, m), 2.51-2.57 (2H, m), 3.06 (2H, d, J=6.8 Hz), 3.45-3.54 (4H, m), 3.78-3.83 (5H, m), 4.15 (2H, t, J=5.1 Hz), 6.81 (1H, d, J=8.6 Hz), 6.95 (2H, d, J=8.8 Hz), 7.31-7.46 (4H, m), 7.88 (1H, s).

REFERENCE EXAMPLE 58

To a solution of methyl 1-isobutyl-8-[4-(2-propoxyethoxy)phenyl]-1,2,3,4-tetrahydro-1-benzazocine-5-carboxylate (1.20 g) in a mixture of ethanol-THF (10-5 ml) was added an aqueous 1N sodium hydroxide solution (5.2 ml) at room temperature. The mixture was stirred at 60° C. for 16 hours and cooled to 0° C. 1N Hydrochloric acid (6 ml) was added and the mixture was extracted with ethyl acetate. The organic layer was washed with saturated brine, and dried with magnesium sulfate. After concentration under reduced pressure, the precipitated crystals were collected by filtration. The crystals were washed with diisopropylether to give 1-isobutyl-8-[4-(2-propoxyethoxy)phenyl]-1,2,3,4-tetrahydro-1-benzazocine-5-carboxylic acid (0.96 g) as yellow crystals.

mp 142-144° C.

$^1$H-NMR (200 MHz, CDCl$_3$) δ 0.94 (3H, t, J=7.4 Hz), 1.00 (6H, d, J=7.0 Hz), 1.40-1.54 (2H, m), 1.56-1.73 (2H, m), 2.06-2.29 (1H, m), 2.48-2.61 (2H, m), 3.07 (2H, d, J=7.6 Hz), 3.48-3.54 (4H, m), 3.80 (2H, t, J=5.0 Hz), 4.15 (2H, t, J=5.0 Hz), 6.84 (1H, d, J=8.8 Hz), 6.96 (2H, d, J=8.8 Hz), 7.33-7.46 (4H, m), 8.00 (1H, s). IR (KBr) 1669, 1607, 1497, 1456, 1422, 1265, 1250, 1194, 1161, 1127 cm$^{-1}$

Elementary analysis C$_{27}$H$_{35}$NO$_4$ Calcd. C, 74.11; H, 8.06; N, 3.20: Found. C, 74.12; H, 8.27; N, 3.04.

REFERENCE EXAMPLE 59

Under argon atmosphere, a mixture of methyl 8-bromo-1-propyl-1,2,3,4-tetrahydro-1-benzazocine-5-carboxylate (1.5 g), 4-(2-butoxyethoxy)phenyl boric acid (1.29 g) and potassium carbonate (1.23 g) in toluene-ethanol-water (45-4.5-4.5 ml) was stirred at room temperature for 1 hour. To the reaction system was added tetrakis-(triphenylphosphine) palladium (0.26 g) was added, and the mixture was refluxed for 4 hours. After cooling to room temperature, water was added and the reaction mixture was extracted with ethyl acetate. The organic layer was washed with saturated brine, and dried with magnesium sulfate. After concentration under reduced pressure, the residue was separated to purify by column chromatography (ethyl acetate:hexane=1:49→1:19→1:9) to give methyl 8-[4-(2-propoxyethoxy)phenyl]-1-propyl-1,2,3,4-tetrahydro-1-benzazocine-5-carboxylate (1.10 g) as a yellow oily material.

$^1$H-NMR (300 MHz, CDCl$_3$) δ 0.94 (3H, t, J=7.5 Hz), 0.98 (3H, t, J=7.4 Hz), 1.40-1.74 (6H, m), 2.54-2.58 (2H, m), 3.15-3.21 (2H, m), 3.46-3.53 (4H, m), 3.79-3.82 (5H, m), 4.15 (2H, t, J=4.8 Hz), 6.76 (1H, d, J=9.0 Hz), 6.95 (2H, d, J=8.7 Hz), 7.32 (1H, d, J=2.1 Hz), 7.36-7.45 (3H, m), 7.82 (1H, s).

REFERENCE EXAMPLE 60

To a solution of methyl 8-[4-(2-propoxyethoxy)phenyl]-1-propyl-1,2,3,4-tetrahydro-1-benzazocine-5-carboxylate (1.10 g) in a mixture of ethanol-THF (20-10 ml) was added an aqueous 1N sodium hydroxide solution (5.0 ml) at room temperature. The mixture was stirred at 60° C. for 16 hours and cooled to 0° C. 1N Hydrochloric acid (6 ml) was added, and the mixture was extracted with ethyl acetate. The organic layer was washed with saturated brine, and dried with magnesium sulfate. After concentration under reduced pressure, the precipitated crystals were collected by filtration. The crystals were washed with diisopropylether to give 8-[4-(2-propoxyethoxy)phenyl]-1-propyl-1,2,3,4-tetrahydro-1-benzazocine-5-carboxylic acid (0.80 g) as yellow crystals.

mp 202-204° C.

$^1$H-NMR (200 MHz, CDCl$_3$) δ 0.94 (3H, t, J=7.4 Hz), 0.98 (3H, t, J=7.6 Hz), 1.35-1.86 (6H, m), 2.52-2.63 (2H, m), 3.11-3.25 (2H, m), 3.48-3.54 (4H, m), 3.80 (2H, t, J=5.1 Hz), 4.15 (2H, t, J=5.1 Hz), 6.77 (1H, d, J=9.6 Hz), 6.96 (2H, d, J=8.8 Hz), 7.33-7.46 (4H, m), 7.98 (1H, s). IR (KBr) 1667, 1607, 1499, 1454, 1418, 1366, 1308, 1267, 1248, 1196, 1169, 1125, 835, 810 cm$^{-1}$

Elementary analysis C$_{26}$H$_{33}$NO$_4$ Calcd. C, 73.73; H, 7.85; N, 3.31: Found. C, 73.46; H, 7.88; N, 3.07.

REFERENCE EXAMPLE 61

4-Amino thiophenol (2.5 g) was dissolved in water (2.5 ml) and isopropanol (10 ml) and triethyhlamine (5.5 ml) was added thereto. The mixture was cooled to −15--10° C.

A solution of 5-(chloromethyl)-1-propyl-1H-imidazole hydrochloride (3.9 g) in water (2.5 ml) was added dropwise thereto at −15--10° C., and the reaction mixture was stirred at the same temperature for 1 hour. After distilling off isopropanol under reduced pressure, methyl isobutyl ketone (25 ml) was added, and the organic layer was washed with water. To the organic layer was added activated carbon (0.1 g) and the mixture was stirred at room temperature for 10 minutes. The organic layer was concentrated and dissolved in methyl isobutyl ketone (30 ml).

Separately, di-p-toluoyl-(D)-tartaric acid (7.7 g) was dissolved in a mixed solution of toluene (90 ml) and methyl isobutyl ketone (60 ml) and to the solution was added water (3.6 ml). Then, the above methyl isobutyl ketone solution was slowly added dropwise over 2 hours. After stirring for 1 hour, aqueous 30% hydrogen peroxide (6.8 g) was added, and the mixture was stirred at room temperature for 24 hours. Methanol (30 ml) was added and the mixture was stirred at 50° C. for 8 hours. Water (30 ml) was added, and the mixture was stirred at room temperature for 5 hours. The precipitated crystals were collected by filtration and washed with water (30 ml) to give (−)-4-{[(1-propyl-1H-imidazol-5-yl)methyl]sulfenyl}phenylamine di-p-toluoyl-D-tartarate monohydrate (7.1 g, 53%).

REFERENCE EXAMPLE 62

To (−)-4-{[(1-propyl-1H-imidazol-5-yl)methyl]sulfenyl}phenylamine di-p-toluoyl-D-tartarate monohydrate (5 g) were added 1N hydrochloric acid (25 ml) and ethyl acetate (15 ml) to effect reverse extraction. To the aqueous layer was added aqueous 25% potassium carbonate solution (25 ml) (pH 9) and the mixture was extracted with 25 ml of ethyl acetate-IPA (4:1) three times. The organic layer was washed with saturated brine (25 ml) and dried with magnesium sulfate. The solvent was distilled off to give (−)-4-{[(1-propyl-1H-imidazol-5-yl)methyl]sulfinyl}phenylamine.

REFERENCE EXAMPLE 63

To a solution of 8-[4-(2-butoxyethoxy)phenyl]-1-isobutyl-1,2,3,4-tetrahydro-1-benzoazocine-5-carboxylic acid (90 g) in THF (7.5 ml) was added DMF (460 mg), followed by addition of thionyl chloride (24.9 g) dropwise at 10-15° C., and the mixture was stirred at the same temperature for 40 minutes.

Separately, to a solution of (−)-4-{[(1-propyl-1H-imidazol-5-yl)methyl]sulfinyl}phenylamine in THF (540 ml) was added pyridine (55.18 g) and the mixture was adjusted to 5° C. or lower. Then, the above acid chloride solution was added dropwise at 5° C. or lower, and the mixture was stirred at the same temperature for 2.8 hours. Water (540 ml) and aqueous 20% citric acid solution (360 ml) were added, and THF was distilled off under reduced pressure, after which the reaction mixture was extracted with ethyl acetate. The extract was washed in turn with water, aqueous saturated sodium bicarbonate solution and water, after which the solvent was distilled off. To the residual material were added acetonitrile (720 ml) and ethyl acetate (720 ml) were added, and then methanesulfonic acid (18.2 g) was added dropwise. The mixture was stirred at room temperature for 1 hour. The precipitated crystals were collected by filtration to give (−)-8-[4-(2-butoxyethoxy)phenyl]-1-isobutyl-N-(4-{[(1-propyl-1H-imidazol-5-yl)methyl]sulfinyl}phenyl)-1,2,3,4-tetrahydro-1-benzoazocine-5-carboxyamide methanesulfonate as yellow crystals (141.8 g, 94.4%).

EXPERIMENTAL EXAMPLE (1) Cloning of Human CCR5 Chemokine Receptor

Cloning of CCR5 gene was conducted from human spleen cDNA by PCR method. Using cDNA (0.5 ng) from spleen (Toyobo, QUICK-Clone cDNA) as a genetic template, primer sets prepared by referring to CCR5 gene nucleotide sequence described by Samson et al. (Biochemistry 35 (11), 3362-3367 (1996)), i.e., SEQ ID NO: 1 (sequence length: 34; sequence type: nucleic acid; chain: single; topology: linear; sequence kind: other nucleic acid, synthetic DNA) described in Experimental Example (1) of WO 99/32100, and SEQ ID NO: 2 (sequence length: 34; sequence type: nucleic acid; chain: single; topology: linear; sequence kind: other nucleic acid, synthetic DNA) described in Experimental Example (1) of WO 99/32100, (25 pmol, respectively), and TaKaRa EX Taq (Takara Shuzo), PCR reaction was carried out in DNA Thermal Cycler 480 (Perkin Elmer). The reaction conditions: 30 cycles of 95° C. for 1 minute, 60° C. for 1 minute, and 75° C. for 5 minutes. The PCR products were subjected to agarose gel electrophoresis, and DNA fragments of about 1.0 kb were collected. The CCR5 gene was cloned using Original TA Cloning Kit (Funakoshi).

(2) Preparation of Expression Plasmid of Human CCR5

After the plasmids obtained above were digested by restriction enzymes XbaI (Takara Shuzo) and BamHI (Takara Shuzo), DNA fragments of about 1.0 kb were collected by agarose gel electrophoresis. The DNA fragments and an expression plasmid for animal cells pcDNA3.1 (Funakoshi), which was previously digested by XbaI and BamHI, were mixed and ligated by DNA Ligation Kit Ver.2 (Takara Shuzo). Transformation of *E. coli* JM109 competent cells (Takara Shuzo) gave plasmid pCKR5.

(3) Introduction of the Human CCR5 Expression Plasmid into CHO-K1 Cells and Expression Thereof CHO-KI cells grown in a tissue culture flask 750 ml (Becton Dickinson) using Ham F12 medium (Nihon Pharm.) containing 10% fetal bovine serum (Lifetech Oriental) were collected by using 0.5 g/L trypsin-0.2 g/L EDTA (Lifetech Oriental). The cells were washed with PBS (Lifetech Oriental), centrifuged (1000 rpm, 5 minutes), and resuspended in PBS. The DNA was introduced into the cells using Gene Pulser (BioRad) according to the following conditions. Namely, $8 \times 10^6$ cells and 10 ug of human CCR5 expression plasmid pCKR5 were placed in a cuvette of 0.4 cm gap, and the mixture was electropolated under conditions of electric voltage of 0.25 kV, and capacitance of less than 960 μF.

Then, the cells were transferred to Ham F12 medium containing 10% fetal bovine serum. After incubation for 24 hours, the cells were collected, centrifuged, and resuspended in Ham F12 medium containing 10% fetal bovine serum and Geneticin (Lifetech Oriental) at a concentration of 500 μg/ml. The cells were diluted to a concentration of $10^4$ cells/ml, and inoculated in 96 well plate (Becton Dickinson), to obtain Geneticin-resistant cells.

The Geneticin-resistant cells were grown in 96 well plate (Becton Dickinson), and CCR5 expressing cells were selected from the resistant cells. Namely, in an assay buffer, (Ham F12 medium containing 0.5% BSA, and 20 mM HEPES (Wako Pure Chemical Ind., pH 7.2)), containing 200 pM [$^{125}$I]-RANTES (Amersham) as a ligand, the cells were subjected to binding reaction at room temperature for 40 minutes. The well plate containing the cells was washed with ice-cooled PBS, added with 1M NaOH in an amount of 50 μl/well and stirred. The cells to which the ligand bound specifically, i.e., CCR5/CHO cells, were selected by measurement of radioactivity by γ-counter.

(4) Evaluation of Compounds Based on CCR5 Antagonist Activity

The CCR5/CHO cells were inoculated in 96 well microplate at a concentration of $5 \times 10^4$ cells/well, and grown for 24 hours. After removal of the medium by aspiration, to each well was added an assay buffer containing a test compound (1 μM), and ($^{125}$I)/RANTES (Amersham) used as a ligand at a concentration of 100 pM. The mixture was subjected to the reaction at room temperature for 40 minutes. After removal of the assay buffer by aspiration, each well was washed with cooled PBS twice. Then, 200 μl MicroScint 20 (Packerd) was added to each well, and the radioactivity of each well was measured by TopCount(Packerd).

According to the method above, inhibitory ratios to CCR5 binding of the test compounds were determined. The results are shown in Table 1.

TABLE 1

| Compound No. | Binding Inhibitory Ratio (%) |
|---|---|
| 1 | 94 |
| 2 | 96 |
| 3 | 91 |
| 4 | 100 |
| 5 | 86 |
| 6 | 98 |
| 7 | 100 |
| 8 | 99 |
| 9 | 100 |
| 14 | 98 |
| 22 | 98 |
| 23 | 97 |
| 26 | 100 |
| 32 | 100 |
| 34 | 97 |
| 35 | 100 |
| 36 | 97 |
| 37 | 100 |
| 38 | 94 |
| 39 | 99 |
| 42 | 90 |
| 45 | 96 |
| 46 | 99 |
| 48 | 97 |
| 49 | 91 |
| 50 | 93 |
| 52 | 96 |
| 53 | 100 |

FORMULATION EXAMPLE 1 (CAPSULES)

| | |
|---|---|
| (1) (S)-8-[4-(2-butoxyethoxy)phenyl]-1-isobutyl-N-(4-[[N-methyl-N-(tetrahydropyran-4-yl)amino]methyl]phenyl]-1,2,3,4-tetrahydro-1-benzazocine-5-carboxamide | 40 mg |
| (2) lactose | 61 mg |
| (3) microcrystalline cellulose | 18 mg |
| (4) magnesium stearate | 1 mg |
| contents of 1 capsule | 120 mg |

After mixing (1), (2), (3) and (4), the mixture is filled in gelatin capsules.

FORMULATION EXAMPLE 2 (CAPSULES)

| | |
|---|---|
| (1) (S)-8-[4-(2-butoxyethoxy)phenyl]-1-isobutyl-N-[4-[[1-propyl-1H-imidazol-5-yl)methyl]sulfinyl]phenyl]-1,2,3,4-tetrahydro-1-benzazocine-5-carboxamide methanesulfonate | 40 mg |
| (2) lactose | 61 mg |
| (3) microcrystalline cellulose | 18 mg |
| (4) magnesium stearate | 1 mg |
| contents of 1 capsule | 120 mg |

After mixing (1), (2), (3) and (4), the mixture is filled in gelatin capsules.

FORMULATION EXAMPLE 3 (CAPSULES)

| | |
|---|---|
| (1) (S)-8-[4-(2-butoxyethoxy)phenyl]-1-propyl-N-[4-[[1-propyl-1H-imidazol-5-yl)methyl]sulfinyl]phenyl]-1,2,3,4-tetrahydro-1-benzazocine-5-carboxamide methansulfonate | 40 mg |
| (2) lactose | 61 mg |
| (3) microcrystalline cellulose | 18 mg |
| (4) magnesium stearate | 1 mg |
| contents of 1 capsule | 120 mg |

After mixing (1), (2), (3) and (4), the mixture is filled in gelatin capsules.

FORMULATION EXAMPLE 4 (TABLETS)

| | |
|---|---|
| (1) (S)-1-isobutyl-8-[4-(2-butoxyethoxy)phenyl]-N-[4-[[1-propyl-1H-imidazol-5-yl)methyl]sulfinyl]phenyl]-1,2,3,4-tetrahydro-1-benzazocine-5-carboxamide | 40 mg |
| (2) mannitol | 51.2 mg |
| (3) microcrystalline cellulose | 18 mg |
| (4) hydroxypropyl cellulose | 3.6 mg |
| (5) croscarmellose sodium | 6 mg |
| (6) magnesium stearate | 1.2 mg |
| contents of 1 tablet | 120 mg |

(1), (2), (3) and (4) are mixed and granulated. To the granules are added (5) and (6) and the mixture is compressed into tablets.

FORMULATION EXAMPLE 5 (TABLETS)

| | |
|---|---|
| (1) (S)-8-[4-(2-butoxyethoxy)phenyl]-1-[(1-methyl-1H-pyrazol-4-yl)methyl]-N-[4-[[(1-propyl-1H-imidazol-5-yl)methyl]sulfinyl]phenyl]-1,2,3,4-tetrahydro-1-benzazocine-5-carboxamide | 40 mg |
| (2) mannitol | 51.2 mg |
| (3) microcrystalline cellulose | 18 mg |
| (4) hydroxypropyl cellulose | 3.6 mg |
| (5) croscarmellose sodium | 6 mg |
| (6) magnesium stearate | 1.2 mg |
| contents of 1 tablet | 120 mg |

(1), (2), (3) and (4) are mixed and granulated. To the granules are added (5) and (6) and the mixture is compressed into tablets.

FORMULATION EXAMPLE 6 (TABLETS)

| | |
|---|---:|
| (1) (S)-8-[4-(2-butoxyethoxy)phenyl]-1-isobutyl-N-[4-[[4-propyl-4H-1,2,4-triazol-3-yl)methyl]sulfinyl]phenyl]-1,2,3,4-tetrahydro-1-benzazocine-5-carboxamide | 40 mg |
| (2) mannitol | 51.2 mg |
| (3) microcrystalline cellulose | 18 mg |
| (4) hydroxypropyl cellulose | 3.6 mg |
| (5) croscarmellose sodium | 6 mg |
| (6) magnesium stearate | 1.2 mg |
| contents of 1 tablet | 120 mg |

(1), (2), (3) and (4) are mixed and granulated. To the granules are added (5) and (6) and the mixture is compressed into tablets.

As described hereinabove, the compound of the formula [I] or a salt thereof of the present invention has a strong CCR5 antagonist activity, and can be advantageously used for prevention and treatment of a variety of human HIV infectious diseases, for example AIDS.

The invention claimed is:

1. (S)-8-[4-(2-Butoxyethoxy)phenyl]-1-isobutyl-N-(4-{[(1-propyl-1H-imidaxol-5-yl)methyl]sulfinyl}phenyl)-1,2,3,4-tetrahydro-1-benzazocine-5-carboxamide, (S)-8-[4-(2-butoxyothoxy) or a salt thereof.

* * * * *

UNITED STATES PATENT AND TRADEMARK OFFICE
CERTIFICATE OF CORRECTION

PATENT NO. : 7,371,772 B2  Page 1 of 1
APPLICATION NO. : 10/484762
DATED : May 13, 2008
INVENTOR(S) : Shiraishi et al.

It is certified that error appears in the above-identified patent and that said Letters Patent is hereby corrected as shown below:

In claim 1, column 114, line 14, please delete "imidaxol" and insert therefor -- imidazol --; and column 114, lines 15-16, please delete "(S)-8-[4-(2-butoxyothoxy)".

Signed and Sealed this

Thirteenth Day of January, 2009

JON W. DUDAS
*Director of the United States Patent and Trademark Office*